(12) United States Patent
Ismagilov et al.

(10) Patent No.: US 10,543,485 B2
(45) Date of Patent: Jan. 28, 2020

(54) SLIP CHIP DEVICE AND METHODS

(71) Applicant: University of Chicago, Chicago, IL (US)

(72) Inventors: Rustem F. Ismagilov, Chicago, IL (US); Wenbin Du, Chicago, IL (US); Liang Li, Chicago, IL (US); Feng Shen, Chicago, IL (US); Kevin Paul Flood Nichols, Chicago, IL (US); Delai Chen, Cambridge, MA (US); Jason Eugene Kreutz, Chicago, IL (US)

(73) Assignee: University of Chicago, Chicago, IL (US)

( * ) Notice: Subject to any disclaimer, the term of this patent is extended or adjusted under 35 U.S.C. 154(b) by 160 days.

(21) Appl. No.: 15/164,788

(22) Filed: May 25, 2016

(65) Prior Publication Data
US 2016/0256870 A1 Sep. 8, 2016

Related U.S. Application Data

(63) Continuation of application No. 13/257,811, filed as application No. PCT/US2010/028316 on Mar. 23, 2010, now Pat. No. 9,415,392.
(Continued)

(51) Int. Cl.
*B01L 3/00* (2006.01)
*B01F 13/00* (2006.01)
(Continued)

(52) U.S. Cl.
CPC .... *B01L 3/502715* (2013.01); *B01F 13/0094* (2013.01); *B01L 3/502738* (2013.01);
(Continued)

(58) Field of Classification Search
CPC ......... B01L 3/502738; B01L 2200/027; B01L 2300/0864; B01L 3/5025; B01F 13/0094
See application file for complete search history.

(56) References Cited

U.S. PATENT DOCUMENTS

| 2,541,413 A | 2/1951 | Gorey |
|---|---|---|
| 3,787,290 A | 1/1974 | Kaye |
| (Continued) | | |

FOREIGN PATENT DOCUMENTS

| CN | 2482070 | 3/2002 |
|---|---|---|
| CN | 1886644 | 12/2006 |
| (Continued) | | |

OTHER PUBLICATIONS

US 7,897,368 B2, 03/2011, Handique et al. (withdrawn)
(Continued)

*Primary Examiner* — Jonathan M Hurst
(74) *Attorney, Agent, or Firm* — Goodwin Procter LLP

(57) ABSTRACT

A device is described having a first surface having a plurality of first areas and a second surface having a plurality of second areas. The first surface and the second surface are opposed to one another and can move relative to each other from at least a first position where none of the plurality of first areas, having a first substance, are exposed to plurality of second areas, having a second substance, to a second position. When in the second position, the plurality of first and second areas, and therefore the first and second substances, are exposed to one another. The device may further include a series of ducts in communication with a plurality of first second areas to allow for a substance to be disposed in, or upon, the plurality of second areas when in the first position.

14 Claims, 11 Drawing Sheets

Specification includes a Sequence Listing.

part I part II

Related U.S. Application Data

(60) Provisional application No. 61/340,872, filed on Mar. 22, 2010, provisional application No. 61/262,375, filed on Nov. 18, 2009, provisional application No. 61/162,922, filed on Mar. 24, 2009.

(51) Int. Cl.
| | |
|---|---|
| *C12Q 1/02* | (2006.01) |
| *C12Q 1/70* | (2006.01) |
| *G01N 21/78* | (2006.01) |
| *G01N 33/543* | (2006.01) |
| *B01L 7/00* | (2006.01) |

(52) U.S. Cl.
CPC ........ *B01L 3/502761* (2013.01); *C12Q 1/025* (2013.01); *C12Q 1/703* (2013.01); *G01N 21/78* (2013.01); *G01N 33/54386* (2013.01); *B01L 3/5025* (2013.01); *B01L 7/52* (2013.01); *B01L 2200/025* (2013.01); *B01L 2200/027* (2013.01); *B01L 2300/0609* (2013.01); *B01L 2300/0809* (2013.01); *B01L 2300/0816* (2013.01); *B01L 2300/0861* (2013.01); *B01L 2300/0864* (2013.01); *B01L 2300/0867* (2013.01); *B01L 2300/0887* (2013.01); *B01L 2300/0893* (2013.01); *B01L 2300/12* (2013.01); *B01L 2300/168* (2013.01); *B01L 2400/065* (2013.01); *H01L 2924/0002* (2013.01)

(56) References Cited

U.S. PATENT DOCUMENTS

| | | | |
|---|---|---|---|
| 3,996,345 | A | 12/1976 | Ullman et al. |
| 4,071,409 | A | 1/1978 | Messing et al. |
| 4,755,363 | A | 7/1988 | Fujita et al. |
| 4,853,336 | A | 8/1989 | Saros et al. |
| 4,963,498 | A | 10/1990 | Hillman et al. |
| 5,026,113 | A | 6/1991 | DiCarlo et al. |
| 5,077,017 | A | 12/1991 | Gorin et al. |
| 5,114,208 | A | 5/1992 | Ikeda et al. |
| 5,169,942 | A | 12/1992 | Johnson et al. |
| 5,185,099 | A | 2/1993 | Delpuech et al. |
| 5,251,670 | A | 10/1993 | Bates et al. |
| 5,264,570 | A | 11/1993 | Johnson et al. |
| 5,478,893 | A | 12/1995 | Ghosh et al. |
| 5,518,892 | A | 5/1996 | Naqui et al. |
| 5,656,493 | A | 8/1997 | Mullis et al. |
| 5,686,315 | A | 11/1997 | Pronovost et al. |
| 5,688,651 | A | 11/1997 | Solomon |
| 5,707,850 | A | 1/1998 | Cole |
| 5,718,509 | A * | 2/1998 | Dunfee ............... B01F 13/0093 206/219 |
| 5,725,017 | A | 3/1998 | Elsberry et al. |
| 5,726,026 | A | 3/1998 | Wilding et al. |
| 5,739,036 | A | 4/1998 | Parris |
| 5,744,305 | A | 4/1998 | Fodor et al. |
| 5,746,978 | A | 5/1998 | Bienhaus et al. |
| 5,772,889 | A | 6/1998 | Gjerde et al. |
| 5,773,258 | A | 6/1998 | Birch et al. |
| 5,805,947 | A | 9/1998 | Miyamoto et al. |
| 5,872,010 | A | 2/1999 | Karger et al. |
| 5,948,624 | A | 9/1999 | Rothschild et al. |
| 5,993,631 | A | 11/1999 | Parton et al. |
| 5,997,636 | A | 12/1999 | Gamarnik et al. |
| 6,013,166 | A | 1/2000 | Heller |
| 6,124,138 | A | 9/2000 | Woudenberg |
| 6,130,098 | A | 10/2000 | Handique et al. |
| 6,140,053 | A | 10/2000 | Koster |
| 6,146,854 | A | 11/2000 | Koster et al. |
| 6,168,948 | B1 | 1/2001 | Anderson et al. |
| 6,171,785 | B1 | 1/2001 | Higuchi |
| 6,180,372 | B1 | 1/2001 | Franzen |
| 6,197,595 | B1 | 3/2001 | Anderson et al. |
| 6,203,989 | B1 | 3/2001 | Goldberg et al. |
| 6,274,726 | B1 | 8/2001 | Laugharn, Jr. et al. |
| 6,277,648 | B1 | 8/2001 | Colpan |
| 6,300,138 | B1 | 10/2001 | Gleason et al. |
| 6,379,929 | B1 | 4/2002 | Burns et al. |
| 6,391,624 | B1 | 5/2002 | Megerle |
| 6,409,832 | B2 | 6/2002 | Weigl et al. |
| 6,426,230 | B1 | 7/2002 | Feistel |
| 6,436,292 | B1 | 8/2002 | Petro |
| 6,451,610 | B1 | 9/2002 | Gorman et al. |
| 6,458,553 | B1 | 10/2002 | Colin |
| 6,465,640 | B1 | 10/2002 | Hood |
| 6,500,617 | B1 | 12/2002 | Stemmer et al. |
| 6,503,707 | B1 | 1/2003 | Baxter-Lowe |
| 6,524,456 | B1 | 2/2003 | Ramsey et al. |
| 6,548,256 | B2 | 4/2003 | Lienau et al. |
| 6,550,497 | B2 | 4/2003 | Thiele et al. |
| 6,565,813 | B1 | 5/2003 | Garyantes |
| 6,567,492 | B2 | 5/2003 | Kiselev et al. |
| 6,569,631 | B1 | 5/2003 | Pantoliano et al. |
| 6,575,188 | B2 | 6/2003 | Parunak |
| 6,606,618 | B2 | 8/2003 | Delo |
| 6,632,653 | B1 | 10/2003 | Astle |
| 6,638,408 | B1 | 10/2003 | Speicher et al. |
| 6,702,256 | B2 | 3/2004 | Killeen et al. |
| 6,705,357 | B2 | 3/2004 | Jeon et al. |
| 6,716,642 | B1 | 4/2004 | Wu et al. |
| 6,717,136 | B2 | 4/2004 | Andersson et al. |
| 6,720,187 | B2 | 4/2004 | Bedingham et al. |
| 6,737,026 | B1 | 5/2004 | Bergh |
| 6,797,056 | B2 | 9/2004 | David |
| 6,808,934 | B2 | 10/2004 | Mutz et al. |
| 6,821,770 | B1 | 11/2004 | Hogan |
| 6,845,968 | B2 | 1/2005 | Killeen et al. |
| 6,852,851 | B1 | 2/2005 | Tooke et al. |
| 6,855,490 | B2 | 2/2005 | Sompuram et al. |
| 6,858,439 | B1 | 2/2005 | Xu et al. |
| 6,883,559 | B2 | 4/2005 | Jeon et al. |
| 6,893,612 | B2 | 5/2005 | Kacian et al. |
| 6,949,355 | B2 | 9/2005 | Yamanishi et al. |
| 6,949,575 | B2 | 9/2005 | Barta et al. |
| 6,994,749 | B2 | 2/2006 | David |
| 7,003,104 | B2 | 2/2006 | Lee |
| 7,015,041 | B2 | 3/2006 | Santarsiero et al. |
| 7,101,663 | B2 | 9/2006 | Godfrey et al. |
| 7,122,301 | B2 | 10/2006 | Shvets et al. |
| 7,122,640 | B2 | 10/2006 | Gjerde et al. |
| 7,126,626 | B2 | 10/2006 | Sawahara et al. |
| 7,129,091 | B2 | 10/2006 | Ismagilov et al. |
| 7,135,180 | B2 | 11/2006 | Truong-Le |
| 7,136,688 | B2 | 11/2006 | Jung et al. |
| 7,169,601 | B1 | 1/2007 | Northrup et al. |
| 7,235,216 | B2 | 6/2007 | Kiselev et al. |
| 7,244,961 | B2 | 7/2007 | Jovanovic et al. |
| 7,252,939 | B2 | 8/2007 | Mori et al. |
| 7,294,308 | B2 | 11/2007 | Kacian et al. |
| 7,294,466 | B2 | 11/2007 | McMillan |
| 7,294,503 | B2 | 11/2007 | Quake et al. |
| 7,297,485 | B2 | 11/2007 | Bornarth et al. |
| 7,306,672 | B2 | 12/2007 | Hansen et al. |
| 7,309,588 | B2 | 12/2007 | Burg et al. |
| 7,314,070 | B2 | 1/2008 | Jeon et al. |
| 7,319,003 | B2 | 1/2008 | Cantor et al. |
| 7,329,485 | B2 | 2/2008 | Zlotnick |
| 7,351,303 | B2 | 4/2008 | Liu et al. |
| 7,375,190 | B2 | 5/2008 | Cheng et al. |
| 7,413,712 | B2 | 8/2008 | Liu et al. |
| 7,465,562 | B2 | 12/2008 | Wangh et al. |
| 7,501,245 | B2 | 3/2009 | Quake et al. |
| 7,556,776 | B2 | 7/2009 | Fraden et al. |
| 7,595,871 | B2 | 9/2009 | Weber |
| 7,608,399 | B2 | 10/2009 | Reed et al. |
| 7,615,274 | B2 | 11/2009 | Ehrfeld et al. |
| 7,629,165 | B2 | 12/2009 | Wyatt et al. |
| 7,648,835 | B2 | 1/2010 | Breidford et al. |
| 7,655,129 | B2 | 2/2010 | Blackburn et al. |
| 7,683,035 | B1 | 3/2010 | Erbacher et al. |
| 7,767,447 | B2 | 8/2010 | Breidenthal et al. |

(56) References Cited

U.S. PATENT DOCUMENTS

| | | |
|---|---|---|
| 7,780,336 B2 | 8/2010 | Breidenthal et al. |
| 7,790,865 B1 | 9/2010 | Heath et al. |
| 7,846,333 B2 | 12/2010 | Pluester et al. |
| 7,851,207 B1 | 12/2010 | Sagripanti |
| 7,867,757 B2 | 1/2011 | Karlsen et al. |
| 7,871,813 B2 | 1/2011 | Wyatt et al. |
| 7,915,030 B2 | 3/2011 | Inoue et al. |
| 7,939,018 B2 | 5/2011 | Bedingham et al. |
| 7,939,249 B2 | 5/2011 | Parthasarathy et al. |
| 7,955,504 B1 | 6/2011 | Jovanovic et al. |
| 7,998,437 B2 | 8/2011 | Berndt et al. |
| 7,998,708 B2 | 8/2011 | Handique et al. |
| 8,043,811 B2 | 10/2011 | Danks et al. |
| 8,052,929 B2 | 11/2011 | Breidenthal et al. |
| 8,057,758 B2 | 11/2011 | Bedingham et al. |
| 8,097,222 B2 | 1/2012 | Scurati |
| 8,137,554 B2 | 3/2012 | Jovanovic et al. |
| 8,187,557 B2 | 5/2012 | Van Atta et al. |
| 8,211,367 B2 | 7/2012 | Wyatt et al. |
| 8,221,705 B2 | 7/2012 | Breidenthal et al. |
| 8,222,023 B2 | 7/2012 | Battrell et al. |
| 8,273,245 B2 | 9/2012 | Jovanovic et al. |
| 8,323,900 B2 | 12/2012 | Handique et al. |
| 8,362,219 B2 | 1/2013 | Gjerde et al. |
| 8,415,103 B2 | 4/2013 | Handique |
| 8,449,830 B2 | 5/2013 | Claussen et al. |
| 8,470,586 B2 | 6/2013 | Wu et al. |
| 8,480,976 B2 | 7/2013 | Breidenthal et al. |
| 8,491,178 B2 | 7/2013 | Breidenthal et al. |
| 8,574,833 B2 | 11/2013 | Jenison et al. |
| 8,615,368 B2 | 12/2013 | Light, II et al. |
| 8,637,250 B2 | 1/2014 | Jenison |
| 8,784,745 B2 | 7/2014 | Nelson et al. |
| 8,828,654 B2 | 9/2014 | Nelson et al. |
| 9,097,710 B2 | 8/2015 | Qin et al. |
| 9,415,392 B2 | 8/2016 | Ismagilov et al. |
| 9,447,461 B2 | 9/2016 | Ismagilov et al. |
| 9,464,319 B2 | 10/2016 | Ismagilov et al. |
| 9,493,826 B2 | 11/2016 | Ismagilov et al. |
| 2001/0048900 A1 | 12/2001 | Bardell et al. |
| 2002/0008029 A1 | 1/2002 | Williams et al. |
| 2002/0012971 A1 | 1/2002 | Mehta |
| 2002/0017464 A1 | 2/2002 | Parce et al. |
| 2002/0022261 A1 | 2/2002 | Anderson et al. |
| 2002/0058332 A1 | 5/2002 | Quake et al. |
| 2002/0076825 A1 | 6/2002 | Cheng et al. |
| 2002/0110835 A1 | 8/2002 | Kumar |
| 2002/0125197 A1 | 9/2002 | Hager et al. |
| 2002/0147317 A1 | 10/2002 | Bentsen et al. |
| 2002/0155032 A1 | 10/2002 | Liu et al. |
| 2002/0172969 A1 | 11/2002 | Burns et al. |
| 2003/0022243 A1 | 1/2003 | Kondejewski et al. |
| 2003/0064414 A1 | 4/2003 | Benecky et al. |
| 2003/0190608 A1 | 10/2003 | Blackburn |
| 2003/0229376 A1 | 12/2003 | Sandhu |
| 2004/0005582 A1 | 1/2004 | Shipwash |
| 2004/0037813 A1 | 2/2004 | Simpson et al. |
| 2004/0072357 A1 | 4/2004 | Stiene et al. |
| 2004/0119070 A1 | 6/2004 | Roach et al. |
| 2004/0137458 A1 | 7/2004 | Archambault et al. |
| 2004/0142479 A1 | 7/2004 | Moerman et al. |
| 2004/0181131 A1 | 9/2004 | Maynard et al. |
| 2004/0184967 A1 | 9/2004 | Parng et al. |
| 2004/0224419 A1 | 11/2004 | Zheng et al. |
| 2004/0228212 A1 | 11/2004 | de Goor et al. |
| 2004/0258571 A1 | 12/2004 | Lee et al. |
| 2005/0009582 A1 | 1/2005 | Vooi-Kia et al. |
| 2005/0019792 A1 | 1/2005 | McBride et al. |
| 2005/0019952 A1 | 1/2005 | Moerman |
| 2005/0042639 A1 | 2/2005 | Knapp et al. |
| 2005/0087122 A1 | 4/2005 | Ismagliov et al. |
| 2005/0172476 A1 | 8/2005 | Stone et al. |
| 2005/0221339 A1 | 10/2005 | Griffiths et al. |
| 2006/0003439 A1 | 1/2006 | Ismagilov et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0163385 A1 | 7/2006 | Link et al. |
| 2006/0188911 A1 | 8/2006 | Otomo et al. |
| 2006/0195047 A1 | 8/2006 | Freeman et al. |
| 2007/0003442 A1 | 1/2007 | Link et al. |
| 2007/0014695 A1 | 1/2007 | Yue et al. |
| 2007/0015545 A1 | 1/2007 | Leifer et al. |
| 2007/0026439 A1 | 2/2007 | Faulstich et al. |
| 2007/0052781 A1 | 3/2007 | Fraden et al. |
| 2007/0077547 A1 | 4/2007 | Shvets et al. |
| 2007/0092914 A1 | 4/2007 | Griffiths et al. |
| 2007/0093894 A1 | 4/2007 | Darouiche |
| 2007/0134739 A1 | 6/2007 | Holmquist et al. |
| 2007/0154355 A1* | 7/2007 | Berndt ............ B01L 3/502715 422/400 |
| 2007/0172954 A1 | 7/2007 | Ismagilov et al. |
| 2007/0184489 A1 | 8/2007 | Griffiths et al. |
| 2007/0189927 A1 | 8/2007 | Ballhorn et al. |
| 2007/0195127 A1 | 8/2007 | Ahn et al. |
| 2007/0202525 A1 | 8/2007 | Quake et al. |
| 2008/0003142 A1 | 1/2008 | Link et al. |
| 2008/0003693 A1 | 1/2008 | Torres |
| 2008/0014589 A1 | 1/2008 | Link et al. |
| 2008/0058039 A1 | 3/2008 | Lee et al. |
| 2008/0107565 A1 | 5/2008 | Vivienne et al. |
| 2008/0108063 A1 | 5/2008 | Lucero et al. |
| 2008/0129736 A1 | 6/2008 | Sun et al. |
| 2008/0153091 A1 | 6/2008 | Brown et al. |
| 2008/0166793 A1 | 7/2008 | Beer et al. |
| 2008/0176757 A1 | 7/2008 | Hassibi et al. |
| 2008/0213215 A1 | 9/2008 | Krishnan et al. |
| 2008/0293045 A1 | 11/2008 | Piepenburg et al. |
| 2009/0010804 A1 | 1/2009 | Withrow, III et al. |
| 2009/0021728 A1 | 1/2009 | Heinz et al. |
| 2009/0035847 A1 | 2/2009 | Cho et al. |
| 2009/0053719 A1 | 2/2009 | Lo et al. |
| 2009/0057149 A1 | 3/2009 | Wegner et al. |
| 2009/0060797 A1 | 3/2009 | Mathies et al. |
| 2009/0062134 A1 | 3/2009 | Linton et al. |
| 2009/0068760 A1 | 3/2009 | Nelson et al. |
| 2009/0069194 A1 | 3/2009 | Ramakrishnan |
| 2009/0117620 A1 | 5/2009 | Fritchie et al. |
| 2009/0176280 A1 | 7/2009 | Hutchison, III et al. |
| 2009/0197248 A1 | 8/2009 | Griffiths et al. |
| 2009/0215050 A1 | 8/2009 | Jenison |
| 2009/0221096 A1 | 9/2009 | Torres |
| 2009/0298191 A1 | 12/2009 | Whitesides et al. |
| 2010/0022414 A1 | 1/2010 | Link et al. |
| 2010/0137152 A1 | 6/2010 | Gorfinkel et al. |
| 2010/0304387 A1 | 12/2010 | Jenison et al. |
| 2010/0308051 A1 | 12/2010 | Weber |
| 2011/0166044 A1 | 7/2011 | Jones et al. |
| 2011/0297866 A1 | 12/2011 | Weber |
| 2011/0303306 A1 | 12/2011 | Weber |
| 2011/0318728 A1 | 12/2011 | Phan et al. |
| 2012/0028342 A1 | 2/2012 | Ismagilov et al. |
| 2012/0077188 A1 | 3/2012 | Nelson et al. |
| 2012/0264132 A1 | 10/2012 | Ismagilov et al. |
| 2012/0329038 A1 | 12/2012 | Ismagilov et al. |
| 2013/0130226 A1 | 5/2013 | Lim et al. |
| 2013/0288348 A1 | 10/2013 | Breidenthal et al. |
| 2013/0331298 A1 | 12/2013 | Rea |
| 2014/0017730 A1 | 1/2014 | Hicke et al. |
| 2014/0038200 A1 | 2/2014 | Jenison et al. |
| 2014/0134619 A1 | 5/2014 | Jenison |
| 2014/0336064 A1 | 11/2014 | Ismagilov et al. |

FOREIGN PATENT DOCUMENTS

| | | |
|---|---|---|
| EP | 0816837 | 1/1998 |
| EP | 1110084 | 7/1999 |
| EP | 1036082 | 5/2002 |
| EP | 996547 | 12/2002 |
| EP | 808456 | 5/2003 |
| EP | 739240 | 6/2004 |
| EP | 1287164 | 10/2004 |
| EP | 1473084 | 11/2004 |
| EP | 1080099 | 2/2006 |

(56) References Cited

FOREIGN PATENT DOCUMENTS

| | | |
|---|---|---|
| EP | 1495119 | 1/2007 |
| EP | 1641564 | 10/2007 |
| EP | 1177318 | 2/2008 |
| EP | 1173623 | 6/2008 |
| EP | 1740722 | 8/2008 |
| EP | 1382676 | 5/2009 |
| EP | 1925678 | 7/2009 |
| EP | 1380642 | 3/2010 |
| EP | 1714134 | 4/2010 |
| EP | 0875584 | 9/2010 |
| EP | 1631685 | 12/2010 |
| EP | 2305809 | 4/2011 |
| EP | 1820552 | 6/2011 |
| EP | 1679383 | 7/2011 |
| EP | 1896180 | 11/2011 |
| EP | 1630228 | 1/2012 |
| EP | 2007905 | 8/2012 |
| EP | 2016186 | 1/2013 |
| EP | 1558934 | 7/2013 |
| EP | 2276828 | 7/2013 |
| GB | 2097692 | 11/1982 |
| JP | 2004-532099 A | 10/2004 |
| JP | 2005-083505 A | 3/2005 |
| JP | 2005-083510 A | 3/2005 |
| WO | WO 1984/002000 | 5/1984 |
| WO | WO 1997/029508 | 8/1997 |
| WO | WO 1998/000231 | 1/1998 |
| WO | WO 1998/002237 | 1/1998 |
| WO | WO 1998/052691 | 11/1998 |
| WO | WO 1997/004297 | 2/1999 |
| WO | WO 2000/013014 | 3/2000 |
| WO | WO 2000/021666 | 4/2000 |
| WO | WO 2001/012327 | 2/2001 |
| WO | WO 2001/077683 | 10/2001 |
| WO | WO 2002/012856 | 2/2002 |
| WO | WO 2002/023163 | 3/2002 |
| WO | WO 2002/025243 | 3/2002 |
| WO | WO 2003/044221 | 5/2003 |
| WO | WO 2004/004906 A1 | 1/2004 |
| WO | WO 2004/038363 | 5/2004 |
| WO | WO 2005/010169 | 2/2005 |
| WO | WO 2005/016529 | 2/2005 |
| WO | WO 2006/088876 | 8/2006 |
| WO | WO 2006/096571 | 9/2006 |
| WO | WO 2006/101851 | 9/2006 |
| WO | WO 2007/009082 | 1/2007 |
| WO | WO 2007/021343 | 2/2007 |
| WO | WO 2007/030501 | 3/2007 |
| WO | WO 2007/044974 | 4/2007 |
| WO | WO 2007/070832 | 6/2007 |
| WO | WO 2007/081385 | 7/2007 |
| WO | WO 2007/081386 | 7/2007 |
| WO | WO 2007/081387 | 7/2007 |
| WO | WO 2007/089541 | 8/2007 |
| WO | WO 2007/089777 | 8/2007 |
| WO | WO 2007/133710 | 11/2007 |
| WO | WO 2007/146923 | 12/2007 |
| WO | WO 2008/002267 | 1/2008 |
| WO | WO 2008/043041 | 4/2008 |
| WO | WO 2008/048673 | 4/2008 |
| WO | WO 2008/063227 | 5/2008 |
| WO | WO 2008/069884 | 6/2008 |
| WO | WO 2008/079274 | 7/2008 |
| WO | WO 2008/097559 | 8/2008 |
| WO | WO 2008/147382 | 12/2008 |
| WO | WO 2009/002849 | 12/2008 |
| WO | WO 2009/012420 | 1/2009 |
| WO | WO 2009/013683 | 1/2009 |
| WO | WO 2009/015390 | 1/2009 |
| WO | WO 2009/018348 | 2/2009 |
| WO | WO 2009/048673 | 4/2009 |
| WO | WO 2009/070640 | 6/2009 |
| WO | WO 2009/070742 | 6/2009 |
| WO | WO 2009/071078 | 6/2009 |
| WO | WO 2009/105648 | 8/2009 |
| WO | WO 2009/149257 | 12/2009 |
| WO | WO 2010/078420 | 7/2010 |
| WO | WO 2010/083795 | 7/2010 |
| WO | WO 2010/094249 | 8/2010 |
| WO | WO 2011/109762 | 9/2011 |
| WO | WO 2013/123238 | 8/2013 |

OTHER PUBLICATIONS

Asiello, P.J., et al., "Miniaturized isothermal nucleic acid amplification, a review," Lab on a Chip, 2011, pp. 1420-1430, vol. 11, No. 8.
United States Patent Office, Office Action for U.S. Appl. No. 14/177,194, dated Apr. 26, 2016, 15 Pages.
United States Patent Office, Office Action for U.S. Appl. No. 14/177,194, dated Aug. 31, 2016, 18 Pages.
United States Patent Office, Office Action for U.S. Appl. No. 15,164,798, dated Sep. 6, 2016, 7 Pages.
Canadian Intellectual Property Office, Canadian Patent Application No. 2,756,463, dated Jul. 22, 2016, 4 Pages.
European Patent Office, Examination Report for European Patent Application No. 10756714.1, dated Nov. 23, 2016, 4 Pages.
Japanese Patent Office, Office Action, Japanese Patent Application No. 2014-266976, dated Sep. 12, 2016, 7 Pages (with English translation).
Korean Intellectual Property Office, Korean Patent Application No. 10-2011-7024884, dated Aug. 23, 2016, 4 Pages (with English translation).
Australian Government, IP Australia, Patent Examination Report No. 2, Australian Application No. 2015200465, dated Apr. 19, 2017, four pages.
Japanese Patent Office, Office Action, Japanese Application No. 2016-116331, dated May 17, 2017, five pages.
Japanese Patent Office, Office Action, Japanese Application No. 2016-116332, dated Feb. 16, 2017, four pages.
Korean Intellectual Property Office, Notice of Preliminary Rejection, Korean Application No. 10-2017-7002166, dated May 5, 2017, six pages.
United States Office Action, U.S. Appl. No. 15/164,798, dated Jan. 10, 2017, 14 pages.
United States Office Action, U.S. Appl. No. 14/177,194, dated Apr. 13, 2017, 15 pages.
Office Action for Japanese Patent Application No. JP 2016-116332, dated Oct. 2, 2017, 6 Pages.
Office Action for U.S. Appl. No. 14/177,194, dated Sep. 27, 2017, 12 Pages.
Abhyankar, Vinay V. et al., "Spatiotemporal Micropatterning of Cells on Arbitrary Substrates", Anal. Chem., vol. 79, (2007), pp. 4066-4073.
Abrams, William R., et al., "Development of a Microfluidic Device for Detection of Pathogens in Oral Samples Using Upconverting Phoshor Technology (UPT)," Ann. N.Y. Acad. Sci. 1098: (2007), pp. 375-388.
Adamson, David N. et al., "Production of Arrays of Chemically Distinct Nanolitre Plugs via Repeated Splitting in Microfluidic Devices", Lab on a Chip, vol. 6, (2006), pp. 1178-1186.
Aharoni, Amir, et al., "High-Throughput Screening of Enzyme Libraries: Thiolactonases Evolved by Fluorescence-Activated Sorting of Single Cells in Emulsion Compartments," Chem. Biol., vol. 12, (2005), pp. 1281-1289.
Ajaev, Vladimir S., et al. "Steady Vapor Bubbles in Rectangular Microchannels", Journal of Colloid and Interface Science, vol. 240, (2001), pp. 259-271.
Ajaev, Vladimir S., et al. "Three-Dimensional Steady Vapor Bubbles in Rectangular Microchannels", Journal of Colloid and Interface Science, vol. 244, (2001), pp. 180-189.
Akselband, Y. et al., "Rapid Mycobacteria Drug Susceptibility Testing Using Gel Microdrop (GMD) Growth Assay and Flow Cytometry", J. Microbiol. Methods, vol. 62, (2005), pp. 181-197.
Alberts, Bruce et al., "Chapter 22—Histology: The Lives and Deaths of Cells in Tissues", Molecular Biology of the Cell (Garland Publishing, 2002), pp. 1259-1312.

(56) References Cited

OTHER PUBLICATIONS

Alizadeh, Ash A. et al., "Genomic-Scale Gene Expression Profiling of Normal and Malignant Immune Cells", Current Opinion in Immunology, vol. 12, No. 2, (2000), pp. 219-225.
Alter, Orly et al., "Singular Value Decomposition for Genome-Wide Expression Data Processing and Modeling", PNAS (2000), vol. 97, No. 18, pp. 10101-10106.
Altreuter, David H. et al., "Combinatorial Biocatalysis: Taking the Lead From Nature", Current Opinion in Biotechnology vol. 10, No. 2, (1999), pp. 130-136.
Anderson, Megan J. et al., "Phase Knowledge Enables Rational Screens for Protein Crystallization," PNAS, vol. 103, No. 45, (2006) pp. 16746-16751.
Andersson, Helene et al., "Microfluidic Devices for Cellomics: A Review," Sensors and Actuators B—Chemical 92, (2003), pp. 315-325.
Androulakis, I.P. et al., "Analysis of Time-Series Gene Expression Data: Methods, Challenges, and Opportunities,", Annual Review of Biomedical Engineering, vol. 9, (2007), pp. 205-228.
Armstrong, Gavin, "Microfluidics: Introducing the Chemstrode," Nature Chemistry, Nov. 14, 2008.
Arrizon, Victor et al., "Talbot Array Illuminators with Liquid Crystal Displays,"0 Opt. Eng., vol. 37, No. 1, (1997), pp. 189-197.
Aryan, Ehsan et al., "A Novel and More Sensitive Loop-Mediated Isothermal Amplification Assay Targeting IS6110 for Detection of *Mycobacterium tuberculosis* Complex," Microbiol Research vol. 165, (2010), pp. 211-220.
Atencia, Javier, et al. "Controlled Microfluidic Interfaces", Nature, 2005, vol. 437, No. 29, pp. 648-655.
Baker, Carolyn N., et al., "Evaluation of Alamar Colorimetric Broth Microdilution Susceptibility Testing Method for Staphylococci and Enterococci," J. Clin. Microbiol., vol. 34, (1996), pp. 2654-2659.
Balakrishnan, Pachamuthu, et al., "Low-Cost Monitoring of HIV Infected Individuals on Highly Active Antiretroviral Therapy (HAART) in Developing Countries", vol. 121, (2005), pp. 345-355.
Balasubramanian, Priya et al., "Confocal Images of Circulating Tumor Cells Obtained Using a Methodology and Technology That Removes Normal Cells," Molecular Pharmaceutics, vol. 6, No. 5, (2009) pp. 1402-1408.
Balslev, Daniela et al., "Cluster Analysis of Activity—Time Series in Motor Learning," Human Brain Mapping, vol. 15, No. 3, (2002), pp. 135-145.
Bang, Hyunwoo et al., "Serial Dilution Microchip for Cytotoxicity Test," Journal of Micromechanics and Microengineering, vol. 14, (2004), pp. 1165-1170.
Bange, Adam et al., Microfluidic Immunosensor Systems, Biosensors and Bioelectronics, vol. 20, (2005), pp. 2488-2503.
Barbieri, Laura et al., "Water Wetting Transition parameters of Perfluorinated Substrates with Periodically Distributed Flat-top Microscale Obstacles," Langmuir, vol. 23, (2007), pp. 1723-1734.
Baret, Jean-Christophe et al., "Fluorescence-Activated Droplet Sorting (FADS): Efficient Microfluidic Cell Sorting based on Enzymatic Activity," Lab Chip, vol. 9, (2009), pp. 1850-1858.
Bar-Joseph, Ziv "Analyzing Time Series Gene Expression Data," Bioinformatics, vol. 20, No. 16 (2004), pp. 2493-2503.
Bar-Nahum, Itsik et al., "Mild, Aqueous, Aerobic, Catalytic oxidation of Methane to Methanol and Acetaldehyde Catalized by a Supported Bipyrimidinylplatinum-Polyoxometalate Hybrid Compound," J. Am. Chem. Soc., vol. 126, (2004), pp. 10236-10237.
Beard, Daniel A. et al., "Dispersion of a Solute in a Microfluidic Channel," Journal of Applied Physics, vol. 89, No. 8, (2001), pp. 4667-4669.
Becker, Frederick F. et al. "Separation of Human Breast-Cancer Cells from Blood by Differential Dielectric Affinity," Proc. Nat'l. Acad. of Sci., vol. 92, (1995) pp. 860-864.
Beebe, David J. et al., "Physics and Applications of Microfluidics in Biology," Rev. Biomed. Eng. vol. 4 (2002) pp. 261-286.
Beer et al., "On-Chip Single-Copy Real-Time Reverse-Transcription PCR in Isolated Picoliter Droplets", Anal. Chem., 2008, 80, 1854-1858.

Beer, Reginald N. et al. "On-Chip, Real-Time, Single-Copy Polymerase Chain Reaction in Picoliter Droplets", Anal. Chem., 2007, v. 79, pp. 8471-8475.
Behrens, Heidi L. et al., "Combining Microdialysis, NanoLC-MS, and MALDI-TOF/TOF to Detect Neuropeptides Secreted in the Crab, Cancer Borealis," Analytical Chemistry, vol. 80, No. 18, (2008), pp. 6949-6958.
Beliaeff, Benoit et al., "The Most "Probable Number" Estimate and its Confidence Limits," Water Res. vol. 27, No. 5, (1993), pp. 799-805.
Benner et al., "Synthetic Biology", Nat. Rev. Genet., Jul. 2005, 6, No. 7, 533-543.
Bergens, Steven H. et al., "A Redox Fuel Cell That Operates with Methane as Fuel at 120 Degrees C," Science, vol. 265, (1994), pp. 1418-1420.
Berger, Rachel Pardes et al., "Multiplex Assessment of Serum Biomarker Concentrations in Well-Appearing Children With Inflicted Traumatic Brain Injury" Pediatric Research, vol. 65, No. 1, pp. 97-102.
Berger, Rachel Pardes, et al., "Urinary S1008 Concentrations are Increased After Brain Injury in Children: A Preliminary Study," Pediatric Critical Care Medicine, vol. 7, No. 6, (2006), pp. 557-561.
Bergh, Sam et al., "Combinatorial Heterogeneous Catalysis: Oxidative Dehydrogenation of Ethane to Ethylene, Selective Oxidation of Ethane to Acetic Acid, and Selective Ammoxidation of propane to Acrylonitrile,", Topics in Catalysis, vol. 23, Nos. 1-4, pp. 65-79.
Bergman, Robert G. et al., "Computational Study of Methane Activation by TpRe(CO)2 and CpRe(CO)2 wit ha Steroelectronic Comparison of Cyclopentadienyl and Scorpianate Ligands," Organometallics, vol. 22,(2008), pp. 2331-2337.
Berthier, Erwin et al., "Managing Evaporation for More Robust Microscale Assays part 2. Characterization of convection and Diffusion for Cell Biology," Lab Chip, vol. 8, (2008), pp. 860-864.
Bhat, Somanath et al., "Single Molecule Detection in Nanofluidic Digital Array Enables Accurate Measurement of DNA Copy Number," Anal. Bioanal. Chem., vol. 394, (2009), pp. 457-467.
Biswal, Sibani Lisa et al., "Micromixing with Linked Chains of Paramagnetic Particles," Analytical Chemistry, vol. 76, No. 21, (2004) pp. 6448-6455.
Blainey et al., "Digital MDA for enumeration of total nucleic acid contamination", Nucleic Acids Res., 2011, 39, e19.
Blicharz, Timothy M. et al., "Fiber-Optic Microsphere-Based Antibody Array for the Analysis of Inflammatory Cytokines in Saliva" Analytical Chemistry, vol. 81, No. 6, (2009) pp. 2106-2114.
Blyth, Brian J. et al, "Validation of Serum Markers for Blood-Brain Barrier Disruption in Traumatic Brain Injury" Journal of Neurotrauma, vol. 26, (2009), pp. 1497-1507.
Boccazzi, Paolo et al., "Gene Expression Analysis of *Escherichia coli* Grown in Miniaturized Bioreactor Platforms for High-Throughput Analysis of Growth and Genomic Data,", App. Microbio. Biotech., vol. 68, (2005), pp. 518-532.
Boedicker, James Q. et al., "Detecting Bacteria and Determining Their Susceptibility to Antibiotics by Stochastic Confinement in Nanoliter Droplets Using Plug-Based Microfluidics," Lab Chip vol. 8, (2008), pp. 1265-1272.
Boom, R. et al., "Rapid and Simple Method for Purification of Nucleic Acids," Journal of Clinical Microbiology, vol. 28, (1990), pp. 495-503.
Boukellal, Hakim et al., "Simple, Robust Storage of Drops and Fluids in a Microfluidic Device,". Lab Chip, vol. 9, (2009), pp. 331-338.
Bourne, James A. "Intracerebral Microdialysis: 30 Years as a Tool for the Neuroscientist," Clinical and Experimental Pharmacology and Physiology, vol. 30, (2003), pp. 16-24.
Brambilla, Don et al., "Multicenter Evaluation of Use of Dried Blood and Plasma Spot Specimens in Quantitative Assays for Human Immunodeficiency Virus RNA: Measurement, Precision, and RNA Stability," Journal of Clinical Microbiology, vol. 41, No. 5, (2003), pp. 1888-1893.
Braslavsky, Ido et al., "Objective-Type Dark-Field Illumination for Scattering from Microbeads" Applied Optics, vol. 40, No. 31, (2001), pp. 5650-5657.

(56) References Cited

OTHER PUBLICATIONS

Bringer, Michelle R. et al., "Microfluidic Systems for Chemical Kinetics that Rely on Chaotic Mixing in Droplets," Phil. Trans. R. Soc. Lond. A vol. 362, (2004), pp. 1087-1104.
Bronzeau, Sandrine et al., "Simultaneous Bioassays in a Microfluidic Channel on Plugs of Different Magnetic Particles", Analytica Chimica Acta, vol. 609 (2008), pp. 105-112.
Brouzes et al., "Droplet microfluidic technology for single-cell high-throughput screening", Proc. Natl. Acad. Sci., 2009, 106, 14195-14200.
Brown, Michael P.S. et al., "Knowledge-Based Analysis of Microarray Gene Expression Data by Using Support Vector Machines," PNAS, vol. 97, No. 1, (2000), pp. 262-267.
Bruls, D.M. et al., Rapid Integrated Biosensor for Multiplexed Immunoassays Based on Actuated Magnetic Nanoparticles, Lab Chip, vol. 9, (2009), pp. 3504-3510.
Burns, Mark A. et al. "Microfabricated structures for integrated DNA analysis", Proc. Natl. Acad. Sci. USA, May 1996, vol. 93, pp. 5556-5561.
Cady, Nathaniel C. et al., "A Microchip-Based DNA Purification and Real-Time PCR Biosensor for Bacterial Detection", Sensors, Proceedings of IEEE 24-27, vol. 3, (2004), pp. 1191-1194.
Calmy, Alexandra et al., "HIV Viral Load Monitoring in Resource-Limited Regions: Optional or Necessary?" CID, vol. 44, (2007), pp. 128-134.
Carpenter, John F. et al., "Long-Term Storage of Proteins," Current Protocols in Protein Science, Unit 4.6.1 Supplement 27, (2002), 6p.
Carrette, Odile et al., "State-of-the-Art Two-Dimensional Gel Electrophoresis: A Key Tool of Proteomics Research," Nature Protocols, vol. 1, No. 2 (2006), pp. 812-823.
Cellar, Nicholas A. et al., "Microfluidic Chip for Low-Flow Push-Pull Perfusion Sampling in Vivo with On-Line Analysis of Amino Acids," Analytical Chemistry, vol. 77, No. 21, (2005), pp. 7067-7073.
Cernak, Ibolja "Animal Models of Head Trauma," NeuroRx Journal of the American Society for Experimental NeuroTherapeutics, vol. 2, (2005), pp. 410-422.
Chabert, Max et al., "Microfluidic High-Throughput Encapsulation and Hydrodynamic Self-Sorting of Single Cells," PNAS, vol. 105, No. 9, (2008), pp. 3191-3196.
Charbonniere, Loie J. et al., "Lanthanide Complexes and Quantum Dots: A Bright Wedding for Resonance Energy Transfer," European Journal of Inorganic Chemistry, (2008), pp. 3241-3251.
Chase, et al., Stimulus-Induced Release of Substances from Olfactory Bulb Using Push-Pull Cannula. Nature, vol. 217 (5127) (1968), pp. 466.
Chayen, Naomi E. "A Novel Technique to Control the Rate of Vapour Diffusion, Giving Larger Protein Crystals," J. Appl. Crystallogr., vol. 30, (1997), pp. 198-202.
Chayen, Naomi E. "Comparative Studies of Protein Crystallization by Vapour-Diffusion and Microbatch Techniques,"Acta Crystallogr. D54, (1998) pp. 8-15.
Chayen, Naomi E. "Turning Protein Crystallization from an Art into a Science," Current Opinion in Structural Biology, vol. 14, (2004), pp. 577-583.
Chayen, Naomi E. et al., "Protein Crystallization: From Purified Protein to Diffraction-Quality Crystal," Nature Methods, vol. 5, No. 2, (2008), pp. 147-153.
Chayen, Naomi E., "Crystallization with oils: a new dimension in macromolecular crystal growth," Journal of Crystal Growth, 1999, vol. 196, pp. 434-441.
Chelliserrykattil et al., "Development of a Quantitative Real-Time Transcription-Mediated Amplification Assay for Simultaneous Detection of Multiple Nucleic Acid Analytes", J Mol. Diagn. 2009, 11, 680.
Chen, Chihchen et al., "Microfluidic Isolation and Transcriptome Analysis of Serum Microvesicles," Lab on a Chip, vol. 10, (2010), pp. 505-511.

Chen, Delai L. et al., "Microfluidic Cartridges Preloaded with Nanoliter Plugs of Reagents: An Alternative to 96-Well Plates for Screening," Current Opinion in Chemical Biology, vol. 10, No. 3, (2006), pp. 226-231.
Chen, Delai L. et al., "The Chemistrode: A Droplet-Based Microfluidic Device for Stimulation and Recording with High Temporal, Spatial, and Chemical Resolution," PNAS, vol. 105, No. 44, (2008), pp. 16843-16848.
Chen, Delai L. et al., "Using Microfluidics to Observe the Effect of Mixing on Nucleation of Protein Crystals,", J. Am. Chem. Soc., vol. 127, (2005), pp. 9672-9673.
Chen, Delai L. et al., "Using Three-Phase Flow of Immiscible Liquids to Prevent Coalescence of Droplets in Microfluidic Channels: Criteria to Identify the Third Liquid and Validation with Protein Crystallization" Langmuir, vol. 23, No. 4, (2007), pp. 2255-2260.
Chen, Delai L. et al., "Using TIRF Microscopy to Quantify and Confirm Efficient Mass Transfer at the Substrate Surface of the Chemistrode,", New Journal of Physics, vol. 11, (2009), 075017, (9pp).
Chen, Grace D. et al., "Concentration and Purification of Human Immunodeficiency Virus Type 1 Virions by Microfluidic Separation of Superparamagnetic Nanoparticles,", Analytical Chemistry, vol. 82, No. 2, (2010), pp. 723-728.
Chen, Zuliang, et al., "Separation of Chromium (III) and Chromium (VI) by Capillary Electrophoresis using 2,6-Pyridinedicarboxylic Acid as a Pre-Column Complexation Agent," Journal of Chromatography A, vol. 927, (2001), pp. 219-227.
Cheng et al., "Research needs and challenges in the development of HIV diagnostic and treatment monitoring tests for use in resource-limited settings", Curr. Opin., HIV AIDS, 2008, 3, 495-503.
Cheng, Ben et al., "Research Needs and Challenges in the Development of HIV Diagnostic and Treatment Monitoring Tests for Use in Resource-Limited Settings,", Current Opinion in HIV and AIDS, vol. 3, (2008), pp. 495-503.
Chiu, Daniel T. et al., "Chemical Transformations in Individual Ultrasmall Biomimetic Containers," Science, vol. 283, (1999), pp. 1892-1895.
Chiu, Daniel T. et al., Droplets for Ultrasmall-Volume Analysis, Analytical Chemistry, vol. 81, No. 13, (2009) pp. 5111-5118.
Choi et al., "Programmable in situ amplification for multiplexed imaging of mRNA expression," Nature Biotechnol, 2010, 28, 1208-1212.
Chu, Kuan-Lun et al., "Nanoporous Silicon Membrane Electrode Assembly for On-Chip Micro Fuel Cell Application," Journal of Microelectromechanical Systems, vol. 15, No. 3, (2006), pp. 671-677.
Chung, Bong Geun et al., "Human Neural Stem Cell Growth and Differentiation in a Gradient-Generating Mcirofluidic Device," Lab Chip, vol. 5, (2005), pp. 401-406.
Chung, Su Eun et al., "Optofluidic Encapsulation and Manipulation of Silicon Microchips Using Image Processing Based Optofluidic Maskless Lithography and Railed Microfluidics," Lab Chip, vol. 9, (2009) pp. 2845-2850.
Clausell-Tormos, Jenifer et al., "Droplet-Based Microfluidic Platforms for the Encapsulation and Screening of Mammalian Cells and Multicellular Organisms," Chemistry & Biology, vol. 15, (2008), pp. 427-437.
Clopper, C.J. et al., "The Use of Confidence or Fiducial Limis Illustrated in the Case of the Binomial," Biometrika vol. 26, No. 4, (1934), pp. 404-413.
Cochran, William G. "Estimation of Bacterial Densities by Means of the Most Probable Number,", Biometrics, vol. 6, (1950), pp. 105-116.
Cohen, Aina E. "An Automated system to Mount Cryo-Cooled Protein Crystals on a Synchrotron Beamline, Using Compact Sample Cassettes and a Small-Scale Robot," J. of Appl. Crystallogr., vol. 35, (2002), pp. 720-726.
Cohen, Jon "The Marketplace of HIV/AID$" Science, New Series, vol. 272, No. 5270 (1996), pp. 1880-1881.
Cohen, Michael H. et al., "Microfabrication of Silicon-Based Nanoporous Particulates for Medical Applications," Biomedical Microdevices, vol. 5, No. 3, (2003), pp. 253-259.

(56) References Cited

OTHER PUBLICATIONS

Collins, Francis S. "Opportunities for Research and NIH," Science, vol. 327, (2010) pp. 36-37.
Compton, "Nucleic acid sequence-based amplification", Nature, 1991, 350, 91-92.
Cookson, P. et al., "A Simple Spectrophotometric Method for the Quantification of Residual Haemoglobin in Platelet Concentrates," Vox Sanguinis, vol. 87, (2004), pp. 264-271.
Cooper, Joshua D. et al., "Evaluation of an Osmotic Pump for Microdialysis Sampling in an Awake and Untethered Rat," Journal of Neuroscience Methods, vol. 160 (2007), pp. 269-275.
Corma, A. et al., "Discovery of New Paraffin Isomerization Catalysts Based on So42-/ZrO2 and Wox/ZrO2 Applying Combinatorial Techniques," Catalysis Today, vol. 81, (2003), pp. 495-506.
Crowe, Suzanne et al., "Monitoring of Human Immunodeficiency Virus Infection in Resource-Constrained Countries," CID, vol. 37, Suppl 1, (2003) pp. S25-S35.
Crowley, Timothy A. et al., "Isolation of Plasma From Whole Blood Using Planar Microfilters for Lab-on-a-Chip Applications," Lab Chip, vol. 5, (2005), pp. 922-929.
Curtis, Kelly A. et al., "Rapid Detection of HIV-1 by Reverse-Transcription, Loop-Mediated Isothermal Amplification (RT-LAMP)" Journal of Virological Methods, vol. 151, (2008), pp. 264-270.
Dai, Jinhua et al., "Electrokinetic Trapping and Concentration Enrichment of DNA in a Microfluidic Channel," Journal of the American Chemical Society, vol. 125, (2003), pp. 13026-13027.
Danna, Erika A. et al., "Transcending the Biomarker Mindset: Deciphering Disease Mechanisms at the Single Cell Level," Curr. Opin. Chem. Biol., vol. 10, (2006), pp. 20-27.
De Baar et al., "One-tube real-time isothermal amplification assay to identify and distinguish human immunodeficiency virus type 1 subtypes A, B, and C and circulating recombinant forms AE and AG", J. Clin. Microbial., 2001, 39, 1895-1902.
De Man, J.C. et al., "MPN Tables, Corrected," Eur. J. Appl. Microbiol. Biotech. vol. 17, No. 5 (1983), pp. 301-305.
Dean et al., "Comprehensive human genome amplification using multiple displacement amplification", Proc. Natl. Acad. Sci., 2002, 99, 5261-5266.
Dear, Paul H. et al., "Happy Mapping: Linkage Mapping Using a Physical Analogue of Meiosis," Nucleic Acids Research, vol. 21, No. 1, (1993), pp. 13-20.
De-Bashan, Luz E. et al., "Removal of ammonium and phosphorus ions from synthetic wastewater by the microalgae *Chlorella vulgaris* coimmobilized in alginate beads with the microalgae growth-promoting bacterium *Azospirillum brasilense*," 2002, vol. 36, pp. 2941-2948.
Defina, Philip et al., "The New Neuroscience Frontier: Promoting Neuroplasticity and Brain Repair in Traumatic Brain Injury," The Clinical Neuropsychologist, vol. 23, No. 8, (2009), pp. 1391-1399.
Dejong, J. B. et al., "New Replication Technique for the Fabrication of Thin Polymeric Microfluidic Devices with Tunable Porosity," Lab Chip—Miniaturisation for Chemistry and Biology, vol. 5, No. 11, (2005), pp. 1240-1247.
Delamarche, Emmanuel et al., Microfluidics for Processing Surfaces and Miniaturizing Biological Assays, Adv. Mater. vol. 17, (2005) pp. 2911-2933.
Delellis, et al., "The Neurometabolic Cascade and Implications of mTBI: Mitigating Risk to the SOF Community," Journal of Special Operations Medicine: A Peer Reviewed Journal for SOF Medical Professionals, vol. 9, No. 4, (2009), pp. 36-42.
Demello, Andrew J. et al., "Control and Detection of Chemical Reactions in Microfluidic Systems," Nature 2006, vol. 442, pp. 392-402.
Dequeant, Mary-Lee et al., "A Complex Oscillating Network of Signaling Genes Underlies the Mouse Segmentation Clock," Science, vol. 314, (2006) p. 1595-1598.
Desai, Tejal A. et al., "Nanoporous Anti-Fouling Silicon Membranes for Biosensor Applications" Biosensors & Bioelectronics, vol. 15, (2000) pp. 453.462.

Dharmasiri, Udara et al., "Highly Efficient Capture and Enumeration of Low Abundance Prostate Cancer Cells Using Prostate-Specific Membrane Antigen Aptamers Immobilized to a Polymeric Microfluidic Device" Electrophoresis, vol. 30, (2009), pp. 3289-3300.
Dhopeshwarkar Rahul et al., "Transient Effects on Microchannel Electrokinetic Filtering with an Ion-Permselective Membrane," Analytical Chemistry, vol. 80, (2008), pp. 1039-1048.
Dhopeshwarkar, Rahul et al., "Electrokinetic Concentration Enrichment Within a Microfluidic Device Using a Hydrogel Microplug," Lab Chip, vol. 5, (2005), pp. 1148-1154.
Dhouib, Kaouthar et al., "Microfluidic Chips for the Crystallization of Biomacromolecules by Counter-Diffusion and On-Chip Crystal X-ray Analysis," Lab Chip, vol. 9, (2009), pp. 1412-1421.
Di Carlo, Dino et al., "Dynamic Single Cell Culture Array". Lab Chip, vol. 6, (2006), pp. 1445-1449.
Di Giusto, Daniel A. et al., "Proximity Extension of Circular DNA Aptamers with Real-Time Protein Detection," Nucleic Acids Research, vol. 33, No. 6, (2005), pp. 33-64.
Diercks, Alan H. et al., "A Microfluidic Device for Multiplexed Protein Detection in Nano-Liter Volumes," Anal. Biochem., vol. 386, (2009), pp. 30-35.
Dimov et al., "Integrated microfluidic tmRNA purification and real-time NASBA device for molecular diagnostics", Lab on a Chip, 2008, 8, 2071-2078.
Dimov, Ivan K. et al., "Integrated Microfluidic tmRNA Purification and Real-Time NASBA Device for Molecular Diagnostics," Lab Chip, vol. 8, (2008), pp. 2071-2078.
Dirks et al., "Triggered Amplification by Hybridization Chain Reaction." Proceedings of the National Academy of Sciences of the United States of America, 2004, 101, No. 43, 1527515278.
Dittrich, Petra S. et al., "Lab-on-a-Chip: Miocrofluidics in Drug Discovery," Nat. Rev., vol. 5, (2006), pp. 210-218.
Dodge, Arash et al., "Electrokinetically Driven Microfluidic Chips with Surface-Modified Chambers for Heterogeneous Immunoassays," Anal. Chem., vol. 73, No. 14, (2001), pp. 3400-3409.
Dong, Yongzhi et al., "Heterogeneous Immunosensing Using Antigen and Antibody Monolayers on Gold Surfaces with Electrochemical and Scanning Probe Detection," Anal. Chem., vol. 72, No. 11, (2000), pp. 2371-2376.
Douglas-Jones, Anthony G. et al., "Molecular Assessment of Sentinel Lymph Node in Breast Cancer Management", Histopathology, No. 55, (2009), pp. 107-113.
Drosten, Christian et al., "Ultrasensitive Monitoring of HIV-I Viral Load by a Low-Cost Real-Time Reverse Transcription-PCR Assay with Internal Control for the 5' Long Terminal Repeat Domain," Clin Chem. vol. 52, (2006), pp. 1258-1266.
Du et al., "SlipChip", Lab Chip, 2009, 9, 2286-2292.
Du, Wen-Bin et al., "High-Throughput Nanoliter Sample Introduction Microfluidic Chip-Based Flow Injection Analysis System with Gravity-Driven Flows," Analytical Chemistry, vol. 77, No. 5, (2005), p. 1330.
Du, Wenbin et al., "SlipChip", Lab Chip, vol. 9, (2009), pp. 2286-2292.
Dube, Simant et al., "Mathmatical Analysis of Copy Number Variation in a DNA Sample Using Digital PCR on a Nanofluidic Device," PLoS One, vol. 3, No. 8, (2008), p. e2876.
Duffy, David C. et al., "Rapid Prototyping of Microfluidic systems in Poly(dimethylsiloxane)," Anal. Chem., vol. 70, No. 23, (1998), pp. 4974-4984.
Durbin, S.D. et al., "Protein Crystallization," Annu. Rev. Phys. Chem. vol. 47, (1996), pp. 171-204.
Edd, Jon F. et al., "Nucleation and Solidification in Static Arrays of Monodisperse Drops," Lab Chip, vol. 9, (2009), pp. 1859-1865.
Eddaoudi, Mohamed et al., "Modular chemistry: Secondary Building Units as a Basis for the Design of Highly Porous and Robust Metal—organic Carboxylate Frameworks," Acc. Chem. Res., vol. 34, (2001), pp. 319-330.
Eisen, Michael B. et al., "Cluster Analysis and Display of Genome-Wide Expression Patterns," Proc. Natl. Acad. Sci., vol. 95, (1998), pp. 14863-14868.
Ekstrand, D. Henric et al., "A Sensitive Assay for the Quantification of Reverse Transcriptase Activity Based on the Use of Carrier-

(56) References Cited

OTHER PUBLICATIONS

Bound Template and Non-Radioactive-Product Detection, with Special Reference to Human-Immunodeficiency-Virus Isolation," Biotechnol. Appl. Biochem. vol. 23, (1996), pp. 95-105.
El-Ali, Jamil, et al., "Cells on Chips," Nature, vol. 442, (2006,) pp. 403-411.
Emamzadah, Soheila et al., "Cyclic Olefin Homopolymer-Based Microfluidics for Protein Crystallization and In Situ X-Ray Diffraction," Acta Crystallogr. vol. D65, (2009), pp. 913-920.
Emsley, Paul, et al., "Coot: Model-Building Tools for Molecular Graphics," Sect. D—Biol. Crystallogr., vol. D60, (2004), pp. 2126-2132.
Eon-Duval, Alex et al., "Purification of Pharmaceutical-Grade Plasmid DNA by Anion-Exchange Chromatography in an RNase-Free Process," J. Chromatogr., vol. 804 (2004), pp. 327-335.
Epstein, Jason R. et al., "Fluorescence-Based Nucleic Acid Detection and Microarrays," Anal. Chim. Acta, vol. 469 (2002) pp. 3-36.
Ernst, Jason et al., "Clustering Short Time Series Gene Expression Data," Bioinformatics, vol. 21 Suppl. 1 (2005), pp. 159-168.
Esch et al., "Detection of Viable Cryptosporidium parvum Using DNA-Modified Liposomes in a Microfluidic Chip", Anal. Chem., 2001, 73, 2952-2958.
Fan, Alice C. et al., "Nanofluidic Proteomic Assay for Serial Analysis of Oncoprotein Activation in Clinical Specimens," Nature Medicine, vol. 15, No. 5, (2009), pp. 566-571.
Fan, Christina et al., "Digital PCR Enables Rapid Prenatal Diagnosis of Fetal Aneuploidy," Am. J. Obstet. Gynecol., (2008), pp. 199.
Fan, H. Christina et al., "Detection of Aneuploidy with Digital Polymerase Chain Reaction," Anal. Chem., vol. 79, No. 19, (2007), pp. 7576-7579.
Fan, H. Christina et al., "Microfluidic Digital PCR Enables Rapid Prenatal Diagnosis of Fetal Aneuploidy," American Journal of Obstetrics & Gynecology, (2009), pp. 543.e1-543.e7.
Fan, Rong et al. "Integrated Barcode Chips for Rapid, Multiplexed Analysis of Proteins in Microliter Quantities of Blood," Nature Biotechnology, vol. 26, No. 12 (2008), pp. 373-1378.
Fang et al., "Loop-Mediated Isothermal Amplification Integrated on Microfluidic Chips for Point-of-Care Quantitative Detection of Pathogens", Anal. Chem., 2010, 82, 3002-3006.
Fekl, Ulrich et al., "Homogeneous Hydrocarbon C—H Bond Activation and Functionalization with Platinum," Adv. Inorg. Chem., vol. 54, (2003), pp. 259-320.
Fidler, Isaiah J. et al., "The Pathogenesis of Cancer Metastasis: the 'Seed and Soil' Hypothesis Revisited," Nature Reviews Cancer, vol. 3, (2003) pp. 453-458.
Filkov, Vladimir et al., "Analysis Techniques for Microarray Time-Series Data" Journal of Computational Biology, vol. 9, No. 2, (2002), pp. 317-330.
Fiscus, et al. "HIV-1 Viral Load Assays for Resource-Limited Settings", PLoS Medicine, vol. 3, No. 10 (2007), pp. 1743-1750.
Franzblau, Scott G. et al., "Rapid Low-Technology MIC Determination with Clinical *Mycobacterium tuberculosis* Isolates by Using the Microplate Alamar Blue Assay," J. Clin. Microbiol., vol. 36, No. 2 (1998), pp. 362-366.
Fu, Elain et al., "Modeling of a Competitive Microfluidic Heterogeneous Immunoassay: Sensitivity of the Assay Response to Varying System Parameters," Anal. Chem., vol. 81, (2009) pp. 3407-3413.
Gambi, Cecilia M.C. et al., "Dynamic percolation in fluorinated water-in-oil microemulsions", Physical Review E. Oct. 1997, v 56, No. 4, pp. 4356-4363.
Gao, Jian et al., "Integration of Single Cell Injection, Cell Lysis, Separation and Detection of Intracellular Constituents on a Microfluidic Chip," Lab Chip, vol. 4, (2004), pp. 47-52.
Garcia-Ruiz, et al., "Investigations on Protein Crystal Growth by the Gel Acupuncture Method," Acta Cryst., D50, (1994), pp. 484-490.
Garcia-Ruiz, J.M. et al., "Investigation on protein crystal growth by the gel acupuncture method," Acta. Cryst,, 1994, vol. D50, pp. 484-490.
Garcia-Ruiz, Juan Ma. et al., "A supersaturation wave of protein crystallization", J. Crystal Growth, 2001, vol. 232, pp. 149-155.
Garthright, Wallace E. et al., "Confidence Intervals for Microbial Density Using Serial Dilutions with MPN Estimates," Biom. J., vol. 38, No. 4, (1996), pp. 489-505.
Gascoyne, Peter R.C. et al., "Isolation of Rare Cells From Cell Mixtures by Dielectrophoresis," Electrophoresis, vol. 30, (2009), pp. 1388-1398.
Geletii, Yu V. et al., "Catalytic-Oxidation of Alkanes by Molecular Oxidation, Oxidation of Methane in the Presence of Platinum Salts and Heteropoly Acids", Kinet. Catal., vol. 24, No. 2, (1983), pp. 413-416.
Genot et al, "Remote Toehold: A Mechanism for Flexible Control of DNA Hybridization Kinetics," JACS, 2011, 133 (7), 2177-2182.
Gerdts, Cory J. et al., "A Synthetic Reaction Network: Chemical Amplification Using Nonequilibrium Autocatalytic Reactions Coupled in Time," J. Am. Chem. Soc., vol. 126, (2004), pp. 6327-6331.
Gerdts, Cory J. et al., "The Plug-Based Nanovolume Microcapillary Protein Crystallization System (MPCS)," vol. D64 (2008), pp. 1116-1122.
Gerdts, Cory J. et al., "Time-Controlled Microfluidic Seeding in nL-Volume Droplets to Separate Nucleation and Growth Stages of Protein Crystallization," vol. 45, (2006), pp. 8156-8160.
Gibson et al., "A Novel Method for Real Time Quantitative RT-PCR", Genome Res., 1996, 6, 995-1001.
Goldman, Ellen R. et al., "Luminescent Quantum Dots Immunoassays," Anal Bioanal Chem., vol. 384 (2006), pp. 560-563.
Goodall, Jennifer L. et al., "Operation of Mixed-Culture Immobilized Cell Reactors for the Metabolism of Meta- and- Para-Nitrobenzoate by *Comamonas* Sp. JS46 and *Comamonas* Sp. J547," 1998, John Wiley & Sons, Inc., pp. 21-27.
Gorris, Hans H. et al., "Mechanistic Aspects of Horseradish Peroxidase Elucidated through Single-Molecule Studies" J. Am. Chem. Soc. vol. 131, (2009), pp. 6277-6282.
Gorris, Hans H. et al., "Stochastic Inhibitor Release and Binding from Single-Enzyme Molecules," PNAS, vol. 104, No. 45, (2007), pp. 17680-17685.
Gratton, Stephanie E.A. et al., "Nanofabricated Particles for Engineered Drug Therapies: A Preliminary Biodistribution Study of PRINT Nanoparticles," ScienceDirect Journal of Controlled Release, vol. 121 (2007), pp. 10-18.
Graugnard et al., "Kinetics of DNA and Rna Hybridization in Serum and Serum-SDS", Nanotechnology, IEEE Transactions, 2010, 9, No. 5, 603-609.
Great Basin Corporation. Isothermal Amplification. Available at www.gbscience.com/technology/iso-amp. Accessed Jan. 6, 2014.
Great Basin Corporation. Sample-to-Result Molecular Diagnostics. Available at www.gbscience.com. Accessed Jan. 6, 2014.
Great Basin Corporation. Technology—Early appropriate treatment of infections is critical for good patient outcomes and to manage treatment costs. Available at www.gbscience.com/technology. Access Jan. 6, 2014.
Greengrass, Vicki et al., "Assessment of the Low-Cost Cavidi ExaVir Load Assay for Monitoring HIV Viral Load in Pediatric and Adult Patients," Acquir Immune Defic Syndr, vol. 52, No. 3, (2009), pp. 387-390.
Griffiths, Andrew D. et al., "Man-Made Enzymes—From Design to In Vitro Compartmentalisation," Curr. Opin. Biotechnol., vol. 11, (2000), pp. 338-353.
Gu, Hao, et al., "Droplets Formation and Merging in Two-Phase Flow Microfluidics", Int. J. Mol. Sci., 2011, vol. 12, pp. 2572-2597.
Guillemette, Maxime D. et al., "Surface Topography Induces 3D Self-Orientation of Cells and Extracellular Matrix Resulting in Improved Tissue Function," Integr. Biol., vol. 1, (2009), pp. 196-204.
Gulliksen, Anja, et al., "Parallel Nanoliter Detection of Cancer Markers Using Polymer Microchips," Lab Chip, vol. 5, (2005), pp. 416-420.
Gunther, Axel et al., "Multiphase Microfluidics: From Flow Characteristics to Chemical and Materials Synthesis," Lab Chip, vol. 6, (2006), pp. 1487-1503.
Gunther, Axel et al., "Transport and Reaction in Microscale Segmented Gas-Liquid Flow,", Lab Chip, vol. 4, (2004), pp. 278-286.

(56) References Cited

OTHER PUBLICATIONS

Hallen, Magnus et al., "A Comparison of Two Different Assays for Determining S-1008 in Serum and Urine," Clinical Chemistry and Laboratory Medicine, vol. 47, pp. 1025-1029.
Halsey, Thomas C. et al., "The Rotary Electrorheological Effect," International Journal of Modern Physics B, vol. 10, No. 23-24, pp. 3019-3027.
Hansen, Carl et al., "Microfluidics in Structural Biology: Smaller, Faster . . . Better," Curr. Opin. Struct. Biol., vol. 13, (2003), pp. 538-544.
Hansen, Carl L. et al., "A Robust and Scalable Microfluidic Metering Method that Allows Protein Crystal Growth by Free Interface Diffusion" Proc. Natl. Acad. Sci. U. S. A., vol. 99, No. 26 (2002), pp. 16531-16536.
Hansen, Carl L., et al., "A Microfluidic Device for Kinetic Optimization of Protein Crystallization and in Situ Structure Determination," J. Am. Chem. Soc., vol. 128, (2006), pp. 3142-3143.
Hatakeyama, Takuji et al., "Microgram-Scale Testing of Reaction Conditions in Solution Using Nanoliter Plugs in Microfluidics with Detection by MALDI-MS," Journal of the American Chemical Society, vol. 128, No. 8, (2006), pp. 2518-2519.
Hathcock, James J. et al., "Flow Effects on Coagulation and Thrombosis," Arterioscler. Thromb. Vasc. Biol., vol. 27, (2007), pp. 1729-1737.
Haudek, Verena J. et al, "Proteome Maps of the Main Human Peripheral Blood Constituents," J Proteome Res, vol. 8, No. 8, (2009), pp. 3834-3843.
Hay Burgess, Deborah C. et al., "Global Health Diagnostics," Nature Publishing Group, vol. 444, Suppl. 1, (2006), pp. 1-2.
Hayes, Ronald L. et al. "Proteomic Identification of Biomarkers of Traumatic Brain Injury" Expert Review of Proteomics, vol. 2, No. 4, (2005), pp. 603-614.
He, Mingyan et al. "Selective encapsulation of single cells and subcellular organelles into picoliter- and femtoliter-volume droplets," Analytical Chemistry, 2005, vol. 77, No. 6, pp. 1539-1544.
He, Wei et al., "In Vivo Quantitation of Rare Circulating Tumor Cells by Multiphoton Intravital Flow Cytometry," Proceedings of the National Academy of Sciences of the United States of America, vol. 104, (2007), pp. 11760-11765.
He, Xinya et al., "Microfluidic Protein patterning on Silicon Mitride Using Solvent-Extracted Poly(Dimethylsiloxane) Channels," Sensors and Actuators B Chem., vol. 129, No. 2, (2008), pp. 811-817.
Hefner, G.J. et al., "Isothermal Amplification and Multimerization of DNA by Bst DNA Polymerase," Biotechniques, vol. 30, No. 4 (2001), pp. 852-856.
Heid et al., "Real Time Quantitative PCR", Genome Res., 1996, 6, 986-994.
Hellweg, Stephanie et al., "Physiotherapy After Traumatic Brain Injury: A Systematic Review of the Literature," Brain Injury, vol. 22, No. 5, (2008), pp. 365-373.
Hellyer et al., "Strand Displacement amplification: a versatile tool for molecular diagnostics", Expert Rev. Mol. Diagn., 2004, 4, 251-261.
Hellyer, Tobin J. et al., "Strand Displacement Amplification: A Versatile Tool for Molecular Diagnostics," Expert Rev Mol Diagn., vol. 4, (2004), pp. 251-261.
Herrmann, Marc et al., „Quantification of Low-Picomolar Concentrations of TNF-.alpha. in Serum Using the Dual-Network Microfluidic ELISA Platform, Anal. Chem., vol. 80, (2008), pp. 5160-5167.
Hill, Craig et al., "Direct-Detection of Microorganisms in Clinical Specimens Using the Gen-Probe Transcription Mediated Amplification System," Clin Chem., vol. 41, No. 6 (1995), pp. S107-S107.
Hill, Craig L. "Progress and Challenges in Polyoxometalate-Based Catalysis and Catalytic Materials Chemistry," J. Mol. Catal., vol. 262, (2007), pp. 2-6.
Hillemann, Doris et al., "Use of the Genotype MTBDR Assay for Rapid Detection of Rifampin and Isoniazid Resistance in *Mycobacterium tuberculosis* Complex Isolates" Journal of Clinical Microbiology vol. 43, pp. 3699-3703.

Hirano, Shoji, et al., "Cluster Analysis of Long Time-Series Medical Datasets," Data Mining and Knowledge Discovery: Theory, tools, and Technology VI, Proceedings of SPIE vol. 5433, No. 2, (2004), pp. 13-20.
Hirst, Evan R. et al., "Bond-Rupture Immunosensors—A Review" Biosensors & Bioelectronics, vol. 23, pp. 1759-1768.
Hlushkou, Dzmitry et al., "The Influence of Membrane Ion-Permselectivity on Electrokinetic Concentration Enrichment in Membrane-Based Preconcentration Units," Lab Chip, vol. 8, (2008), pp. 1153-1162.
Holtze, C. et al., "Biocompatible Surfactants for Water-in-fluorocarbon Emulsions," vol. 8, (2008), pp. 1632-1639.
Honda, Masahiro et al., "Serum Glial Fibrillary Acidic Protein Is a Highly Specific Biomarker for Traumatic Brain Injury in Humans Compared With S-1008 and Neuron-Specific Enolase" Journal of Trauma, Injury, Infection and Critical Care, vol. 69, No. 1 (2010), pp. 104-109.
Hosaka, Norimitsu et al., "Rapid Detection of Human Immunodeficiency Virus Type 1 Group M by a Reverse Transcription-Loop-Mediated Isothermal Amplification Assay," J. Virol. Methods, vol. 157, (2009), pp. 195-199.
Hourfar, Michael K. et al., "High-Throughput Purification of Viral RNA Based on Novel Aqueous Chemistry for Nucleic Acid Isolation," Clin. Chem., vol. 51, No. 7 (2005), pp. 1217-1222.
Hsieh, H. Ben et al., "High Speed Detection of Circulating Tumor Cells," Biosensors & Bioelectronics vol. 21, (2007), pp. 1893-1899.
Hu, Guoqing et al., "A Microfluidic Chip for Heterogeneous Immunoassay Using Electrokinetical Control," Microfluid. Nanofluid, vol. 1, (2005), pp. 347-355.
Hu, Li-Hong et al., "Synthesis and Biological Activity of Amide Derivatives of Ginkolide A," Journal of Asian Natural Products Research, University of Chicago, vol. 3, (2012), pp. 219-227.
Huang, Bo et al., "Counting Low-Copy Number Proteins in a Single Cell," Science, vol. 315, No. 5808, (2007), pp. 81-84.
Huang, Jing et al., "A Yeast Genetic System for Selecting Small Molecule Inhibitors of Protein-Protein Interactions in Nanodroplets," Proc. Natl. Acad. Sci., vol. 94, (1997), pp. 13396-13401.
Huebner, A. et al., "Quantitative detection of protein expression in single cells using droplet microfluidics," Chemical Communications, 2007, pp. 1218-1220.
Huebner, A. et al., "Static Microdroplet Arrays: A Microfluidic Device for Droplet Trapping, Incubation and Release for Enzymatic and Cell-Based Assays," Lab on a Chip, vol. 9, (2009) pp. 692-698.
Hughes, Michael D. et al., "Monitoring Plasma HIV-1 RNA Levels in Addition to CD4(+) Lymphocyte Count Improves Assessment of Antiretroviral Therapeutic Response," Annals of Internal Medicine, vol. 126, No. 12 (1997), pp. 929-938.
Hui, Elliot E. et al., "Micromechanical Control of Cell-Cell Interactions," Proceedings of the National Academy of Sciences of the United States of America, vol. 104, (2007), pp. 5722-5726.
Hurley, Margaret A. et al., "Automated Statistical Analysis of Microbial Enumeration by Dilution Series", J. Appl. Bacteriol, vol. 55, (1983), pp. 159-164.
Ichikawa, Naoki et al., "Interface Motion of Capillary-Driven Flow in Rectangular Microchannel," Journal of Colloid and Interface Science, vol. 280, (2004), pp. 155-164.
Ichimura, Kunihiro, "Molecular Amplification of Photochemical Events" Journal of Photochemistry and Photobiology A—Chemistry, vol. 158, (2003), pp. 205-214.
Inoue, Tomoya et al., "Microfabricated Multiphase Reactors for the Direct Synthesis of Hydrogen Peroxide from Hydrogen and Oxygen," Ind. Eng. Chem. Res., vol. 46, (2007), pp. 1153-1160.
International Patent Application No. PCT/US2008/071374: International Search Report dated Aug. 31, 2009, 7 pages.
International Patent Application No. PCT/US2010/028316. International Search Report and Written Opinion dated May 10, 2010, 8 Pages.
Irimia, Daniel et al., "Spontaneous Migration of Cancer Cells Under Conditions of Mechanical Confinement" Integrative Biology, vol. 1, (2009), pp. 506-512.

(56) References Cited

OTHER PUBLICATIONS

Irish, Jonathan M. et al., "Altered B-Cell Receptor Signaling Kinetics Distinguish Human Follicular Lymphoma B Cells From Tumor-Infiltrating Nonmalignant B Cells," Blood, vol. 108, (2006), pp. 3135-3142.
Irish, Jonathan M. et al., "Single Cell Profiling of Potentiated Phospho-Protein Networks in Cancer Cells," Cell, vol. 118, (2004), pp. 217-228.
Ito, Hiroshi et al., "Chemical Amplification in the Design of Dry Developing Resist Materials" Polymer Engineering and Science, vol. 23, pp. 1012-1018.
Ito, Hiroshi, "Chemical Amplification Resists for Microlithography," Adv. Polym. Sci, vol. 172, (2005), pp. 37-245.
Iverson, Grant L. et al., "Challenges Associated with Post-Deployment Screening for Mild Traumatic Brain Injury in Military Personnel," Clinical Neuropsychologist, vol. 23, No. 8, (2009), pp. 1299-1314.
Izutsu, Ken-ichi et al., "Freeze-Drying of Proteins in Glass Solids Formed by Basic Amino Acids and Dicarboxylic Acids," Chemical & Pharmaceutical Bulletin, vol. 57, (2009), pp. 43-48.
Jahnisch, Klaus et al., "Chemistry in MIcrostructured Reactors," Angew. Chem. Int. Ed. vol. 43, (2004), pp. 406-446.
Jain, K.K., "Neuroprotection in Traumatic Brain Injury," Drug Discovery Today, vol. 13 (23-24): (2008), pp. 1082-1089.
Jarvius, Jonas et al., "Digital Quantification Using Amplified Single-Molecule Detection," Nature Methods, vol. 3, No. 9, (2006), pp. 725-727.
Jeffreys, Alec J. et al., "Repeat Unit Sequence Variation in Minisatellites: A Novel Source of DNA Polymorphism for Studying Variation and Mutation by Single Molecule Analysis" Cell, vol. 60, (1990), pp. 473-485.
Jennings, Cheryl et al., "Comparison of Two Human Immunodeficiency Virus (HIV) RNA Surrogate Assays to the Standard HIV RNA Assay," Journal of Clinical Microbiology, vol. 43, No. 12, (2005), pp. 5950-5956.
Jeon, Noo Li et al., "Generation of Solution and Surface Gradients Using Microfluidic Systems," Langmuir, Vo. 16, (2000), pp. 8311-8316.
Jeon, Noo Li et al., "Neutrophil Chemotaxis in Linear and Complex Gradients of Interleukin-8 Formed in a Microfabricated Device," Nature Biotechnology, vol. 20, (2002), pp. 826-830.
Jeong, Yong-Joo et al., "Isothermal DNA Amplification in Vitro: The Helicase-Dependent Amplification System", Cell Mol Life Sci., vol. 66, (2009), pp. 3325-3336.
Johnson, David et al., "Biochemical Parameters of Recovery in Acute Severe Head-Injury," British Journal of Neurosurgery, vol. 7, No. 1, (1993), pp. 53-59.
Jones, C.J. et al., "Selective Oxidation of Methane to Methanol Catalyzed, with C—H Activation, by Homogeneous, Cationic Gold," Angew. Chem. Int. Ed., vol. 43, (2004), pp. 4626-4629.
Jones, P.A. et al., "Graphical Display of Variability and Inter-Relationships of Pressure Signals in Children with Traumatic Brain Injury," Physiological Measurement, vol. 24, No. 1, (2003) pp. 201-211.
Kaigala, Govind V., "Automated Screening Using Microfluidic Chip-Based PCR and Product Detection to Assess Risk of BK Virus-Associated Nephropathy in Renal Transplant Recipients" Electrophoresis (2006), vol. 27, pp. 3753-3763.
Kalinina, Olga, et al., "Nanoliter Scale PCR with TaqMan Detection," Nucleic Acids Research, vol. 25, No. 10, (1997), pp. 1999-2004.
Kanatzidis, Mercouri G. "Beyond Silica: Nonoxidic Mesostructured Materials," Adv. Mater. vol. 19, (2007), pp. 1165-1181.
Kartalov, Emil P. et al., "High-Throughput Multi-Antigen Microfluidic Fluorescence Immunoassays," BioTechniques, vol. 49, No. 1, (2006), pp. 85-90.
Keats, Jonathon et al., "Jargon Watch: Valedictocracy, ISS Toolbag, Chemstrode," Wired Magazine 17.03, Feb. 23, 2009.

Kemp, David J. et al., "Colorimetric Detection of Specific DNA Segments Amplified by Polymerase Chain Reactions," Proc. Natl. Acad. Sci., vol. 86, (1989), pp. 2423-2427.
Kennedy, Robert T et al., "In Vivo Monitoring of Amino Acids by Direct Sampling of Brain Extracellular Fluid at Ultralow Flow Rates and Capillary Electrophoresis," Journal of Neuroscience Methods, vol. 114, (2002), pp. 39-49.
Keymer, Juan E. et al., "Bacterial Metapopulations in Nanofabricated Landscapes," PNAS, vol. 103, No. 46, (2006), pp. 17290-17295.
Kim, Byoung Chan et al., "Quantitative Detection of HIV-1 Particles Using HIV-1 Neutralizing Anti body-Conjugated Beads," Anal Chem., vol. 81, No. 6 (2009), pp. 2388-2393.
Kim, Choong et al., "A Serial Dilution Microfluidic Device Using a Ladder Network Generating Logarithmic or Linear Concentrations," Lab Chip, vol. 8, (2008), pp. 473-479.
Kim, Hyun Jung et al., "Defined Spatial Structure Stabilizes a Synthetic Multispecies Bacterial Community," PNAS, vol. 105, No. 47, (2008), pp. 18188-18193.
Kim, Sung Jae et al., "Concentration Polarization and Nonlinear Electrokinetic Flow Near a Nanofluidic Channel," Physical Review Letters, vol. 99, (2007) pp. 044501.
Kim, Sung Jae et al., "Self-Sealed Vertical Polymeric Nanoporous-Junctions for High-Throughput Nanofluidic Applications," Analytical Chemistry, vol. 80, No. 9, (2008), pp. 3507-3511.
Kimura, et al., "Inference of S-System Models of Genetic Networks Using a Cooperative Coevolutionary Algorithm," Bioinformatics, vol. 21, No. 7, (2005), pp. 1154-1163.
Kinzelman, Julie L. et al., "Use of IDEXX Colilert-18 and Quanti-Tray/2000 as a Rapid and Simple Enumeration Method for the Implementation of Recreational Water Monitoring and Notification Programs," Lake and Reserv. Manag., vol. 21, No. 1 (2005), pp. 73-77.
Kiss, Margaret Macris et al., "High-Throughput Quantitative Polymerase Chain Reaction in Picoliter Droplets," Anal. Chem., vol. 80, No. 23 (2008), pp. 8975-8981.
Kline, et al., "D Blood Typing and Subtyping Using Plug-Based Microfluidics," Analytical Chemistry, vol. 80, No. 16, (2008), pp. 6190-6197.
Kobayashi, Juta et al., "A Microfluidic Device for Conducting Gas-Liquid-Solid Hydrogenation Reactions," Science, vol. 304, (2004), pp. 1305-1308.
Kobayashi, Juta, et al., "Multiphase Organic Synthesis in Microchannel Reactors," Chem.—Asian J. , vol. 1, (2006), pp. 22-35.
Kobeissy, Firas H. et al. "Psychoproteomic Analysis of Rat Cortex Following Acute Methamphetamine Exposure," Journal of Proteome Research, vol. 7, No. 5, (2008), pp. 1971-1983.
Kobeissy, Firas H. et al., "Novel Differential Neuroproteomics Analysis of Traumatic Brain Injury in Rats" Molecular & Cellular Proteomics, vol. 5, (2005), pp. 1887-1898.
Koh, Chee G. et al., "Integrating Polymerase chain Reaction, Valving, and Electrophoresis in a Plastic Device for Bacterial Detection", Anal. Chem., vol. 75, (2003), pp. 4591-4598.
Kontos, Hermes A. et al., "Oxygen Radicals in Cerebral Vascular Injury," Circulation Research,vol. 57, No. 4, (1985), pp. 508-516.
Koster, Sarah et al., Influence of Internal Capsid Pressure on Viral Infection by Phage Lambda. Biophysical Journal, vol. 97, No. 6, (2009), pp. 1525-1529.
Kottegoda, Sumith et al., "Demonstration of Low Flow Push-Pull Perfusion," Journal of Neuroscience Methods, vol. 121, No. 1, (2002), pp. 93-101.
Koumura, A. et al., "A Novel Calpain Inhibitor, ((1s)-4(((1s)-1-Benzyl-3-Cyclopropylamino-2,3-Di-Oxopropyl)Amino)Carbonyl-)-3-Methylbutyl) Carbamic Acid 5-Methoxy-3-Oxapentyl Ester, Protects Neuronal Cells from Cerebral Ischemia-Induced Damage in Mice," Neuroscience, vol. 157, No. 2, (2008), pp. 309-318.
Kraeft, Stine-Kathrein et al., "Reliable and Sensitive Identification of Occult Tumor Cells Using the Improved Rare Event Imaging System" Clinical Cancer Research, vol. 10, (2004), pp. 3020-3028.
Kralj, Jason G. et al., "Integrated Continuous Microfluidic Liquid-Liquid Extraction," Lab Chip, vol. 7, No. 2, (2007), pp. 256-263.
Kreutz et al., "Theoretical Design and Analysis of Multivolume Digital Assays with Wide Dynamic Range Validated Experimentally with Microfluidic Digital PCR", Anal. Chern., 2011 83, 8158-8168.

(56) References Cited

OTHER PUBLICATIONS

Kreutz, James E. et al., "Laterally Mobile, Functionalized Self-Assembled Monolayers at the Fluorous—Aqueous Interface in a Plug-Based Microfluidic System: Characterization and Testing with Membrane Protein Ctystallization," J. Am. Chem. Soc., vol. 131, (2009), pp. 6042-6043.
Kreutz, Jason E. et al., "Evolution of Catalysts Directed by Genetic Algorithms in a Plug-Based Microfluidi Device Tested with Oxidation of Methane by Oxygen," J. Am Chem Soc., vol. 132, No. 9, (2010), pp. 3128-3132.
Krivacic, Robert T. et al., "A Rare-Cell Detector for Cancer" PNAS, vol. 101, No. 29, (2004), pp. 10501-10504.
Krstenansky, John L. et al., "Biocatalytic Combinatorial Synthesis," Bioorganic & Medicinal Chemistry, vol. 7, No. 10, pp. 2157-2162.
Krutzik, Peter O. et al., "High-Content single-Cell Drug Screening with Phosphospecific Flow Cytometry," Nat. Chem. Biol., vol. 4, No. 2 (2008), pp. 132-142.
Kulakovich, Olga et al., "Enhanced Luminescence of CdSe Quantum Dots on Gold Colloids" Nano Letters, vol. 2, pp. 1449-1452.
Kumar, Vineet et al., "In Situ Precipitation and Vacuum Drying of Interferon Alpha-2a: Development of a Single-Step Process for Obtaining Dry, Stable Protein Formulation," International Journal of Pharmaceutics, vol. 366, (2009), pp. 88-98.
Labbett, Wendy et al., "Comparative Evaluation of the ExaVir Load Version 3 Reverse Transcriptase Assay for Measurement of Human Immunodeficiency Virus Type 1 Plasma Load," J. Clin. Microbiol., vol. 47, No. 10, (2009), pp. 3266-3270.
Labinger, Jay A. et al., "Understanding and Exploiting c-H Bond Activation," Nature, vol. 417, (2002), pp. 507-514.
Lacharme, F. et al., "Magnetic Beads Retention Device for Sandwich Immunoassay: Comparison of Off-Chip and On-Chip Antibody Incubation," Microfluid. Nanofluid, vol. 7, (2009), pp. 479-487.
Lai, Siyi et al., Design of a Compact Disk-Like Microfluidic Platform for Enzyme-Linked Immunosorbent Assay, Anal. Chem., vol. 76, No. 7, (2004), pp. 1832-1837.
Lam, Kit s. et al., "The One-Bead-One-Compound Combinatorial Library Method," Chem. Rev., vol. 97, (1997), pp. 411-448.
Lapizco-Encinas, Blanca H. et al., "An Insulator-Based (Electrodeless) Dielectrophoretic Concentrator for Microbes in Water", Journal of Microbiological Methods, vol. 62, (2005) pp. 317-326.
Lau, Billy T.C. et al., "A Complete Microfluidic Screening Platform for Rational Protein Crystallization," J. Am. Chem. Soc., vol. 129, (2007), pp. 454-455.
Laws, Derek R. et al., "Bipolar Electrode Focusing: Simultaneous Concentration Enrichment and Separation in a Microfluidic Channel Containing a Bipolar Electrode" Analytical Chemistry, vol. 81 (2009), pp. 8923-8929.
Leamon, John H. et al., "Overview: Methods and Applications for Droplet Compartmentalization of Biology," Nature Methods, vol. 3, (2006), pp. 541-543.
Leardi, Riccardo et al., "Genetic Algorithms in Chemistry," J. Chromatogr. A, vol. 1158, (2007), pp. 226-233.
Leclerc, E. et al., "Study of Osteoblastic Cells in a Microfluidic Environment" Biomaterials, vol. 27, (2007), pp. 586-595.
Lee, Jeong Yong et al., Metal-Organic Framework Materials as Catalysts, Soc. Rev., vol. 38, (2009), pp. 1450-1459.
Leng et al., "Agarose droplet microfluidics for highly parallel and efficient single molecule emulsion PCR", Lab on a Chip, 2010,10, 2841-2843.
Lersch, Martin et al., "Mechanistic Aspects of C—H Activation by Pt. Complexes," Chem. Rev., vol. 105, (2005), pp. 2471-2526.
Li et al., "A New Class of Homogeneous Nucleic Acid Probes Based on Specific Displacement Hybridization", Nucleic Acids Research, 2002, 30, No. e5.
Li et al., "Dead-End Filling of SlipChip Evaluated Theoretically and Experimentally as a Function of the Surface Chemistry and the Gap Size between the Plates for Lubricated and Dry SlipChips", Langmuir, 2010, 26, 12465-12471.

Li et al., "Rational, modular adaptation of enzyme-free DNA circuits to multiple detection methods", Nucl. Acids Res., 2011, 1-13.
Li, Liang et al., "A Plug-Based Microfluidic System for Dispensing Lipidic Cubic Phase (LCP) Material Validated by Crystallizing Membrane Proteins in Lipidic Mesophases," Microfluid Nanofluid , vol. 8, (2010), pp. 789-798.
Li, Liang et al., "Multiparameter Screening on SlipChip Used for Nanoliter Protein Crystallization Combining Free Interface Diffusion and Microbatch Methods," J. Am. Chem. Soc., vol. 132, (2010), pp. 112-119.
Li, Liang et al., "Nanoliter Microfluidic Hybrid Method for Simultaneous Screening and Optimization Validated with Crystallization of Membrane Proteins," PNAS vol. 103, No. 51, (2006), pp. 19243-19248.
Li, Liang et al., "Protein Crystallization Using Microfluidic Technologies Based on Valves, Droplets, and SlipChip," Annu. Rev. Biophys. vol. 39, (2010), pp. 139-158.
Li, Liang et al., "Simple Host-Guest Chemistry to Modulate the Process of Concentration and Crystallization of Membrane Proteins by Detergent Capture in a Microfluidic Device," J. Am. Chem. Soc., vol. 130, 2008, pp. 14324-14328.
Li, Liang et al., "User-Loaded SlipChip for Equipment-Free Multiplexed Nanoliter-Scale Experiments," J. Am. Chem. Soc., vol. 132, (2010), pp. 106-111.
Li, Liang et al., "Using a Multifunction Microfluidic Device to Inject Substrate into an Array of Preformed Plugs without Cross-Contamination: Comparing Theory and Experiments," Anal. Chem., vol. 79, No. 7, (2007), pp. 2756-2761.
Li, Xu et al., "Paper-Based Microfluidic Devices by Plasma Treatment" Analytical Chemistry, vol. 80, (2008), pp. 9131-9134.
Li, Zhaohui, et al., "Detection of Single-Molecule DNA Hybridization using Enzymatic Amplification in an Array of Femtoliter-Sized Reaction Vessels," J. Am. Chem. Soc., vol. 130, (2008), pp. 12622-12623.
Liang, Ru-Qiang, et al., "Colorimetric Detection of Protein Microarrays Based on Nanogold Probe Coupled with Silver Enhancement" Journal of Immunological Methods, vol. 285, (2004), pp. 157-163.
Liao, Warren T., "Clustering of Time Series Data—A Survey." Pattern Recognition, vol. 38, No. 11, (2005), pp. 1857-1874.
Lim, C.T. et al., "Bead-Based Microfluidic Immunoassays: The Next Generation," Biosens. Bioelectron, vol. 22, (2007), pp. 1197-1204.
Lin, Jessica et al., "A Symbolic Representation of Time Series, with Implications for Streaming Algorithms," DMKD, (2003), San Diego, CA.
Lin, Minren et al., "Direct Catalytic Conversion of Methane to Acetic Acid in an Aqueous Medium," Letters to Nature, vol. 368, (1994), pp. 613-615.
Linder, Vincent et al., "Application of Surface biopassivated Disposable Poly(Dimethylsiloxane)/Glass Chips to a Heterogeneous Competitive human Serum Immunoglobulin G Immunoassay with Incorporated Internal Standard," Electrophoresis, vol. 23, (2002), pp. 740-749.
Linder, Vincent et al., "Reagent-Loaded Cartridges for Valveless and Automated Fluid Delivery in Microfluidic Devices," Anal. Chem.vol. 77, No. 1, (2005), pp. 64-71.
Lisi, T.L. et al., "Comparison of Microdialysis and Push-Pull Perfusion for Retrieval of Serotonin and Norepinephrine in the Spinal Cord Dorsal Horn," Journal of Neuroscience Methods, vol. 126, No. 2, (2003) pp. 187-194.
Liu et al., "Solving the "World-to-Chip" Interface Problem with a Microfluidic Matrix", Anal. Chern., 2003, 75, 4718-4723.
Liu, Jian et al., "A Nanoliter Rotary Device for Polymerase Chain Reaction," Electrophoresis, vol. 23, (2002), pp. 1531-1536.
Liu, Ming Chen, et al.,"Extensive Degradation of Myelin Basic Protein Isoforms by Calpain Following Tramatic Brain Injury," Journal of Neurochemistry, vol. 98, (2006), pp. 700-712.
Liu, Ming Cheng et al., "Comparing Calpain- and Caspase-3-Mediated Degradation Patterns in Traumatic Brain Injury by Differential Proteome Analysis," Biochemical Journal vol. 394, (2006) pp. 715-725.

(56) References Cited

OTHER PUBLICATIONS

Liu, Ming Cheng et al., "Ubiquitin C-Terminal Hydrolase-L1 as a Biomarker for Ischemic and Traumatic Brain Injury in Rats," European Journal of Neuroscience, vol. 31, No. 4, (2010), pp. 722-732.
Liu, Weishan et al., "SlipChip for Immunoassays in Nanoliter Volumes," Anal Chem., vol. 82, (2010), pp. 3276-3282.
Liu, Weishan, et al., "Isolation, Incubation, and Parallel Functional Testing and Identification by Fish of Rare Microbial Single-Copy Cells from Multi-Species Mixtures Using the Combination of Chemistrode and Stochastic Confinement," Lab Chip, vol. 9, No. 15, (2009), pp. 2153-2162.
Liu, Ying et al., "Dynamics of Coalescence of Plugs with a Hydrophilic Wetting Layer Induced by Flow in a Microfluidic Chemistrode". Langmuir, vol. 25, No. 5, (2009), pp. 2854-2859.
Livak et al., "Analysis of Relative Gene Expression Data Using Real-Time Quantitative PCR and the 2-A,AcT Method", 2001, 25, 402-408.
Lizardi , Paul M. et al., "Mutation Detection and Single-Molecule counting Using Isothermal Rolling-Circle Amplification," National Genetics, vol. 19, (1998), pp. 225-232.
Lo, Tsz-Yan M. et al., "Pediatric Brain Trauma Outcome Prediction Using Paired Serum Levels of Inflammatory Mediators and Brain-Specific Proteins" Journal of Neurotrauma, vol. 26, pp. 1479-1487.
Lo, Y.M. Dennis, et al., "Digital PCR for the Molecular Detection of Fetal Chromosomal Aneuploidy," Proc. Natl. Acad. Sci., vol. 104, No. 32, (2007), pp. 13116-13121.
Locascio, Joseph J. et al., "Time Series Analysis in the Time Domain and Resampling Methods for Studies of Functional Magnetic Resonance Brain Imaging," Human Brain Mapping, vol. 5, No. 3, (1997), pp. 168-193.
Long, De-Liang, et al., "Towards Polyoxometalate-Integrated Nanosystems," Chem.-Eur. J. vol. 12, (2006), pp. 3699-3706.
Love, J. Christopher, et al., A Microengraving Method for Rapid Selection of Single Cells Producing Antigen-Specific Antibodies, Nature Biotechnol., vol. 24, No. 6, (2006), pp. 703-707.
Loyer, Milton W., et al., "Interval Estimation of the Density of Organisms Using a Serial-Dilution Experiment," Biometrics, vol. 40, No. 4, (1984) pp. 907-916.
Lu, Miao-Jen et al., "Detection of Elevated Signaling Amino Acids in Human Diabetic Vitreous by Rapid Capillary Electrophoresis," Experimental Diabetes Research, vol. 2007, Article ID 39765, 6p.
Lun, Fiona M.F. et al., "Microfluidics Digital PCR Reveals a Higher Than Expected Fraction of Fetal DNA in Maternal Plasma," vol. 54, (2008), pp. 1664-1672.
Lutz et al., "Microfluidic lab-on-a-foil for nucleic acid analysis based on isothermal recombinase polymerase amplification (RPA)", Lab on a Chip, 2010, 10, 887-893.
MacDougall, David S. et al., "Quantitative Measurement of HIV RNA Techniques Clinical Applications," J. of Int'l Assoc. of Physicians in AIDS Care, vol. 2, No. 11 (1996), pp. 9-14.
Macek, K., and Be{hacek over (c)}va{hacek over (r)}ova, H., "Papers, Ready-For-Use Plates and Flexible Sheets for Chromatography," Chromatographic Reviews, vol. 15, No. 1, (1971), pp. 1-28.
MacKay et al., "Real-time PCR in virology", Nucleic Acids Res., 2002, 30, 1292-1305.
Madou, Marc, et al., "Lab on a CD," Annu. Rev. Biomed. Eng., vol. 8, (2006), pp. 601-628.
Maerkl, Sebastian J. et al., "A Systems Approach to Measuring the Binding Energy Landscapes of Transcription Factors" Science, vol. 315, (2007), pp. 233-237.
Maier, Wilhelm F, et al., "Combinatorial and High-Throughput Materials Science," S Angew. Chem.-Int. Edit., vol. 46, (2007), pp. 6016-6067.
Maiorella, Brian, et al., "Crossflow Microfiltration of Animal Cells," Biotechnology and Bioengineering, vol. 37, (1991), pp. 121-126.
Majchrowicz, "Beyond Antiretroviral Access: Low-Cost Laboratory Tests Needed for the Developing World," AIDS, vol. 17, Suppl 4, (2003), pp. S13-S15.

Makinen, Johanna, et al., Automated Purification of Borrelia Burgdorferi s.l. PCR Products with KingFisher Magnetic Particle Processor Prior to Genome Sequencing, J. Magnetism and Magnetic Materials, vol. 225, (2001), pp. 134-137.
Marcy, Yann, et al., "Nanoliter Reactors Improve Multiple Displacement Amplification of Genomes from Single Cells," PLoS Genetics, vol. 3, No. 9, (2007), pp. 1702-1708.
Markoulatos, P., et al., "Multiplex Polymerase Chain Reaction: A practical Approach," J. Clin. Lab. Anal., vol. 16, (2002), pp. 47-51.
Marriott, Gerard, "Time-Resolved Delayed Luminescence Image Microscopy Using an Europium Ion Chelate Complex," Biophysical Journal, vol. 67, (1994), pp. 957-965.
Martin, Anandi, et al., "Resazurin Microtiter Assay Plate Testing of *Mycobacterium tuberculosis* Susceptibilities to Second-Line Drugs: Rapid, Simple, and Inexpensive Method," Antimicrobial Agents and Chemotherapy, vol. 47, No. 11, (2003), pp. 3616-3619.
Martin, James E. et al., "Strong Intrinsic Mixing in Vortex Magnetic Fields," Physical Review, vol. 80, (2009), pp. 016312.
Martin, James E., et al., "Simulation of the Athermal Coarsening of Composites Structured by a Uniaxial Field," Journal of Chemical Physics vol. 108, No. 9, (1998), pp. 3765-3787.
Martinez, Andres et al., "FLASH: A Rapid Method for Prototyping Paper-Based Microfluidic Devices," Lab Chip, vol. 8, (2008), pp. 2146-2150.
Martinez, Andres W. et al., "Patterned Paper as a Platform for Inexpensive, Low-Volume, Portable Bioassays," Angew. Chem. Int. Ed. vol. 46, (2007), pp. 318-1320.
Martinez, Andres W. et al., "Simple Telemedicine for Developing Regions: Camera Phones and Paper-Based Microfluidic Devices for Real-Time, Off-Site Diagnosis," Analytical Chemistry, vol. 80, No. 10, (2008), pp. 3699-3707.
Matsubara, Yasutaka et al., "Application of On-Chip Cell Cultures for the Detection of Allergic Response". Biosensors & Bioelectronics, vol. 19, (2004), pp. 741-747.
Matsubara, Yasutaka et al., "Microchamber Array based DNA Quantification and Specific Sequence Detection from a Single Copy via PCR in Nanoliter Volumes," Biosensors and Bioelectronics, vol. 20, (2005), pp. 1482-1490.
Mazutis, Linas, et al., "Droplet-Based Microfluidic Systems for High-Throughput Single DNA Molecule Isothermal Amplification and Analysis," Anal. Chem., vol. 81, No. 12, (2009), pp. 4813-4821.
McCormack, Devin et al., "Photoacoustic Detection of Melanoma Micrometastasis in Sentinel Lymph Nodes". Journal of Biomechanical Engineering—Transactions of the Asme, vol. 131 ( 2009).
McDonald, J. Cooper, et al., "Poly(Dimethylsiloxane) as a Material for Fabricating Microfluidic Devices," Accounts of Chem. Res., vol. 35, No. 7, (2002), pp. 491-499.
McPherson, A. et al., "Crystallization of Biological Macromolecules," Cold Spring Harbor Laboratory Press, (1999).
Meier, Matthias et al., "Plug-Based Microfluidics with Defined Surface Chemistry to Miniaturize and Control Aggregation of Amyloidogenic Peptides," Angewandte Chemie-International Edition, vol. 48, No. 8, (2009), pp. 1487-1489.
Melle, Sonia et al., "Chain Model of a Magnetorheological Suspension in a Rotating Field," Journal of Chemical Physics, vol. 118, No. 21, pp. 9875-9881.
Melle, Sonia et al., "Structure and Dynamics of Magnetorheological Fluids in Rotating Magnetic Fields," Physical Review E, vol. 61, vol. 4, pp. 4111-4117.
Mellors, John W. et al., "Prognosis in HIV-1 Infection Predicted by the Quantity of Virus in Plasma," Science, New Series, vol. 272, No. 5265, (1996), pp. 1167-1170.
Meyvantsson, Ivar et al., "Cell Culture Models in Microfluidic Systems". Annual Review of Analytical Chemistry 1, 423-449 (2008).
Michels, Peter C. et al., "Combinatorial Biocatalysis: A Natural Approach to Drug Discovery," Trends in Biotechnology, vol. 16, No. 5, pp. 210-215.
Miller, M. Craig et al., "Significance of Circulating Tumor Cells Detected by the CellSearch System in Patients with Metastatic Breast Colorectal and Prostate Cancer". Journal of Oncology 2010, Article ID 617421, 8 pages.

(56) References Cited

OTHER PUBLICATIONS

Miller, Oliver J., et al., "Directed Evolution by In Vitro Compartmentalization," Nat. Methods, vol. 3, No. 7, (2006), pp. 561-570.
Mohamed, et al., "Isolation of Tumor Cells Using Size and Deformation," Journal of Chromatography, (2009) pp. 8289-8295.
Mohamed, Hisham et al. "Development of a Rare Cell Fractionation Device: Application for Cancer Detection," IEEE Transactions on Nanobioscience, vol. 3, No. 4 (2004), pp. 251-256.
Monckton, Darren G. et al., "Minisatellite "Isoallele" Discrimination in Pseudohomozygotes by Single Molecule PCR and Variant Repeat Mapping," Genomics, vol. 11, (1991), pp. 465-467.
Moorthy, Jaisree et al., "In Situ Fabricated Porous Filters for Microsystems," Lab Chip, vol. 3, (2003), pp. 62-66.
Morales, D.M. et al., "Experimental Models of Traumatic Brain Injury: Do we really need to build a better mousetrap?"Neuroscience, vol. 136, No. 4, (2005), pp. 971-989.
Morris, L.D. et al., "Use of a New HemoCue System for Measuring Haemoglobin at Low Concentrations," Clinical and Laboratory Haematology, vol. 23, No. 2, (2001), pp. 91-96.
Morton, Keith J. et al., "Hydrodynamic Metamaterials: Microfabricated Arrays to Steer, Refract, and Focus Streams of Biomaterials," Proceedings of the National Academy of Sciences of the United States of America, vol. 105, (2008), pp. 7434-7438.
Moser, Y. et al., On-Chip Immuno-Agglutination Assay with Analyte Capture by Dynamic Manipulation of Superparamagnetic Beads, Lab Chip, vol. 9, (2009), pp. 3261-3267.
Mountzouros, Kenneth T. et al., "Detection of Complement-Mediated Antibody-Dependent Bactericidal Activity in a Fluorescence-Based Serum Bactericidal Assay for Group B Neisseria Meningitidis," J. Clin. Microbiol.,vol. 38, No. 8, (2000), pp. 2878-2884.
Murakami, Yoshihiro, et al., "On-Chip Micro-flow Plystyrene Bead-Based Immunoassay for Quantitative Detection of Tacrolimus(FK506)," Anal. Biochem., vol. 334, (2004), pp. 111-116.
Murshudov, Garib N. et al., "Refinement of Maromolecular Structures by the Maximum-Likelihood Method," Acta Crystallographica Section D-Biological Crystallography, vol. 53, (1997), pp. 240-255.
Myers, R.D. et al., "Simultaneous Comparison of Cerebral Dialysis and Push-Pull Perfusion in the Brain of Rats: A Critical Review," Neuroscience and Biobehavioral Reviews, vol. 22, No. 3, (1998), pp. 371-387.
Nacht et al., "Molecular characteristics of non-small cell lung cancer", Proc. Natl. Acad. Sci., 2001, 98, 15203-15208.
Nagrath, Sunitha et al., "Isolation of Rare Circulating Tumour Cells in Cancer Patients by Microchip Technology" Nature, vol. 450, (2007), pp. 1235-U10.
Nam, Jwa-Min et al., "Nanoparticle-Based Bio-Bar Codes for the Ultrasensitive Detection of Proteins" Science, vol. 301, pp. 1884-1886.
Neuman De Vegvar, Henry E., et al., "Microarray Profiling of Antiviral Antibodies for the Development of Diagnostics, Vaccines, and Therapeutics," Clin. Immunol., vol. 111, (2004), pp. 196-201.
Ng, Joseph D. et al., "In Situ X-ray Analysis of Protein Crystals in Low-Birefringent and X-ray Transmissive Plastic Microchannels," Acta Crystallogr. , vol. D64, (2008), pp. 189-197.
Ng, Joseph D. et al., "Protein Crystallization by Capillary Counterdiffusion for Applied Crystallographic Structure Determination," J. Struct. Biol., vol. 142, (2003), pp. 218-231.
Ng, Joseph D. et al., "Protein crystallization by capillary counterdiffusion for applied crystallographic structure determination," Journal of Structural Biology, 2003, vol. 142, pp. 218-231.
Niemela, S.I. et al., "A Comparison of the International Standards Organisation Reference Method for the Detection of Coliforms and *Escherichia coli* in Water with a Defined Substrate Procedure," J. Appl. Microbiol., vol. 95, (2003), pp. 1285-1292.
Niemeyer, Christof M. et al., "Immuno-PCR: High Sensitivity Detection of Proteins by Nucleic Acid Amplification" Trends in Biotechnology, vol. 23, No. 4, (2006), pp. 208-216.
Nisisako, Takasi et al., "Formation of Droplets Using Branch Channels in a Microfluidic Circuit," SICE, Aug. 2002, pp. 1262-1264.

Nisisako, Takasi et al., "Synthesis of Monodisperse Bicolored Janus Particles with Electrical Anisotropy Using a Microfluidic Co-Flow System," Advanced Materials, vol. 18, (2006), pp. 1152-1156.
Nosworthy, Neil J. et al., "A New Surface for Immobilizing and Maintaining the Function of Enzymes in a Freeze-Dried State," Biomacromolecules, vol. 10, (2009), pp. 2577-2583.
Notomi, Tsugunori et al., Loop-Mediated Isothermal Amplifictaion of DNA, Nucleic Acids Res., vol. 38, No. 12, (2000), pp. e63.
O'Brien, J. et al., "Investigation of the Alamar Blue (Resazurin) Fluorescent dye for the Assessment of Mammalian Cell Cytotoxicity," Molecular Toxicology, vol. 164, (2001), pp. 132-132.
Oehler, V.G. et al., "Absolute Quantitative Detection of ABL Tyrosine Kinase Domain Point Mutations in Chronic Myeloid Leukemia Using a Novel Nanofluidic Platform and Mutation-Specific PCR," vol. 23, (2009), pp. 396-399.
Office Action dated Aug. 14, 2014 for U.S. Appl. No. 13/440,371.
Office Action dated Dec. 18, 2013 for U.S. Appl. No. 13/440,371.
Office Action dated Feb. 28, 2014 for U.S. Appl. No. 13/467,482.
Office Action dated Jul. 31, 2014 for U.S. Appl. No. 13/467,482.
Ohji, Hiroshi, et al., "Macro Porous Silicon Formation for Micromachining," Micromachining and Microfabrication Process Technology III, SPIE vol. 3223, No. 189, (1997), pp. 29-30.
Ohrenberg, Arne et al., Application of Data Mining and Evolutionary Optimization in Catalyst Discoery and High-Throughput Experimentation—Techniques, Strategies, and Software, QSAR Comb. Sci., vol. 24, (2005), pp. 29-37.
Okie, Susan et al., "Traumatic Brain Injury in the War Zone" The New England Journal of Medicine, vol. 352, No. 20, (2005) pp. 2043-2047.
Olson, Eric N., "The Microarray Data Analysis Process: From Raw Data to Biological Significance," The Am. Soc. For Experimental NeuroTherapeutics, vol. 3, (2006), pp. 373-383.
Onal, Yucel et al., "Application of a Capillary Microreactor for Selective Hydrogenation of .alpha.,.beta.—Unsaturated Aldehydes in Aqueous Multiphase Catalysis," Chem. Eng. Technol., vol. 28, No. 9, (2005), pp. 972-978.
O'Neill, Roger A. et al., "Isoelectric Focusing Technology Quantifies Protein Signaling in 25 Cells," Proceedings of the National Academy of Sciences of the United States of America, vol. 103, (2006), pp. 16153-16158.
Ong, Siew-Min et al., "A Gel-Free 3D Microfluidic Cell Culture System" Biomaterials, vol. 29, (2008), pp. 3237-3244.
Ottens, Andrew K. et al., "Neuroproteomics in Neurotrauma," Mass Spectrometry Reviews, vol. 25, (2006), pp. 380-408.
Ottens, Andrew K. et al., "Novel Neuroproteomic Approaches to Studying Traumatic Brain Injury Neurotrauma," Progress in Brain Research, vol. 161, (2007), pp. 401-418.
Ottesen, Elizabeth A. et al., "Microfluidic Digital PCR Enables Multigene Analysis of Individual Environmental Bacteria," Science, vol. 314, No. 5804, (2006), pp. 1464-1467.
Otwinowski, Zbyszek et al., "Processing of X-Ray Diffraction Data Collected in Oscillation Mode," Methods in Enzymology, vol. 276, (1997), pp. 307-326.
Paegel, Brian M. et al., "Microfluidic Serial Dilution Circuit" Analytical Chemistry, vol. 78, (2006), pp. 7522-7527.
Pai, Nittika Pant et al., "Evaluation of Diagnostic Accuracy, feasibility and Client Preference for Rapid Oral Fluid-Based Diagnosis of HIV Infection in Rural India," PLoS ONE, Issue 4, (2007), pp. e367.
Pan, Chu-Hsiang et al., "A Visual DNA Chip for Simultaneous Detection, Genotyping and Differentiation of Wild-type and Vaccine-Type Classical Swine Fever Virus" Taiwan Veterinary Journal, No. 34, No. 2 (2008), pp. 66-76.
Papa, Linda et al., "Ubiquitin C-Terminal Hydrolase is a Novel Biomarker in Humans for Severe Traumatic Brain Injury," Critical Care Medicine, vol. 38, No. 1 (2010), pp. 138-144.
Parekkadan, Biju et al., "Cell-Cell Interaction Modulates Neuroectodermal Specification of Embryonic Stem Cells" Neuroscience Letters, vol. 438, (2008), pp. 190-195.
Paris, Pamela L. et al., "Functional Phenotyping and Genotyping of Circulating Tumor Cells from Patients with Castration Resistant Prostate Cancer" Cancer Letters, vol. 277, (2009), pp. 164-173.

(56) References Cited

OTHER PUBLICATIONS

Park, Jungwook et al., "A Calcium Ion-Selective Electrode Array for Monitoring the Activity of HepG2/C3As in a Microchannel," Sensors and Actuators B, vol. 174, (2012), pp. 473-477.
Park, Sungsu et al., "Influence of Topology on Bacterial Social Interaction" Proceedings of the National Academy of Sciences of the United States of America, vol. 100, (2003), pp. 13910-13915.
Periana, Roy A. et al., "Platinum Catalysts for the High-Yield Oxidation of Methane to a Methanol Derivative," Science, vol. 280, No. 5363, (1998), pp. 560-564.
Perry, John J. et al., "Design and Synthesis of Metal-Organic Frameworks Using Metal-Organic Polyhedra as Supermolecular Blocks," Chem. Soc. Rev., vol. 38, (2009), pp. 1400-1417.
Persidis, Aris et al., "High-Throughput Screening," Nat. Biotechnol., vol. 16 (1998), pp. 488-489.
Petronis, Sarunas et al., "Model Porous Surfaces for Systematic Studies of Material-Cell Interactions," Journal of Biomedical Materials Research—Part A vol. 66 (3), (2003), pp. 707-721.
Phan, Sieu et al., "A Novel Pattern Based Clustering Methodology for Time-Series Microarray Data," International Journal of Computer Mathematics, vol. 84, No. 5, (2007), pp. 585-597.
Piche et al., "Optimization of in Vitro Transcription and Full-Length cDNA Synthesis Using the T4 Bacteriophage Gene 32 Protein", J Biomol. Tech., 2005, 16, 239-247.
Pichonat, Tristan et al., "Development of Porous Silicon-Based Miniature Fuel Cells," Journal of Micromechanics and Microengineering, vol. 15, (2005), pp. S179-S184.
Picuri et al., "Universal Translators for Nucleic Acid Diagnosis" Journal of the American Chemical Society, 2009, 131, No. 26, 9368-9377.
Piepenburg, Olaf et al., "DNA Detection Using Recombination Proteins," PLoS Biol., vol. 4, No. 7, (2006), pp. e204.
Pihl, Johan et al., "Microfluidics for Cell-Based Assays," Materials Today, vol. 8, No. 12, (2005), pp. 46-51.
Pikal, Michael J. et al., "Solid State Chemistry of Proteins: II. The Correlation of Storage Stability of Freeze-Dried Human Growth Hormone (hGH) with Structure and Dynamics in the Glassy Solid," Journal of Pharmaceutical Sciences, vol. 97, No. 12 (2008), pp. 5106-5121.
Pike, Brian R. et al., "Regional Calpain and Caspase-3 Proteolysis of Alpha-Spectrin After Traumatic Brain Injury," Neuroreport, vol. 9, No. 11, (1998), pp. 2437-2442.
Pineda, Jose A. et al., "Clinical Significance of All-Spectrin Breakdown Products in Cerebrospinal Fluid After Severe Traumatic Brain Injury" Journal of Neurotrauma, vol. 24, No. 1 (2007), pp. 354-366.
Pipper, Juergen et al., "Catching Bird Flu in a Droplet," Nature Medicine, vol. 13, No. 10, (2007), pp. 1259-1263.
Plotkin, Steven S. "Generalization of Distance to Higher Dimensional Objects," Proceedings of the National Academy of Sciences of the United States of America, vol. 104, No. 38, (2007), pp. 14899-14904.
Pollack, M.G. et al., "Electrowetting-based actuation of droplets for integrated microfluidics," Lab Chip, 2002, vol. 2, pp. 96-101.
Pompano, Rebecca R. et al., "Rate of Mixing Controls Rate and Outcome of Autocatalytic Processes: Theory and Microfluidic Experiments with Chemical Reactions and Blood Coagulation," Biophysical Journal, vol. 95, No. 3, (2008), pp. 1531-1543.
Potts, Matthew B. et al., "Models of Traumatic Cerebellar Injury," Cerebellum, vol. 8, No. 3, (2009) pp. 211-221.
Powers, Mark J. et al., "A Microfabricated Array Bioreactor for Perfused 3D Liver Culture" Biotechnology and Bioengineering, vol. 78, (2002), pp. 257-269.
Pregibon, Daniel C. et al., "Multifunctional Encoded Particles for High-Throughput Biomolecule Analysis," Science, vol. 315, (2007), pp. 1393-1396.
Preiser, Wolfgang et al., "HIV-1 Viral Load Assays for Resource-Limited Settings: Clades Matter," PLoS Medicine, vol. 3, No. 12, (2006), pp. 2460.

Proost, P. et al., "The Role of Chemokines in Inflammation" International Journal of Clinical & Laboratory Research, vol. 26, (1996), pp. 211-223.
Proust, Anna et al., "Functionalizaiton of Polyoxometalates: Towards Advanced Applications in Catalysis and Materials Science," Chem. Commun., (2008), pp. 837-1852.
Qian et al., "Scaling up Digital Circuit Computation with DNA Strand Displacement Cascades" Science, 2011, 332, No. 6034, 1196-1201.
Raghupathi, Ramesh et al., "Cell Death Mechanisms Following Traumatic Brain," Brain Pathology, vol. 14, No. 2, (2004), pp. 215-222.
Rah, Tatsukiet al., "The Novel Free Radical Scavenger, Edaravone, Increases Neural Stem Cell Number Around the Area of Damage Following Rat Traumatic Brain Injury. Neurotoxicity Research," vol. 16, No. 4, (2009), pp. 378-389.
Ravula, Surendra K. et al., "Spatiotemporal Localization of Injury Potentials in DRG Neurons During Vincristine-Induced Axonal Degeneration," Neuroscience Letters, vol. 415, (2007), pp. 34-39.
Rea, et al. Point-of-Care Molecular Diagnostic Testing. Created Dec. 12, 2012 20:17. Published: Dec. 12, 2012. Published on IVD Technology. Available at http://www.ivdtechnology.com/print/3097. Accessed Jan. 6, 2014.
Rida, A. et al., "Manipulation of Self-Assembled Structures of Magnetic Beads for Microfluidic Mixing and Assaying," Anal Chem., vol. 77, No. 21, (2004), pp. 6239-6246.
Riegger, L. et al., "Read-Out Concepts for Multiplexed Bead-Based Fluorescence Immunoassays on Centrifugal Microfluidic Platforms," Sensors and Actuators A, vol. 126, (2006), pp. 455-462.
Rifai, Nader et al., Protein Biomarker Discovery and Validation: The Long and Uncertain Path to Clinical Utility, Nat. Biotechnol., vol. 24, No. 8 (2006), pp. 971-983.
Ringger, N.C. et al., "A Novel Marker for Traumatic Brain Injury: CSF Alpha II-Spectrin Breakdown Product Levels" Journal of Neurotrauma, vol. 21, pp. 1443-1456.
Rissin, David M. et al., "Digital Concentration Readout of Single Enzyme Molecules Using Femtoliter Arrays and Poisson Statistics" Nano Letters, vol. 6, pp. 520-523.
Rissin, et al., Digital Readout of Target Binding with Attomole Detection Limits via Enzyme Amplification in Femtoliter Arrays, J. Am. Chem. Soc., vol. 128 (2006), pp. 6286-6287.
Roach, L. Spencer et al., "Controlling Nonspecific Protein Adsorption in a Plug-Based Microfluidic System by Controlling Interfacial Chemistry Using Fluorous-Phase Surfactants," Anal. Chem.,vol. 77, No. 3, (2005), pp. 785-796.
Rodemerck, U. et al., "Application of a Genetic Algorithm and a Neural Network for the Discovery and Optimization of New Solid Catalytic Materials," Applied Surface Science, vol. 223, (2004), pp. 168-174.
Rodriguez-Villarreal, Angeles Ivan et al., "High Flow Rate Microfluidic Device for Blood Plasma Separation Using a Range of Temperatures," Lab Chip, vol. 10, (2010), pp. 211-219/.
Romano, Joseph W. et al., "NASBA Technology: Isothermal RNA Amplification in Qualitative and Quantitative Diagnostics," Immunol Invest., vol. 26, Nos. 1&2, (1997), pp. 15-28.
Rowat, Amy C. et al., "Tracking Lineages of Single Cells in Lines Using a Microfluidic Device" Proceedings of the National Academy of Sciences of the United States of America, vol. 106, (2090), pp. 18149-18154.
Rowe, Laura et al., "Active 3-D Microscaffold System With Fluid Perfusion for Culturing in Vitro Neuronal Networks" Lab Chip, vol. 7, (2007), pp. 475-482.
Ryan, Colleen et al., "Rapid Assay for Mycobacterial Growth and Antibiotic Susceptibility Using Gel Microdrop Encapsulation," J. Clin. Microbiol., vol. 33, No. 7, (1995), pp. 1720-1726.
Ryu, WonHyoung et al., "The Construction of Three-Dimensional Micro-Fluidic Scaffolds of Biodegradable Polymers by Solvent Vapor Based Bonding of Micro-Molded Layers," Biomaterials, vol. 28 (2007), pp. 1174-1184.
Sachs, Karen et al., "Causal Protein-Signaling Networks Derived from Multiparameter Single-Cell Data," Science, vol. 308 (2005), pp. 523-529.

(56) References Cited

OTHER PUBLICATIONS

Sakaki, Kelly et al., "RoboSCell: An Automated Single Cell Arraying and Analysis Instrument" Biomedical Microdevices, vol. 11, (2009), pp. 1317-1330.

Sakudo, Akikazu et al., "Efficient Capture of Infectious H5 Avian Influenza Virus Utilizing Magnetic Beads Coated With Anionic Polymer," Biochem. Biophys. Res. Commun., vol. 377, (2008), pp. 85-88.

Salemme, F.R. et al., "A Free Interface Diffusion Technique for the Crystallization of Proteins for X-Ray Crystallography," Archives of Biochemistry and Biophysics, vol. 151, (1972), pp. 533-539.

Sanishvili, Ruslan et al., "A 7 .mu.M Mini-Beam Improves Diffraction Data From Small or Imperfect Crystals of Macromolecules," Biol. Crystallography, vol. D64, (2008), pp. 425-435.

Sang, Takeshi et al., "Immuno-PCR: Very Sensitive Antigen Detection by Means of Specific Antibody-DNA Conjugates" Science, vol. 258, pp. 120-122.

Sasuga, Yasuhiro et al., Single-Cell Chemical Lysis Method for Analyses of Intracellular Molecules Using an Array of Picoliter-Scale Microwells, Anal. Chem., vol. 80, No. 23, (2008), pp. 9141-9149.

Sato, Kiichi et al., "Determination of Carcinoembryonic Antigen in Human Sera by Integrated Bead-Bed Immunoasay in a Microchip for Cancer Diagnosis," Anal. Chem.vol. 73, No. 6, (2001), pp. 1213-1218.

Schmitz, Christian H.J. et al., "Dropspots: A Picoliter Array in a Microfluidic Device," Lab Chip, vol. 9, (2009), pp. 44-49.

Scott, Lesley E. et al., "Evaluation of the Abbott m2000 RealTime Human Immunodeficiency Virus Type 1 (HIV-1) Assay for HIV Load Monitoring in South Africa Compared to the Roche Cobas AmpliPrep-Cobas Amplicor, Roche Cobas AmpliPrep-Cobas TagMan HIV-1, and BioMerieux NucliSENS EasyQ HIV-1 Assays," J. Clin. Microbiol. , vol. 47, (2009), pp. 2209-2217.

Seelig et al., "Enzyme-Free Nucleic Acid Logic Circuits," Science, Dec. 8, 2006, 1585-1588.

Selvin, Paul R. "Principles and Biophysical Applications of Lanthanide-Based Probes," Annu. Rev. Biophys. Biomol. Struct., vol. 31, (2002), pp. 275-302.

Senkan, Selim, "Combinatorial Heterogeneous Catalysis—A New Path in an Old Field," Angew Chem.-Int. Edit., vol. 40, (2001), pp. 312-329.

Seong, Gi Hun et al., "Efficient Mixing and Reactions within Microfluidic Channels Using Microbead-Supported Catalysts" JACS, 2002, vol. 124, pp. 13360-13361 (Published Online Oct. 17, 2002).

Seong, Gi Hun et al., "Fabrication of Microchambers Defined by Photopolymerized Hydrogels and Weirs within Microfluidic Systems: Application to DNA Hybridization", Anal. Chem., 2002, vol. 74, pp. 3372-3377 (Published Online Jun. 6, 2002).

Shamoo et al., "Crystal structure of a replication fork single-stranded DNA binding protein (T4 gp32) complexed to DNA", Nature, 1995, 376, 362-366.

Sharma, Rajesh K. et al., "Multiplex Immunoassay Analysis of Biomarkers in Clinically Accessible Quantities of Human Aqueous Humor," Molecular Vision, vol. 15, (2009), pp. 60-69.

Shaw, C.T. et al., "Using Cluster Analysis to Classify Time Series," Physica D. vol. 58, (1992), pp. 288-298.

Shen et al., "Digital Isothermal Quantification of Nucleic Acids via Simultaneous Chemical Initiation of Recombinase Polymerase Amplification Reactions on SlipChip", Analytical Chemistry, 2011, 83, 3533-3540.

Shen et al., "Multiplexed Quantification of Nucleic Acids with Large Dynamic Range Using Multivolume Digital RT-PCR on a Rotational SlipChip Tested with HIV and Hepatitis C Viral Load", JACS, 2011, 133, 17705-17712.

Shen, Feng et al., "Digital PCR on a SlipChip," Anal. Chem., vol. 10, (2010), pp. 2666-2672.

Shen, Feng et al., "Nanoliter Multiplex PCR Arrays on a SlipChip," Analytical Chemistry, vol. 82, No. 11, (2010), pp. 4606-4612.

Shen, Hong et al., "A Microfluidic Chip Based Sequential Injection System with Trapped Droplet Liquid—Liquid Extraction and Chemiluminescence Detection," Lab Chip, vol. 6, (2006), pp. 1387-1389.

Sherlock, Gavin, "Analysis of Large-Scale Gene Expression Data," Current Opinion in Immunology, vol. 12, (2000), pp. 201-205.

Shestopalov, Ilya, "Multi-step synthesis of nanoparticles performed on millisecond time scale in a microfluidic droplet-based system," Lab Chip, 2004, vol. 4, pp. 3-8.

Shestopalov, Ilya., et al., "Multi-Step Synthesis of Nanoparticles Performed on Millisecond Time Scale in a Microfluidic Droplet-Based System", Lab-Chip, 2004, vol. 4, pp. 316-321.

Shi, Weiwei et al., "Droplet-Based Microfluidic System for Individual Caenorhabditis Elegans Assay," Lab on a Chip, vol. 8, (2008), pp. 1432-1435.

Shih, le-Ming et al., "Evidence That Genetic Instability Occurs at an Early Stage of Colorectal Tumorigenesis," Cancer Research, vol. 61, (2001), pp. 818-822.

Shilov, Alexander E. et al., "Activation of C—H Bonds by Metal Complexes," Chem. Rev., vol. 97, No. 8, (1997), pp. 2879-2932.

Shim, et al., "Control and Measurement of the Phase Behavior of Aqueous Solutions Using Microfluidics," Journal of the American Chemical Society, vol. 129, (2007), pp. 8825-8835.

Shim, Jung-uk et al., Simultaneous Determination of Gene Expression and Enzymatic Activity in Individual Bacterial Cells in Microdroplet Compartments, J. Am. Chem. Soc., vol. 131, (2009), pp. 15251-15256.

Shimazawa, Masamitsu et al., "A Novel Calpain Inhibitor, ((1S)-1-((((1S)-1-Benzyl-3-Cyclopropylamino-2,3-di-oxopropyl)amino)carbon-yl)-3-methylbutyl)carbamic Acid 5-Methoxy-3-oxapentyl Ester (SNJ-1945), Reduces Murine Retinal Cell Death In Vitro and In Vivo," Journal of Pharmacology and Experimental Therapeutics, vol. 332, No. 2, (2010), pp. 380-387.

Shumway, Robert H. et al., "Time Series Analysis and Its Applications With R Examples," Springer Science Business Media, LLC: New York, NY, 2006, 12p.

Sia, Samuel K. et al., "An Integrated Approach to a Portable and Low-Cost Immunoassay for Resource-Poor Settings" Angewandte Chemie-International Edition, vol. 43, pp. 498-502.

Sickmann, Albert et al., "Towards a High Resolution Separation of Human Cerebrospinal Fluid," Journal of Chromatography B—Analytical Technologies in the Biomedical and Life Sciences, vol. 771, No. 1-2, (2002), pp. 167-196.

Sikes, Hadley D. et al., "Antigen Detection Using Polymerization-Based Amplification" Lab Chip, vol. 9, pp. 653-656.

Sikes, Hadley D. et al., "Using Polymeric Materials to Generate an Amplified Response to Molecular Recognition Events" Nature Materials, vol. 7, pp. 52-56.

Siman, Robert et al., "A Panel of Neuron-Enriched Proteins as Markers for Traumatic Brain Injury in Humans," Journal of Neurotrauma, vol. 26, No. 11, (2009), pp. 1867-1877.

Sindelka, Radek et al., "Intracellular Expression Profiles Measured by Real-Time PCR Tomography in the Xenopus Laevis Ooocyte," Nucleic Acids Research, vol. 36, No. 2, (2008), pp. 387-392.

Sista, Ramakrishna et al., "Development of a Digital Microfluidic Platform for Point of Care Testing," Lab Chip, vol. 8, (2008), pp. 2091-2104.

Sista, Ramakrishna et al., "Heterogeneous Immunoassays Using Magnetic Beads on a Digital Microfluidic Platform," Lab Chip, vol. 8, (2008), pp. 2188-2196.

Sohn, Kee-Sun et al., "Genetic Algorithm-Assisted Combinatorial Search for a New Green Phosphor for Use in Tricolor White LEDs," J. Comb. Chem., vol. 8, (2006), pp. 44-49.

Sollier, Elodie et al., "Passive Microfluidic Devices for Plasma Extraction From Whole Human Blood," Sensors and Actuators B: Chemical, vol. 141 (2009), pp. 617-624 (2009).

Solomon, Sunil S. et al., "Dried Blood Spots (DBS): A Valuable Tool for HIV Surveillance in Developing/Tropical Countries," International Journal of STD & AIDS, vol. 13, (2002), pp. 25-28.

Song et al., "A Microfluidic System for Controlling Reaction Networks in Time", Angew. Chem.-Int. Edit., 2003, 42, 768-772.

(56) References Cited

OTHER PUBLICATIONS

Song, Helen et al., "A Microfluidic System for Controlling Reaction Networks in Time," Angew. Chem. Int. Ed., vol. 42, No. 7, (2003), pp. 768-772.
Song, Helen et al., "Experimental Test of Scaling of Mixing by Chaotic Advection in Droplets Moving Through Microfluidic Channels," Applied Physics Letters, vol. 83, No. 22, (2003), pp. 4664-4666.
Song, Helen et al., "Millisecond Kinetics on a Microfluidic Chip Using Nanoliters of Reagents. Journal of the American Chemical Society," vol. 125, No. 47, (2003), pp. 14613-14619.
Song, Helen et al., "On-Chip Titration of an Anticoagulant Argatroban and Determination of the Clotting Time Within Whole Blood or Plasma Using a Plug-Based Microfluidic System," Analytical Chemistry, vol. 78, No. 14, (2006), pp. 4839-4849.
Song, Helen et al., "Reactions in Droplets in Microfluidic Channels," Angew. Chem. Int. Ed. vol. 45, (2006), pp. 7336-7356.
Souteyrand, Yves, P. et al., "Free Care at the Point of Service Delivery: a Key Component for Reaching Universal Access to HIV/AIDS Treatment in Developing Countries," AIDS, vol. 22, No. 1, (2008), S161-S168.
Spaid, Michael et al., "High Throughput Analysis Using Microemulsions for Reagent Encapsulation," 7.sup.th International Conference on Miniaturized Chemical and Biochemical Analysis Systems, Oct. 2003, pp. 445-448.
Spokoyny, Alexander M. et al., "Infinite Coordination Polymer Nano- and Microparticle Structures," Chem. Soc. Rev., vol. 38, (2009), pp. 1218-1227.
Spurgeon, Sandra L. et al., "High Throughput Gene Expression Measurement with Real Time PCR in a Microfluidic Dynamic Array," PLoS ONE, vol. 3, Issue 2, (2008), pp. e1662.
Squires, Todd M. et al., "Microfluidics: Fluid Physics at the Nanoliter Scale," vol. 77, (2005), pp. 977-1026.
Stahl, Shannon S. et al., Homogeneous Oxidation of Alkanes by Electrophili Late Transition Metals, Angew. Chem. Int. Ed., vol. 37, (1998), pp. 2180-2191.
Steegen, Kim et al., "Evaluation of Two Commercially Available Alternatives for HIV-1 Viral Load Testing in Resource-Limited Settings," Journal of Virological Methods, vol. 146 (2007), pp. 178-187.
Sterne, Theodore E. "Some Remarks on Confidence or Fiducial Limits," Biometrika, vol. 41, No. 1/2 (1954), pp. 275-278.
Stoll, Monika et al., "A Genomic-Systems Biology Map for Cardiovascular Function," Science, vol. 294, No. 5547, (2001), pp. 1723-1726.
Story, Craig M. et al., "Profiling Antibody Responses by Multiparametric Analysis of Primary B Cells," PNAS, vol. 105, No. 46, (2008), pp. 17902-1790.
Stuart, Jeffrey N. et al., "The Chemistry of Thought: Neurotransmitters in the Brain," Analytical Chemistry, vol. 76, No. 7, (2004), pp. 120-128.
Sugiura, Shinji et al., "Interfacial Tension Driven Monodispersed Droplet Formation from Microfabricated Channel Array", Langmuir, 2001, vol. 17, pp. 5562-5566.
Sundberg et al., "Spinning Disk Platform for Microfluidic Digital Polymerase Chain Reaction", Anal. Chem., 2010, 82, 1546-1550.
Sung, Wang Chou et al,, "Chip-based microfluidic devices coupled with electrospray ionization-mass spectrometry," Electrophoresis, 2005, vol. 26, pp. 1783-1791.
Sykes et al., "Quantitation of Targets for PCR by Use of Limiting Dilution", Biotechniques, 1992, 13, 444-449.
Szabo, Zsofia et al., "Voluntary Exercise May Engage Proteasome Function to Benefit the Brain After Trauma," Brain Research, vol. 1341, (2010) pp. 25-31.
Takats, Zoltan et al., "Ambient Mass Spectrometry Using Desorption Electrospray Ionization (DESI): Instrumentation, Mechanisms and Applications in Forensics, Chemistry, and Biology," Journal of Mass Spectrometry, vol. 40, No. 10, (2005), pp. 1261-1275.
Takeuchi, Shoji et al., "Controlling the Shape of Filamentous Cells of *Escherichia coli*," Nano Lett., vol. 5, No. 9 (2005), pp. 1819-1823.
Talasaz, AmirAli H. et al., "Isolating Highly Enriched populations of Circulating Epithelial Cells and Other Rare Cells From Blood Using a Magnetic Sweeper Device". Proceedings of the National Academy of Sciences of the United States of America, vol. 106, (2009), pp. 3970-3975.
Tan, Swee Jin et al., "Microdevice for the Isolation and Enumeration of Cancer Cells From Blood". Biomedical Microdevices, vol. 11, (2009), pp. 883-892.
Tanaka, Hideo et al., "Ethanol Production from starch by a Coimmobilized Mixed Culture System of Aspergillus awamori and Zymomonas mobilis," Biotechnology and Bioengineering,1986, vol. XXVIII, pp. 1761-1768.
Taton, Andrew T. et al., "Scanometric DNA Array Detection with Nanoparticle Probes" Science, vol. 289, pp. 1757-1760.
Teh, Shia-Yen et al., "Droplet Microfluidics," Lab Chip, vol. 8 (2008), pp. 198-220.
Tewhey, Ryan et al., "Microdroplet-Based PCR Enrichment for Large-Scale Targeted Sequencing," Nat. Biotechnol. vol. 27, (2009), pp. 1025-1031.
Tharp, William G. et al., "Neutrophil Chemorepulsion in Defined Interleukin-8 Gradients in Vitro and in Vivo" Journal of Leukocyte Biology, vol. 79, (2006), pp. 539-554.
The Neurochemical and Metabolic Cascade Following Brain Injury—Moving from Animal-Models to Man. Journal of Neurotrauma, vol. 12, No. 5, (1995) pp. 903-906.
Theberge, Ashleigh B. et al., "Microdroplets in Microfluidics: An Evolving Platform for Discoveries in Chemistry and Biology," Angew. Chem. Int. Ed., 2010, vol. 49, pp. 5846-5868.
Thiel, Johannes et al., "Heteroatom-Controlled Kinetics of Switchable Polyoxometalate Frameworks," J. Am. Chem. Soc., vol. 131, (2009), pp. 4180-4181.
Thomas, Sydney et al., "Review of Ways to Transport Natural Gas Energy From Countries Which Do Not Need the Gas for Domestic Use," Energy, vol. 28, (2003), pp. 1461-1477.
Thorsen, Todd et al., "Microfluidic Large-Scale Integration," Science, vol. 298, (2002), pp. 580-584.
Thorsen, Todd, et al., "Dynamic Pattern Formation in a Vesicle-Generating Microfluidic Device", Phys. Rev. Lett., 2001, vol. 86, No. 18, pp. 4163-4166.
Thorslund, Sara et al., "A Hybrid Poly(Dimethylsiloxane) Microsystem for On-Chip Whole Blood Filtration Optimized for Steroid Screening," Biomed Microdevices Biomed Microdevices, vol. 8, (2006), pp. 73-79.
Tice, Joshua et al., "Effects of Viscosity on Droplet Formation and Mixing in Microfluidic Channels," Analytica Chimica Acta, vol. 507, No. 1, (2004), pp. 73-77.
Tice, Joshua et al., "Formation of Droplets and Mixing in Multiphase Microfluidics at Low Values of the Reynolds and the Capillary Numbers," Langmuir, vol. 19, No. 22 (2003), pp. 9127-9133.
Titomanlio, G. et al., "Capillary Experiments of Flow Induced Crystallization of HDPE," AIChE Journal, Jan. 1990, vol. 36, No. 1, pp. 13-18.
Toh, Yi-Chin et al., "A Novel 3D Mammalian Cell Perfusion-Culture System in Microfluidic Channels," Lab Chip, No. 7, (2007), pp. 302-309.
Torkkeli, Altti et al., "Droplet Manipulation on a Superhydrophobic Surface for Microchemical Analysis," The 11.sup.th International Conference on Solid-State Sensors and Actuators, Jun. 2001, 4 pages.
Tourovskaia, Anna et al., "Local Induction of Acetylcholine Receptor Clustering in Myotube Cultures Using Microfluidic Application of Agrin," Biophysical Journal, vol. 90, (2006), pp. 2192-2198.
Tranchemontagne, David J. et al., "Reticular Chemistry of Metal-Organic Polyhedra," Angew. Chem.-Int. Edit., vol. 47, (2008), pp. 5136-5147.
Tsigdinos, George A. et al., Molybdovanadophosphoric Acids and Their Salts, J Inorg. Chem., vol. 7, (1968), pp. 437-441.
Tsongalis et al., "Branched DNA Technology in Molecular Diagnostics" American journal of clinical pathology, 2006, 126, No. 3, 448-453.

(56) References Cited

OTHER PUBLICATIONS

Tucci, Sonia et al., "Glutamate Measured by 6-s Resolution Brain Microdialysis: Capillary Electrophoretic and Laser-Induced Fluorescence Detection Application," Journal of Chromatography B-Analytical Technologies in the Biomedical and Life Sciences, vol. 694, No. 2, (1997), pp. 343-349.
Tuteja, Anish et al., "Robust Omniphobic Surfaces," Proc. Natl. Acad. Sci. U. S. A., vol. 105, (2008), pp. 18200-18205.
U.S. Appl. No. 14/177,190, filed Feb. 10, 2014, Ismagilov et al.
U.S. Appl. No. 14/177,194, filed Feb. 10, 2014, Ismagilov et al.
UNAIDS, "UNAIDS/WH Report on the Global AIDS Epidemic", UNAIDS/WHO, 2008, 362 pages.
Underhill, Gregory et al., "High-Throughput Analysis of Signals Regulating Stem Cell Fate and Function," Current Opinion in Chemical Biology, vol. 11, (2007), pp. 357-366.
Unger, Marc A. et al., "Monolithic Microfabricated Valves and Pumps by Multilayer Soft Lithography," Science, vol. 288, No. 5463 (2000), pp. 113-116.
United States Office Action, U.S. Appl. No. 14/177,194, dated Apr. 26, 2016, 14 Pages.
Unknown author, "Extending the idea of using plugs for crystallization of proteins: screening and crystallization directly inside a capillary inside which the structure may be determined," protein.sub.--crystals.sub.--capillary.sub.--MB.sub.--1.FH10, 1 page.
Unknown author, "Extending the idea of using plugs for crystallization of proteins: screening and crystallization directly inside a capillary inside which the structure may be determined," protein.sub.--crystals.sub.--capillary.sub.--VD.sub.--1.FH10, 1 page.
Unknown author, "HIV/AIDS Policy Fact Sheet," The Henry Kaiser Family Foundation, (Nov. 2009), 3p. http://www.kff.org/hivaids/upload/7029-05.pdf.
Unknown author, "Separating Nucleation and Growth," 8 slides.
Unknown author, "The CCP4 Suite: Programs for Protein Crystallography", Acta Cryst (1994), D50, pp. 760-763.
Unknown author, "The Global HIV Challenge: Assessing Progress, Identifying Obstacles, Renewing Commitment," UNAIDS Report on the Global Aids Epidemic, Executive Summary (2008).
Unknown author, "Towards Universal Access—Scaling Up Priority HIV/AIDs Interventions in the Health Sector," WHO UNAIDS, Progress Report, 2009, 164 pages.
Urdea, Mickey et al., "Requirements for High Impact Diagnostics in the Developing World," vol. 444, Suppl 1, (2006), pp. 73-79.
US 7,897,368, 03/2011, Handique et al (withdrawn).
Uttamchandani, Mahesh et al., "Small Molecule Microarrays: Recent Advances and Applications," Curr. Opin. Chem. Biol., vol. 9, (2005), pp. 4-13.
Uttayarat, Pimpon et al. "Topographic Guidance of Endothelial Cells on Silicone Surfaces with Micro- to Nanogrooves: Orientation of Actin Filaments and Focal Adhesions" Journal of Biomedical Materials Research Part A 75A, (2005), pp. 668-680.
Vagin, Alexei et al., "MOLREP: An Automated Program for Molecular Replacement," J. Appl. Cryst., vol. 30, (1997), pp. 1022-1025.
Vail, J.H. et al., "Enumeration of Waterborne *Escherichia coli* With Petrifilm Plates: Comparison to Standard Methods," J. Environ. Qual., vol. 32, No. 1 (2003), pp. 368-373.
Valero, S. et al., "DoE Framework for Catalyst Development Based on Soft Computing Techniques," Comput. Chem. Eng., vol. 33, (2009), pp. 225-238.
Van Delinder, Virginia et al., "Separation of Plasma From Whole Human Blood in a Continuous Cross-Flow in a Molded Microfluidic Device," Anal. Chem., vol. 78, (2006), pp. 3765-3771.
Van Ness et al., "Isothermal Reactions for the Amplification of Oligonucleotides" Proceedings of the National Academy of Sciences, 2003, 100, No. 8, 4504-4509.
Van Staden, J.F. "Membrane Separation in Flow Injection Systems," Fresenius J. Anal Chem. vol. 352, (1995), pp. 271-302.
Vandenabeele, Steven et al., "A Comprehensive Analysis of Hydrogen Peroxide-Induced Gene Expression in Tobacco," Proceedings of the National Academy of Sciences of the United States of America, vol. 100, No. 26 (2003), pp. 16113-16118.
Vargaftik, M.N. et al., "Highly Selective Partial Oxidation of Methane to Methyl Trifluoroacetate," J. Chem. Soc.-Chem. Commun. ,(1990), pp. 1049-1050.
Vet et al., "Multiplex detection of four pathogenic retroviruses using molecular beacons", Proc. Natl. Acad. Sci., 1999, 96, 6394-6399.
Villa-Diaz, Luis Gerardo et al., "Microfluidic Culture of Single Human Embryonic Stem Cell Colonies," Lab Chip, vol. 9, (2009), pp. 1749-1755.
Vincent, Myriam et al., "Helicase-Dependent Isothermal DNA Amplification," European Molecular Biology Organization Embo Rep., vol. 5, No. 8 (2004), pp. 795-800.
Vogelstein, Bert et al., "Digital PCR", PNAS, vol. 96, No. 16, Aug. 3, 1999, pp. 9236-9241.
Vozzi, Giovanni et al., "Fabrication of PLGA Scaffolds Using Soft Lithography and Microsyringe Deposition," Biomaterials, vol. 24, (2003), pp. 2533-2540.
Vozzi, G. et al., "Microsyringe-Based Deposition of Two-Dimensional and Three-Dimensional Polymer Scaffolds with a Well-Defined Geometry for Application to Tissue Engineering," Tissue Engineering, vol. 8, No. 6 (2002), pp. 1089-1098.
Vriamont, Nicolas et al., "Design of a Genetic Algorithm for the Simulated Evolution of a Library of Asymmetric Transfer Hydrogenation Catalysts," Chem.—Eur. J., vol. 15, (2009), pp. 6267-6278.
Wages, S.A. et al., "Sampling Considerations for Online Microbore Liquid-Chromatography of Brain Dialysate," Analytical Chemistry, vol. 58, No. 8, (1986), pp. 1649-1656.
Walker et al., "Strand displacement amplification—an isothermal, in vitro DNA amplification technique", Nucleic Acids Res., 1992, 20, 1691-1696.
Walker, G. Terrance et al., "Strand Displacement Amplification—An Isothermal, In Vitro DNA Amplification Technique," Nucleic Acids Res., vol. 20, No. 7 (1992), pp. 1691-1696.
Walker, Glenn M. et al., "A Linear Dilution Microfluidic Device for Cytotoxicity Assays," Lab Chip, vol. 7, (2007), pp. 226-232.
Walt, David R., "Fibre Optic Microarrays," Chem. Soc. Rev., vol. 39, (2010), pp. 38-50.
Wang, Min et al., "Palladium-Silver Thin Film for Hydrogen Sensing (Sensors and Actuators" B: Chemical, vol. 123(1), (2007), pp. 101-106.
Wang, Qiangbin et al., "Photonic Interaction Between Quantum Dots and Gold Nanoparticles in Discrete Nanostructures through DNA Directed Self-Assembly," Chemical Communications, vol. 46, 2010, pp. 240-242.
Wang, Ying-Chih et al., "Million-Fold Preconcentration of Proteins and Peptides by Nanofluidic Filter," Analytical Chemistry, vol. 77, (2005), pp. 4293-4299.
Warden, Deborah, "Military TBI During the Iraq and Afghanistan Wars," J. Head Trauma Rehabil., vol. 21, No. 5, (2006), pp. 398-402.
Warren, Luigi et al., Transcription Factor Profiling in Individual Hematopoietic Progenitors by Digital RT-PCR, Proc. Natl. Acad. Sci. U. S. A., vol. 103, No. 47 (2006), pp. 17807-17812.
Watson, Christopher J. et al., "In Vivo Measurements of Neurotransmitters by Microdialysis Sampling," Analytical Chemistry, vol. 78, No. 5, (2006), pp. 1391-1399.
Webb, Anna et al., "Guidance of Oligodendrocytes and Their Progenitors by Substratum Topography" Journal of Cell Science, vol. 108, (1995), pp. 2747-2760.
Weight, Ryan M. et al., "Photoacoustic Detection of Metastatic Melanoma Cells in the Human Circulatory System" Optics Letters, vol. 31, (2006), pp. 2998-3000.
Weinberg, David R. et al., "Competitive Oxidation and Protonation of Aqueous Monomethylplatinum(II) Complexes: A Comparison of Oxidants," Organometallics, vol. 26, (2007), pp. 167-172.
Weiss, David J. et al., "In Vivo Microdialysis as a Tool for Monitoring Pharmacokinetics," Trac-Trends in Analytical Chemistry, vol. 19, No. 10, (2000), pp. 606-616.
Wen, Ji-Kai et al., "A Visual DNA Chip for Simultaneous Detection of Hepatitis B Virus, Hepatitis C Virus and Human Immunodeficiency Virus Type-1" Biosensors & Bioelectronics, vol. 19, pp. 685-692.

(56) References Cited

OTHER PUBLICATIONS

Wheeler, M.B. et al., "Toward Culture of Single Gametes: The Development of Microfluidic Platforms for Assisted Reproduction" Theriogenology, vol. 68, (2007), S178-S189.
Wheeler, Rob C. et al., "Mesoscale Flow Chemistry: A Plug-Flow Approach to Reaction Optimisation," Org. Process Res. Dev., vol. 11, (2007), pp. 704-710.
Whitesides, George M. et al., "The Origins and the Future of Microfluidics," Nature, vol. 442, (2006), pp. 368-373.
Wismuller, Axel et al., "Cluster Analysis of Biomedical Image Time-Series" International Journal of Computer Vision, vol. 42, No. 2, (2002), pp. 103-128.
Wojcik, Barbara E. et al., "Traumatic Brain Injury Hospitalizations of US Army Soldiers Deployed to Afghanistan and Iraq," American Journal of Preventive Medicine, vol. 38, No. 1, (2010), pp. S108-S116.
Wolf, D. et al., "An Evolutionary Approach in the Combinatorial Selection and Optimizaiton of catalytic Materials," Appl. Catal. A-Gen., vol. 200, (2000), pp. 63-77.
Wong, Amy P. et al., "Partitioning Microfluidic Channels With Hydrogel to Construct Tunable 3-D Cellular Microenvironments," Science Direct Biomaterials, vol. 29, (2008), pp. 1853-1861.
Wong, Pak Kin et al., "Electrokinetic Biopressor for Concentrating Cells and Molecules," Anal. Chem., vol. 76, No. 23, (2004), pp. 6908-6914.
Woodward, R.L., "How Probable is the Most Probable Number" J. Am. Water Works As. vol. 49, (1957), pp. 1060-1068.
Wu, Liang, et al., "Droplet Formation in Microchannels Under Static Conditions," Appl. Phys. Lett. vol. 89, (2006), pp. 144106.
Xia, Younan et al., "Soft Lithography" Angewandte Chemie—International Edition, vol. 37, No. 5, (1998) pp. 551-575.
Xiong, Ye et al., "Emerging Treatments for Traumatic Brain Injury," Expert Opinion on Emerging Drugs, vol. 14, No. 1, (2009), pp. 67-84.
Yamanaka, Ichiro et al., "Oxidation of Methane and Benzene with Oxygen Catalyzed by Reduced Vanadium Species at 40.degree. C," J. Mol. Catal. A-Chem., vol. 133, (1998), pp. 251-254.
Yang, Jianing et al., "High Sensitivity PCR Assay in Plastic Micro Reactors," Lab Chip, vol. 2, (2002), pp. 179-187.
Yang, Liying et al., "Optimization of an Enrichment Process for Circulating Tumor Cells From the Blood of Head and Neck Cancer Patients Through Depletion of Normal Cells," Biotechnology and Bioengineering, vol. 102, No. 2, (2009), pp. 521-534.
Yang, Sung-Yi et al., "Microflow Cytometry Utilizing a Magnetic Bead-Based Immunoassay for Rapid Virus Detection," Biosensors and Bioelectronics, vol. 24, (2008), pp. 855-862.
Yeh, Chia-Hsien et al., "An Immunoassay Using Antibody-Gold Nanoparticle Conjugate, Silver Enhancement and Flatbed Scanner," Microfluidics and Nanofluidics, vol. 6, (2009), pp. 85-91.
Yeung, K.Y. et al., "Principal Component Analysis for Clustering Gene Expression Data," Bioinformatics, vol. 17, No. 9, (2001), pp. 763-774.
Yin et al., "Programming Biomolecular Self-Assembly Pathways", Nature, 2008, 451, No. 7176, 318-322.
Younes-Metzler, Osnat et al., "Microfabricated High-Temperature Reactor for Catalytic Partial Oxidation of Methane," Applied Catalysis A: General, vol. 284, (2005), pp. 5-10.
Yu, Ji et al., "Probing Gene Expression in Live Cells, One Protein Molecule at a Time," Science, vol. 311, (2006), pp. 1600-1603.
Yuan, Yong J. et al., "Bond Rupture of Biomolecular Interactions by Resonant Quartz Crystal," Analytical Chemistry, vol. 79, (2007), pp. 9039-9044.
Yuen, Po Ki et al., "Microfluidic Devices for Fluidic Circulation and Mixing Improve Hybridization Signal Intensity on DNA Arrays," Lab Chip, vol. 3, (2003), pp. 46-50.
Zhang et al., "A DNA-Origami Chip Platform for Label-Free SNP Genotyping Using Toehold-Mediated Strand Displacement", Small, 2010, 6, No. 17, 1854-1858.

Zhang et al., "Control of DNA Strand Displacement Kinetics Using Toehold Exchange" Journal of the American Chemical Society, 2009, 131, No. 47, 17303-17314.
Zhang et al., "Engineering Entropy-Driven Reactions and Networks Catalyzed by DNA.", Science, 2007, 318, No. 5853, 1121-1125.
Zhang, Qingquan et al., "Microfluidic Droplet Trapping Array as Nanoliter Reactors for Gas-Liquid Chemical Reaction," Electrophoresis, vol. 30, No. 18, (2009), pp. 3181-3188.
Zhang, Xin et al., "New Triple Microbore Cannula System for Push-Pull Perfusion of Brain Nuclei of the Rat," Journal of Neuroscience Methods, vol. 32, (1990), pp. 93-104.
Zhang, Y.H. et al., "Microfluidic DNA Amplification—A Review," Analytica Chimica Acta, vol. 63, No. 2, (2009), pp. 115-125.
Zhang, Yi et al., "Putting the Invader Assay to Work: Laboratory Application and Data Management," Methods Mol. Biol., vol. 578, (2009), pp. 363-377.
Zhang, Zhiqun et al., Calpain-Mediated Collapsin Response Mediator Protein-1,-2, and -4 Proteolysis After Neurotoxic and Traumatic Brain Injury, Journal of Neurotrauma, vol. 24, No. 3, (2007), pp. 460-472.
Zheng, Bo et al., "A Droplet-Based, Composite PDMS/Glass Capillary Microfluidic system for Evaluating Protein Crystallization Conditions by Microbatch and Vapor-Diffusion Methods With On-Chip X-ray Diffraction," Angew. Chem. Int. Ed., vol. 43, (2004), pp. 2508-2511.
Zheng, Bo et al., "A Microfluidic Approach for Screening Submicroliter volumes Against Multiple Reagents by Using Preformed Arrays of Nanoliter Plugs in a Three-Phase Liquid/Liquid/Gas Flow," Angew. Chem. Int. Ed., vol. 44, (2005), pp. 2520-2523.
Zheng, Bo et al., "Formation of Arrayed Droplets of Soft Lithography and Two-Phase Fluid Flow, and Application in Protein Crystallization," Advanced Materials, vol. 16, No. 15, (2004), pp. 1365-1368.
Zheng, Bo et al., "Formation of Droplets of Alternating Composition in Microfluidic Channels and Applications to Indexing of Concentrations in Droplet-Based Assays", Analytical Chemistry, 2004, vol. 76, pp. 4977-4982.
Zheng, Bo et al., "Screening of Protein Crystallization Conditions on a Microfluidic Chip Using Nanoliter-Size Droplets," J. Am. Chem. Soc., vol. 125, (2003), pp. 11170-11171.
Zheng, Bo et al., "Using Nanoliter Plugs in Microfluidics to Facilitate and Understand Protein Crystallization," Current Opinion in Structure Biology, vol. 15, (2005), pp. 548-555.
Zheng, Siyang et al., "Membrane Microfilter Device for Selective Capture, Electrolysis and Genomic Analysis of Human Circulating Tumor Cells," Journal of Chromatography A, vol. 1162, (2007), pp. 154-161.
Zhou, Xuechang et al., "Nanoliter Dispensing Method by Degassed Poly(dimethylsiloxand) Microchannels and Its Application in Protein Crystallization," Anal. Chem., vol. 79, No. 13, (2007), pp. 4924-4930.
Ziatdinov, Vadim R. et al., "Carboxylic Solvents and O-Donor Ligand Effects on CH Activation by Pt(II)," J. Am. Chem. Soc., vol. 128, (2006), pp. 7404-7405.
Zieglschmid, V. et al., "Detection of Disseminated Tumor Cells in Peripheral Blood" Critical Reviews in Clinical Laboratory Sciences, vol. 42, (2005), pp. 155-196.
Zimmermann, Bernhard G. et al., "Digital PCR: A Powerful New Tool for Noninvasive Prenatal Diagnosis?" Prenatal Diagnosis, vol. 28, (2008), pp. 1087-1093.
Office Action for U.S. Appl. No. 15/164,798, dated Dec. 11, 2017, 17 Pages.
Request for Interference Pursuant to 37 C.F.R § 41.202, U.S. Appl. No. 15/164,798, May 27, 2016, 1782 pages.
United States Examiner's Answer to Appeal Brief, U.S. Appl. No. 15/164,798, dated Feb. 28, 2019, 13 pages.

\* cited by examiner

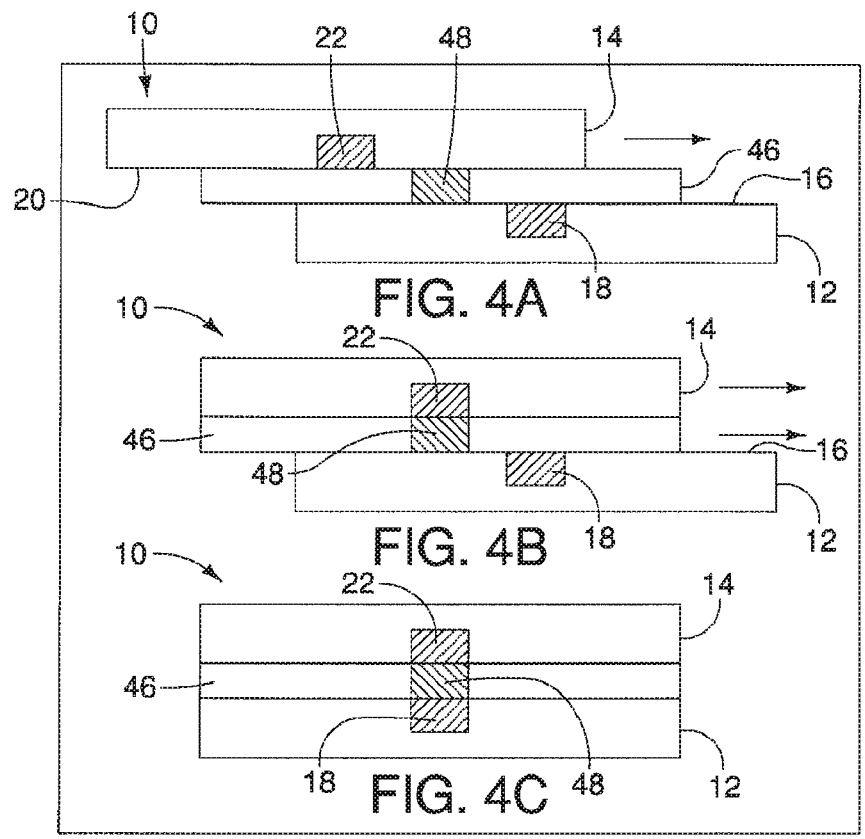
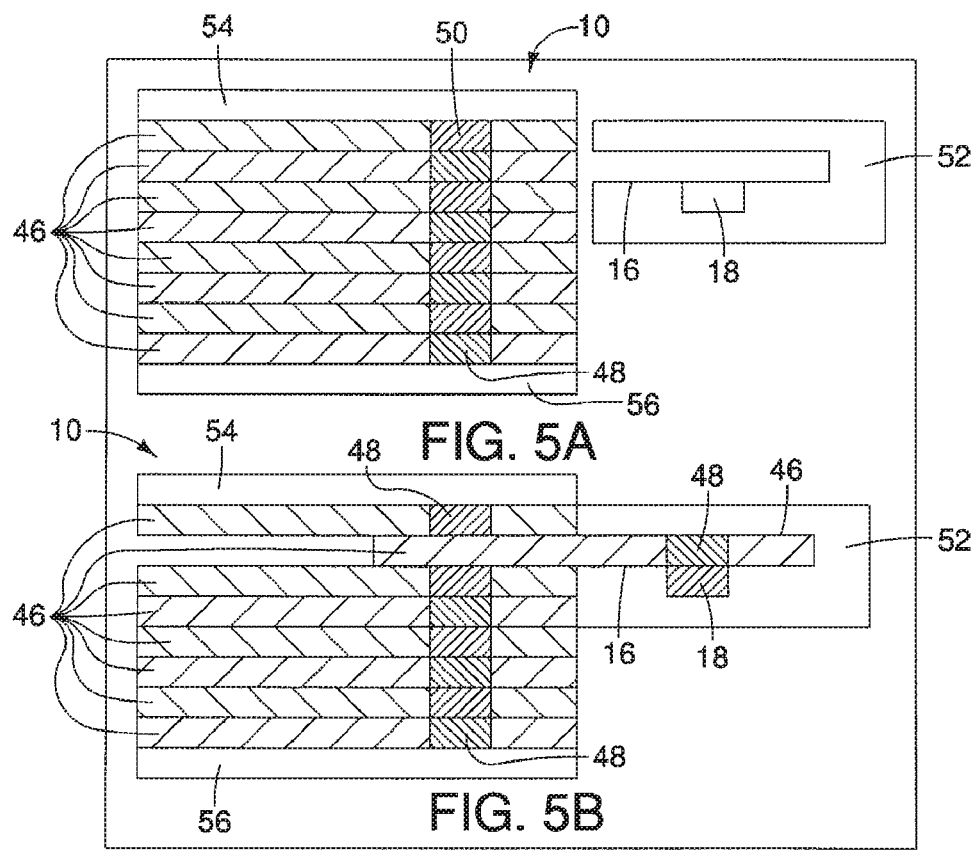

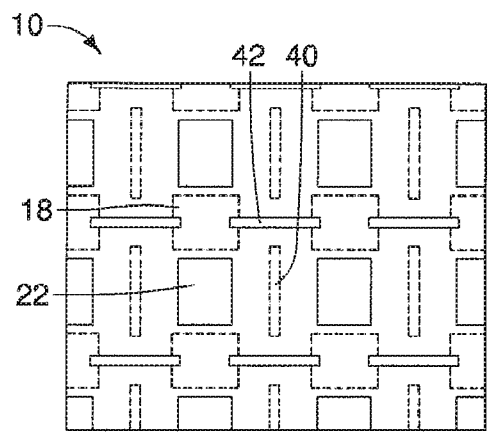
FIG. 8A, part I
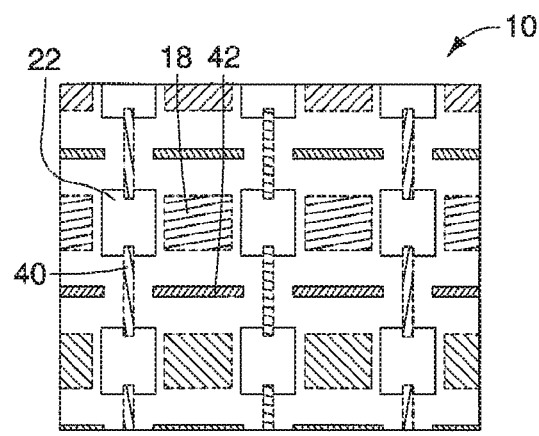
FIG. 8C, part I
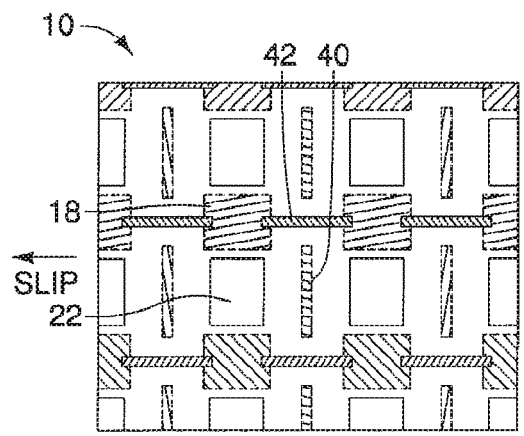
FIG. 8A, part II
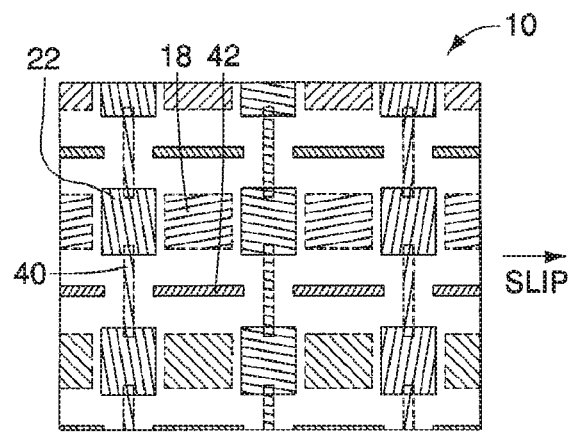
FIG. 8C, part II
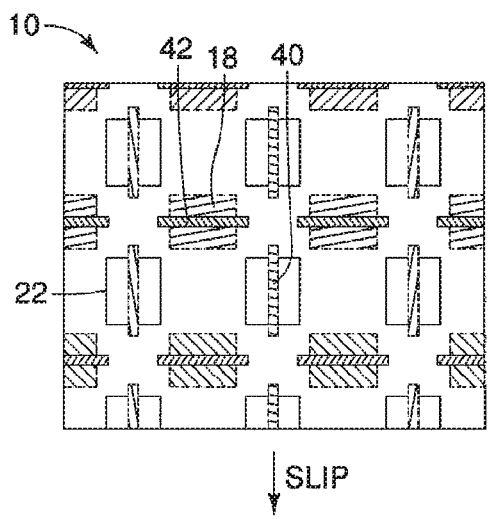
FIG. 8B
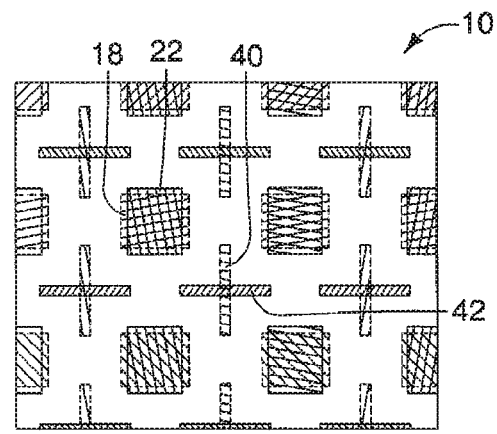
FIG. 8D

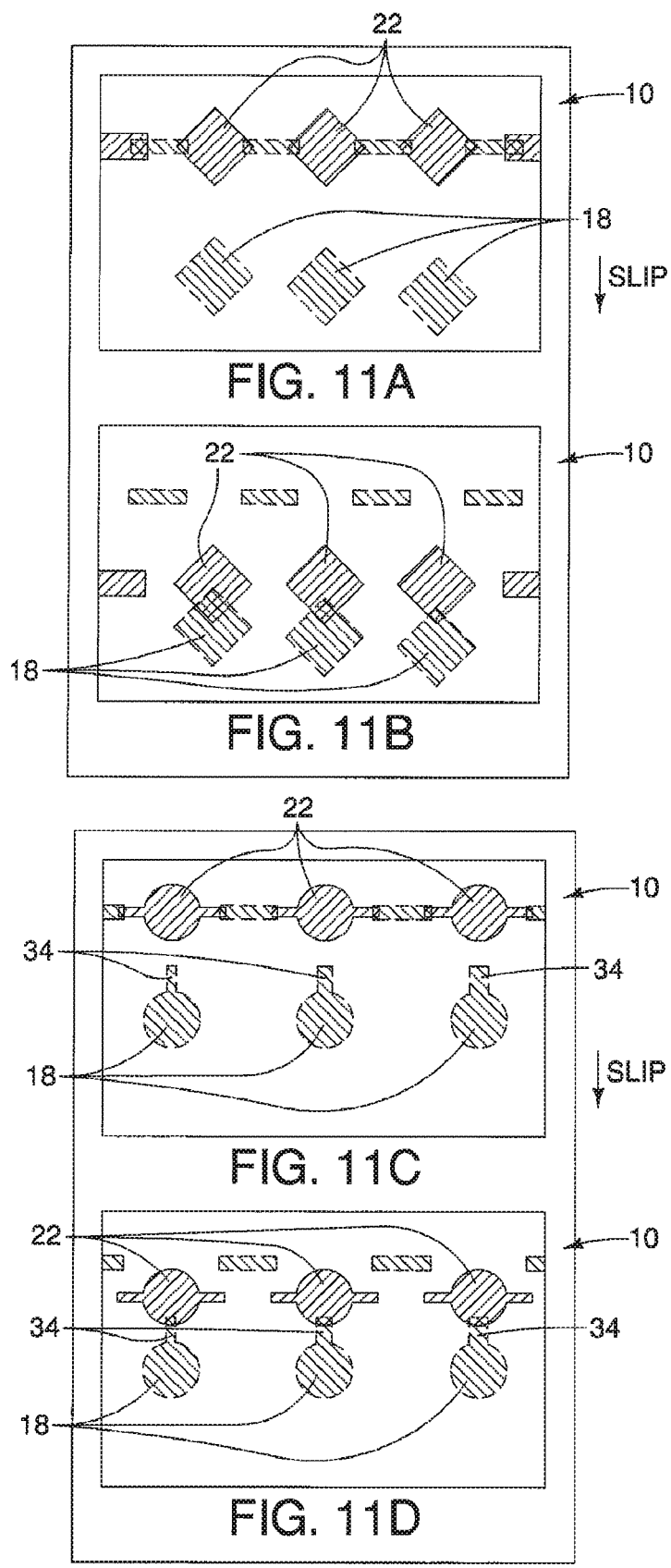

```
                        SEQUENCE LISTING

<160> NUMBER OF SEQ ID NOS: 48

<210> SEQ ID NO 1
<211> LENGTH: 21
<212> TYPE: DNA
<213> ORGANISM: Artificial Sequence
<220> FEATURE:
<223> OTHER INFORMATION: synthetic primer

<400> SEQUENCE: 1
gcgattgatg gtgatacggt t                                              21

<210> SEQ ID NO 2
<211> LENGTH: 24
<212> TYPE: DNA
<213> ORGANISM: Artificial Sequence
<220> FEATURE:
<223> OTHER INFORMATION: synthetic primer

<400> SEQUENCE: 2
agccaagcct tgacgaacta aagc                                           24

<210> SEQ ID NO 3
<211> LENGTH: 20
<212> TYPE: DNA
<213> ORGANISM: Artificial Sequence
<220> FEATURE:
<223> OTHER INFORMATION: synthetic pBad primer

<400> SEQUENCE: 3
gcgtcacact ttgctatgcc                                                20

<210> SEQ ID NO 4
<211> LENGTH: 24
<212> TYPE: DNA
<213> ORGANISM: Artificial Sequence
<220> FEATURE:
<223> OTHER INFORMATION: synthetic pBad primer

<400> SEQUENCE: 4
gcttctgcgt tctgatttaa tctg                                           24

<210> SEQ ID NO 5
<211> LENGTH: 20
<212> TYPE: DNA
<213> ORGANISM: Artificial Sequence
<220> FEATURE:
<223> OTHER INFORMATION: synthetic E coli nlp primer

<400> SEQUENCE: 5
ataatcctcg tcatttgcag                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic E coli nlp primer

<400> SEQUENCE: 6
```

```
gacttcgggt gattgataag                                              20
```

<210> SEQ ID NO 7
<211> LENGTH: 21
<212> TYPE: DNA
<213> ORGANISM: Artificial Sequence
<220> FEATURE:
<223> OTHER INFORMATION: synthetic S pyogene fah primer

<400> SEQUENCE: 7

```
ttaaatacgc taaagccctc t                                            21
```

<210> SEQ ID NO 8
<211> LENGTH: 20
<212> TYPE: DNA
<213> ORGANISM: Artificial Sequence
<220> FEATURE:
<223> OTHER INFORMATION: synthetic S pyogene fah primer

<400> SEQUENCE: 8

```
agggtgctta atttgacaag                                              20
```

<210> SEQ ID NO 9
<211> LENGTH: 21
<212> TYPE: DNA
<213> ORGANISM: Artificial Sequence
<220> FEATURE:
<223> OTHER INFORMATION: synthetic S pyrogene OppA primer

<400> SEQUENCE: 9

```
cccagttcaa ttagattacc c                                            21
```

<210> SEQ ID NO 10
<211> LENGTH: 20
<212> TYPE: DNA
<213> ORGANISM: Artificial Sequence
<220> FEATURE:
<223> OTHER INFORMATION: synthetic S pyrogene OppA primer

<400> SEQUENCE: 10

```
ttgacttagc ctttgctttc                                              20
```

<210> SEQ ID NO 11
<211> LENGTH: 20
<212> TYPE: DNA
<213> ORGANISM: Artificial Sequence
<220> FEATURE:
<223> OTHER INFORMATION: synthetic S pneumoniae cinASP primer

<400> SEQUENCE: 11

```
ggctgtagga gacaatgaag                                              20
```

<210> SEQ ID NO 12
<211> LENGTH: 22
<212> TYPE: DNA
<213> ORGANISM: Artificial Sequence
<220> FEATURE:
<223> OTHER INFORMATION: synthetic S pneumoniae cinASP primer

<400> SEQUENCE: 12

```
ctttgttgac agacgtagag tg                                           22
```

<210> SEQ ID NO 13
<211> LENGTH: 20
<212> TYPE: DNA
<213> ORGANISM: Artificial Sequence

```
<220> FEATURE:
<223> OTHER INFORMATION: synthetic S pneumoniae plySP primer

<400> SEQUENCE: 13
atttcgagtg ttgcttatgg                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic S pneumoniae plySP primer

<400> SEQUENCE: 14
gtaaagtgag ccgtcaaatc                                              20

<210> SEQ ID NO 15
<211> LENGTH: 22
<212> TYPE: DNA
<213> ORGANISM: Artificial Sequence
<220> FEATURE:
<223> OTHER INFORMATION: synthetic E faecium bglB primer

<400> SEQUENCE: 15
tcttcatttg ttgaatatgc tg                                           22

<210> SEQ ID NO 16
<211> LENGTH: 20
<212> TYPE: DNA
<213> ORGANISM: Artificial Sequence
<220> FEATURE:
<223> OTHER INFORMATION: synthetic E faecium bglB primer

<400> SEQUENCE: 16
tggaatcgaa cctgttatc                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic E faecalis ace primer

<400> SEQUENCE: 17
tagttggaat gaccgagaac                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic E faecalis ace primer

<400> SEQUENCE: 18
agtgtaacgg acgataaagg                                              20

<210> SEQ ID NO 19
<211> LENGTH: 21
<212> TYPE: DNA
<213> ORGANISM: Artificial Sequence
<220> FEATURE:
<223> OTHER INFORMATION: synthetic P aerugino vic primer

<400> SEQUENCE: 19
ttccctcgca gagaaaacat c                                            21
```

```
<210> SEQ ID NO 20
<211> LENGTH: 21
<212> TYPE: DNA
<213> ORGANISM: Artificial Sequence
<220> FEATURE:
<223> OTHER INFORMATION: synthetic P aerugino vic primer

<400> SEQUENCE: 20
cctggttgat caggtcgatc t                                              21

<210> SEQ ID NO 21
<211> LENGTH: 21
<212> TYPE: DNA
<213> ORGANISM: Artificial Sequence
<220> FEATURE:
<223> OTHER INFORMATION: synthetic S agalactia cpsY primer

<400> SEQUENCE: 21
cgacgataat tccttaattg c                                              21

<210> SEQ ID NO 22
<211> LENGTH: 24
<212> TYPE: DNA
<213> ORGANISM: Artificial Sequence
<220> FEATURE:
<223> OTHER INFORMATION: synthetic S agalactia cpsY primer

<400> SEQUENCE: 22
tcaggactgt ttatttttat gatt                                           24

<210> SEQ ID NO 23
<211> LENGTH: 19
<212> TYPE: DNA
<213> ORGANISM: Artificial Sequence
<220> FEATURE:
<223> OTHER INFORMATION: synthetic Pseu general 16S primer

<400> SEQUENCE: 23
gacgggtgag taatgccta                                                 19

<210> SEQ ID NO 24
<211> LENGTH: 20
<212> TYPE: DNA
<213> ORGANISM: Artificial Sequence
<220> FEATURE:
<223> OTHER INFORMATION: synthetic Pseu general 16S primer

<400> SEQUENCE: 24
cactggtgtt ccttcctata                                                20

<210> SEQ ID NO 25
<211> LENGTH: 21
<212> TYPE: DNA
<213> ORGANISM: Artificial Sequence
<220> FEATURE:
<223> OTHER INFORMATION: synthetic S aureous nuc primer

<400> SEQUENCE: 25
gcgattgatg gtgatacggt t                                              21

<210> SEQ ID NO 26
<211> LENGTH: 24
<212> TYPE: DNA
<213> ORGANISM: Artificial Sequence
<220> FEATURE:
<223> OTHER INFORMATION: synthetic S aureous nuc primer
```

```
<400> SEQUENCE: 26
agccaagcct tgacgaacta aagc                                              24

<210> SEQ ID NO 27
<211> LENGTH: 25
<212> TYPE: DNA
<213> ORGANISM: Artificial Sequence
<220> FEATURE:
<223> OTHER INFORMATION: synthetic S epid agrC primer

<400> SEQUENCE: 27
gatgatatta atctatttcc gtttg                                             25

<210> SEQ ID NO 28
<211> LENGTH: 24
<212> TYPE: DNA
<213> ORGANISM: Artificial Sequence
<220> FEATURE:
<223> OTHER INFORMATION: synthetic S epid agrC  primer

<400> SEQUENCE: 28
tcaggactgt ttatttttat gatt                                              24

<210> SEQ ID NO 29
<211> LENGTH: 22
<212> TYPE: DNA
<213> ORGANISM: Artificial Sequence
<220> FEATURE:
<223> OTHER INFORMATION: synthetic S mutans dltA primer

<400> SEQUENCE: 29
agatatgatt gcaacaattg aa                                                22

<210> SEQ ID NO 30
<211> LENGTH: 20
<212> TYPE: DNA
<213> ORGANISM: Artificial Sequence
<220> FEATURE:
<223> OTHER INFORMATION: synthetic S mutans dltA primer

<400> SEQUENCE: 30
cgcatgattg atttgataag                                                   20

<210> SEQ ID NO 31
<211> LENGTH: 20
<212> TYPE: DNA
<213> ORGANISM: Artificial Sequence
<220> FEATURE:
<223> OTHER INFORMATION: synthetic P mirabil aad primer

<400> SEQUENCE: 31
cgctattaac cttgctgaac                                                   20

<210> SEQ ID NO 32
<211> LENGTH: 20
<212> TYPE: DNA
<213> ORGANISM: Artificial Sequence
<220> FEATURE:
<223> OTHER INFORMATION: synthetic P mirabil aad primer

<400> SEQUENCE: 32
cctttctcac tcaccacatc                                                   20

<210> SEQ ID NO 33
```

```
<211> LENGTH: 23
<212> TYPE: DNA
<213> ORGANISM: Artificial Sequence
<220> FEATURE:
<223> OTHER INFORMATION: synthetic MRSA mecA primer

<400> SEQUENCE: 33
caagatatga agtggtaaat ggt                                          23

<210> SEQ ID NO 34
<211> LENGTH: 23
<212> TYPE: DNA
<213> ORGANISM: Artificial Sequence
<220> FEATURE:
<223> OTHER INFORMATION: synthetic MRSA mecA primer

<400> SEQUENCE: 34
tttacgactt gttgcatacc atc                                          23

<210> SEQ ID NO 35
<211> LENGTH: 22
<212> TYPE: DNA
<213> ORGANISM: Artificial Sequence
<220> FEATURE:
<223> OTHER INFORMATION: synthetic C troplicalis ctr primer

<400> SEQUENCE: 35
caatcctacc gccagaggtt at                                           22

<210> SEQ ID NO 36
<211> LENGTH: 22
<212> TYPE: DNA
<213> ORGANISM: Artificial Sequence
<220> FEATURE:
<223> OTHER INFORMATION: synthetic C troplicalis ctr primer

<400> SEQUENCE: 36
tggccactag caaaataagc gt                                           22

<210> SEQ ID NO 37
<211> LENGTH: 20
<212> TYPE: DNA
<213> ORGANISM: Artificial Sequence
<220> FEATURE:
<223> OTHER INFORMATION: synthetic C glabrata cgl primer

<400> SEQUENCE: 37
ttatcacacg actcgacact                                              20

<210> SEQ ID NO 38
<211> LENGTH: 24
<212> TYPE: DNA
<213> ORGANISM: Artificial Sequence
<220> FEATURE:
<223> OTHER INFORMATION: synthetic C glabrata cgl primer

<400> SEQUENCE: 38
cccacatact gatatggcct acaa                                         24

<210> SEQ ID NO 39
<211> LENGTH: 22
<212> TYPE: DNA
<213> ORGANISM: Artificial Sequence
<220> FEATURE:
<223> OTHER INFORMATION: synthetic C albicans calb primer

<400> SEQUENCE: 39
```
tttatcaact tgtcacacca ga                                          22

<210> SEQ ID NO 40
<211> LENGTH: 20
<212> TYPE: DNA
<213> ORGANISM: Artificial Sequence
<220> FEATURE:
<223> OTHER INFORMATION: synthetic C albicans calb primer

<400> SEQUENCE: 40
atcccgcctt accactaccg                                             20

<210> SEQ ID NO 41
<211> LENGTH: 23
<212> TYPE: DNA
<213> ORGANISM: Artificial Sequence
<220> FEATURE:
<223> OTHER INFORMATION: synthetic K pneumonia cim primer

<400> SEQUENCE: 41
aatttaacct ggtttgataa gaa                                         23

<210> SEQ ID NO 42
<211> LENGTH: 26
<212> TYPE: DNA
<213> ORGANISM: Artificial Sequence
<220> FEATURE:
<223> OTHER INFORMATION: synthetic K pneumonia cim primer

<400> SEQUENCE: 42
caaaatatga actatcagaa agattg                                      26

<210> SEQ ID NO 43
<211> LENGTH: 18
<212> TYPE: DNA
<213> ORGANISM: Artificial Sequence
<220> FEATURE:
<223> OTHER INFORMATION: synthetic K pneumonia acoA primer

<400> SEQUENCE: 43
taacggcaaa gacgctaa                                               18

<210> SEQ ID NO 44
<211> LENGTH: 19
<212> TYPE: DNA
<213> ORGANISM: Artificial Sequence
<220> FEATURE:
<223> OTHER INFORMATION: synthetic K pneumonia acoA primer

<400> SEQUENCE: 44
tgaccagggc ttctacttc                                              19

<210> SEQ ID NO 45
<211> LENGTH: 20
<212> TYPE: DNA
<213> ORGANISM: Artificial Sequence
<220> FEATURE:
<223> OTHER INFORMATION: synthetic primer 1

<400> SEQUENCE: 45
gcgtcacact ttgctatgcc                                             20

<210> SEQ ID NO 46
<211> LENGTH: 24
<212> TYPE: DNA

```
<213> ORGANISM: Artificial Sequence
<220> FEATURE:
<223> OTHER INFORMATION: synthetic primer 2

<400> SEQUENCE: 46
gcttctgcgt tctgatttaa tctg                                          24

<210> SEQ ID NO 47
<211> LENGTH: 23
<212> TYPE: DNA
<213> ORGANISM: Artificial Sequence
<220> FEATURE:
<223> OTHER INFORMATION: synthetic A1352 sense primer

<400> SEQUENCE: 47
graacccact gcttaassct caa                                           23

<210> SEQ ID NO 48
<211> LENGTH: 23
<212> TYPE: DNA
<213> ORGANISM: Artificial Sequence
<220> FEATURE:
<223> OTHER INFORMATION: synthetic A1355 antisense primer
<220> FEATURE:
<221> NAME/KEY: misc_feature
<222> LOCATION: (14)..(14)
<223> OTHER INFORMATION: n is a, c, g, or t

<400> SEQUENCE: 48
gagggatctc tagnyaccag agt                                           23
```

SLIP CHIP DEVICE AND METHODS

This application is a continuation of U.S. application Ser. No. 13/257,811, filed Sep. 20, 2011 which claims priority to PCT/US2010/28316 filed Mar. 23, 2010, which claims priority to U.S. Provisional Patent Application Ser. No. 61/162,922 filed on Mar. 24, 2009, and entitled "Slip Chip Device And Methods"; U.S. Provisional Patent Application Ser. No. 61/262,375, filed on Nov. 18, 2009, and entitled "Slip Chip Device And Methods"; and U.S. Provisional Patent Application Ser. No. 61/340,872, filed on Mar. 22, 2010, and entitled "Slip Chip Device And Methods", the entireties of all of which are incorporated herein by reference.

This invention was made with government support under grant numbers EB012946, GM074961 and OD003584 awarded by the National Institutes of Health and grant number CHE-0526693 awarded by the National Science Foundation. The government has certain rights in the invention.

BACKGROUND

Known devices and methods for carrying out a reaction are limited in the way two or more substances may be exposed to one another. Such devices employ a series of chambers configured for subjecting a substance to a specific processing step, but require each chamber to be individually filled and/or exposed to another chamber for carrying out a reaction in that chamber. These devices are not designed to minimize the possibility of cross-contamination or contamination from external sources. Moreover, to perform multiple reactions with multiple substances, these devices must be re-loaded with additional substances, thus taking additional time and increased chance of contamination. Accordingly, it is a time-consuming process to perform each combination of reactions for a specific substance.

BRIEF SUMMARY

The present invention includes a device and method for carrying out a reaction. In one embodiment the device includes a base having a first surface, at least one first area located along a portion of the first surface where the at least one first area is configured to maintain at least one first substance. A plate having a second surface is opposed to the first surface and at least one second area is located along a portion of the second surface, where the at least one second area is configured to maintain at least one second substance, where at least one of the first surface of the base and the second surface of the plate is configured to move relative to the other between a first position, where one of the at least one first area is only exposed to one of the at least one second areas and form a closed system.

In another embodiment, the device for carrying out a reaction includes a base having a first surface and a plurality of areas formed along a portion of the first surface, where each of the plurality of first areas is configured to maintain at least one first substance. A plate having a second surface is opposed to the first surface and a plurality of second areas is formed along a portion of the second surface. Each of the plurality of second areas is configured to maintain at least one second substance wherein at least one of the first surface of the base and the second surface of the plate is configured to slide relative to the other between a first position, where at least some of the plurality of the first areas are not exposed to any of the plurality of the second areas, and a second position in a direction substantially perpendicular to the normal of the first surface, wherein in the second position at least one of the plurality of the first areas and at least one of the plurality of the second areas are only exposed to one another.

In another embodiment of the present invention, the device includes a base having a first surface and a first area located along a portion of the first surface where the first area is configured to maintain at least one first substance. A first duct is formed along a portion of the first surface and is not exposed to the first area. A plate having a second surface is opposed to the first surface and a second area is located along a portion of the second surface, where the second area is configured to maintain at least one second substance wherein the first surface and the second surface are configured to slide relative to one another between a first position and a second position, wherein in the first position the first duct is exposed to the second area and the first area and the second area are not exposed to one another, and wherein in the second position the first area and the second area are only exposed to one another.

In another embodiment of the present invention the device includes a base having a first surface and a first plurality of first areas located along a portion of the first surface, where the first plurality of first areas have a first pattern and are configured to maintain at least one first substance. A first set of ducts is formed along a portion of the first surface and are not exposed to the first plurality of first areas. A plate having a second surface is opposed to the first surface and a plurality of second areas are located along a portion of the second surface, the plurality of second areas having a pattern substantially similar to the pattern of the first plurality of first areas where the plurality of second areas are configured to maintain at least one second substance, wherein the first surface and the second surface are configured to slide relative to one another between a first position, where the first set of ducts is exposed to the plurality of second areas, and a second position, where at least one of the first plurality of first areas and at least one of the plurality of second areas are only exposed to one another.

In another embodiment of the present invention the device includes a base having a first surface, a first area located along a portion of the first surface, and the first area configured to maintain at least one first substance. An upper plate has a second surface facing the first surface and has a second area located along a portion of the second surface and is configured to maintain at least one second substance. An intermediate plate is disposed between the first surface of the base and the second surface of the upper plate and the intermediate plate has an opening formed therethrough, wherein the base, the upper plate and the intermediate plate are configured to slide relative to one another from a first position where the first area is not exposed to the second area via the opening to a second position where the first area is exposed to the second area via the opening.

Yet another embodiment of the present invention includes a kit for carrying out a reaction including a base having a first surface and a first area located along a portion of the first surface where the first area is configured to maintain at least one first substance, and a plate having a second surface and a second area located along a portion of the second surface, where the second area is configured to maintain at least one second substance, and at least one of a first substance in the first area, and a second substance in the second area, and a substrate disposed between the first surface and the second surface, wherein the first surface of the base and the second surface of the plate are configured such that when fitted together, they are opposed to each other and move relative to the other between a first position, where the first area and the second area are not exposed to one another, and a second position where the first area and the second area are only exposed to one another.

Yet another embodiment of the present invention includes a kit for carrying out a reaction including a base having a first surface, a first area located along a portion of the first surface and configured to maintain at least one first substance and a first duct formed along a portion of the first surface and not exposed to the first area, a plate having a second surface and a second area located along a portion of the second surface and configured to maintain at least one second substance, and at least one of a first substance in the first area, a second substance in the second area, and a substrate disposed between the first surface and the second surface, wherein the first surface and the second surface are configured such that when fitted together they slide relative to one another between a first position and a second position, wherein in the first position, the first duct is exposed to the second area, and the first area and the second area are not exposed to one another, and wherein in the second position, the first area and the second area are only exposed to one another.

Yet another embodiment of the present invention includes a kit for carrying out a reaction including a base having a first surface, a first plurality of first areas located along a portion of the first surface, where the plurality of first areas have a first pattern and are configured to maintain at least one first substance, and a first set of ducts formed along a portion of the first surface and not exposed to the first plurality of first areas. The embodiment further includes a plate having a second surface and a plurality of second areas located along a portion of the second surface where the plurality of second areas have a pattern substantially similar to the pattern of the first plurality of first areas and the plurality of second areas are configured to maintain at least one second substance, and at least one of a first substance in the first area, a second substance in the second area, and a substrate disposed between the first surface and the second surface, where the first surface and the second surface are configured such that when fitted together they slide relative to one another between a first position, where the first set of ducts is exposed to the plurality of second areas, and a second position, where at least one of the first plurality of first areas and at least one of the plurality of second areas are only exposed to one another.

Yet another embodiment of the present invention includes a kit for carrying out a reaction including a base having a first surface and a first area located along a portion of the first surface, where the first area is configured to maintain at least one first substance, an upper plate having a second surface and a second area located along a portion of the second surface configured to maintain at least one second substance, an intermediate plate disposed between the first surface of the base and the second surface of the upper plate having an opening formed therethrough, and at least one of a first substance in the first area, a second substance in the second area, and a substrate disposed between the first surface and the second surface, wherein the base, the upper plate and the intermediate plate are configured such that the intermediate plate can be disposed between the first and second surfaces and can slide relative to the base and upper plate from a first position, where the first area is not exposed to the second area via the opening, to a second position, where the first area is exposed to the second area via the opening.

Yet another embodiment of the present invention includes a method for carrying out a reaction, the method includes the steps of providing a device in a first position where the device comprises a base having a first surface, a first area located along a portion of the first surface where the first area is configured to maintain at least one first substance, a first substance in the first area, a plate having a second surface opposed to the first surface, a second area located along a portion of the second surface, where the second area is configured to maintain at least one second substance, and a second substance in the second area, wherein the first surface of the base and the second surface of the plate are configured to move relative to one another, and wherein the first area and the second area are not exposed to one another when in the first position, and moving the device from the first position into a second position by moving the first surface of the base and the second surface of the plate relative to one another, and wherein in the second position, the first area and the second area are only exposed to one another, thereby reacting the first and second substances.

Yet another embodiment of the present invention includes a method for carrying out a reaction, the method includes the steps of providing a device in a first position, the device including a base having a first surface, a plurality of first areas formed along a portion of the first surface, where each of the plurality of first areas is configured to maintain at least one first substance, at least one first substance in at least one of the plurality of first areas, a plate having a second surface opposed to the first surface, wherein the first surface of the base and the second surface of the plate are configured to move relative to one another in a direction substantially perpendicular to the normal of the first surface, a plurality of second areas formed along a portion of the second surface, where each of the plurality of second areas is configured to maintain at least one second substance, at least one second substance in at least one of the plurality of second areas, and where at least some of the plurality of first areas are not exposed to any of the plurality of second areas in the first position, and moving the device from the first position to a second position, wherein in the second position at least one of the plurality of the first areas and at least one of the plurality of the second areas are only exposed to one another, thereby reacting the at least one first and second substances.

Yet another embodiment of the present invention includes a method for carrying out a reaction, the method includes the steps of providing a device in a first position, with the device including a base having a first surface, a first area located along a portion of the first surface, where the first area is configured to maintain at least one first substance, at least one first substance maintained in the first area, a first duct formed along a portion of the first surface and not exposed to the first area, a plate having a second surface opposed to the first surface, wherein the first surface and the second surface are configured to slide relative to one another from the first position to a second position, a second area located along a portion of the second surface, where the second area is configured to maintain at least one second substance, and at least one second substance maintained in the second area, wherein when in the first position, the first duct is exposed to the second area, and the first area and the second area are not exposed to one another, and moving the device from the first position into the second position, wherein in the second position, the first area and the second area are only exposed to one another, thereby reacting the at least one first and second substances.

Yet another embodiment of the present invention includes a method for carrying out a reaction, the method including the steps of providing a device in a first position, wherein the device includes a base having a first surface, a first plurality of first areas located along a portion of the first surface, where the first plurality of first areas have a first pattern and are configured to maintain at least one first substance, at least one first substance maintained in at least one first area, a first set of ducts formed along a portion of the first surface and not exposed to the first plurality of first areas, a plate having a second surface opposed to the first surface, wherein the first surface and the second surface are configured to slide relative to one another, a plurality of second areas located along a portion of the second surface, the plurality of second areas having a pattern substantially similar to the pattern of the first plurality of first areas, the plurality of second areas configured to maintain at least one second substance, and at least one second substance maintained in at least one of the second areas, wherein in the first position the first set of ducts is exposed to the plurality of second areas, and moving the device from the first position into a second position, wherein in the second position, at least one of the first plurality of first areas and at least one of the plurality of second areas are only exposed to one another, thereby reacting the at least one first and second substances.

Yet another embodiment of the present invention includes a method for carrying out a reaction, the method including the steps of providing a device in a first position, wherein the device includes a base having a first surface, a first area located along a portion of the first surface, where the first area is configured to maintain at least one first substance, at least one first substance in the first area, an upper plate having a second surface facing the first surface, a second area located along a portion of the second surface configured to maintain at least one second substance, at least one second substance in the second area, and an intermediate plate disposed between the first surface of the base and the second surface of the upper plate having a opening formed therethrough, wherein the base, the upper plate and the intermediate plate are configured to slide relative to one another, and wherein in the first position the first area is not exposed to the second area via the opening, and moving the device from the first position into a second position, wherein in the second position, the first area is exposed to the second area via the opening, thereby reacting the at least one first and second substances.

Yet another embodiment of the present invention includes a kit for offering an inventory of reagents, receiving from the customer a desired subset of reagents, and delivering a kit to the customer, wherein the kit includes a base having a first surface and a first area located along a portion of the first surface, where the first area is configured to maintain at least one first substance, and a plate having a second surface and an second area located along a portion of the second surface, where the second area is configured to maintain at least one second substance, and either a first substance in the first area or a second substance in the second area, wherein the first surface of the base and the second surface of the plate are configured such that when fitted together they are opposed to each other and move relative to the other between a first position, where the first area and the second area are not exposed to one another, and a second position, where the first area and the second area are exposed to one another, and wherein at least one of the first substance and the second substance is an element of the desired subset of reagents.

Yet another embodiment of the present invention includes a kit for offering an inventory of reagents, receiving from the customer a desired subset of reagents, and delivering a kit to the customer, wherein the kit includes a base having a first surface, a first plurality of first areas located along a portion of the first surface, where the first plurality of first areas have a first pattern and are configured to maintain at least one first substance, and a first set of ducts formed along a portion of the first surface that are not exposed to the first plurality of first areas, a plate having a second surface and a plurality of second areas located along a portion of the second surface where the plurality of second areas have a pattern substantially similar to the pattern of the first plurality of first areas, and where the plurality of second areas configured to maintain at least one second substance, and at least one of a first substance in the first area and a second substance in the second area, wherein the first surface and the second surface are configured such that when fitted together they slide relative to one another between a first position, where the first set of ducts is exposed to the plurality of second areas, and a second position, where at least one of the first plurality of first areas and at least one of the plurality of second areas are only exposed to one another.

BRIEF DESCRIPTION OF THE DRAWINGS

FIG. 4A is a side view of a slip chip device according to another embodiment of the invention in a first position.

FIG. 4B is a side view of the slip chip device shown in FIG. 4A in a second position.

FIG. 4C is a side view of the slip chip device shown in FIG. 4A in a third position.

FIG. 5A is a side view of a slip chip device according to another embodiment of the invention in a first position.

FIG. 5B is a side view of the slip chip device shown in FIG. 5A in a second position.

FIG. 8A, part I and FIG. 8A, part II are partial top views of a slip chip device in first position according to another embodiment of the invention.

FIG. 8B is a partial view of a slip chip device shown in FIG. 8A in a second position.

FIG. 8C, part I and FIG. 8C, part II are partial views of a slip chip device shown in FIG. 8A in a third position.

FIG. 8D is a partial view of a slip chip device shown in FIG. 8A in a fourth position.

FIG. 11A is a partial top view of a slip chip device according to another embodiment of the invention in a first position.

FIG. 11B is a partial top view of the slip chip device shown in FIG. 11A in a second position.

FIG. 11C is a partial top view of a slip chip device according to another embodiment of the invention in a first position.

FIG. 11D is a partial top view of the slip chip shown in FIG. 11C in a second position.

DETAILED DESCRIPTION OF THE DRAWINGS AND THE PRESENTLY PREFERRED EMBODIMENTS

Figures 1A, 1B:
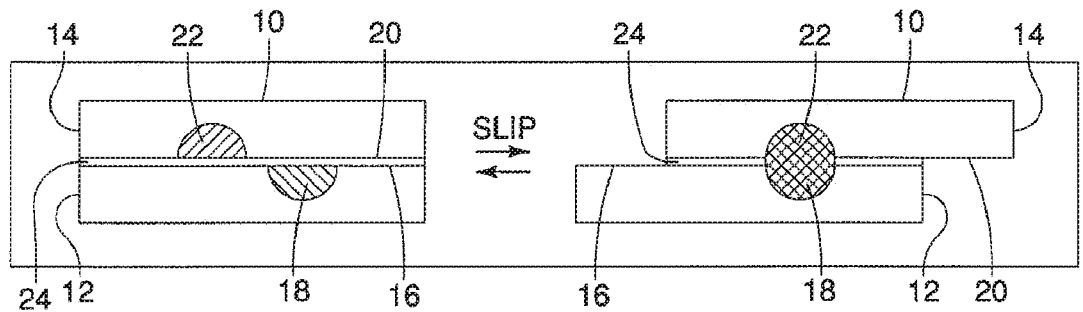
FIG. 1A is a side view of a slip chip device according to one embodiment of the invention in a first position.
FIG. 1B is a side view of the slip chip device of the embodiment shown in FIG. 1A in a second position.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. While not intending to be bound by theory, in several of the examples below the inventors propose theories by which the invention is believed to operate. Any statements which propose a scientific theory by which an invention is believed to operate are not intended as, and should not be treated as, a limitation on the claimed invention.

As used in the specification and the appended claims, the singular forms "a," "an" and "the" indicate plural references unless the context clearly dictates otherwise. Thus, for example, reference to "a substance" includes a single substance as well as a plurality of substances, reference to "an area" includes a single area as well as a plurality of areas, "a duct" includes a single duct as well as a plurality of ducts, and so forth.

The term "area" as used herein refers to a site where two or more substances are exposed to one another. The "area" may also refer to a portion along a surface that is capable of maintaining a substance therein or therealong. The "area" may take on a physical structure such as a hole, a well, cavity, or indentation, and have any cross-sectional shape along its length, width or depth, such as rectangular, circular, or triangular.

The term "between" when used in the context of moving between "a first position" and a "second position" may mean to move only from a first position to a second position, move only from a second position to a first position, or move from a first position to a second position and from the second position to the first position.

The term "closed system" may refer to a system that can exchange heat and energy but not matter, with its surroundings. For certain embodiments, the closed system can be one in which liquid cannot be exchanged with its surroundings, but gases, such as water vapor or oxygen, can be. For certain embodiments, the closed system can be one in which liquid water cannot be exchanged with its surroundings, but gases, such as water vapor or oxygen, or substances that can permeate a lubricating layer or substrate, can be. also be non-Newtonian fluids, for example shear-thickening fluids. May also be gels, including hydrogels. May also be carbohydrate-rich or lipid-rich phases, including lipidic cubic phase and other lipid mesophases. In some embodiments, permeability to gases may be desirable, for example in some applications that use live cells and tissues inside the Slip-Chip.

The term "duct" may refer to a three-dimensional enclosure through which a substance may be transported. Alternatively, it can also refer to an open groove or a trench in a surface through which a substance may also be transported. A duct can assume any form or shape such as tubular or cylindrical, have a uniform or variable (e.g., tapered) diameter along its length, and have one or more cross-sectional shapes along its length such as rectangular, circular, or triangular. As used herein, the term "duct" includes microducts that are of dimensions suitable for use in devices. A duct may be connected to at least one other duct through another duct, area, or any other type of conduit.

In certain embodiments areas may also be ducts, and in certain embodiments ducts may also be areas.

As mentioned above, the duct can have any cross-sectional shape (circular, oval, triangular, irregular, square or rectangular, or the like) and can be covered or uncovered. In embodiments where it is completely covered, at least one portion of the duct can have a cross-section that is completely closed, or the entire duct may be completely enclosed along its entire length with the exception of inlet(s) and outlet(s). A duct generally will include characteristics that facilitate control over substance transport, e.g., structural characteristics and/or physical or chemical characteristics (hydrophobicity vs. hydrophilicity) or other characteristics that can exert a force on a fluid. The substance within the duct may partially or completely fill the duct. In some cases where an open duct is used, the substance, such as a fluid, may be held within the duct, for example, using surface tension (i.e., a concave or convex meniscus).

The duct may be of any size, for example, having a largest dimension perpendicular to the direction of flow of a substance, for example a fluid, of less than about 50 mm, less than about 5 mm, less than about 2 mm, less than about 1 mm, less than about 500 microns, less than about 200 microns, less than about 60 microns, less than about 50 microns, less than about 40 microns, less than about 30 microns, less than about 15 microns, less than about 10 microns, less than about 3 microns, less than about 1 micron, less than about 300 nm, less than about 100 nm, less than about 30 nm, or less than about 10 nm. In some cases the dimensions of the duct may be chosen such that a substance is able to freely flow through, or into, an area or other ducts. The dimensions of the duct may also be chosen, for example, to allow a certain volumetric or linear flow rate of fluid in the duct. Of course, the number of ducts and the shape of the ducts can be varied by any method known to those of ordinary skill in the art.

The term "exposed" as used herein is a form of communication between two or more elements. These elements may include a substance, an area, a duct, a passage, a channel, a lumen, or any combination thereof. In some instances, "exposed" may mean that two or more substances are in fluidic communication with each other, or alternatively, it may mean that two or more substances react with one another.

The term "fluidic communication," as used herein, refers to any duct, channel, tube, pipe, or pathway through which a substance, such as a liquid, gas, or solid may pass substantially unrestricted when the pathway is open. When the pathway is closed, the substance is substantially restricted from passing through. In embodiments where a substrate is present, a substance may pass from one reaction area to another through the substrate when the device is in the closed position, if the reaction areas are spatially positioned to allow diffusion via the substrate versus passage via a pathway. Typically, limited diffusion of a substance through the material of a plate, base, and/or a substrate, which may or may not occur depending on the compositions of the substance and materials, does not constitute fluidic communication.

The terms "react" or "reaction" refer to a physical, chemical, biochemical, or biological transformation that involves at least one substance, e.g., reactant, reagent, phase, carrier-fluid, or plug-fluid and that generally involves (in the case of chemical, biochemical, and biological transformations) the breaking or formation of one or more bonds such as covalent, noncovalent, van der Waals, hydrogen, or ionic bonds. The term includes typical photochemical and electrochemical reactions, typical chemical reactions such as synthetic reactions, neutralization reactions, decomposition reactions, displacement reactions, reduction-oxidation reactions, precipitation, crystallization, combustion reactions, and polymerization reactions, as well as covalent and non-covalent binding, phase change, color change, phase formation, dissolution, light emission, changes of light absorption or emissive properties, temperature change or heat absorption or emission, conformational change, and folding or unfolding of a macromolecule such as a protein.

The term "substance" as used herein refers to any chemical, compound, mixture, solution, emulsion, dispersion, suspension, molecule, ion, dimer, macromolecule such as a polymer or protein, biomolecule, precipitate, crystal, chemical moiety or group, particle, nanoparticle, reagent, reaction product, solvent, or fluid, and any one of which may exist in the solid, liquid, or gaseous state, and which is typically the subject of an analysis.

A device 10 for carrying out a reaction is shown in FIGS. 1A and 1B. FIGS. 1A and 1B are a cross-sectional view of the device 10 taken along a longitudinal axis. The device 10 includes a base 12 and a plate 14. A first surface 16 is formed along a portion of the base 12. A first area 18 is located along a portion of the first surface 16. A second surface 20 is formed along a portion of the plate 14 and has a second area 22 located along a portion of the second surface 20. The first and second surfaces 16, 20 may be fixedly opposed to one another and may be substantially planar, or alternatively, may have complimentary surface characteristics to permit relative movement between the first and second surfaces 16, 20. Moreover, the second surface 20 may be complex, non-planar, and/or nonparallel to the first surface 16. The first and second surfaces 16, 20 are capable of interfacing closely with one another, and in some embodiments, pressure sealing techniques may be employed, e.g., by using external means to urge the pieces together (such as clips, springs, pneumatic or hydraulic means, or clamping apparatuses). Moreover, to ensure that uniform pressure is applied over the first and second surfaces 16, 20, the shape of the surfaces may vary to ensure when pressure is applied in discrete locations along the device 10, a uniform pressure across the surfaces 16, 20 results. For example, when the two surfaces are conical, pressure may be applied to bring two surfaces into close contact. One or more of the plates may be designed to deform as the pressure is applied, to re-distribute local pressure into uniform pressure over entire surface.

In some embodiments, areas are filled with reagents that, when exposed to one another, consume a gas, or cause a decrease in pressure, and are configured such that they form a closed system. For example, at least one first area may contain sodium hydroxide and at least one second area may be filled with carbon dioxide. Once the parts of the device 10 are moved to expose the at least one first area to the second area, the reaction of the sodium hydroxide with the carbon dioxide can form a partial vacuum. This partial vacuum produces a force acting to hold the base 12 and the plate 14 of the device 10 together.

The first and second surfaces 16, 20 may be planar or nonplanar. For example, the surfaces can be cylindrical. The relative motion in a cylindrical device 10 of the base 12 and plate 14 will be rotational. If the relative motion of base 12 and plate 14 is to be carried out manually, a handle could be fixed to either base 12, plate 14 or both. It will be apparent to one skilled in the art that the surfaces 16, 20 can be other closely interfacing shapes. The first and second surfaces may be concentric spheres.

The first and second surfaces 16, 20 may be made out of the same material as the base 12 and plate 14, respectively. Alternatively, the surfaces 16, 20 may be made out of any other suitable material having a low coefficient of friction and may have hydrophobic or hydrophilic properties. Moreover, the first and second areas 18, 22 may also be made out of a different material, or have different properties, than the first and second surfaces 16, 20 or the base 12 and plate 14, respectively.

Figure 2:
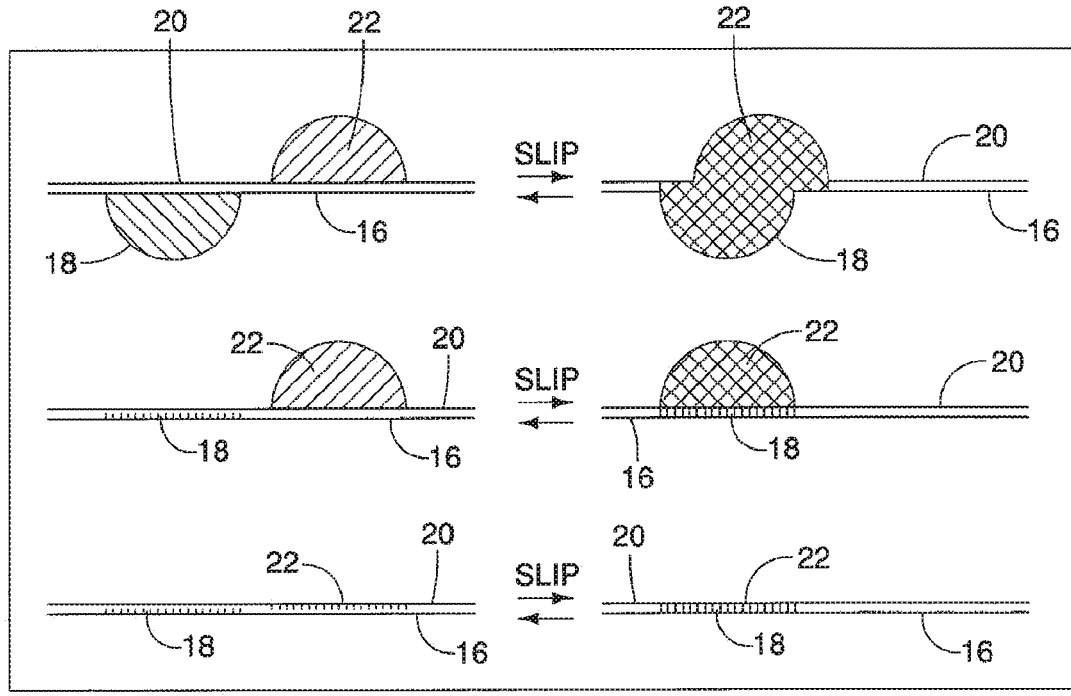
FIG. 2 is a partial view of a slip chip device according to another embodiment of the invention.

Both the first area 18 and the second area 22, as shown in the FIGS. 1A and 1B embodiment, are areas 23 configured to maintain a substance therein. However, the first area 18 and the second area 22 may also be a surface pattern 25 of a substance, as shown in FIG. 2, or a through hole, as shown in FIG. 4. As shown in FIG. 2, it is not necessary that the first area 18 and the second area 22 have the same structural configuration, or maintain the same substance, as the other.

Areas 18, 22 may also contain porous materials, for example porous glass, aluminum oxide, or cellulose matrix found in paper. Such areas may be made by deposition of the matrix into the area. Alternatively, they may be made by patterning a porous layer and filling the porous layer around the areas. For example, paper may be patterned by methods described in Martinez, A. W., Phillips, S. T., Carrilho, E., Thomas III, S. W., Sindi, H., Whitesides, G. M., Simple telemedicine for developing regions: Camera phones and paper-based microfluidic devices for real-time, off-site diagnosis (2008) Analytical Chemistry, 80 (10), pp. 3699-3707, Martinez, A. W., Phillips, S. T., Butte, M. J., Whitesides, G. M. Patterned paper as a platform for inexpensive, low-volume, portable bioassays (2007) Angewandte Chemie—International Edition, 46 (8), pp. 1318-1320, Martinez, A. W. FLASH: A rapid method for prototyping paper-based microfluidic devices (2008) Lab Chip, and Macek, K., Bečvářová, H. Papers, ready-for-use plates, and flexible sheets for chromatography (1971) Chromatographic Reviews, 15 (1), pp. 1-28, and other materials may be patterned by methods described in Vozzi, G., Flaim, C., Ahluwalia, A., Bhatia, S. Fabrication of PLGA scaffolds using soft lithography and microsyringe deposition (2003) Biomaterials, 24 (14), pp. 2533-2540, Desai, T. A., Hansford, D. J., Leoni, L., Essenpreis, M., Ferrari, M. Nanoporous anti-fouling silicon membranes for biosensor applications (2000) Biosensors and Bioelectronics, 15 (9-10), pp. 453-462, Pichonat, T., Gauthier-Manuel, B. Development of porous silicon-based miniature fuel cells (2005) Journal of Micromechanics and Microengineering, 15 (9), pp. S179-S184, Cohen, M. H., Melnik, K., Boiarski, A. A., Ferrari, M., Martin, F. J. Microfabrication of silicon-based nanoporous particulates for medical applications (2003) Biomedical Microdevices, 5 (3), pp. 253-259, De Jong, J., Ankoné, B., Lammertink, R. G. H., Wessling, M. New replication technique for the fabrication of thin polymeric microfluidic devices with tunable porosity (2005) Lab on a Chip—Miniaturisation for Chemistry and Biology, 5 (11), pp. 1240-1247, Ohji, H., Lahteenmaki, S., French, P. J. Macro porous silicon formation for micromachining (1997) Proceedings of SPIE—The International Society for Optical Engineering, 3223, pp. 189-197, Chu, K.-L., Gold, S., Subramanian, V., Lu, C., Shannon, M. A., Masel, R. I. A nanoporous silicon membrane electrode assembly for on-chip micro fuel cell applications (2006) Journal of Microelectromechanical Systems, 15 (3), pp. 671-677, Petronis, S., Gretzer, C., Kasemo, B., Gold, J. Model porous surfaces for systematic studies of material-cell interactions (2003) Journal of Biomedical Materials Research—Part A, 66 (3), pp. 707-721, Wang, M., Feng, Y. Palladium-silver thin film for hydrogen sensing (2007) Sensors and Actuators, B: Chemical, 123 (1), pp. 101-106, to fill and/or coat the regions around the areas, all of which are incorporated herein by reference.

Referring back to the embodiment shown in FIGS. 1A and 1B, the first and second surfaces 16, 20 are substantially opposed to one another. A substrate 24 may be disposed between the first and second surfaces 16, 20 to help maintain a substance within each area 18, 22, or may operate to protect each area 18, 22 from cross-contamination. The substrate 24 is typically comprised of a material that is substantially inert with respect to the substances that will be in contact with and/or transported through the device 10. The substrate 24 is also typically comprised of a material that is substantially immiscible with the substances that will be in contact with and/or transported through the device 10.

The substrate 24 may be a hydrocarbon or a fluorinated substance, Fluorinated substances that can be used in the invention include but are not limited to fluorocarbons, perfluorocarbons, alkyl and aryl fluorocarbons, halofluorocarbons, fluorinated alcohols, fluorinated oils, and liquid fluoropolymers including perfluoropolyethers). Examples include, but are not limited to, perfluorooctyl bromide, perfluorooctylethane, octadecafluorodecahydronaphthalene, 1-(1, 2, 2, 3, 3, 4, 4, 5, 5, 6, 6-undeca-fluorocyclohexyl) ethanol, $C_6F_{11}C_2H_4OH$, Flourinert (3M), Krytox oils, Fomblin oils, and Demnum oils. Hydrocarbon substances include but are not limited to, alkanes or mixtures of alkanes (e.g. paraffin oils such as hexane, hexadecane, and mineral oil), other organic materials and polymers. Other fluid material includes silicon oils and various greases (e.g. Dow Corning high vacuum grease, Fomblin vacuum grease, Krytox greases), and ionic fluids. Fluids can also be non-Newtonian fluids, for example shear-thickening fluids, gels, including hydrogels, and carbohydrate-rich or lipid-rich phases, including lipidic cubic phase and other lipid mesophases. In some embodiments, permeability to gases may be desirable, for example in some applications that use live cells and tissues inside the SlipChip. Surfactants may be added to the substrate, for example to cause or prevent surface aggregation and/or to influence the stability of substances. Lubricating powders or bead could also be used. Variations or versions of some of the above materials may apply here and include but are not limited to various Teflon beads or powders which could be composed of PTFE, PFA or FEP Teflon materials. Other dry lubricants include graphite, molybdenum disulfide and tungsten disulfide. The substrate may also be a solid membrane. For example, if bead-based reagents are used in an area, the membrane may be capable of preventing motion of the beads from an area 18 to an area 22 while still allowing diffusion of other substances from area 18 to area 22. Such a membrane could be, for example, a Teflon membrane or a polycarbonate membrane or a cellulose membrane or any other membranes. In certain embodiments, typically when the substrate 24 is a liquid, it may partially fill areas and/or ducts of the device. In particular, in certain embodiments, surface tension may cause substrate 24 to divide a sample fluid present in a volume into separate plugs or droplets separated by substrate 24. If the volume varies in cross-section along its length, the substrate 24 may, for example, be mostly present in the portions of the volume with a larger cross-sectional area, for example in ducts, and the sample may be mostly present in the portions of the volume with a larger cross-sectional area.

FIG. 1A further illustrates the device 10 in a first position, referred to as "Position A," and FIG. 1B illustrates the device in a second position, referred to as "Position B". The device 10, when in the first position, is in an orientation where the first surface 16 is opposed to the second surface 20 and is configured to move in a direction substantially perpendicular to the normal of the second surface 20 such that the vertical distance (as defined when the device is oriented as shown in FIG. 1A) between the first surface 16 and the second surface 20 remains at a substantially constant value. The distance, or gap, between the first surface 16 and the second surface 20 may vary depending on the existence of a substrate and the type of substrate. In certain embodiments, the distance may vary in different device positions, for example due to design or due to surface roughness. Generally speaking, the gap may range anywhere from 0.2 nanometers to 20 micrometers.

When in the first position, the first area 18 and the second area 22 each contain a substance, but the first and second areas 18, 22 and therefore the substances, are not exposed to one another. When in the second position, at least one of the base 12 or the plate 14 moves relative to the other in a direction perpendicular to the normal of the base 12 thereby exposing the first and second areas 18, 22 to each other. In this embodiment, as depicted in FIGS. 1A and 1B, the first and second areas 18, 22 are only exposed to one another when one overlaps with the other. However, the level of exposure and overlap may vary, and as shown in FIG. 2, the second position may be reached when only a portion of the first and the second areas 18, 22 overlap. It is also contemplated that other configurations will allow two or more areas to be exposed to each other without any of the areas overlapping, as will be discussed later with respect to other embodiments of the present invention. Independent of how the first and second areas 18, 22 are exposed to one another, the exposure allows the substances in the first and second areas 18, 22 to react with each other.

However, in each of the embodiments discussed herein it is contemplated that when the device 10 is in the second position there may be at least one first area 18 and corresponding second area 22 overlapping such that no other substance will be exposed to, or in communication with, that first and second areas 18, 22. Accordingly, respective first and second areas 18, 22 will not be exposed to, or in communication with, any channel, duct, inlet, outlet, or any other structure that is configured to provide a substance therein.

At least one of the base 12 and plate 14 may further move with respect to the other to separate the first and second areas 18, 22 such that they are no longer exposed to each other. The base 12 and/or plate 14 may move back to the first position, or move to a third position that is different from the first position to separate the first and second areas 18, 22. The relative movement between the base 12 and plate 14 may be guided by a guide/track (not shown) configuration, or a ball bearing configured to slidingly engage the base 12 and the plate 14 in order to limit the direction and amount of relative movement between the base 12 and the plate 14. In addition, the relative movement between the base 12 and the plate 14 may be automated. In any of the embodiments discussed herein, the device 10 may also include a detector, such as an imaging or sensor components to record and/or measure reactions within the device 10. Examples of such detectors and imaging devices can be found in U.S. Publication No. 2009/0010804 and WO 2008/002267, both of which are incorporated herein by reference. The detector may be any detector suitable to detect the may be selected from the group consisting of: a web camera, a digital camera, a digital camera in a mobile phone and a video camera, as described in published patent application WO 2008/002267, incorporated by reference herein in its entirety. Alternatively, the detector can be a camera or imaging device which has adequate lighting and resolution for spatially resolving individual signals produced by the device, as described in US 2009/0010804, incorporated by reference in its entirety. In this regard, an imaging device of the present invention can be any known in the art that is compatible with the various designs and configurations of the instant device. For example, the camera can employ any common solid state image sensor including a charged coupled device (CCD), charge injection device (CID), photo diode array (PDA), or complementary metal oxide semiconductor (CMOS). The device may incorporate markers, such as lines, dots or visible substances in ducts and/or areas to enable registration and/or analysis. Registration marks may be included on the device to allow for automatic correction of optical aberrations, or adjustment of the image for the angle and orientation at which the picture was taken. For detecting fluorescent output, chirped excitation/readout can be used. For example blue excitation light may be shined on the device for, for example, nanoseconds, then turned off, and fluorescence may be detected a, for example, nanosecond later. Then, ten nanoseconds later, for example, another image is collected (without an initial excitation flash) to produce a background intensity image for subtraction. In this manner, fluorescence can be analyzed even in daylight. For safety, the detector could be designed to automatically recognize the device, for example if the device comprised a recognizable pattern, such that the detector would only produce the excitation light when pointed at the device. Sia, et al., Angewandte Chemie International Edition, (43), 4, 498-502, incorporated by reference herein, describes additional means for detecting signals in multifluidic devices, including using pulse modulation to reduce noise. Detection can also be improved by using the polarization of excited/emitted light, as is known to those skilled in the art.

It can be appreciated that the number, configuration, or orientation of first and/or second areas 18, 22 is application dependent and may vary from application to application and can include an infinite number of configurations. Accordingly, by way of example, FIGS. 3A-D illustrates another embodiment of the device 10. In this and other figures where appropriate, solid lines indicate features associated with the plate 14 and the second surface 20 and dashed lines indicate features associated with the base 12 and first surface 16. In this embodiment, the device 10 includes the base 12 having one first area 18 and the plate 14 now having two second areas 22. The two second areas 22 are located along a portion of the second surface 20, but are separate and not directly exposed to each other.

Depending on the relative movement between the base 12 and the plate 14, the first area 18 may be exposed to only one of the second areas 22, the other second area, or simultaneously to both of the second areas 22. For instance, as shown in Position A of FIG. 3A, the first area 18 is not exposed to the two second areas 22 and the two second areas 22, in this position, are also not exposed to each other.

Figure 3A:
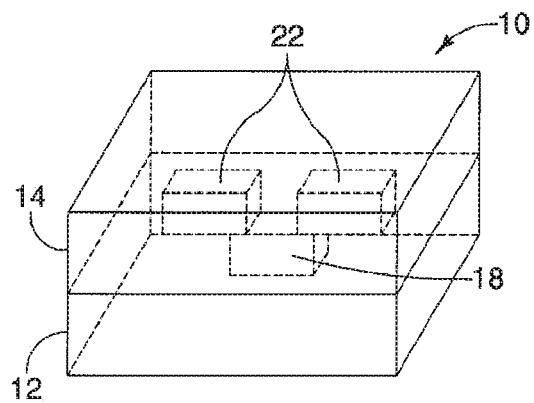
FIG. 3A is a perspective view of a slip chip device according to another embodiment of the invention in a first position.
Figure 3B:
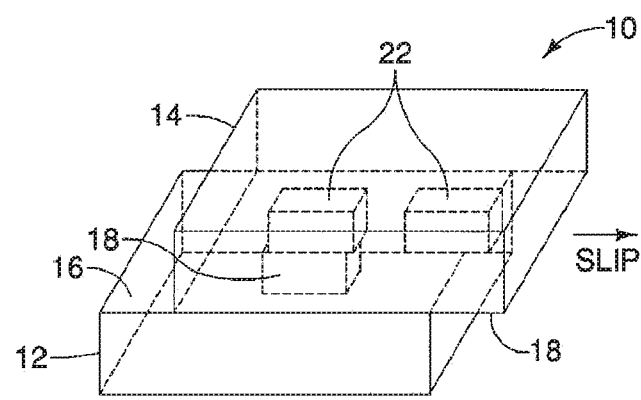
FIG. 3B is a side view of the slip chip device shown in FIG. 3A in a second position.
Figure 3C:
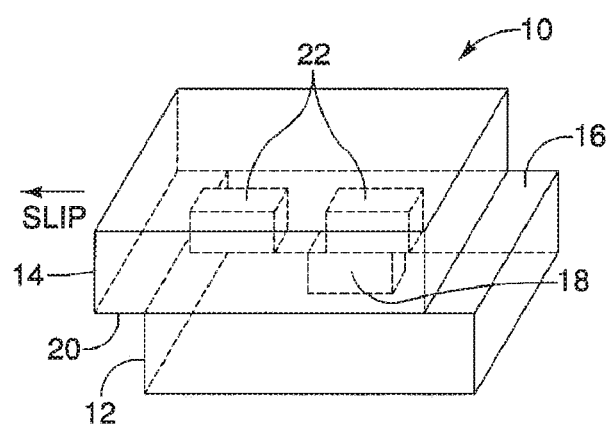
FIG. 3C is a side view of the slip chip device shown in FIG. 3A in a third position.
Figure 3D:
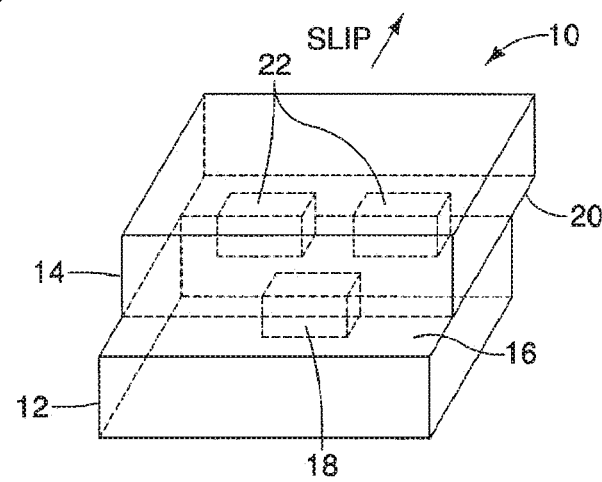
FIG. 3D is a side view of the slip chip device shown in FIG. 3A in a fourth position.

The base 12 and/or plate 14 may move relative to the other from Position A, of FIG. 3A, to another position such that the first area 18 is now only exposed to one of the second areas 22, as shown in Position B in FIG. 3B, or is only exposed to the other of the second areas 22, as shown in Position C in FIG. 3C, or is simultaneously exposed to both the second areas 22 as shown in Position D in FIG. 3D. The base 12 and/or plate 14 may further move from the second position to additional positions that will allow for different configurations and reactions. Of course, the sequence in which the first area 18 and at least one of the two second areas 22 are exposed to the other will govern the substances to be reacted and the reaction itself.

The embodiment of FIGS. 3A-D only contains one plate 14, however, there are other embodiments that contemplate using more than one plate 14. For example, in the embodiment shown in FIGS. 4A-C, between the plate 14 and the base 12 is an intermediate plate 46. Similar to the plate 14 and base 12, the intermediate plate 46 is configured to slide relative to either element and further defines an opening 48 therein.

As shown in FIGS. 4A-C, the device 10 in this embodiment is configured to have three different substances disposed therein, with one substance being disposed within, or along, the first area 18, a second substance being disposed within, or along, the second area 22 and a third substance being disposed within, or along, the opening 48. The first surface 16, the second surface 20, and the intermediate plate 46 are all configured to move relative to one another. In this embodiment, the device 10 is configured to move from a first position, Position A in FIG. 4A, where the first area 18, the second area 22, and the opening 48 are not exposed to one another, to a second position, Position B in FIG. 4B, where the second area 22 is exposed to the opening 48, and to a third position, Position C in FIG. 4C, where the first area 18, second area 22, and opening 48 are all exposed to one another to allow for the three substances to react. It can be appreciated that the order in which the areas 18, 22 and the opening 48 are exposed to one another, if at all, can vary and the number of intermediate plates 48 may vary depending on the application.

The embodiment of the device 10 in FIGS. 5A and B, is one example having more than one intermediate plate 46 in a stacked configuration. This embodiment includes a plurality of intermediate plates 46, with each of the plurality of intermediate plates 46 having an opening 48 therethrough to form, when aligned with the other openings 48, a continuous column 50. A substance then may be disposed within the column 50 through one of the openings 48 or via an inlet port (not shown). The stack of intermediate plates 46 can be used for multiple substance testing, or be used to fill and store a plurality of intermediate plates 46 for future tests. A holder (not shown) may also be included to provide stability, control of relative movement of plates 46, and control of evaporation of a substance contained by the plates 46.

As mentioned above, this embodiment of the device 10 may be used for multiple substance testing. For example, one intermediate plate 46 can be moved relative to the other intermediate plates 46, or partially "slipped" out, in at least a first direction from a first position, Position A of FIG. 5A, to a second position, Position B of FIG. 5B, such that the opening 48 of that intermediate plate 46 can be exposed to the first area 18 along the first surface 16 of the base 12 which is in the form of a receiving structure 52 configured to receive the intermediate plate 46.

The stack of intermediate plates 46 may have a biasing mechanism or system to apply a biasing force when one of the intermediate plates 46 is removed such that the column 50 is kept intact. For example, the stack of intermediate plates 46 may be bounded by an upper plate 54 and a lower plate 56, such that when the top intermediate plate 46 is removed the biasing mechanism will push the remaining stack of plates upwardly such that the next intermediate plate 46 is now adjacent to the upper plate 54.

Alternatively, the intermediate plate 46 that is exposed to the first surface 16 may be slipped in a direction substantially perpendicular to the first direction and in a direction substantially opposite from the first direction such that that intermediate plate 46 is placed within the stack of intermediate plates 46 but the opening 46 is no longer in communication of the column 50, and the column 50 is no longer intact. The remaining openings 48 in the intermediate plates 46 may then be subsequently slipped out and caused to be exposed to another, or the same, first area 18 of the receiving structure 52. It can be appreciated that a plurality of intermediate plates 46 may be used for a single device 10, and the embodiment described above is exemplary of the multiple contemplated configurations. Moreover, the features discussed herein with respect to the embodiments having only the base 12 and the plate 14 without the intermediate plate 46 may also be accomplished in embodiments having one or more intermediate plates 46.

In certain embodiments, any of the base or plates may be replaced with another new base or plate containing, where the new base or plate has a different configuration of areas and/or a different substance in its areas. For example, a device may be used to conduct a solid-phase reaction, such as an on-bead synthetic reaction, in an area on a base. The reagents for this reaction would be added in one or more steps using any of the techniques described herein. After the reaction is complete, the plate may be removed and replaced by a new plate, containing ducts and/or areas suitable for assaying the products of the reaction that are located on the beads within the area of the base. Optionally, the plate may have reagents preloaded to conduct the assay. In another embodiment, the reaction product may be cleaved off the beads in the base and allowed to diffuse into a reaction area on the plate, and then the base is removed and a new base is added containing ducts and/or areas and/or reagents for further reactions and/or assays.

Figure 6A:
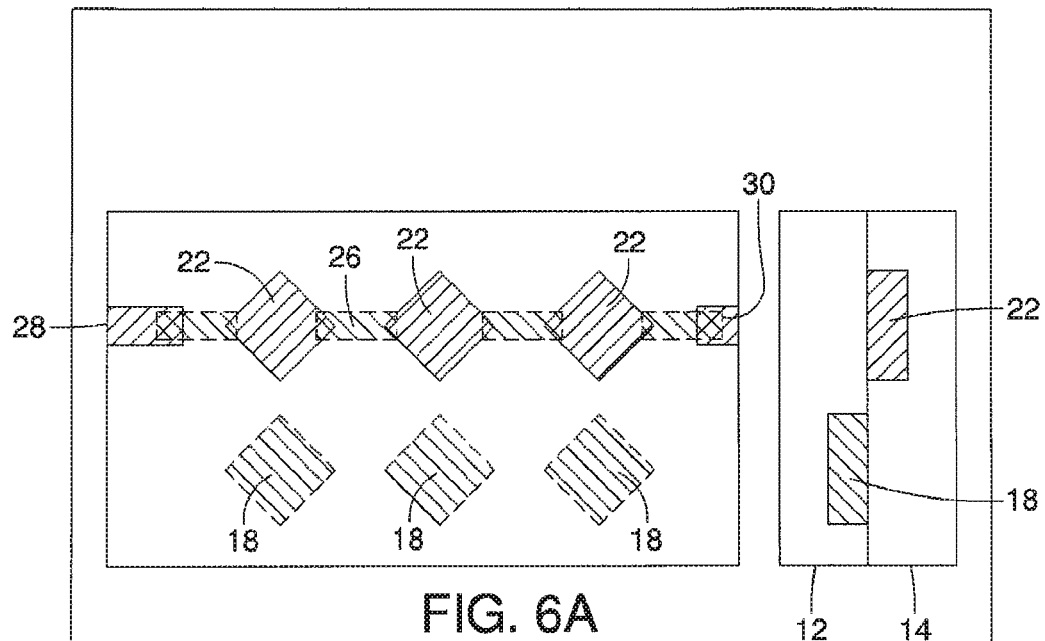
FIG. 6A is a top view and a cross-sectional view of a slip chip device according to another embodiment of the invention in a first position.
Figure 6B:
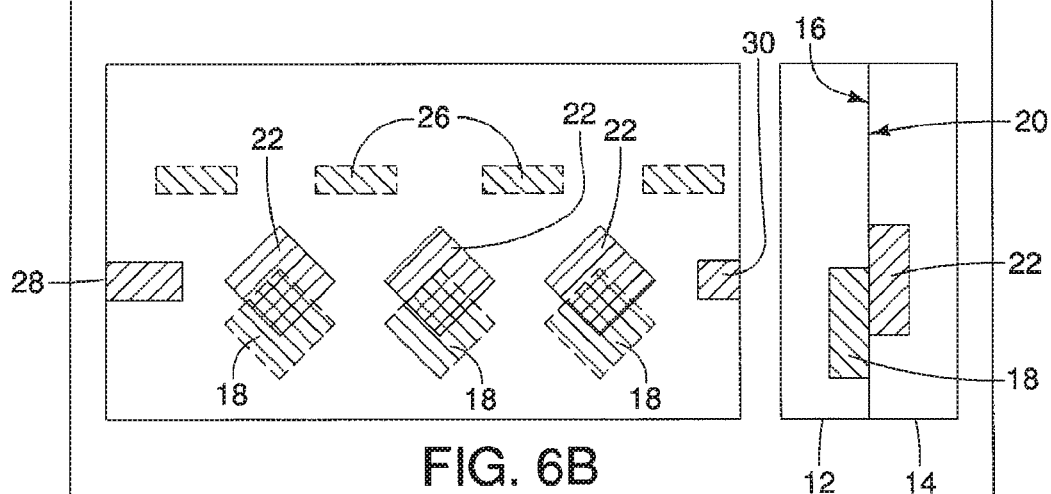
FIG. 6B is a top view and a cross-sectional view of the slip chip device of the embodiment shown in FIG. 6A in a second position.

Moving on to the two plate embodiment shown in FIGS. 6A and 6B, the number and configuration of first areas 18 may also be greater than one and coincide with the number of second areas 22. FIGS. 6A and B are top fragmentary views of one embodiment of the device 10, having the base 12 illustrated in dashed lines and the plate 14 illustrated in solid lines, with a plurality of first and second areas 18, 22. A series of discrete ducts 26 are formed along a portion of the first surface 16. The series of discrete ducts 26 are independent from one another and do not independently form a continuous fluidic path. The number of discrete ducts 26 may range from one to more than one. The physical characteristics may vary between each duct 26 of the series of ducts 26 and are application dependent.

The series of discrete ducts 26 are spaced apart from, and not in communication with, the plurality of first areas 18. One or more of the discrete ducts 26 may include an inlet duct 28 and another may be an outlet duct 30. The inlet duct 28 and the outlet duct 30 may be formed along the first 16 or second 20 surface, and it is not required that the inlet duct 28 and the outlet duct 30 be formed along the same surface 16, 20. In the embodiment shown in FIGS. 6A-B, the inlet duct 28 and outlet duct 30 are formed along the second surface 18. In some embodiments having a plurality of first and second areas 18, 22, the number of inlet ducts 28 will be less than half the total number of areas 18, 22 for that particular embodiment. In other embodiments, the number of outlet ducts 30 will be less than half the total number of areas 18, 22.

When in the first position, as shown as Position A in FIG. 6A, the first and second surfaces 16, 20 are fixedly opposed to one another and the plurality of second areas 22 are exposed to the series of discrete ducts 26, for example, to allow fluid communication between the series of ducts 26 and the second areas 22 to dispose a first substance along, or within, the second areas 22. In this embodiment, the first substance is provided to the series of discrete ducts 26 and the second areas 22 via the inlet duct 28. Any excess substance is exited via the outlet duct 30.

Once the substance is disposed within or along the second areas 22, the base 12 and/or plate 14 may move relative to one another towards the second position, shown as Position B of FIG. 6B. When in Position B, the fluidic communication between the series of discrete ducts 26 and the second areas 22 is broken, and no additional substance provided by the inlet duct 28 may be disposed within or along the second areas 22. The second position, referred to as Position B, is user defined, and in this embodiment is attained when each second area 22 is exposed with the respective first area 18. The exposure of each second area 22 to the respective first area 18 allows the first substance to communicate, and possibly react, with any other substance that is disposed within or along the first areas 18. The base 12 and/or plate 14 may then be moved to another position, if necessary.

A device may be configured with an inlet duct or area in a base capable of being dipped into a sample. The inlet duct or area may be concave, in order to capture a sample, or may contain a wicking material. An inlet duct or area designed for capturing sample may be exposed to the environment, that is, not covered by an opposing plate, in a first, loading position, but covered by an opposing plate in a second position, after motion of the base and opposing plate relative to one another.

Figure 7A:
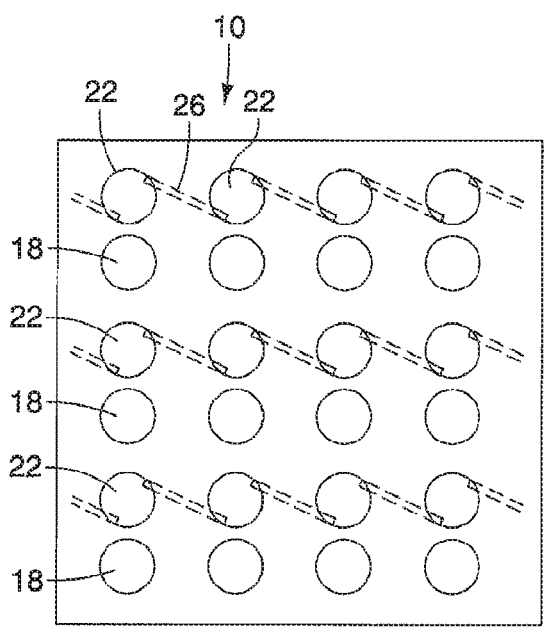
FIG. 7A is a partial view of a slip chip device according to another embodiment of the invention in a first position.
Figure 7B:
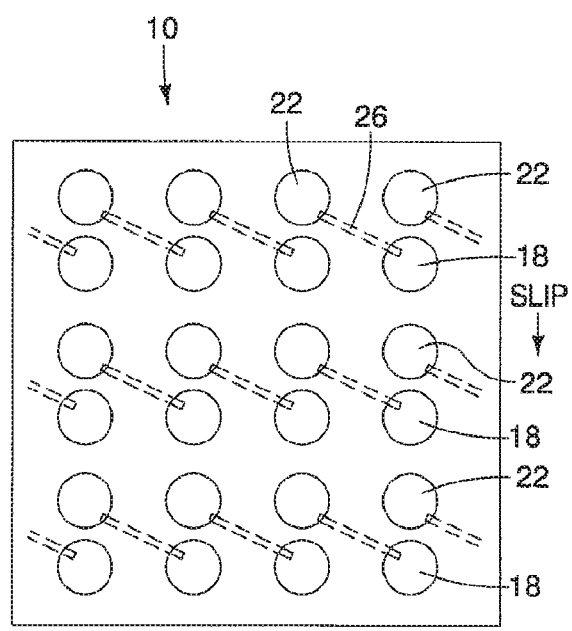
FIG. 7B is a partial view of the slip chip device shown in FIG. 7A in a second position.

In an alternative embodiment, as shown in FIGS. 7A and 7B, the first and second areas 18, 22 may be formed along, or within, the same surface. For example, in this embodiment, the first and second areas 18, 22 are formed along the first surface 16 of the base 12. The ducts 26 in this embodiment are formed along the second surface 20 of the plate 14.

In this embodiment, the device 10 is configured to move from a first position, Position A of FIG. 7A, where two or more second areas 22 are in fluidic communication with, or exposed to, the ducts 26, but where none of the first and second areas 18, 22 are exposed to one another, to a second position, Position B of FIG. 7B. When in the second position, corresponding first and second areas 18, 22 are exposed to one another via one of the ducts 26. Specifically, the relative movement between the first and second positions caused the ducts 26 to move with respect to the first 18 and second 22 area from the first position, Position A, where each duct 26 was exposed two adjacent second areas 22 and allowed for fluidic communication therebetween to the second position, Position B, shown in FIG. 7B, where each duct 26 is now exposed to one first area 18 and one corresponding second area 22. Accordingly, as shown in this embodiment, the first and second areas 18, 22 may be exposed to one another via the duct 26 and it is not required that the first and second areas 18, 22 physically overlap. However, the number and orientation of the areas 18, 22 configured to be exposed to each other via the duct is application dependent.

In any embodiment discussed above, the relative movement between the base 12 and the plate 14 of the device 10, and any intermediate plates 46, may vary in direction and in distance. For example, unlike the single direction of movement disclosed in FIGS. 4A-C, the embodiment of the device 10 shown in FIGS. 8A-D illustrates a plurality of first and second areas 18, 22, with each set of areas having its own set of discrete ducts 26 in a matrix configuration. Specifically, the device 10 of this embodiment includes a plurality of first areas 18 on the first surface 16 of the base 12, and has a series of first ducts 40 formed within the first surface 16 that are not in direct fluid communication with the first areas 18. The second surface 20 of the plate 14 includes a plurality of second areas 22 and a series of second ducts 42 formed therein that are not in direct fluidic communication with the second areas 22.

When in the first position, as shown as Position A in FIG. 8A, the first surface 16 is fixedly opposed to the second surface 20 in an orientation such that the first areas 18 are in fluidic communication, or exposed, to the second set of ducts 42, but the second areas 22 are not in fluidic communication, or exposed to, the first areas 18 or the first set of ducts 40. When in this position, the first areas 18 can be filled with a substance, or each row of first areas 18 can be filled with a different substance. The relative movement in the first direction between the first surface 16 and the second surface 20 to the second position, Position B in FIG. 8B, isolates each one of the first area 18 and a corresponding one of the second set of ducts 42 from other first areas 18 and second set of ducts 42. Further movement in a second direction, to Position C in FIG. 8C, which is substantially perpendicular to the first direction, causes the second areas 22 to be in fluidic communication, or exposed to, the first set of ducts 40 and allows the second areas 22 to be filled with another substance, or each column of second areas 22 can be filled with a different substance. Further movement to Position D in FIG. 8D, in a direction opposite from the first direction, causes the first areas 18 to be at least partially exposed to the second areas 22. It can be appreciated that devices 10 may have a greater or lesser number of rows and columns and the relative movement between the first surface 16 and the second surface 20 may vary depending on the particular application.

As mentioned above, the device 10 when moving between any two positions moves in a direction substantially perpendicular to the normal of the first surface 16. Accordingly, the direction may be linear, rotational, or a combination of both. In some instances, two-dimensional motion (e.g., X-Y motion) may be accomplished through a combination of linear and/or rotational movements. For example, sliding and rotating means may be employed to effect linear and rotational sliding motion. In addition, such means for producing relative sliding motion may be constructed from, for example, motors, levers, pulleys, gears, hydraulics, pneumatics, a combination thereof, or other electromechanical or mechanical means known to one of ordinary skill in the art. Other examples of methods of controlling the motion of one part relative to another include, but are not limited to, sliding guides, rack and pinion systems (U.S. Pat. No. 7,136,688), rotational plates (U.S. Pat. No. 7,003,104), slider assemblies (US 2007/015545 and US 2008/0058039), guide grooves (U.S. Pat. Nos. 5,805,947 and 5,026,113), piezoelectric actuators (US 2005/0009582), ball bearings and notches (U.S. Pat. No. 2,541,413) and drive cables (U.S. Pat. No. 5,114,208). These patents and patent applications are incorporated herein by reference in their entireties.

Moreover, motion of the base 12 and plate 14 or plates relative to one another may be constrained by notches, retainers, and/or a system of holes and mating pins, for example, as are typically used alone or in combination in electrical connectors. Also, the motion of the base 12 and plate 14 or plates relative to one another may be constrained by a case, posts, grooves and ridges, gears, or, for example in the case of rotational motion, a central axle. In certain embodiments, the device 10 is configured to be manipulated by a robot.

Figure 9A:
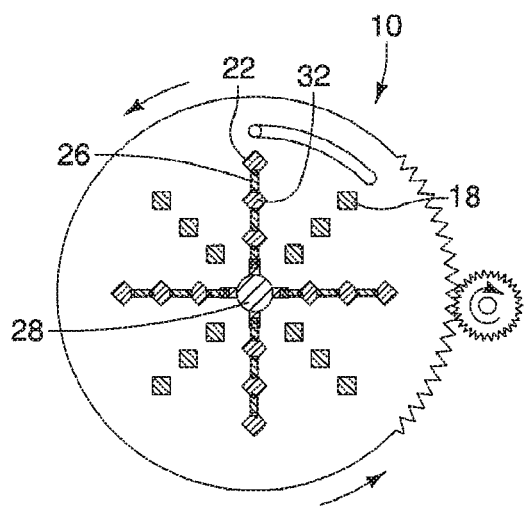
FIG. 9A is a top view of a slip chip device according to another embodiment of the invention in a first position.
Figure 9B:
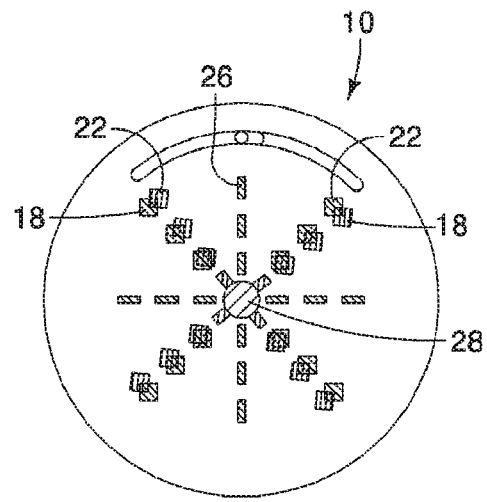
FIG. 9B is a top view of the slip chip device shown in FIG. 9A in a second position.

For example, in the embodiment shown in FIGS. 9A and 9B, the relative movement between the first and second surfaces 16, 20 is rotational in nature. Specifically, the device shown in FIG. 9A moves from the first position, Position A, where the second areas 22 are in fluidic communication with the series of ducts 26 and an inlet duct 28. It can be appreciated that in this embodiment, there may be no outlet duct 30. The way in which the first substance is disposed in, or along, the second areas 22 may vary. For example, an external pump may create a line pressure to help dispose the first substance 32 in, or along, the second areas 22. Alternatively, and as shown in the embodiment in FIGS. 9A-B, the rotation of the entire device 10 creates a centrifugal force that helps the first substance 22 to travel from the inlet duct 28 to the second areas 22.

The base 12 and plate 14 are then moved from the first position, Position A, to the second position, Position B shown in FIG. 9B, by relative rotational movement. In this position, at least one first area 18 is exposed to at least one second area 22. The relative rotational movement may be caused, in part, by, for example, an automated gear assembly 36 or by manual movement.

Figure 10A:
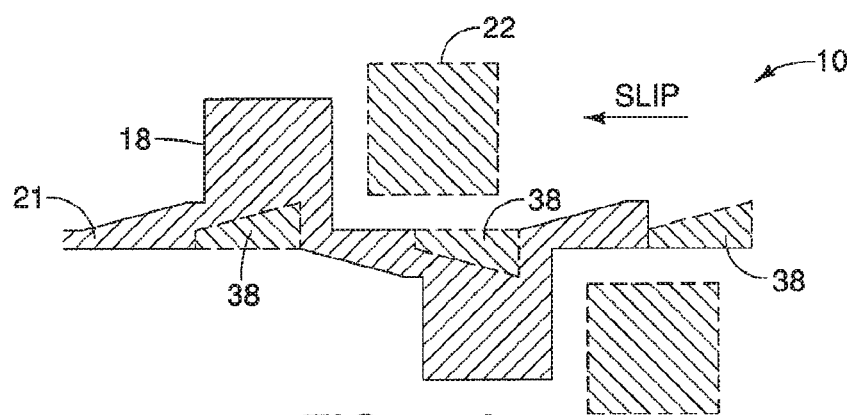
FIG. 10A is a partial top view of a slip chip device according to another embodiment of the invention in a first position.
Figure 10B:
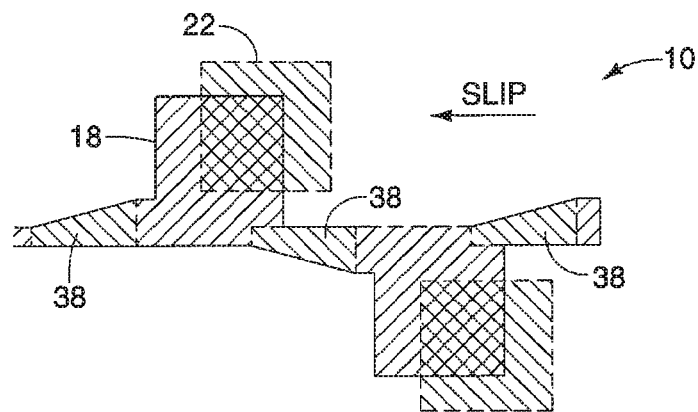
FIG. 10B is a partial top view of the slip chip device shown in FIG. 10B in a second position.

The pattern and shape of each embodiment of the device 10 may also vary and is application dependent. For example, in an alternate embodiment, shown in FIGS. 10A and 10B, the first area 18 is a continuous channel 21, configured to maintain a substance, formed within the first surface 16. A series of post members 38 are formed along the second surface 20, adjacent to the second areas 22 that do not impede the continuality of the first area 18 when in the first position, Position A in FIG. 10A. When in Position A, the first area 18 is not exposed to the second areas 22. However, when moved into the second position, Position B, the series of post members 38 engage with a portion of the first area 18, such as to compartmentalize the previously continuous channel 21 into a plurality of discrete first areas 18 that are not in fluid communication with the other discrete first areas 18. Each of the discrete first areas 18, when in Position B shown in FIG. 10B, is exposed to the second areas 22.

Moreover, a combination of a post member 38 along the second surface 18 and the first area 18 along the first surface 16 may be used to generate pressure as the surfaces 16, 18 move relative to one another. For example, positive pressure may be generated in front of the direction of the post member 38, and negative pressure may be generated behind. It may be used to load a substance into the device 10 or dispose substance out of the device 10, or move a substance within the device 10, or to introduce separations as discussed infra, including filtrations. Flow may also be generated by such movement.

In addition to the variance of the shape of the first and second areas 18, 22 between embodiments, the amount of exposure and the relative exposure between each respective set of first and second areas 18, 22, may also vary and is application dependent. For example, the embodiment of the device 10 shown in FIGS. 11A and 11B varies the amount of exposure between each respective set of first and second areas 18, 22 when in the second position, Position B as shown in FIG. 10B. The varied, or graduated, amount of exposure between each set of first and second areas 18, 22 can be achieved by, for example configuring the pattern of the first set of areas 18 and the second set of areas 22.

For example, the amount of exposure, or diffusion, between the first and second areas 18, 22 may be attained in a number of ways. For example, as shown in FIGS. 11A and 11B, the first and second areas 18, 22 are substantially square shaped with the amount of overlap between each set of the first and second areas 18, 22 varied by the graduated diagonal pattern of the first areas 18 when in the second position as shown in FIG. 11B. Alternatively, in the embodiment shown in FIGS. 11C and 11D, the amount of exposure, or diffusion, is controlled by varying the shape and/or diameter of an inlet portion 34 of the second area 22 that is exposed to the first area 18 when in the second position as shown in FIG. 11D. As discussed herein, gradients may be generated by controlling diffusion of substances between areas of the device. The level of diffusion in each step of the method of gradient generation of the present invention may be controlled according to the slip position of the device. Gradients of the present invention are useful in studying biological phenomena that depend on gradient concentration, such as cell-surface interactions, high-throughput screening using arrays of cells, and in cell-based biosensors. In particular, studies involving chemotaxis, haptotaxis and migration take advantage of the relatively compact and stable gradients achievable by the present invention. As chemotactic cells may be sensitive to concentration differences as small as 2% between the front and back of the cell, gradients with a resolution on the order of a single cell (10-100 μm, 2-20% per 100 μm) can be useful. The invention provides the ability to generate gradients of proteins, surface properties, and fluid streams containing growth factors, toxins, enzymes, drugs, and other types of biologically relevant molecules. In addition, gradients of diffusible substances having chemoattractant or chemorepellent properties can play an important role in biological pattern formation, and angiogenesis and axon pathfinding provide examples of processes that can make use of gradients. The invention also provides the superimposition of gradients (similar or dissimilar) of different substances in studying higher organisms. The sawtooth gradients of the present invention can also be used in investigating biological processes. The gradients of the present invention may be used for additional applications as described in US 2004/0258571, U.S. Pat. Nos. 6,705,357, 7,314,070 and 6,883,559, the entireties of all of which are herein incorporated by reference.

Figure 12A:
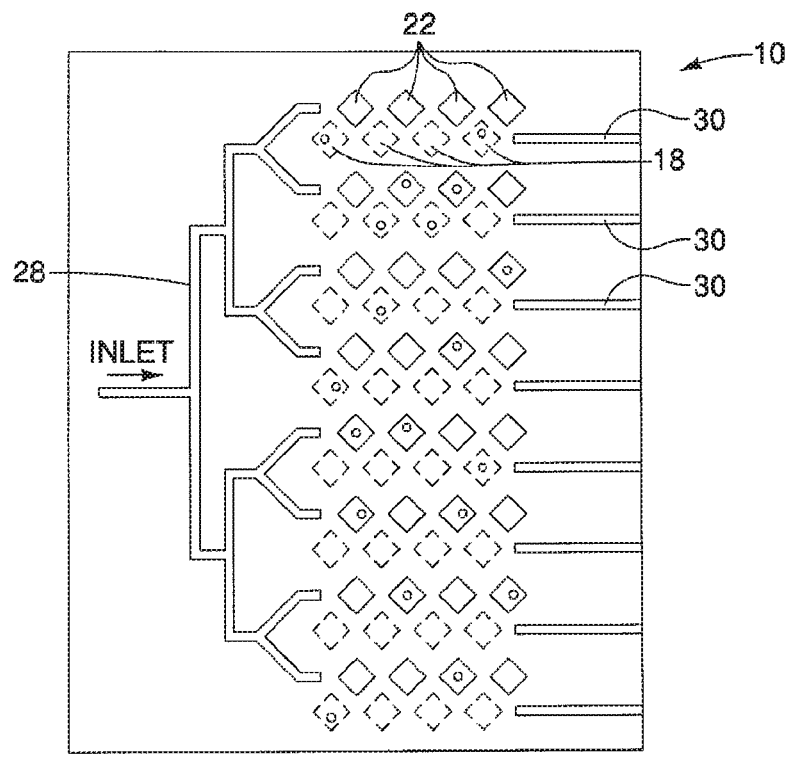
FIG. 12A is a top view of a slip chip device according to another embodiment of the invention in a first position.

Other embodiments exist of the device 10 where the first and second areas 18, 22 form a continuous channel to expose two or more substances to each other. For example, embodiment of the device 10 as shown in FIGS. 12A and B, includes an inlet duct 28 in a branch-like formation formed along the second surface 20. Also formed within, or along, the second surface 20 are multiple series of the second areas 22. The multiple series of second areas 22 and the inlet duct 28 however, are not directly in fluidic communication with, or exposed to, each other when in the first position, Position A as shown in FIG. 12A. A multiple series of first areas 18 are formed within, or along, the first surface 16 along with multiple outlet ducts 30, each of which is aligned with each series of first areas 18, but are not in direct fluid communication with, or exposed to, each other when in Position A.

Figure 12B:
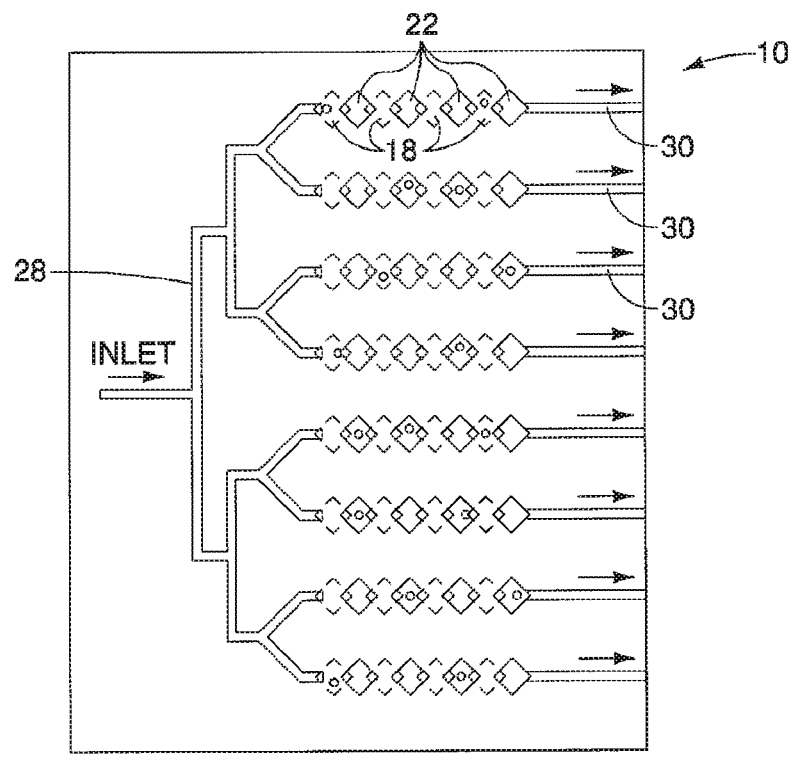
FIG. 12B is a top view of the slip chip device shown in FIG. 12A in a second position.

In this embodiment, a substance or a series of substances may be placed within or along each of the first areas 18. When the first and second surfaces 16, 20 move relative to each other from the first position to the second position, Position B as shown in FIG. 12B, a first area 18 and a second area 22 for each series of areas 18, 22 overlap, or are exposed to one another, to form a continuous series of first and second areas 22, 22, as shown in FIG. 12B. Additionally, when in the second position, Position B as shown in FIG. 12B, at least one of the first areas 18 is exposed to, or in fluidic communication with, one branch of the inlet duct 28. Moreover, one of the second areas 22 is exposed to, or in fluidic communication with, one of the outlet ducts 30 forming a continuous path between the inlet duct 28 and the outlet duct 30 to allow a substance to be exposed to the series of first areas 18. The orientation and number of branches of the inlet duct 28 and outlet ducts 30 may vary and is application dependant. However, as can be seen in this embodiment, a plurality of substances may be placed within or formed along each of the first areas 18 and can react with the substance provided by the inlet duct 28 when in the second position, Position B.

Figures 13A, 13B:
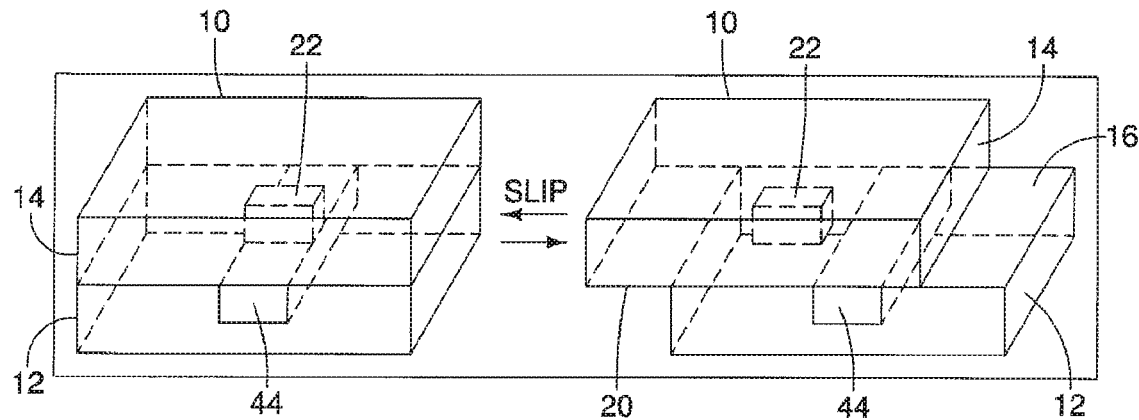
FIG. 13A is a perspective view of a slip chip device according to another embodiment of the invention in a first position.
FIG. 13B is a perspective view of the slip chip device shown in FIG. 13A in a second position.

Continuous channels may also be used to preload other reactions areas. For example in an alternative embodiment of the device 10, as shown in FIGS. 13A and 13B, the device 10 may be configured to fill, or preload, a number of second areas 22 with a substance. In this embodiment, the base 12 has a continuous channel 44 configured to carry a first substance. The second area 22 of the plate 14 and continuous channel 44 of the base 12 are configured to move from a first position, Position A shown in FIG. 13A, where the second area 22 or areas 22 are not in fluidic communication, or exposed, to the continuous channel 44, to a second position, Position B as shown in FIG. 13B, where at least a portion of the second area 22, or areas 22, are exposed, or in fluidic communication, with the channel 44 and thereby filling, or disposing, the substance within, or along, the second area 22. The base 12, and/or plate 14, are then configured to move relative to one another to a third position (not shown) such that the second area 22, or areas 22, are now filled with the substance. The plate 14 preloaded with the filled substance may then be used for subsequent uses, some of which are described herein. It can be appreciated that the base 12 may instead have the discrete first areas 18 and the continuous channel 44 be formed within the plate 14 (not shown in this figure). Moreover, instead of preloading the areas, this embodiment may also be used for exposing a second substance within the second area 22 to continuous channel 44 filled with the first substance within, or along, the first surface 16, or vice versa.

Figure 14A:
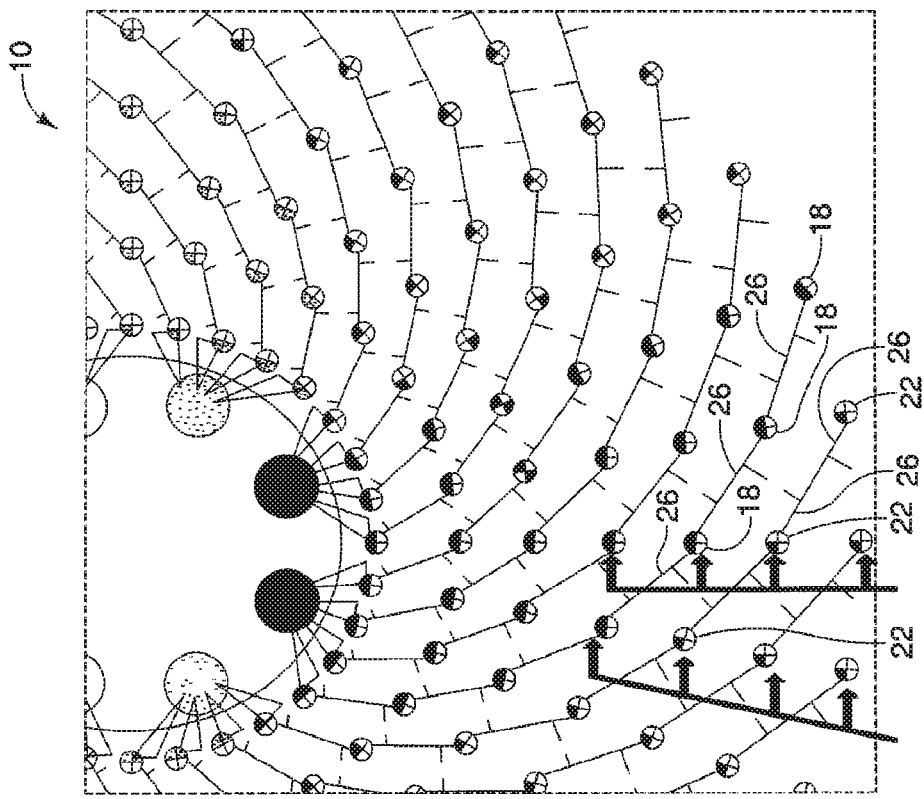
FIG. 14A is a partial top view of a slip chip device according to another embodiment of the present invention in a first position.
Figure 14B:
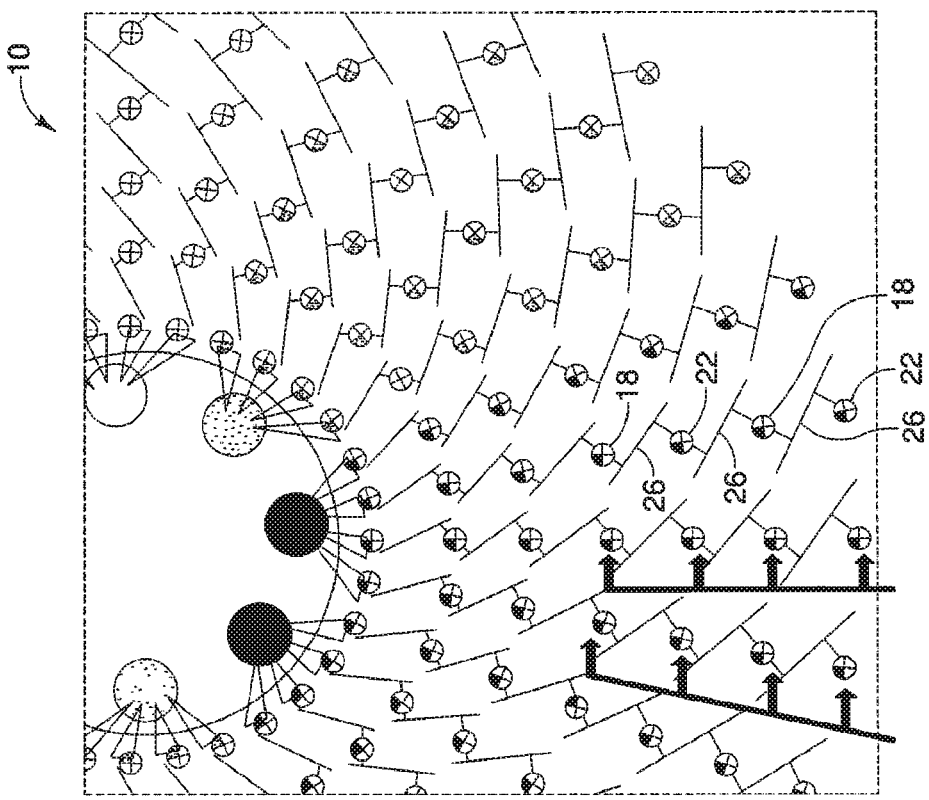
FIG. 14B is a partial top view of the slip chip device shown in FIG. 14A in a second position.

In another embodiment a fragmentary view of which is shown in FIGS. 14A and 14B the relative movement between the first and second surfaces 16, 20 is rotational in nature. The first and second etc. areas 18, 22 may be formed along, or within, the same surface. The inlet duct 28 and series of ducts 26 in this embodiment are formed along the second surface 20. In this embodiment, the device is configured to rotate from a first position, Position A as shown in FIG. 14A, where a set of two or more first areas 18, a set of two or more second areas 22, etc. are each in fluidic communication with, or exposed to, a corresponding set of ducts 26, but where none of the first and second etc. areas 18, 22 are exposed to one another. For example, as shown in FIGS. 14A and 14B, when in Position A, as shown in FIG. 14A, seven first areas 18 are exposed to one another via a series of radially connected ducts 26 but are not exposed to any of second areas 22.

In a second position, Position B, as shown in FIG. 14B, the first and second surfaces 16, 20 are then moved from the first position, Position A, to the second position, Position B, by relative rotational movement. In this position, at least one first area 18 is exposed to at least one second area 22, etc. When in Position B, corresponding first and second, etc. areas 18, 22 are exposed to one another via a series of spirally connected ducts 26. For example, as shown in FIGS. 14A and 14B, the relative movement between the first and second positions caused the ducts to move with respect to the first and second areas, etc. 18, 22 from the first position, Position A, where each duct was exposed to adjacent first areas 18 and allowed for fluidic communication between the row of first areas 18 to Position B, where each duct is now exposed to one first area 18, one corresponding second area 22, etc. via a series of spirally connected ducts 26. The first and second surfaces 16, 20 may then be moved from the second position, Position B, to a third position, Position C (not shown in FIG. 14A or 14B), by relative rotational movement in the same direction as the motion from Position A to Position B. In this position as in Position A, two or more first areas 18, two or more second areas 22, etc. are in fluidic communication with, or exposed to, the ducts 26, but where none of the first and second etc. areas 18, 22 are exposed to one another. In this third position, Position C, two or more first areas 18 are exposed to one another via a series of ducts 26 connected radially but are not exposed to second areas 22 etc.

The first and second surfaces 16, 20 may then be moved from the third position, Position C, to a fourth position, Position D (not shown in FIG. 14A or 14B), by further relative rotational movement. In this position as in Position B, at least one first area 18 is exposed to at least one second area etc. 22 via a series of spiraling ducts 26.

In each sequential slip position each duct originating from an inlet duct 28 slips over to the next adjacent first or second etc. area 18, 22. For each sequential slip position the ducts 26 alternate between connecting rows of first areas 18, rows of second areas 22, etc. and connecting a first area 18 to a second area 22 etc. via a spiraling series of ducts 26.

In certain embodiments of the invention the areas retain an amount of the substances they are exposed to. This can be done by functionalization of the surface of an area, deposition of a material on an area, attaching a monomer in a polymerization reaction (such as peptide or DNA synthesis) to an area, etc. Prior to assembling this device the areas could be loaded with beads or gels that are trapped, thus whatever absorbs, adsorbs, or reacts with these beads or gels is also trapped. This device also comprises an outlet duct or alternative outlet such as a gas-permeable element. Although the above description pertains to a device with one base and one plate, alternative embodiments may include a plurality of intermediate plates as described for FIGS. 5A-B.

Potential uses for this device include running assays of enzyme activity, cell viability, cell adhesion, cell binding etc., screening for catalytic activity or selectivity, screening for storage ability or sequestration (such as absorption of gas or trapping of toxic compounds, etc.), and testing various properties such as electrical, magnetic, optical, etc.

The invention described herein may also be used for the synthesis of radioisotopes. Typical methods for making radioisotopes are disclosed in U.S. Pat. Nos. 7,235,216; 6,567,492; 5,264,570; and 5,169,942, the entireties of all of which are incorporated herein by reference. These multistep methods may be performed by controlling conditions at each subsequent slip position of the device.

The materials used to form the substrates and the devices 10 of the invention as described above are selected with regard to physical and chemical characteristics that are desirable for proper functioning of the device 10. In microfluidic applications, the first and second surfaces 16, 20, first and second areas, 18, 22, and ducts 26, 28, 30, are typically fabricated from a material that enables formation of high definition (or high "resolution") features, e.g., microchannels, chambers, mixing features, and the like, that are of millimeter, micron or submicron dimensions. That is, the material should be capable of microfabrication using, e.g., dry etching, wet etching, laser etching, laser ablation, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto, for example, polymer channels can be formed on the surface of a glass substrate using photo-imageable polyimide. Also, all device materials used are preferably chemically inert and physically stable with respect to any substance with which they come into contact when used to introduce a fluid (e.g., with respect to pH, electric fields, etc.). Suitable materials for forming the present devices include, but are not limited to, polymeric materials, ceramics (including aluminum oxide, silicon oxide, zirconium oxide, and the like), semiconductors (including silicon, gallium arsenide, and the like) glass, metals, composites, and laminates thereof.

Glass Etching Fabrication of Slip Chip:

The device 10 may be composed of two pieces of glass slides with complementary patterns were made with using standard photolithographic and wet chemical etching techniques. (See He, et al., Sens Actuators B Chem. 2008 Feb. 22; 129(2): 811-817, for example.) Soda-lime glass plates with chromium and photoresist coating were obtained from Telic Company (Valencia, Calif.). The glass plate with photoresist coating was aligned with a photomask containing the design of the microducts and areas using a Karl Suss, MJBB3 contact alighner. The photomask may also contain marks to align the mask with the plate. The glass plate and photomask were then exposed to UV light for 1 min. The photomask was removed, and the glass plate was developed by immersing it in 0.1 mol/L NaOH solution for 2 min. Only the areas of the photoresist that were exposed to the UV light dissolved in the solution. The exposed underlying chromium layer was removed using a chromium etchant (a solution of 0.6:0.365 M $HClO_4/(NH_4)_2Ce(NO_3)_6$). The plate was rinsed with Millipore water and dried with nitrogen gas, and the back of the glass plate was taped with PVC sealing tape (McMaster-Carr) to protect the back side of glass. The taped glass plate was then carefully immersed in a plastic container with a buffered etching agent composed of 1:0.5:0.75 mol/L $HF/NH_4F/HNO_3$ to etch the soda-lime glass at the temperature of 40° C. The etching speed was controlled by the etching temperature, and the area and duct depth was controlled by the etching time. After etching, the tape was removed from the plates. The plate was then thoroughly rinsed with Millipore water and dried with nitrogen gas. The remaining photoresist was removed by rinsing with ethanol, and the remaining chromium coating was removed by immersing the plate in the chromium etchant. The surface of the glass plate were rendered hydrophobic by silanization with tridecafluoro-1,1,2,2-tetrahydrooctyl-1-trichlorosilane (United Chemical Technologies, Inc.). Access holes were drilled with a 0.76 mm diameter diamond drill bit.

One method to establish fluidic communication between two or more areas of the SlipChip includes the use of a channel with at least one cross-sectional dimension in the nanometer range, a nanochannel, which can be embedded in the SlipChip. The nanochannels could be embedded into multilayer SlipChip. The height of nanochannel can be varied with nanometer scale resolution, for instance this would prohibit transfer of micron sized cells between the wells, but enable transfer of proteins, vesicles, micelles, genetic material, small molecules, ions, and other molecules and macromolecules, including cell culture media and secreted products. The width, length, and tortuosity of the nanochannels can also be manipulated in order to control transport dynamics between wells. Nanochannels can be fabricated as described in Bacterial metapopulations in nanofabricated landscapes, Juan E. Keymer, Peter Galajda, Cecilia Muldoon, Sungsu Park, and Robert H. Austin, PNAS Nov. 14, 2006 vol. 103 no. 46 17290-17295, or by etching nanochannels in the first glass piece and bringing it in contact with the second glass piece, optionally followed by a bonding step. Applications include filtration, capturing of cells and particles, long term cell culture, and controlling interactions among cells and cellular colonies and tissues.

Devices 10 of the PDMS/Glass type may also be made using soft lithography (McDonald, J. C.; Whitesides, G. M. Accounts Chem. Res. 2002, 35, 491-499.) similarly as described previously (Angew. Chem. Int. Ed. 2004, 43, 2508-2511). The device used contains two layers, each layer was composed of a thin membrane of PDMS with ducts and areas, and a 1 mm thick microscope glass slides with size of 75 mm×25 mm. To make the device, the glass slides were cleaned and subjected to an oxygen plasma treatment. Dow-Corning Sylgard 184 A and B components were mixed at a mass ratio of 5:1, and poured onto the mold of the SlipChip. A glass slide was placed onto the PDMS before cure. A glass bottom with iron beads were place onto the glass slides to make the PDMS membrane thinner. The device were pre-cured for 7 hour at room temperature, then move to 60° C. oven and cured overnight. After cure, the device were peeled off the mold and silanized with tridecafluoro-1,1,2,2-tetrahydrooctyl-1-trichlorosilane. Access holes were drilled with a 0.76 mm diameter diamond drill bit.

Polymeric materials suitable for use with the invention may be organic polymers. Such polymers may be homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. Generally, at least one of the substrate or a portion of the device 10 comprises a biofouling-resistant polymer when the microdevice is employed to transport biological fluids. Polyimide is of particular interest and has proven to be a highly desirable substrate material in a number of contexts. Polyimides are commercially available, e.g., under the tradename Kapton®, (DuPont, Wilmington, Del.) and Upilex® (Ube Industries, Ltd., Japan). Polyetheretherketones (PEEK) also exhibit desirable biofouling resistant properties. Polymeric materials suitable for use with the invention include silicone polymers, such as polydimethylsiloxane, and epoxy polymers.

The devices 10 of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, that has been co-extruded with a second, thin layer of a thermal adhesive form of polyimide known as KJ®, also available from DuPont (Wilmington, Del.).

The device can be fabricated using techniques such as compression molding, injection molding or vacuum molding, alone or in combination. Sufficiently hydrophobic material can be directly utilized after molding. Hydrophilic material can also be utilized, but may require additional surface modification. Further, the device can also be directly milled using CNC machining from a variety of materials, including, but not limited to, plastics, metals, and glass. Microfabrication techniques can be employed to produce the device with sub-micrometer feature sizes. These include, but are not limited to, deep reactive ion etching of silicon, KOH etching of silicon, and HF etching of glass. Polydimethylsiloxane devices can also be fabricated using a machined, negative image stamp. In addition to rigid substrates, flexible, stretchable, compressible and other types of substrates that may change shape or dimensions may be used as materials for certain embodiments of the SlipChip. In certain embodiments, these properties may be used to, for example, control or induce slipping.

In some instances, the base 12 and plate 14 and substrate may be made from the same material. Alternatively, different materials may be employed. For example, in some embodiments the base 12 and plate 14 may be comprised of a ceramic material and the substrate may be comprised of a polymeric material.

The device may contain electrically conductive material on either surface 16, 20. The material may be formed into at least one area or patch of any shape to form an electrode. The at least one electrode may be positioned on one surface 16 such that in a first position, the at least one electrode is not exposed to at least one first area on the opposing surface 20, but when the two parts of the device 12, 14 are moved relative to one another to a second position, the at least one electrode overlaps the at least one area 18. The at least one electrode may be electrically connected to an external circuit. The at least one electrode may be used to carry out electrochemical reactions for detection and/or synthesis. If a voltage is applied to at least two electrodes that are exposed to a substance in an area or a plurality of areas in fluidic communication or a combination of areas and ducts in fluidic communication, the resulting system may be used to carry out electrophoretic separations, and/or electrochemical reactions and/or transport. Optionally, at least one duct and/or at least one area may be present on the same surface as the at least one electrode and may be positioned so that in a first position, none of the at least one duct and the at least one electrode are exposed to an area 18 on the opposing surface, but when the two parts of the device 12, 14 are moved relative to one another to a second position, the at least one duct and/or at least one area and the at least one electrode overlaps the at least one area 18.

Several embodiments of the current invention require movement of a substance through, into, and/or across at least one duct and/or area. For example movement of a substance can be used for washing steps in immunoassays, removal of products or byproducts, introduction of reagents, or dilutions.

Loading of a substance may be performed by a number of methods, as described herein. Loading may be performed either to fill the ducts and areas of the device, for example by designing the outlets to increase flow resistance when the substance reaches the outlets. This approach is valuable for volume-limited samples or to flow the excess volume through the outlets, while optionally capturing analyte from the substance. Analytes can be essentially any discrete material which can be flowed through a microscale system. Analyte capture may be accomplished for example by preloading the areas of the device with capture elements that are trapped in the areas (such as particles, beads or gels, retained within areas via magnetic forces or by geometry or with relative sizes of beads and ducts or with a membrane), thus whatever absorbs, adsorbs, or reacts with these beads or gels is also trapped. These areas will then retain an amount or component or analyte of the substances they are exposed to. This can also be done by functionalization of the surface of an area, deposition of a material on an area, attaching a monomer in a polymerization reaction (such as peptide or DNA synthesis) to an area, etc.

Other examples of capture elements include antibodies, affinity-proteins, aptamers, beads, particles and biological cells. Beads may be for example, polymer beads, silica beads, ceramic beads, clay beads, glass beads, magnetic beads, metallic beads, inorganic beads, and organic beads can be used. The beads or particles can have essentially any shape, e.g., spherical, helical, irregular, spheroid, rod-shaped, cone-shaped, disk shaped, cubic, polyhedral or a combination thereof. Capture elements are optionally coupled to reagents, affinity matrix materials, or the like, e.g., nucleic acid synthesis reagents, peptide synthesis reagents, polymer synthesis reagents, nucleic acids, nucleotides, nucleobases, nucleosides, peptides, amino acids, monomers, cells, biological samples, synthetic molecules, or combinations thereof. Capture elements optionally serve many purposes within the device, including acting as blank particles, dummy particles, calibration particles, sample particles, reagent particles, test particles, and molecular capture particles, e.g., to capture a sample at low concentration. Additionally the capture elements may be used to provide particle retention elements. Capture elements are sized to pass or not pass through selected ducts or membranes (or other microscale elements). Accordingly, particles or beads will range in size depending on the application.

A substance may be introduced to fill the majority of reaction areas and ducts. Filling may be continued further to provide excess sample, larger than the volume of areas and ducts. Introducing a volume of substance which is greater than the volume of areas and ducts will increase the amount of analyte which may be captured within the capture. Introducing a wash fluid after the introduction of a substance may be performed to wash the capture elements and analytes which are bound to the capture elements. Subsequent further slipping may be performed to conduct reactions and analysis of the analytes.

The approach described above is beneficial when analyzing samples with low concentrations of analytes, for example rare nucleic acids or proteins, markers and biomarkers of genetic or infectious disease, environmental pollutants, etc. (See e.g., U.S. Ser. No. 10/823,503, incorporated herein by reference). Another example includes the analysis of rare cells, such as circulating cancer cells or fetal cells in maternal blood for prenatal diagnostics. This approach may be beneficial for rapid early diagnostics of infections by capturing and further analyzing microbial cells in blood, sputum, bone marrow aspirates and other bodily fluids such as urine and cerebral spinal fluid. Analysis of both beads and cells may benefit from stochastic confinement (See e.g., PCT/US08/71374, incorporated herein by reference).

In certain embodiments, the device 10 may be used for rapid detection and drug susceptibility screening of bacteria in samples, including complex biological matrices, without pre-incubation. Unlike conventional bacterial culture and detection methods, which rely on incubation of a sample to increase the concentration of bacteria to detectable levels, this method may be used to confine individual bacteria into areas nanoliters in volume. When single cells are confined into areas of small volume such that the loading is less than one bacterium per area, the detection time is proportional to area volume. Confinement increases cell density and allows released molecules to accumulate around the cell, eliminating the pre-incubation step and reducing the time required to detect the bacteria. This approach may be called 'stochastic confinement'. The device may, for example, be used to determine an antibiogram—or chart of antibiotic sensitivity—of bacteria, such as methicillin-resistant *Staphylococcus aureus* (MRSA) to many antibiotics in a single experiment and to measure the minimal inhibitory concentration (MIC) of the drugs against such strains. In addition, this device may be used to distinguish between sensitive and resistant strains of *S. aureus* in samples of human blood plasma. The device also enables multiple tests to be performed simultaneously on a single sample containing bacteria. The device provides a method of rapid and effective patient-specific treatment of bacterial infections and could be extended to a variety of applications that require multiple functional tests of bacterial samples on reduced timescales.

Stochastic confinement has been used in other systems. See for example, "Detecting bacteria and determining their susceptibility to antibiotics by stochastic confinement in nanoliter droplets using plug-based microfluidics", Boedicker J. Q., Li L., Kline T. R., Ismagilov R. F. Lab on a chip 8(8):1265, 2008 August, published U.S. patent application 60/962,426, M. Y. He, J. S. Edgar, G. D. M. Jeffries, R. M. Lorenz, J. P. Shelby and D. T. Chiu, Anal. Chem., 2005, 77, 1539-1544; Y. Marcy, T. Ishoey, R. S. Lasken, T. B. Stockwell, B. P. Walenz, A. L. Halpern, K. Y. Beeson, S. M. D. Goldberg and S. R. Quake, PLoS Genet., 2007, 3, 1702-1708; A. Huebner, M. Srisa-Art, D. Holt, C. Abell, F. Hollfelder, A. J. Demello and J. B. Edel, Chem. Commun., 2007, 1218-1220; S. Takeuchi, W. R. DiLuzio, D. B. Weibel and G. M. Whitesides, Nano Lett., 2005, 5, 1819-1823; P. Boccazzi, A. Zanzotto, N. Szita, S. Bhattacharya, K. F. Jensen and A. J. Sinskey, App. Microbio. Biotech., 2005, 68, 518-532; V. V. Abhyankar and D. J. Beebe, Anal. Chem., 2007, 79, 4066-4073. Similar techniques have been used for single molecule and single enzyme work. (H. H. Gorris, D. M. Rissin and D. R. Walt, Proc. Natl. Acad. Sci. U.S.A., 2007, 104, 17680-17685; A. Aharoni, G. Amitai, K. Bernath, S. Magdassi and D. S. Tawfik, Chem. Biol., 2005, 12, 1281-1289; O. J. Miller, K. Bernath, J. J. Agresti, G. Amitai, B. T. Kelly, E. Mastrobattista, V. Taly, S. Magdassi, D. S. Tawfik and A. D. Griffiths, Nat. Methods, 2006, 3, 561-570; J. Huang and S. L. Schreiber, Proc. Natl. Acad. Sci. U.S.A, 1997, 94, 13396-13401; D. T. Chiu, C. F. Wilson, F. Ryttsen, A. Stromberg, C. Farre, A. Karlsson, S. Nordholm, A. Gaggar, B. P. Modi, A. Moscho, R. A. Garza-Lopez, A. Orwar and R. N. Zare, Science, 1999, 283, 1892-1895; J. Yu, J. Xiao, X. J. Ren, K. Q. Lao and X. S. Xie, Science, 2006, 311, 1600-1603), the entireties of all of which are incorporated by reference. The device also enables simultaneous execution of numerous assays of bacterial function from a single bacterial sample in the same experiment, which is especially useful for rapid antibiotic susceptibility screening. Previously, gel microdroplets had been utilized for susceptibility screening. (Y. Akselband, C. Cabral, D. S. Shapiro and P. McGrath, J. Microbiol. Methods, 2005, 62, 181-197; C. Ryan, B. T. Nguyen and S. J. Sullivan, J. Clin. Microbiol., 1995, 33, 1720-1726.)

The device may be used to detect organisms. The term "organism" refers to any organisms or microorganism, including bacteria, yeast, fungi, viruses, protists (protozoan, micro-algae), archaebacteria, and eukaryotes. The term "organism" refers to living matter and viruses comprising nucleic acid that can be detected and identified by the methods of the invention. Organisms include, but are not limited to, bacteria, archaea, prokaryotes, eukaryotes, viruses, protozoa, *mycoplasma*, fungi, and nematodes. Different organisms can be different strains, different varieties, different species, different genera, different families, different orders, different classes, different phyla, and/or different kingdoms. Organisms may be isolated from environmental sources including soil extracts, marine sediments, freshwater sediments, hot springs, ice shelves, extraterrestrial samples, crevices of rocks, clouds, attached to particulates from aqueous environments, and may be involved in symbiotic relationships with multicellular organisms. Examples of such organisms include, but are not limited to *Streptomyces* species and uncharacterized/unknown species from natural sources.

Organisms included genetically engineered organisms. Further examples of organisms include bacterial pathogens such as: *Aeromonas hydrophila* and other species (spp.); *Bacillus anthracis; Bacillus cereus*; Botulinum neurotoxin producing species of *Clostridium; Brucella abortus; Brucella melitensis; Brucella suis; Burkholderia mallei* (formally *Pseudomonas mallei*); *Burkholderia pseudomallei* (formerly *Pseudomonas pseudomallei*); *Campylobacter jejuni; Chlamydia psittaci; Clostridium botulinum; Clostridium botulinum; Clostridium perfringens; Coccidioides immitis; Coccidioides posadasii; Cowdria ruminantium* (Heartwater); *Coxiella burnetii*; Enterovirulent *Escherichia coli*/group (EEC Group) such as *Escherichia coli*—enterotoxigenic (ETEC), *Escherichia coli*—enteropathogenic (EPEC), *Escherichia coli*—O157:H7 enterohemorrhagic (EHEC), and *Escherichia coli*—enteroinvasive (EIEC); *Ehrlichia* spp. such as *Ehrlichia chaffeensis; Francisella tularensis; Legionella pneumophilia; Liberobacter africanus; Liberobacter asiaticus; Listeria monocytogenes*; miscellaneous enterics such as *Klebsiella, Enterobacter, Proteus, Citrobacter, Aerobacter, Providencia,* and *Serratia; Mycobacterium bovis; Mycobacterium tuberculosis; Mycoplasma capricolum; Mycoplasma mycoides* ssp *mycoides; Peronosclerospora philippinensis; Phakopsora pachyrhizi; Plesiomonas shigelloides; Ralstonia solanacearum* race 3, biovar 2; *Rickettsia prowazekii; Rickettsia rickettsii; Salmonella* spp.; *Schlerophthora rayssiae varzeae; Shigella* spp.; *Staphylococcus aureus; Streptococcus; Synchytrium endobioticum; Vibrio cholerae* non-O1; *Vibrio cholerae* O1; *Vibrio parahaemolyticus* and other Vibrios; *Vibrio vulnificus; Xanthomonas oryzae; Xylella fastidiosa* (citrus variegated chlorosis strain); *Yersinia enterocolitica* and *Yersinia pseudotuberculosis*; and *Yersinia pestis*. Further examples of organisms include viruses such as: African horse sickness virus; African swine fever virus; Akabane virus; Avian influenza virus (highly pathogenic); Bhanja virus; Blue tongue virus (Exotic); Camel pox virus; Cercopithecine herpesvirus 1; Chikungunya virus; Classical swine fever virus; Coronavirus (SARS); Crimean-Congo hemorrhagic fever virus; Dengue viruses; Dugbe virus; Ebola viruses; Encephalitic viruses such as Eastern equine encephalitis virus, Japanese encephalitis virus, Murray Valley encephalitis, and Venezuelan equine encephalitis virus; Equine morbillivirus; Flexal virus; Foot and mouth disease virus; Germiston virus; Goat pox virus; Hantaan or other Hanta viruses; Hendra virus; Issyk-kul virus; Koutango virus; Lassa fever virus; Louping ill virus; Lumpy skin disease virus; Lymphocytic choriomeningitis virus; Malignant catarrhal fever virus (Exotic); Marburg virus; Mayaro virus; Menangle virus; Monkeypox virus; Mucambo virus; Newcastle disease virus (WND); Nipah Virus; Norwalk virus group; Oropouche virus; Orungo virus; Peste Des Petits Ruminants virus; Piry virus; Plum Pox Potyvirus; Poliovirus; Potato virus; Powassan virus; Rift Valley fever virus; Rinderpest virus; Rotavirus; Semliki Forest virus; Sheep pox virus; South American hemorrhagic fever viruses such as Flexal, Guanarito, Junin, Machupo, and Sabia; Spondweni virus; Swine vesicular disease virus; Tickborne encephalitis complex (flavi) viruses such as Central European tickborne encephalitis, Far Eastern tick-borne encephalitis, Russian spring and summer encephalitis, Kyasanur forest disease, and Omsk hemorrhagic fever; Variola major virus (Smallpox virus); Variola minor virus (Alastrim); Vesicular stomatitis virus (Exotic); Wesselbron virus; West Nile virus; Yellow fever virus; and South American hemorrhagic fever viruses such as Junin, Machupo, Sabia, Flexal, and Guanarito.

Further examples of organisms include parasitic protozoa and worms, such as: *Acanthamoeba* and other free-living amoebae; *Anisakis* sp. and other related worms *Ascaris lumbricoides* and *Trichuris trichiura; Cryptosporidium parvum; Cyclospora cayetanensis; Diphyllobothrium* spp.; *Entamoeba histolytica; Eustrongylides* sp.; *Giardia lamblia; Nanophyetus* spp.; *Shistosoma* spp.; *Toxoplasma gondii*; Filarial nematodes and *Trichinella*. Further examples of analytes include allergens such as plant pollen and wheat gluten.

Further examples of organisms include fungi such as: *Aspergillus* spp.; *Blastomyces dermatitidis*; *Candida*; *Coccidioides immitis*; *Coccidioides posadasii*; *Cryptococcus neoformans*; *Histoplasma capsulatum*; Maize rust; Rice blast; Rice brown spot disease; Rye blast; *Sporothrix schenckii*; and wheat fungus. Further examples of organisms include worms such as *C. Elegans* and pathogenic worms or nematodes.

Sample may obtained from a patient or person and includes blood, feces, urine, saliva or other bodily fluid. Food samples may also be analyzed. Samples may be any sample potentially comprising an organism. Environments for finding organisms include, but are not limited to, geothermal and hydrothermal fields, acidic soils, sulfotara and boiling mud pots, pools, hot-springs and geysers where the enzymes are neutral to alkaline, marine actinomycetes, metazoan, endo and ectosymbionts, tropical soil, temperate soil, arid soil, compost piles, manure piles, marine sediments, freshwater sediments, water concentrates, hypersaline and super-cooled sea ice, arctic tundra, Sargasso sea, open ocean pelagic, marine snow, microbial mats (such as whale falls, springs and hydrothermal vents), insect and nematode gut microbial communities, polar bear nostrils, plant endophytes, epiphytic water samples, industrial sites and ex situ enrichments. Additionally, a sample may be isolated from eukaryotes, prokaryotes, myxobacteria (epothilone), air, water, sediment, soil or rock, a plant sample, a food sample, a gut sample, a salivary sample, a blood sample, a sweat sample, a urine sample, a spinal fluid sample, a tissue sample, a vaginal swab, a stool sample, an amniotic fluid sample, a fingerprint, aerosols, including aerosols produced by coughing, skin samples, tissues, including tissue from biopsies, and/or a buccal mouthwash sample.

To monitor the presence and metabolically active bacteria in the device, a fluorescent viability indicator alamarBlue® may be added to the cultures. The active ingredient of alamarBlue is the fluorescent redox indicator resazurin. (J. O'Brien and F. Pognan, Toxicology, 2001, 164, 132-132.) Resazurin is reduced by electron receptors used in cellular metabolic activity, such as NADH and FADH, to produce the fluorescent molecule resofurin. Therefore, fluorescence intensity in an area is correlated with the presence and metabolic activity of a cell, in this case, a bacterium. Because resazurin indicates cell viability, resazurin-based assays have been used previously in antibiotic testing. (S. G. Franzblau, R. S. Witzig, J. C. McLaughlin, P. Torres, G. Madico, A. Hernandez, M. T. Degnan, M. B. Cook, V. K. Quenzer, R. M. Ferguson and R. H. Gilman, J. Clin. Microbiol., 1998, 36, 362-366; A. Martin, M. Camacho, F. Portaels and J. C. Palomino, Antimicrob. Agents Chemother., 2003, 47, 3616-3619; K. T. Mountzouros and A. P. Howell, J. Clin. Microbiol., 2000, 38, 2878-2884; C. N. Baker and F. C. Tenover, J. Clin. Microbiol., 1996, 34, 2654-2659.) Resazurin may be used to detect both the presence of a live bacterium and the response of bacteria to drugs, such as antibiotics. Stochastic confinement decreases detection time because in an area that has the bacterium, the bacterium is at an effectively higher concentration than in the starting solution, and the signal-to-noise required for detection is reached sooner since the product of reduction of resazurin accumulates in the area more rapidly.

Detecting low concentrations of species (down to single molecules and single bacteria) is a challenge in food, medical, and security industries. The device may allow one to concentrate such samples and perform analysis. For example, a sample containing small amounts of DNA of interest in the presence of an excess of other DNA may be amplified. Amplification may be detected if areas are made small enough that some areas contain single DNA molecules of interest, and other areas contain no DNA molecules of interest. This separation into areas effectively creates areas with higher DNA of interest concentration than in the original sample. Amplification of DNA in those areas, for example by PCR, may lead to higher signal than amplification of the original sample. In addition, localization of bacteria in areas by a similar method may create a high local concentration of bacteria (1 per very small area), making them easier to detect. For some bacteria that use quorum sensing, this may be a method to activate and detect them. Such bacteria may be inactive/non-pathogenic and difficult to detect at low concentrations due to lack of activity, but at a high concentration of bacteria, the concentration of a signaling molecule increases, activating the bacteria. If a single bacterium is localized in an area, the signaling molecule produced by a bacterium cannot diffuse away and its concentration will rapidly increase, triggering activation of the bacterium, making it possible for detection. In addition, the device may be used to localize cells and bacteria by creating gels or matrixes inside areas. Bacteria and other species (particles and molecules) may be collected and concentrated into plugs by flowing air through a fluid such as water, and then using that fluid to fill a plurality of areas. This results in concentrated sample-containing areas because some of the areas do not contain any of the analyte.

PCR techniques are disclosed in the following published US patent applications and International patent applications: US 2008/0166793, WO 08/069884, US 2005/0019792, WO 07/081386, WO 07/081387, WO 07/133710, WO 07/081385, WO 08/063227, US 2007/0195127, WO 07/089541, WO 07030501, US 2007/0052781, WO 06096571, US 2006/0078893, US 2006/0078888, US 2007/0184489, US 2007/0092914, US 2005/0221339, US 2007/0003442, US 2006/0163385, US 2005/0172476, US 2008/0003142, and US 2008/0014589, all of which are incorporated by reference herein in their entirety.

The following articles, describing methods for concentrating cells and/or chemicals by making small volume areas with low numbers of items to no items being incorporated into the areas, with specific applications involving PCR, are incorporated by reference herein: Anal Chem. 2003 Sep. 1; 75(17):4591-8. Integrating polymerase chain reaction, valving, and electrophoresis in a plastic device for bacterial detection. Koh C G, Tan W, Zhao M Q, Ricco A J, Fan Z H; Lab Chip. 2005 April; 5(4):416-20. Epub 2005 Jan. 28. Parallel nanoliter detection of cancer markers using polymer microchips. Gulliksen A, Solli L A, Drese K S, Sorensen O, Karlsen F, Rogne H, Hovig E, Sirevåg R.; Ann N Y Acad Sci. 2007 March; 1098:375-88. Development of a microfluidic device for detection of pathogens in oral samples using upconverting phosphor technology (UPT). Abrams W R, Barber C A, McCann K, Tong G, Chen Z, Mauk M G, Wang J, Volkov A, Bourdelle P, Corstjens P L, Zuiderwijk M, Kardos K, Li S, Tanke H J, Sam Niedbala R, Malamud D, Bau H; Sensors, 2004. Proceedings of IEEE 24-27 Oct. 2004 Page(s):1191-1194 vol. 3. A microchip-based DNA purification and real-time PCR biosensor for bacterial detection. Cady, N. C.; Stelick, S.; Kunnavakkam, M. V.; Yuxin Liu; Batt, C. A.; Science. 2006 Dec. 1; 314(5804):1464-7. Microfluidic Digital PCR Enables Multigene Analysis of Individual Environmental Bacteria. Elizabeth A. Ottesen, Jong Wook Hong, Stephen R. Quake, Jared R. Leadbetter; Electrophoresis 2006, 27, 3753-3763. Automated screening using microfluidic chip-based PCR and product detection to assess risk of BK virus associated nephropathy in renal transplant recipients. Govind V. Kaigala, I, Ryan J. Huskins, Jutta Preiksaitis, Xiao-Li Pang, Linda M. Pilarski, Christopher J. Backhouse; Journal of Microbiological Methods 62 (2005) 317-326. An insulator-based (electrodeless) dielectrophoretic concentrator for microbes in water. Blanca H. Lapizco-Encinas, Rafael V. Davalos, Blake A. Simmons, Eric B. Cummings, Yolanda Fintschenko; Anal. Chem. 2004, 76, 6908-6914. Electrokinetic Bioprocessor for Concentrating Cells and Molecules. Pak Kin Wong, Che-Yang Chen, Tza-Huei Wang, and Chih-Ming Ho; Lab Chip, 2002, 2, 179-187. High sensitivity PCR assay in plastic micro reactors. Jianing Yang, Yingjie Liu, Cory B. Rauch, Randall L. Stevens, Robin H. Liu, Ralf Lenigk and Piotr Grodzinski; Anal. Chem. 2005, 77, 1330-1337. High-Throughput Nanoliter Sample Introduction Microfluidic Chip-Based Flow Injection Analysis System with Gravity-Driven Flows. Wen-Bin Du, Qun Fang, Qiao-Hong He, and Zhao-Lun Fang; Science Vol 315 5 Jan. 2007, 81-84. Counting Low-Copy Number Proteins in a Single Cell. Bo Huang, Hongkai Wu, Devaki Bhaya, Arthur Grossman, Sebastien Granier, Brian K. Kobilka, I, Richard N. Zare; Nature Biotechnology Vol 22 (4), April 2004. A nanoliterscale nucleic acid processor with parallel architecture. Hong J W, Studer V, Hang G, Anderson W F, and Quake S R; Electrophoresis 2002, 23, 1531-1536. A nanoliter rotary device for polymerase chain reaction. Jian Liu, Markus Enzelberger, and Stephen Quake; Biosensors and Bioelectronics 20 (2005) 1482-1490. Microchamber array based DNA quantification and specific sequence detection from a single copy via PCR in nanoliter volumes. Yasutaka Matsubara, Kagan Kerman, Masaaki Kobayashi, Shouhei Yamamura, Yasutaka Morita, Eiichi Tamiya; US Patent Application 2005/0019792, "Microfluidic device and methods of using same"; and Nature Methods 3, 541-543 (2006) "Overview: methods and applications for droplet compartmentalization of biology" John H Leamon, Darren R Link, Michael Egholm & Jonathan M Rothberg.

Flourogenic media, which change color in the presence of specific bacteria, can also be used to detect cells. Chromogenic media include, for example, Difco mEl agar, Merck/EMD Chromocult™ Coliform Agars, Chromocult™ Enterococci Agar/Broth, or Fluorocult® LMX Broth, BL agar, IDEXX Colilert, CPI ColiTag and Merck/EMD ReadyCult®. Typical enzyme substrates linked to chromogens or fluorogens include ONPG, CPRG, and MUG. These are also available in ready-to-use format, e.g. BBL ml agar and 'convenience' packs, e.g. IDEXX Colilert, CPI ColiTag and Merck/EMD ReadyCult®.

To perform an antibiotic screen, areas may contain antibiotics, and the areas filled with the sample may be allowed to incubate to permit growth of microorganisms. Antibiotics are recognized and are substances which inhibit the growth of or kill microorganisms. Examples of antibiotics include, but are not limited to, chlorotetracycline, bacitracin, nystatin, streptomycin, polymicin, gramicidin, oxytetracyclin, chloramphenicol, rifampicin, cefsulodin, cefotiam, mefoxin, penicillin, tetracycline, minocycline, doxycycline, vancomycin, kanamycin, neomycin, gentamycin, erythromycin, cephalosporins, geldanamycin, and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone. Additional examples of antibiotics that may be used are in US 2007/0093894 A1, hereby incorporated by reference in its entirety. Detection of differences in growth and microbial populations in the absence and presence of each antibiotic would provide information on antibiotic susceptibility. First the bacteria in the sample are counted. Then, the bacteria sample is exposed to areas containing different growth media and different antibodies along with some as "blank" media and "blank" antibiotics areas, and areas are assayed for bacterial growth.

Other applications include detecting bacteria for applications in homeland security and safety of the food chain and water. It is also possible to apply these methods of detection to the areas of sepsis, bioenergy, proteins, enzyme engineering, blood clotting, biodefense, food safety, safety of water supply, and environmental remediation. The following patents and patent applications are hereby incorporated by reference in their entireties: WO 2005-010169 A2, U.S. Pat. No. 6,500,617, WO 2007-009082 A1.

Examples of means to cause movement of a substance include, but are not limited to, centrifugal force, for example when the device contains an array of areas in fluidic communication is used, gradients of surface tension, osmotic pressure, capillary pressure, positive or negative pressure, generated externally, for example using pumps or syringes, slipping, for example by compressing or expanding an area containing fluid, electric forces, electroosmotic forces, magnetic forces, and chemical reactions or processes, which may be initiated externally or initiated by slipping.

For example a plurality of liquid or solid substances may be brought into that together produce a gaseous product, thereby generating pressure. For example a solution of sulfuric acid and a carbonate salt may be used. Alternatively, a catalyst may be added to an area containing substances that do not react or only react slowly in the absence of the catalyst but which react more rapidly in the presence of the catalyst. One example is a mixture of sodium bicarbonate with a solid acid, for example tartaric acid, activated by addition of water, acting as a catalyst. A number of such mixtures capable of being activated by catalysts are used as baking powders. Alternatively, substances may be brought together such that a gaseous substance is consumed, thereby generating negative pressure and inducing motion of a substance in a device. For example, sodium hydroxide and carbon dioxide will react in such a manner. Phase transitions may also be used to induce motion of a substance in a device. In addition, wicking may be used. For example a first area may contain, or be composed of a material that absorbs a substance in order to induce motion. In another example of inducing movement of a substance, differential pressures due to surface tension and flow resistance can be used to drive flow after slipping, even without applying external pressure. In one instance, a device may contain one or more main channels through which flow is desired as well as an array of one or more capillary channels, which are smaller than the main channel and therefore have a higher capillary pressure than the main channel. The device can be slipped to bring the main channel(s) into fluidic communication with the array of capillary channels, thus creating a fluidic path that has higher pressure in the capillary channels than in the main channel, which drives flow into the main channel. The device and the slipping motion can be tuned to provide control over the rate and duration of flow. For example, reservoirs of fluid that are open to the atmosphere can be located at controlled distances the capillary and/or main channel, to control the pressure due to flow resistance. These reservoirs can optionally be connected via a duct to the capillary and/or main channel, to further decrease flow resistance and thus increase the flow rate. This could for example be used to drive flow through a washing channel, to wash during an immunoassay, or to drive slow flow over a perfusion culture of cells or a suspension of beads.

The device of the present invention can be used to load multiple areas with the same substance easily and economically. For example, with respect to FIGS. 12A and 12B, the device can be manufactured to include multiple, areas 22 and areas 18. In the open position, each area is connect to each other and to an inlet 28, allowing easy loading. In the closed position, each of the areas 18 and 22 are isolated from each other, allowing, for example, detection of small amount of substances in individual areas (e.g., through stochastic confinement of single molecules, beads, cells and bacteria). Methods for detecting small amounts of substances in individual areas are described in, for example, PCT/US08/071374, PCT/US07/02532, and PCT/US08/71370, all incorporated by reference herein.

The device of the present invention can also be used to easily load a first substance into multiple areas preloaded with various second substances. For example, with respect to FIGS. 12A and 12B, each area 18 and 22 may contain a different first substance, which may be attached to the surface of the areas (e.g., different antibiotics). When a second substance (e.g., a sample containing a bacteria) is loaded into the device in the open position through inlet 28, it will load into each area. After the device is slipped into the closed position, individual areas can be monitored for the affect of the first substance on the second substance. Methods for measuring susceptibility of bacteria to antibiotics are described in PCT/US08/71374, incorporated by reference herein.

Embodiments of the invention described herein may be used for microbial culturing. For example, anaerobic microbes may be cultured in devices made of glass in which the microbes have been loaded anaerobically. The anaerobes could then be manipulated, grown, analyzed etc. without exposing the organism to oxygen. Such devices may be used in applications such as analyzing aerobic or anaerobic microbes, analyzing intestinal biota, diagnostics, determining antibiotic susceptibility of anaerobic infections. Applications of these microbial culturing devices are disclosed in patent applications PCT/US08/71374 and PCT/US08/71370. After microbial species have been confined to areas of the device they may be manipulated via multistep processes such that conditions (i.e., anaerobic, chemical, etc.) are controlled at each subsequent slip position. For example, a microbe may be confined in the initial slip position, then stimulated to produce a virulence factor in the following slip position and then in a final slip position the virulence factor may be contacted with a detection reagent.

Additionally, embodiments of the invention described herein may be used for culturing and manipulating prokaryotic and eukaryotic cells including multicellular organisms such as nematodes. For example organisms may be cultured in devices designed to supply cells and organisms with nutrients in the first slip position, supply stimuli in the second slip position and remove waste products in the third slip position. Optional additional slip positions may be used to capture products secreted by the organisms within the device as disclosed in patent applications PCT/US08/71374 and PCT/US08/71370. The device may be designed to be compatible with high resolution imaging of the confined organisms.

Similarly, the device of the present invention can be designed to load multiple areas with different substances easily and economically. For example, in FIGS. 8A-D, the device is manufactured to include multiple areas 18 on one surface and multiple areas 22 on the opposing surface. In position A, parallel rows of areas 22 can be loaded with different, first substances. After slipping into position C, parallel columns of areas 18 can be loaded with different, second substances. In position D, the various first and second substances can combine, forming an array of different reactions. In this embodiment, for example, a device containing 10 areas in each of 10 rows and 10 areas in each of 10 columns can be used to set up 100 reactions. In other embodiments, the device could contain areas configured in the same locations as standard multiwell plates which may contain, for example, 6, 24, 96, 384, 1536, 3456, or 9600 sample wells. In other embodiments, the device could contain at least about 1, 2, 3, 4, 5, 6, 7, 8, 9, 10, 20, 24, 30, 40, 48, 50, 60, 70, 80, 90, 96, 100, 200, 300, 384, 400, 500, 512, 1000, 1500, 1536, 2000, 2500, 3000, 3456, 3500, 4000, 4500, 5000, 6000, 7000, 8000, 9000, 9600, 10000, 1500, 2000, 2500, 3000, 4000, 5000, 6000, 7000, 8000, 9000, 10000, 20000, 30000, 40000, 50000, 60000, 70000, 80000, 90000, 100000, 200000, 200000, 400000, 500000, 600000, 700000, 800000, 900000, 1000000 or more areas. Standard multiwell configurations are described in US 20070015289, incorporated by reference herein in its entirety. For example, a device can contain an array of 100,000 areas, wherein each area is a cube approximately 200 micrometers on a side, enabling 1 milliliter of sample to be divided into 100,000 volumes of 10 nL each. Such a device can be used, for example to detect analytes present at very low concentrations.

In some embodiments the device of the present invention can be preloaded with substances and stored prior to use. For example, if one or more substances are dried into the areas, a solution could be added to the device in the open position to rehydrate/dissolve the substances. Methods of drying substances for storage are described in US 2008/0213215, US2009/0057149 and U.S. Pat. No. 7,135,180, incorporated by reference herein in their entireties.

The present invention can be used with plug technology, such as disclosed in U.S. Pat. No. 7,129,091 and patent publications US 2007/0172954, US 2006/0003439, US 2005/0087122, PCT/US08/71374, PCT/US08/71370, and PCT/US07/26028 to the same inventor, all incorporated by reference herein in their entireties. For example, an area can comprise a channel on a base capable of being filled with an array of plugs. The device can comprise an opposing plate containing a set of at least one areas that, in a first position, each overlap at least one plug in the array of plugs, and in a second position, do not overlap any plugs of the array of plugs.

One embodiment of such device 10 is shown in FIGS. 12A-B. One way to manufacture the device 10 shown in FIGS. 12A-B is out of glass. The glass slide with areas or channels were made by etching as described above. The area size is approximately 130×50 µm and depth is about 15 µm. There are 2048 areas in each layer of the device, which were composed of 32 rows of 64 areas. All 32 row areas connected to a single inlet by a Y shape tree distribution style. After slipping, the device generated 4096 individual compartments. The size of the device was 1 cm×2 cm.

Two pieces of glass slides with complementary patterns were aligned under microscope to make through-channels and clamped with paper clips. When the areas are aligned, they formed a continuous channel connected with inlet. And the other end of the channel connected with a bigger channel which went all way down to the edge of the device.

FC-40 was first injected via the inlet to fill all the channels. Since the glass was silanized and FC-40 wet the glass, the oil not only filled all the channels, but also all contact area between two glass layers. Air was pushed in through the inlet to replace FC-40, while keep the contacted area of two layer still wet by FC-40. And also, there are small amount of FC-40 residue in channel or a FC-40 thin layer still covers the surface of the channel. A solution of 0.5 µM fluoroscein in 10 mM Tris pH 7.8 was injected into the channels through the inlet.

In some embodiments, the sample loaded into the device may have beads, such as those capable of immobilizing a substance or magnetic beads. Beads can be confined into different areas in the device by sizing the ducts that connect the areas in the open position to be smaller than the beads. Magnetic beads can additionally be directed or trapped in specific areas by applying a focused magnetic field to the area. In some embodiments, the areas are loaded with beads containing a first substance (e.g., a first amino acid). By slipping the device between an open and closed position (or through several different open and closed positions), the beads can be washed, deprotected, reacted with a second substance (e.g. a second amino acid), washed, etc. In this manner, arrays of new molecules (e.g. polypeptides) can be formed. Ultimately, the new molecule could be released from the bead and either analyzed or even collected. Examples of the types of beads that may be used in the present invention are listed in US 2009/0035847, WO 2009/018348, WO 2009/013683, WO 2009/002849 and WO 2009/012420, all incorporated by reference herein in their entireties.

In some embodiments, the speed of mixing of first and second substances can be increased by slipping the device between the open and closed positions multiple times.

In some embodiments, multiple areas are aligned to allow consecutive addition of substances (and possibly further reactions) by slipping more than one time into further closed positions. In this embodiment, the slipping can be in the same or different directions as described with respect to FIGS. 14A and 14B, discussed supra.

In some embodiments, the volume of the areas is controlled such that mixing of two areas is quantitative allowing the concentration of the substances to be monitored. In some embodiments, multiple areas are aligned allowing for serial dilution of substance when the device is slipped into further closed positions. For example, a first set of at least one first areas on a base can be filled with a substance, for example via ducts, in a first position, and then sequentially the area can be moved into different positions, where, in each position, the at least one first area is exposed to one of a second set of pre-filled areas, for example on an opposing plate, that contains a diluent, for example a buffer. The exposure at each position is maintained for enough time for the substance to be fully diluted with the diluents. At each successive position, the substance is diluted by volume of diluents. If, for example, a first area contains 1 nanoliter of substance and each of a set of five second areas are 9 nanoliters in volume, after the first area is exposed to each of the second areas in turn, the second areas will be filled with substances diluted approximately 10-fold, 100-fold, 1,000-fold, 10,000-fold and 100,000-fold. The second set of areas may then be exposed to further areas and substances to conduct further reactions.

In an alternative embodiment, a row containing a plurality of first areas on a base can be filled with a substance, for example via ducts, in a first position, and then sequentially the plurality of areas can be moved into different positions, where, in each position, each one of the plurality of first areas is exposed to a corresponding second set of pre-filled areas, for example on an opposing plate, that each contain a diluent, and where each one of the plurality of first areas is exposed to a different number of areas in the second set of pre-filled areas. For example, four first areas can be filled in a first position, and then in a second position, a first area is exposed to a diluting area, but the other three first areas are not. In a third position, the first and second areas are exposed to diluting areas, but the remaining two are not. In a fourth position, the first, second and third areas are exposed to diluting areas, but the remaining one is not. The result of these actions is to fill a series of four first areas differing in concentration that may then be moved to at least one further positions at which they are exposed to reagents, for, for example, assaying protein binding or inhibition activity. It will be apparent to one skilled in the art that the number of first areas and second areas in this example could be readily varied to any desired value, subject to the available area on the device, and the amount of substance available.

Using these techniques, solutions for, for example, protein activity assays, and/or protein-binding assays, in which a large range of protein and/or inhibitor concentrations are needed to get accurate data, can quickly be prepared using small amounts of material.

In some embodiments, areas on a first surface are aligned with those on the opposing second surface so that the area on the second surface bridges two or more areas on the first surface in the closed position. In this embodiment, the formed bridge allows for controlled diffusion from one area on the first surface to another area on the first surface via the bridging area on the second surface. This embodiment is especially useful for protein crystallization.

A few exemplarily experiments were conducted to illustrate the usefulness of this device for protein crystallization. One experiment conducted, referred to as "Crystallization of RC on SlipChip (L16L025-26)," incorporated the use of the device 10 illustrated in FIGS. 6A-B. Specifically, the experiment occurred on an aligned PDMS/glass SlipChip (patterned as FIGS. 6A-B, 25 mm×75 mm size). The gap between the two layers was filled by FC-40 before use. The device contains 160 areas for protein and 160 areas for precipitants on two layers, which are complementary for sliding. All of the areas have a depth of 100 µm and width of 300 µm, and a changing length was used to control the volume in the range of 8.8 to 14.2 nL. 16 precipitants and reaction center sample were loaded onto the SlipChip by pipetting. Each precipitant filled an array of 10 areas with volumes from 8.8 nL to 14.2 nL (with a steady increment of 0.6 nL between neighboring areas), the protein fills all 160 areas opposite to the precipitant areas, with a volume of 14.2 to 8.8 nL. 16 precipitants included No. 1 to No. 14 of CrystalScreen kit (Hampton Research) and two identical control solutions: 4 M $(NH_4)_2SO_4$ in 50 mM $Na_2HPO_4/NaH_2PO_4$ pH 6.0. When loading each precipitant, a 100 µL pipetter was used. 40 µL of solution was loaded into the pipetter. To load the solution into the SlipChip, the end of the pipetter tip was pushed against the corresponding inlet hole. The solution was then pushed out and pipetter tip was released when the whole channel was filled. Once all precipitants were loaded into the chip, the reaction center sample (~24 mg/mL in 4.5% TEAP, 7% 1,2,3-heptanetriol, 0.08% LDAO and 20 mM $Na_2HPO_4/NaH_2PO_4$ pH 6.0. A 10 µL pipetter was used and ~6 µL of RC sample was loaded onto the Chip. Sliding was achieved by hand and RC was brought into contact with the correlated precipitants. After one day's incubation, only the control precipitant generated crystals. The other 14 conditions did not yield crystals even after one week.

Another experiment, referred to as "Crystallization of lysozyme in hybrid device (notebook page L16L032)" occurred on an aligned PDMS/glass SlipChip embodiment shown in FIGS. 6A-B and 7A-B. On an aligned PDMS/glass SlipChip (25 mm×75 mm size), which consisted of both FID (FIGS. 7A-B) and microbatch styles (FIGS. 6A-B), one precipitant (30% PEG 5000 MME, 1 M NaCl in 0.1 M NaOAc pH 4.8) was loaded into 16 different ports through 16 inlets. Precipitant filled 12 areas connected with each inlet. These 12 areas were composed of 6 areas for microbatch optimization of mixing ratio and 6 areas for optimization of free interface diffusion. For the microbatch experiment, the mixing volume of protein to precipitants were: 7.8 nL: 15.8 nL; 9.4 nL: 14.2 nL; 11.0 nL: 12.6 nL; 12.6 nL: 11.0 nL; 14.2 nL: 9.4 nL; 15.8 nL:7.8 nL. For FID, the protein volume and precipitants used were both 16 nL. There was a bridging duct with cross section of 50 μm×50 μm which connected the protein and precipitant areas, with a distance of 160 μm, 220 μm, 280 μm, 320 μm, 360 μm, 400 μm. The same pipetting procedure for pipetting precipitants was performed as described above. Lysozyme sample (~120 mg/mL in 0.1 M NaOAc pH 4.8) was loaded into the chip using the same procedure of loading protein as described above. Within 30 minutes' incubation, crystals started to appear, first in microbatch style and then FID style.

Yet another experiment, referred to as "Crystallization of lysozyme, thaumatin in FID (L16L24, L16L095)" was conducted on the embodiment shown in FIGS. 7A-B, referred to as the PDMS/glass SlipChip with FID style. First, the bottom layer containing areas of protein sample and precipitants was immersed in FC-40 contained in a Petri-dish. 7.5 nL solutions of precipitants from Crystal Screen (Hampton research) and double concentrated wizard I (Emerald BioSystems) were deposited into the precipitant areas. To deposit 7.5 nL of solution, the solution was first aspirated into a piece of Teflon tubing (100 μm I.D. and 250 μm O.D.) which was connected to a 10 μL syringe by another piece of Teflon tubing (~360 μm I.D.). The two pieces of Teflon tubing were sealed by wax. The syringe was driving by a syringe pump. The pump was set to use 10 mL syringe at an infusion rate of 300 μL/min. It was set at volume mode and 7.5 μL was designated to be dispensed every time. Considering the offset of syringe size, the actually dispensed volume is 7.5 nL.

It can also be appreciated that the device 10 of the present invention can be combined with other microfluidic crystallization techniques, including those described in U.S. Pat. Nos. 6,409,832; 6,994,749; 7,306,672; 7,015,041; and 6,797,056, all of which are incorporated by reference herein.

Moreover, the device of the present invention can be used to carry out vapor diffusion crystallization experiments. Vapor diffusion experiments are described in patent applications WO/2006/101851 and U.S. Publication No. 2005/0087122 and U.S. Pat. Nos. 6,808,934 and 4,755,363, all incorporated by reference herein. In some embodiments useful for vapor diffusion crystallization experiments, at least one first area can be connected to at least one second area via at least one duct or third area wherein the duct or third area contains a first substance. In some embodiments, the at least one first area contains a second substance to be crystallized dissolved in a solvent, and the at least one second area contains at least one third substance dissolved in the same solvent such that the osmotic pressures of the solution in the at least one first area and at least one second area differ, for example, by differing in the concentration of a salt. Typically, the solution in the second area contains a higher salt concentration than the solution in the first area. The first substance may be a gas such as air or an oil, but may be any substance through which the solvent can equilibrate between the first and second areas. Typically, some portion of the solvent, for example, water, will diffuse towards equilibrium, moving from the solution of lower salt concentration, which contains the second substance to be crystallized, to the solution of higher salt concentration. This diffusion will concentrate the second substance to be crystallized, thereby making it more likely to crystallize. It will be apparent that all of the techniques described herein, for example, moving a suitable base and a suitable plate that contain the appropriate areas and/or ducts relative to one another, can be used to prepare the solutions necessary for such experiments.

After deposition, the top layer containing the connecting "necks" was aligned on top of the bottom layer to connect the correlated areas for protein samples. After alignment, the two layers were clamped using four paper clips. Thaumatin solution (~80 mg/mL in water) and lysozyme solution (22 mg/mL) were injected into the areas through the inlets, respectively. After all the sample areas were all filled by one of the two samples, sliding was performed manually. The previous deposition was performed in such a way that the precipitants from Crystal Screen would be connected to the thaumatin sample by "necks" while those from double concentrated Wizard I would be connected to the lysozyme sample. Within five days, thaumatin was crystallized with condition 29 (0.8 M Sodium potassium tartrate in 0.1 M HEPES pH 7.5) of Crystal Screen and lysozyme was crystallized with condition 16 (3.75 M NaCl in 0.1 M sodium potassium phosphate buffer pH 6.2) of double concentrated Wizard I.

In some embodiments, a substance is immobilized in an area. For example, catalyst, analyte, and biomolecules (i.e., carbohydrates, peptides, proteins, DNA, antibodies, etc.) can be immobilized using known methods, such as those described in U.S. Pat. Nos. 4,071,409, 5,478,893, 7,319,003, 6,203,989, 5,744,305 and 6,855,490, all of which are incorporated by reference herein.

The devices of the present invention can be analyzed using a variety of known detection methods (optical, x-ray, MALDI, FP/FCS, FCS, fluorometric, colorimetric, chemiluminescence, bioluminescence, scattering, Surface Plasmon Resonance, electrochemical, electrophoresis, lasers, mass spectrometry, Raman spectrometry, FLIPR™ (Molecular Devices), etc.). The device can be analyzed directly when suitable materials are used (i.e., optically transparent materials used for optical detection methods). For those detection methods, such as optical absorption, in which the signal is a function of pathlength, multiple areas can be formed on the device such that they contain identical contents, but differ only in pathlength. In this way, the chances are increased that the signal obtained from at least one of the areas will be within the dynamic range of the detector. A computer system configured to account for the differing pathlengths could be used to obtain the final desired result, for example an analyte concentration. The device alternatively can be opened and individual areas analyzed or designed to allow slippage into a further position that allows for access to individual areas (e.g., through access holes). In some embodiments, amplification of the reaction areas may be conducted (e.g. silver-based amplification, microphage amplification, etc.).

In some embodiments, once loaded into a duct, an electric field can be used to separate constituents of a sample (electrophoresis).

The device of the present invention can be used to study and perform coagulation/clotting, protein aggregation, protein crystallization (including the use of lipidic cubic phase), crystallization and analysis of small molecules, macromolecules, and particles, crystallization and analysis of polymorphs, crystallization of pharmaceuticals, drugs and drug candidates, biomineralization, nanoparticle formation, the environment (via aqueous and air sampling), culturing conditions (e.g., stochastic confinement, lysis of cells, etc.), drug susceptibility, drug interactions, etc. Techniques for crystallization are described in US patent and publications U.S. Pat. No. 7,129,091, US 2007/0172954, US 2006/0003439, and US 2005/0087122, incorporated by reference in their entireties. Methods for assaying blood coagulation/clotting are described in PCT/US07/02532, incorporated by reference in its entireties, and are further discussed infra. These methods, as individual tests or their combinations, include PT, aPTT, ACT, INR, assays for individual coagulation factors, measurement of fibrinogen concentration, measurement of platelet function, thrombelastography and various modifications of this method, and viscosimetric methods. These methods can be deployed on slipchip, and can be enhanced by taking advantage of the movement of the layers of the SlipChip. Protein aggregation assays are described in U.S. Pat. Nos. 6,949,575; 5,688,651; 7,329,485; and 7,375,190 and US publication 2003/0022243, incorporated by reference in their entirety. The study of culturing conditions is described in PCT/US08/71370, incorporated by reference in its entirety. The device of the present invention can be used in various assays, including high throughput screening (e.g. one first substance with many, different second substances; many, different first substances with many, different second substances), multiplex assays (e.g. PCR, Taqman, immunoassays (e.g. ELISA, etc.)), sandwich immunoassays, chemotaxis, ramification amplification (RAM), etc. The device of the present invention can be used for various syntheses, including catalysis, multistep reactions, immobilized multistep synthesis (e.g., small molecule, peptide and nucleic acid syntheses), solid state synthesis, radioisotope synthesis, etc. Finally, the device of the present invention can be used for purification and enrichment of samples.

As discussed above, embodiments of the invention described herein may be used for assaying coagulation and platelet function of blood samples. For example the invention provides a device and method that may be used to assay blood clotting. The method includes contacting blood fluid from a subject with at least two patches, where each of the patches includes stimulus material which is capable of initiating a clotting pathway when contacted with a blood fluid from a subject. The stimulus material in one patch differs from the stimulus material in the other patch; or the concentration of stimulus material in the one patch differs from the second patch; or one patch has a surface area different from the other patch; or one patch has a shape different from the other patch; or one patch has a size different from the other patch. The method includes determining which patch initiates clotting of the blood fluid from the subject. The invention may be used for all standard coagulation and platelet function assays. Techniques for assaying coagulation and platelet function in a microfluidic device are described in the following patent application and herein incorporated by reference: PCT/US07/02532 (publication number WO 2007/089777).

In some embodiments, the device can contain areas that are used as positive or negative controls. To make positive controls, the analyte that is being tested for in other areas on the device can be preloaded in the control areas, such that when the device parts are moved as described herein, the pre-loaded analyte is exposed to reactions and detected using the same method as the sample to be measured. When a positive control does not give the expected result, it can be sign of improper storage or usage of the device. Similarly, negative control areas can be prepared that contain no analyte, which would be expected to give no signal when exposed to the reagents for analysis. Additive verification controls can also be used to determine integrity of the assay. Using the techniques of the present invention, a known amount, X, of analyte can be added to the sample containing the unknown amount of analyte, and then both the sample containing additional material and the original sample containing the unknown amount are assayed for analyte concentration using the same method, preferably on the same device to give results Y, for the unknown sample, and Z, for the unknown sample with added amounts of analyte. The difference between Z and Y should be X, and any deviation from X indicates a problem with the assay, such as degradation of the assay reagents.

Optionally, a detectable, such as a colored, substance, for example, black ink, or a dye, can be placed in specific control areas of the device and located such that, movement of the parts of the device in the manner needed to carry out the desired reactions in other regions of the device exposes the colored substance to other areas on either the same or different part of the device such that a specific known detectable pattern is created. If the expected pattern is not created, it can be a sign of improper storage of the device, leakage of the device, or incomplete motion of the parts of the device through the desired sequence of motions. In some embodiments, the expected pattern is a barcode. The pattern may be read by a human or a machine.

In other embodiments, a user adds sample to a device, slips through one or more steps, and a readout is obtained as a pattern of areas that convey information about the presence of analytes and their concentrations.

One method of measuring concentration is to take advantage of multiplexing many assays with different response characteristics, and then using statistics to calculate the expected value and the confidence interval. This is analogous to approaches used in the computer industry such as is done with RAID for disks and the HP approach to constructing supercomputers using many potentially faulty chips.

Alternatively, reactions can be set up in different areas such that each area displays a different threshold response. That is, each area has a different sensitivity to the analyte. For example, for a given analyte, sets of areas can be set up to only give a response if the concentration exceeds, for example an array of, for example, 16 areas divided into sets of, for example, four areas can be formed, where each set only gives a response if, for example, 20, 25, 30 or 35 concentration units are present. After a sample is introduced to the 16 areas, if, for example, the sample really contains the substance at 27 concentration units, then the concentration can be reported as between 25 and 30 concentration units with high confidence if all the areas with thresholds of 20 and 25 concentration units respond and none with thresholds of 30 and 35 concentration units respond. Successively greater deviations from this response pattern will result in successively lower degrees of confidence in the reported result.

Mechanisms for generating a threshold response are reported in PCT US2008/071374, PCT/US07/02532, and PCT/US08/71370, all incorporated by reference herein in its entirety. In one embodiment of the device, a first area on the plate of a device comprises the sample to be analyzed. A second area on the base of a device comprises a capture area. The capture area contains a substance capable of capturing an amount of the analyte just below the threshold level. The threshold for detection is set by the amount of the substance capable of capturing analyte in the capture area. For example, the capturing substance could be surface- or bead-bound antibodies, aptamers or other molecules selective for the analyte. The device is slipped in order to expose the sample to be analyzed to the capture area. If beads are used, a membrane could be disposed between the base and plate to prevent their movement outside the capture area. After a time sufficient to allow exchange has occurred, the device is slipped again to expose the sample to be analyzed to an exchange area placed on the base. The exchange area contains bound catalyst capable of being displaced by the analyte. The catalyst may be, for example, functionalized gold nanoparticles capable of being bound by bead- or surface-bound antibodies or aptamers. Catalyst will only be displaced in the exchange area if the capacity of the capture area is exceeded, leading to analyte being carried over to the exchange area. The device is then slipped again to exposed displaced catalyst in the first area to a detection area located on the base. The detection area contains substances that react in the presence of the catalyst to produce a detectable signal. For example, if the catalyst is a functionalized gold nanoparticle, the detection area may be comprised of two areas one of which contains, for example, silver(I) and the other of which contains a reducing agent, such as hydroquinone. They two areas may be located so that they are not exposed to one another until the first area containing catalyst is slid over them. Once they are both exposed to catalyst, the gold nanoparticle catalyzes reduction of silver to form detectable silver metal. It will be apparent to one skilled in the art that, at each step of the process, the device should be left in position for a time sufficient for the reaction to occur, and that the dimensions and other characteristics of the device could be optimized, taking into account diffusion, for example, to make this time longer or shorter.

In some embodiments, measuring concentration can be done by measuring intensity or time to reach intensity. Time resolution can be automatic or manual. For visual or photometric detection, the device may include a computer with a timer to control or signal at what time or times an image should be acquired or a test area observed.

The device may optionally contain a timer region. The timer region could contain a standard reaction that indicates when the device should be moved from one position to the next. A reaction that undergoes an abrupt visible transition could be used. Preferably the timer region reaction or reactions are carried out in separate areas and are initiated by the same movements that initiate the reactions to be timed.

Alternatively, a concentration can be determined geometrically by filling a volume with capture sites, introducing the analyte at one end, side or edge of the volume and choosing the conditions such that the analyte binds quickly relative to the rate of diffusion of the molecule and the rate at which the substance carrying the analyte flows through the volume so that the analyte saturates the capture sites as it diffuses and/or flows across the volume. If a color change or other detectable difference occurs when the analyte is bound to capture sites, measuring the length or size of the capture zone directly gives a measure of the amount of analyte. Alternatively, a competitive strategy in which a complex of a capture molecule and a labeled analyte is pre-formed in the volume, then added analyte displaces the labeled analyte, and finally the labeled analyte is detected as described elsewhere herein and as will be apparent to one skilled in the art.

The present invention could be used to for determining copy number variation of a target polynucleotide in a genome of a subject including amplification based techniques such as is described in US 2009/0069194, PCR reactions, such as is described in US 2008/0129736 and WO 2008/063227, assays of nucleic acid and protein targets, such as are described in US 2008/0108063, US 2007/0134739, WO 2008/063227, WO 2008/043041 and U.S. Pat. No. 7,413,712, noninvasive fetal gene screening, such as is described in US 2007/0202525, polynucleotide sequencing, such as is described in U.S. Pat. No. 7,501,245 and WO 06/088876, cell-based assays such as are described in US 2008/0107565, US 2007/0077547, U.S. Pat. No. 7,122,301, US 2009/0062134 and WO 2008/063227, biosensors, such as are described in US 2009/0068760, and high throughput screening, such as is described in WO 2007/081387, all of which are incorporated by reference herein. SlipChip may be used to analyze a few cells obtained from a mammalian embryo, including human, mouse, rat, bovine and other embryos. Tests may include genetic tests, including those to establish the presence or absence of certain genes or mutations in genes, detection of chromosomal abnormalities including inversions and deletions. PCR, FISH, whole genome amplification and comparative genomic hybridization and other technologies may be used on SlipChip. Tests may be applied for embryo selection, embryo screening, preimplantation genetic diagnosis, to enable gene therapy, to enable in-vitro fertilization, and other applications. Conditions for which tests may be performed include cystic fibrosis, Beta-thalassemia, sickle cell disease and spinal muscular atrophy type 1, myotonic dystrophy, Huntington's disease and Charcot-Marie-Tooth disease; fragile X syndrome, haemophilia A and Duchenne muscular dystrophy. PCR, FISH and other techniques for analysis and amplification of nucleic acids may be used, as described in this application. SlipChip may be used to analyze bilirubin or bilirubin-albumin complex in blood of neonates.

Embodiments of the invention described herein may be used for PCR-based single nucleotide polymorphism (SNP) genotyping or quantitative measurement of gene expression by real-time PCR in applications such as plant and animal diagnostics, food and water safety testing, ecology, agricultural genetics and human disease research. For example the pathogen E. coli O157:H7 which has been found in ground beef, unpasteurized milk, bottled juices and sewage contaminated water, and individual virulence genes of the pathogen can be rapidly screened for and identified by performing parallel PCR in the device described herein.

In addition, the present invention can be used to assay enzyme concentration and/or activity of enzymes, including but not limited to glycosidases, peptidases, esterases, phosphatases, peroxidases, sulfatases, phospholipases, luciferases, Cytochrome P450, kinases, lipases, phospholipases, oxidases, secretases, proteases, and peptidases, and to carry out immunoassays, using for example reagents sold by Life Technologies, Carlsbad, Calif. and/or Biosynth, Switzerland.

Figure 15:
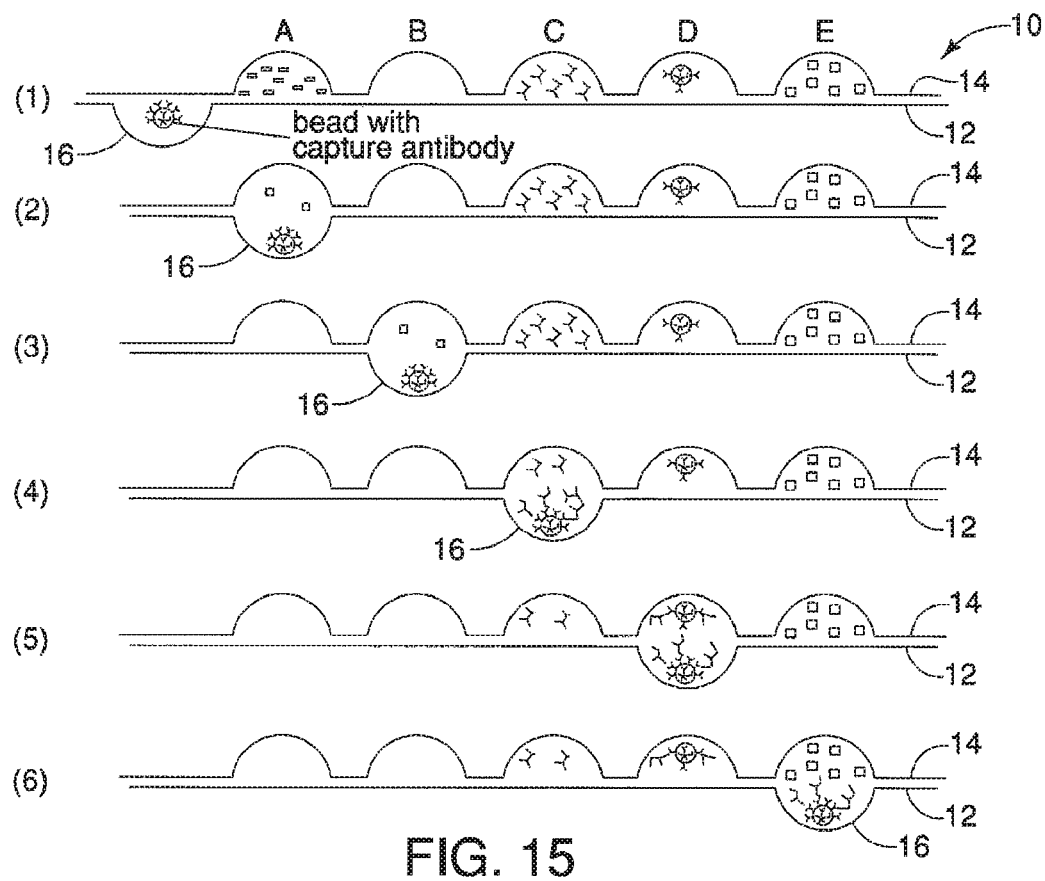
FIG. 15 is a partial side view of a slip chip device accordingly to another embodiment of the invention.

The device can be used to perform a heterogeneous immunoassay without a washing step. For example, in one embodiment, a partial view of which is shown in FIG. 15, a plate 14 of the device 10 contains an area A, optionally B, C, D, and E, all of which are preloaded with appropriate reagents or beads. In a first position, the sample containing the analytes is loaded into the at least one area A. Anti-analyte capture antibodies are loaded into an area F on the opposing base. The capture antibody may be immobilized, for example on beads or on the surface of the area F. When the base and plate are moved relative to one another to a second position, the area F is exposed to area A, and analyte molecules bind to the capture antibody. In a third, optional position, area F is exposed to area B, which contains buffer and/or other reagents that help remove potential interfering molecules. In a fourth position area F is exposed to area C, which contains detection antibody. The detection antibody is chosen to bind strongly to the analyte. The detection antibody may be labeled with an enzyme. Alternatively, it may also be labeled with a fluorescent tag or other tags, or may be unlabeled, depending on the specific immunoassay configuration. In a fifth position, area F is exposed to area D. Area D contains an antibody which binds to the detection antibody, but with an affinity that is weaker than the detection antibody-antigen interaction. The antibody in D may be immobilized on either beads or the surface of area D. The antibody in area D removes excessive detection antibody from the solution. In a sixth position, area F is exposed to area E. Area E contains a substrate solution, which may be converted to a product in the presence of the enzyme that is linked to the detection antibody. This step is optional for some immunoassay configurations. Typically, in each position area F is only exposed to one of areas A, B, C, D, and E. The device can be configured to perform a single such immunoassay on a single sample or a plurality of samples, or many different such immunoassays on a single sample or a plurality of samples.

The device may be used to perform sample preparation and for sample storage. For example, the device may be used to remove cells from blood using filtration and for adding reagents to preserve a blood sample. Plasma may be filtered from blood using the device by first introducing the blood into an input volume in a device comprised of at least one first area and/or ducts. The input volume is exposed to at least one second area separated from the input volume by a membrane, such that some or all of the plasma passes through the membrane into the at least one second area. Excess plasma may be collected in at least one third area exposed to the at least one second area but not directly to the input volume. Optionally, in the same device, the at least one second area may be filled with plasma as described above, and other at least one fourth area may be filled with whole blood by exposure through, for example, a disrupted membrane, or no membrane.

After filling areas with plasma, they can be used for a variety of reactions and manipulations. For example, by using the relative motion of the parts of the device to expose the at least one second area to additional areas, plasma can be preserved by addition of citrate or EDTA to prevent coagulation. Other preservatives or reagents can be added similarly. The whole device may be then stored and transported for analysis. For analysis, all or some of the plasma can be removed from areas and used in other assays outside of the device. In addition, the at least one area containing plasma may be moved into additional positions to perform additional analysis. This analysis could be done using reagents preloaded in additional areas on the device. This analysis could also be performed using user-added reagents; this method is attractive for assays that involve those reagents that are difficult to preload and that are easier to add immediately prior to the assay. Optionally, assays can be performed on the device at the time of sample collection, or at a later time, for example, in a setting in which external temperature is more readily controlled, or external detectors are available.

The device can be used with, and/or incorporate, a chemistrode for sampling (See: Chen, et al., PNAS, Nov. 4, 2008, vol. 105, no. 44 16843-16848; Keats, J., "Jargon Watch," Wired Magazine 17.03, Feb. 23, 2009; Armstrong, G., Nature Chemistry (14 Nov. 2008), doi: 10.1038/nchem.89, Research Highlights.).

A single device could be used to store and/or perform a single assay or a plurality of assays on samples from a single patient, or to store and/or perform a single assay or a plurality of assays on samples from a plurality of patients. Other types of sample preparation and storage can also be performed, for example for preparing and storing other bodily fluids, or environmental samples. Additionally, the areas 18, 22, the ducts 26, or combinations of areas 18, 22 and ducts 26 of one embodiment of the device 10, may constitute a separation path or a separation area. Separation may be carried out by the methods known in the art, using chromatography, electrical potentials including gel and capillary electrophoresis, hydrodynamic separations, filtration, separations by centrifugations, separations based on magnetic and optical forces. A variety of species may be separated including molecules including proteins and nucleic acids, macromolecules, particles and cells. Patents and published applications discussing the separation path or area include U.S. Pat. Nos. 5,707,850; 5,772,889; 5,948,624; 5,993,631; 6,013,166; 6,274,726; 6,436,292; 6,638,408; 6,716,642; 6,858,439; 6,949,355; and U.S. Publication No. 2002/0076825. These patents and patent applications are incorporated herein by reference in their entirety.

Membranes can be incorporated into the SlipChip. For example, a dialysis membrane may be used to concentrate macromolecules on chip, for example for macromolecular and protein crystallization. Membranes can be used to perform other separations, for example separate cells, including blood cells, and to separate components of blood and other biological fluids.

Slipping the two plates relative to one another may be used to carry out a transformation for example: reconfiguring separation path or area, capturing a separated product, bringing reagents to the separation path or area to detect, visualize or analyze.

In some embodiments, the slip chip can be used for two stage reactions. For example, a slip chip capable of moving between a first, second and third position can be configured with areas such that at least one first area overlaps at least one second area in the second position, and the second areas are smaller (for example one-tenth or one-twentieth the size) than the at least one third area that the first area overlaps in the third position. Such a device may be used for a two-stage protein crystallization experiment. The at least one first area is filled with protein to be crystallized. The at least one second area is pre-filled or user-filled with a substance expected to induce nucleation, for example a higher concentration of precipitant, or a solution of methyl-β-cyclodextrin or a solution of another substance capable of removing detergent. The at least one third area may contain, for example, a lower concentration of precipitant. To use the chip, first, areas would be filled. Then, the device would be moved to the first position to nucleation, and either held there for a time sufficient to induce nucleation or moved continuously across the first position such that the at least one first area and at least one second area are in contact for a time sufficient to induce nucleation. The time could be, for example, 1 second, 30 seconds, or 5 minutes. The device would then be moved to the third position. The small size of the at least one second area prevents significant dilution of the sample.

In some embodiments, a user-loaded SlipChip can be used to perform multiplexed nanoliter-scale experiments by combining a sample with multiple different reagents, each at multiple mixing ratios. The mixing ratios, characterized, for example, by diluting a fluorescent dye, can be controlled by the volume of each of the combined areas. Such a SlipChip design was used to screen the conditions for crystallization of a soluble protein, glutaryl-CoA dehydrogenase from *Burkholderia pseudomallei*, against 48 different reagents; each reagent was tested at 11 different mixing ratios, for a total of 528 crystallization trials, each on the scale of ~12 nL. This experiment was conducted using 3 identical SlipChip devices, each screening 16 different reagents. The total consumption of the protein sample was ~10 µL. Conditions for crystallization were successfully identified. The crystallization experiments were successfully scaled up in plates using the conditions identified in the SlipChip. Crystals were characterized by X-ray diffraction and provided a protein structure in a different space group and at a higher resolution than the structure obtained by conventional methods. The user-loaded SlipChip reliably handles fluids of diverse physicochemical properties, such as viscosities and surface tensions. Quantitative measurements of fluorescence intensities and high-resolution imaging were straightforward to perform in these glass SlipChips. Surface chemistry was controlled using fluorinated lubricating fluid, analogous to the fluorinated carrier fluid used in plug-based crystallization. This approach can be used in a number of areas beyond protein crystallization, especially those areas where droplet-based microfluidic systems have demonstrated successes, including, for example, measurements of enzyme kinetics and blood coagulation, cell-based assays, and chemical reactions.

In certain embodiments, the SlipChip can be used to combine a sample with many different reagents, each at many different mixing ratios, to perform multiplexed nanoliter-scale experiments in a user-loaded fashion. In certain embodiments, this can be done without the need for equipment external to the SlipChip, such as extra fluid-handling equipment. Multiplexed experiments are common in the areas of biological assays, chemical synthesis, crystallization of proteins and any area where chemical space is widely explored. U.S. Patent Application 61/162,922, incorporated by reference in its entirety herein, describes additional features and embodiments of the SlipChip. Wide exploration of chemical space benefits from technologies for faster experiments and lower consumption of samples, both to make these processes more productive and to reduce the amount of chemical waste. Microfluidic technology has both the capacity for high throughput screening and the ability to manipulate fluids on nanoliter and smaller scales. Although various microfluidic systems have been developed for such applications, these systems often require pumps, valves, or centrifuges. Certain embodiments of the SlipChip can be used to perform multiplexed microfluidic reactions without pumps or valves and its operation, in certain embodiments, requires only pipetting of a sample into the chip followed by slipping one part of the chip relative to another to combine the sample with pre-loaded reagents and initiate the reactions. (Additional exemplary means of configuring the SlipChip for slipping are described in Chung, et al., Lab Chip, 2009, 9, 2845-2850, incorporated by reference herein in its entirety.) In certain embodiments of the SlipChip the sample is combined with pre-loaded reagents. For certain embodiments, pre-loading the reagents onto the chips in a centralized facility and distributing chips to researchers is attractive to dramatically simplify the experiment for the user. In certain embodiments, a SlipChip does not have to be pre-loaded with reagents. The inventors have demonstrated that the SlipChip can be used to perform multiplexed nanoscale experiments with many different reagents, each at multiple different mixing ratios, allowing exploration of chemical space on the regional scale.

The inventors used this approach to screen conditions for crystallization of a soluble protein. Obtaining crystals of proteins remains one of the bottlenecks to solving their structures and elucidating their functions at the molecular level. Getting "diffraction-quality" crystals requires high throughput screening of multiple precipitants at various concentrations, i.e., performing, for example hundreds or thousands of crystallization trials. Microfluidic technology using either valves or droplets to accurately handle nanoliter and even picoliter volumes has been described, and has also been applied to crystallization of proteins. Although these two approaches can successfully crystallize proteins, most individual laboratories are still setting up crystallization trials by pipetting microliters of solutions into 96-well plates, suggesting that there is still a need for a system for crystallizing proteins that is simple, inexpensive, fast, and controllable. Here we describe embodiments of a user-loaded SlipChip that satisfies these criteria.

In some embodiments of a user-loaded SlipChip, the two plates of the SlipChip can be aligned such that the sample areas and sample ducts are aligned to form a continuous fluidic path, and the reagent areas and reagent ducts are offset. The sample can be loaded through a continuous fluidic path formed by overlapping sample areas (top plate) with sample ducts (bottom plate). The device can be slipped such that the reagent areas (bottom plate) and reagent ducts (top plate) are now aligned. Reagents can be loaded into the individual fluidic paths formed by overlapping reagent areas and sample areas. The device can be slipped a second time, and the sample areas from the top plate are exposed to the reagent areas of the bottom plate. The order of loading reagents and sample can be determined by the user.

In one embodiment of the invention, the SlipChip was used to screen a protein sample against 16 different precipitants, at 11 mixing ratios each, for a total of 176 experiments, each on the scale of ~12 nL, and requiring only 3.5 µL of the protein sample for all of the experiments. The SlipChip contained 16 separate fluidic paths for the reagents, each path with 11 areas, and a single, continuous fluidic path for the protein sample with 176 areas. In some embodiments of the SlipChip, the inlets for fluidic paths of reagents were spaced in a way to match the spacing of areas in a 96-well plate and spacing of tips in a multichannel pipettor. This SlipChip consisted of two plates. The top plate contained separate inlets for the reagent and the sample, ducts for the sample, and areas for the reagent. The bottom plate contained ducts for the reagent which were connected to an inlet on the top plate, areas for the samples, and an outlet. The two plates were separated by a layer of lubricating fluid, for which the inventors used fluorocarbon, a mixture of per-fluoro-tri-n-butylamine and perfluoro-di-n-butylmethylamine (FC-40). When the two plates were first assembled, the inlet and areas for the reagent in the top plate were aligned on top of the ducts for the reagent in the bottom plate. In this orientation, each reagent was pipetted into the inlet, flowed through the ducts, and filled the areas. After loading the reagents, the top plate of the chip was "slipped" to a new orientation, where the ducts for the sample in the top plate were aligned on top of the areas for the sample in the bottom plate. In this orientation, the sample was pipetted into the inlet, flowed through the ducts, and filled the areas. After loading both sample and reagents, the top plate of the chip was slipped again to position the areas for the reagent on top of the areas for the sample and initializing the interaction between the reagent and the sample by diffusion.

In one embodiment of a user-loaded SlipChip the top plate consisted of an outlet duct, a reagent inlet, a sample inlet aligned to sample ducts, and reagent areas. The bottom plate consisted of an outlet aligned with reagent ducts and sample areas. The top plate and bottom plate were assembled and filled with fluorocarbon to generate a SlipChip ready for use. In this orientation, a continuous fluidic path was formed by the reagent inlet, the reagent areas, and the outlet. A reagent was introduced by pipetting. The reagent flowed through the continuous fluidic path and filled the reagent areas. The chip could be slipped into a second position. In this second position, a continuous fluidic path was formed by the sample inlet, the sample ducts, and the sample areas. The sample may be introduced by pipetting. The sample flowed through the continuous fluidic path and filled the sample areas. The chip could be slipped again into the third position, where the reagent areas were aligned on top of the sample areas, and the sample and reagent in the aligned areas combined by diffusion.

In certain embodiments, during the slipping steps an undesired thin film of reagent solution can form between the two plates of the SlipChip. This thin film can, in certain embodiments, connect the duct for the reagent to the area for the reagent instead of keeping them separated. Cross-contamination after the slipping steps can be minimized by controlling the contact angle between the solutions (sample or reagents) and the plates of the SlipChip, measured under the lubricating fluid. The inventors measured the contact angle under the lubricating fluid used for certain embodiments, fluorocarbon (FC), and determined that, for certain embodiments, a contact angle above ~130° is preferred to minimize cross-contamination. To confirm this, when the inventors loaded a solution of reagents containing no surfactants and having a contact angle of 139°, reagents did not get trapped between the plates of the SlipChip after the first slipping step. The contact angle preference was found to be the same for the second slipping step; when the inventors added surfactant to the sample solution, the contact angle dropped to 110°, and a thin film of the surfactant solution was trapped between the two plates of the SlipChip. To minimize this problem for certain embodiments, the inventors spin-coated the plates with thin layers of fluorinated ethylene propylene (FEP) increasing the contact angle to 154°. After spin coating, the slipping steps were performed without cross-contamination.

Using this embodiment of the SlipChip, the inventors controlled the volumes, and thus the mixing ratio, of both the sample and reagents that were combined into each trial. The inventors designed this SlipChip with areas for reagent and samples such that the total volume of a trial, created by slipping to combine the two areas, was always ~12 nL, and the mixing ratio of reagent and sample in each trial varied from 0.67:0.33 to 0.33:0.76 by volume, with nine evenly spaced ratios in between.

Experimental results using a fluorescent dye solution as the sample and a buffer solution as the reagent confirmed that this design did lead to a controlled mixing ratio in each of the 11 areas. The relationship between the relative concentrations of the sample from the experiment and the predicted concentrations based on the design showed good agreement: the disparity between the experimental and predicted concentrations was lower than 10% for all except one of the areas.

In one embodiment of the present invention, the SlipChip had areas for the sample in the bottom plate containing a fluorescent dye solution and areas for the reagent in the top plate containing a buffer solution. Each area was a different size and held a different volume of fluid. Areas ranged in volume from 8 nL (relative volume of 0.67) to 4 nL (relative volume of 0.33). Once the chip was slipped to combine the reagents and the sample, the total volume of a trial was always 12 nL. A graph of the relative concentrations of the diluted sample from the experiment plotted against the relative concentrations that were predicted based on the designed volume showed good agreement between the experimental and predicted concentrations (slope=0.98; $R^2$=0.9938). The concentration was inferred from the measurements of fluorescent intensities. A histogram of the number of areas with different disparity values was generated. The disparity was calculated as the percentage difference in concentration between the experiment results and the predicted concentration, and takes into account errors and deviations in fabrication of the areas, filling of the areas, slipping, and measurements of intensity.

The inventors identified the variability in reagent concentrations using this approach with crystallization of a model membrane protein, the photosynthetic reaction center (RC) from *Blastochloris viridis*. Seven replicate trials, each with 11 different mixing ratios of a precipitant (3.2 M $(NH_4)_2SO_4$ in 40 mM $NaH_2PO_4/Na_2HPO_4$, pH 6.0) and RC, were performed on the SlipChip and were reproducible. Different mixing ratios were randomly arranged across the rows of the SlipChip. That is, instead of beginning at a mixing ratio of 0.33 precipitant to 0.67 protein and ending at a mixing ratio of 0.67 precipitant to 0.33 protein with evenly spaced mixing ratios in between, the areas were arranged from left to right in the following order with regard to the relative precipitant concentration: 0.33, 0.63, 0.4, 0.57, 0.47, 0.5, 0.53, 0.43, 0.6, 0.37, and 0.67. This arrangement was chosen so that any artifacts of manufacturing or evaporation that might systematically skew the results from one side to another could be easily differentiated from the effects of mixing ratios. This arrangement also kept the distance between two adjacent areas similar, keeping the duct length similar to the area size, making fabrication of the SlipChip simpler. The results obtained were the same as when the different mixing ratios were arranged sequentially across the rows of the SlipChip, indicating that any effects due to manufacturing or evaporation are minimal.

To help understand the behavior of crystallization, the inventors digitally re-arranged the microphotographs of the areas in order of increasing concentration of the precipitant. At mixing ratios of precipitant to protein from 0.33:0.67 to 0.43:0.57, none of the seven trials formed protein crystals. At a mixing ratio of 0.47:0.53, one trial formed protein crystals, and at 1:1 four trials formed protein crystals. At mixing ratios of 0.53:0.47, 0.57:0.43 and 0.6:0.4, all seven trials formed protein crystals. At 0.63:0.37, all seven trials formed precipitate. At 0.67:0.33, two trials formed protein crystals while the remaining five formed precipitate. Crystallization of RC was found to be sensitive to precipitant concentration. As the inventors increased the relative concentration of precipitant, the inventors observed a transition from the protein remaining in solution to crystallizing to precipitating. Decreasing protein concentration was observed to reduce nucleation to a certain extent. Crystallization outcome was not monotonic with mixing ratio, with regions of larger single crystals separated by regions of microcrystals. In addition to the seven rows used for the seven experiments described here, on this chip two rows were intentionally left blank and the additional seven trials were performed at a higher concentration of precipitant.

The inventors also screened the conditions for crystallization of protein samples using many different reagents, each at many different mixing ratios, on a single user-loaded SlipChip. The inventors chose a soluble protein as the target: glutaryl-CoA dehydrogenase from *Burkholderia pseudomallei*. The protein sample was obtained from the Seattle Structural Genomics Center for Infectious Disease (SSGCID). It was screened in parallel without the use of a SlipChip to yield crystals under vapor diffusion conditions in conditions using 20% (w/v) PEG-3000, 0.1 M HEPES pH 7.5, 0.2M NaCl (PDBid 3D6B). These crystals yielded a structure of 2.2 Å resolution and space group $P2_12_12_1$ (PDBid 3D6B). Without any knowledge of those crystallization conditions, the protein was screened on an embodiment of the SlipChip against 48 different reagents from a home-made screening kit based on the Wizard screen. For each reagent, 11 different mixing ratios of protein sample and reagent were screened, ranging from 0.33:0.67 to 0.67:0.33 as described above. The screen successfully identified two conditions for crystallization of the protein. From these results, optimal conditions were chosen: a 0.57:0.43 mixing ratio with 45% (w/v) PEG-400, 0.2 M $MgCl_2$ and 0.1 M Tris, pH 7.8 and a 0.67:0.33 mixing ratio with 30% (w/v) PEG-8000 and 0.1 M Hepes, pH 7.8. The latter condition is similar, but not identical, to the one identified by using traditional technologies at SSGCID. Each of these conditions was reproduced in area plates, and crystals were obtained in both cases. The crystals from the area plates diffracted X-rays at resolutions of 1.6 Å, space group P21 and 2.9 Å, space group P212121 respectively. Consequently, the inventors determined the structure of the protein at the resolution of 1.73 Å, with the data set collected from the crystal that diffracted X-rays to the higher resolution, 1.6 Å, and the inventors could assign the loops missing in the 2.2 Å $P2_12_12_1$ structure.

In some embodiments the SlipChip does not require external equipment for operation. For example, in certain embodiments, the sliding can be done manually. In certain embodiments internal guides can be used to constrain the motion of the plates relative to one another. In some embodiments, the results of a reaction or reactions carried out on the device can be read out without specialized equipment, for example, using widely available equipment e.g., a camera on a cell phone, or by eye, or using a barcode scanner. In certain embodiments, readout is facilitated by having each area of the device function as a pixel in a digital display, wherein different results produce different overall patterns that can be perceived and/or interpreted by a human and/or a machine.

In certain embodiments of the present invention, a user-loaded, SlipChip can be used to perform multiplexed reactions by screening many different reagents against a substrate at different mixing ratios and accurately meter nanoliter volumes. Certain embodiments of the SlipChip can be delivered to researchers preloaded with reagents at multiple mixing ratios or user-loaded at the site of use, depending on the requirements of a given application. The fluid paths can be designed to include extra ducts to increase fluidic resistance and to provide adequate filling of all areas. This method is functionally akin to the droplet-based hybrid method where many different conditions are screened in a droplet-based array. The inventors have demonstrated the use of the SlipChip in screening conditions for crystallization for a soluble protein. X-ray diffraction data for the protein were obtained by replicating crystallization conditions in well plates, demonstrating that crystallization conditions identified in a SlipChip can be reliably scaled up outside of the SlipChip. Crystallization by free interface diffusion on a different embodiment of a SlipChip can be performed and, in yet another embodiment, a composite SlipChip can be used to perform both microbatch and free interface diffusion crystallizations in parallel.

In addition to crystallization, user-loaded SlipChip embodiments are applicable to a number of other multiplexed reactions and assays where testing both different reagents and their concentrations is desirable. A fluorinated lubricating fluid, for example, can be used to directly transfer established approaches for control of surface chemistry into certain embodiments of the SlipChip. Assays similar to those performed in plug-based systems, such as those using enzymes, and cells can be performed in certain embodiments of the SlipChip. The inventors found imaging certain embodiments of the SlipChip to be readily accomplished, as positions of all areas are defined. Certain embodiments of user-loaded SlipChips can be used for those applications where droplet-based approaches, especially the hybrid approach, have been demonstrated. In general, attractive applications of user-loaded SlipChips include diagnostics, drug discovery, combinatorial chemistry, biochemistry, molecular biology and materials science.

Example

Chip Design and Fabrication. Slipchip was fabricated using glass etching fabrication of SlipChip as described elsewhere in this application, except for the following changes: In this example, ~45 minutes of etching was used to yield a depth of ~60 μm. Access holes were drilled with a diamond drill bit 0.030 inches in diameter. The surfaces of the etched glass plates were cleaned with Millipore water, followed by ethanol and subjected to an oxygen plasma treatment before silanization or Fluorinated Ethylene Propylene (FEP) coating.

Spin Coating FEP. An aqueous emulsion of FEP (TE-9568, Dupont) was first diluted 4 times with Millipore water before use. Following plasma cleaning the SlipChip device, the solution was evenly spread onto the device by using a plastic pipette. For spin coating, the spin speed was set at 1500 rpm and the process was executed for 30 seconds, or the spin speed was set at 2000 rpm and the process was executed for 30 seconds. Once the coating was finished, the SlipChip was transferred to a 120° C. oven and incubated for 10 minutes. After incubation, the SlipChip was baked at 250° C. on a hot plate for 10 minutes, followed by baking while increasing the temperature to 265° C. for another 10 minutes. After baking, the SlipChip was sintered at 340° C. on a hot plate for 1 minute. The sintered Chip was then cooled to room temperature.

Assembling the SlipChip. The SlipChip was assembled under FC-40. The bottom plate was first immersed into FC-40 in a Petri dish, with the patterns facing up. The top plate was then laid on top of the bottom plate, with the patterns facing down. The two plates were aligned into the position, by moving them relative to each other and then fixed by using four micro binder clips. The SlipChip was ready for use after the extra FC-40 on the surface was removed.

Measuring Contact Angles. The plate of the SlipChip was first immersed into fluorocarbon in a tank. The plate, facing down, was clamped by two micro binderclips on each end to create a gap between the plate and the bottom of the tank. 5 μL of the measured aqueous solution was pipetted into the gap, and the aqueous droplet contacted the plate due to its buoyancy in the surrounding fluorocarbon. The contact angle of the droplet on the substrate was then measured by using an optical contact angle meter (Ramé-Hart Instrument Co., Model 500).

Food Dye Assays. All the solutions used for food dye assays were filtered with a 0.45 μm PVDF syringe filter before use. Four food dyes (brown, pink, red, and blue, Ateco, Glen Cove, N.Y.) were diluted ~10 times from their stock solutions and were pipette-loaded into 16 reagent ducts. To load each duct, 4 μL of dye was first pushed through the inlet using a pipette until the dye solution emerged from the outlet. After loading reagents, the SlipChip was slipped to form a continuous fluidic path for the sample. A green dye was diluted 20 times and then loaded through the sample inlet. Using a pipette 4 μL of dye was loaded into the Chip until all the sample ducts were fully filled. Once the sample was loaded, the SlipChip was slipped again to mix the solutions by diffusion.

Quantifying Mixing Ratio. The loading procedure was similar to that for the food dye assays. Two solutions, the fluorescent solution (44.8 μM Alexa-488 in 10 mM Tris, pH 7.8) and the buffer (10 mM Tris, pH 7.8), were used. The outermost four fluidic paths, each path containing 11 areas, were loaded with the fluorescent solution, and the remaining 12 fluidic paths were loaded with the buffer. The fluorescent solution was also used as the sample. After the areas for the reagent and areas for the sample were combined, the SlipChip was incubated for one hour in the dark to allow complete mixing. The SlipChip was then slipped a second time to separate the areas for the reagent from those for the sample. The outermost four fluidic paths containing the fluorescent solution were not diluted, providing a control for calibrating intensity measurements.

Quantifying Mixing Ratio: Measuring Fluorescence. To confirm that the fluorescence intensity of Alexa-488 is linearly correlated with the concentration in the working range of the fluorescent microscope, the inventors made a dilution curve on a SlipChip. First, four solutions, including one buffer (10 mM Tris, pH 7.8) and three solutions at concentrations of ¼, ½, and 1 times the concentrations of the original Alexa-488 solution (44.8 micromolar in 10 mM Tris pH 7.8), were loaded into four separated fluidic paths in a pre-assembled user-designed SlipChip. The top plate was slipped relative to the bottom plate so that all the areas were separated. The fluorescence intensity of the loaded areas on the bottom plate was then measured by using a Leica DMI6000 microscope (Leica Microsystems) with a 10×0.4 NA Leica objective and a Hamamatsu ORCAER camera. A GFP filter was used to collect Alexa-488 fluorescence. An exposure time of 4 ms was used. Images were acquired and analyzed by using Metamorph imaging system version 6.3r1 (Universal Imaging). To extract the intensity of the fluorescent signal, a region of 100 pixels by 100 pixels was selected in the middle of every area of interest. The average integrated intensity of the regions belonging to areas with the same Alexa-488 concentration (five areas for each concentration) was plotted against the corresponding concentration to obtain a calibration curve.

The fluorescent measurement was then performed by using the sample areas. The inventors measured the fluorescence intensity of the areas in the bottom plate. This ensured that the working parameters for measuring fluorescence intensity were consistent. The same setup for the fluorescent microscope was used in this experiment as was used in making the dilution curve. The intensity from the measurements was then converted to concentration based on the dilution curve. To calibrate the microscope, the fluorescence intensity of a fluorescence reference slide for GFP was recorded and used for background correction. Images were acquired and analyzed by using Metamorph imaging system version 6.3r1 (Universal Imaging).

Quantifying Mixing Ratio: Characterization of area sizes. The wet etching of glass is assumed to be isotropic, and the speed of etching is the same in all directions. The size of the areas after etching was measured by using a Leica MZ 16 Stereoscope calibrated by a micro-ruler and the volume of the areas were calculated accordingly.

Quantifying Mixing Ratio: Data analysis. To calibrate the intensity measurements, the background intensity was first subtracted from all the fluorescent images. The intensity of each area was then extracted from the integrated intensity of a 100 pixel by 100 pixel region located at the center of each area. The dilution ratio for each area was obtained by dividing the intensity of that area by the intensity of a area of the same size that did not get diluted.

RC crystallization. A sample of the photosynthetic reaction center (RC) from *Blastochloris viridis* was obtained. The loading procedure was similar to that for the food dye assays. The precipitant (3.2 M $(NH_4)_2SO_4$ in 40 mM $NaH_2PO_4/Na_2HPO_4$, pH 6.0) was loaded into seven reagent ducts and the protein sample (36 mg/mL RC in 0.07% (w/v) LDAO, 7% (w/v) 1,2,3-heptanetriol, 4.5% (w/v) triethylamine phosphate (TEAP), 17 mM $Na_2HPO_4/NaH_2PO_4$, pH 6.0) was loaded into the sample duct. The SlipChip containing the trials was then stored in FC-70 in a Petri dish at room temperature in the dark. The trials were monitored over 10 days to check for the formation of crystals.

Crystallization of glutaryl-CoA dehydrogenase from *Burkholderia pseudomallei* in SlipChip. The protein sample was obtained from the Seattle Structural Genomics Center for Infectious Disease (SSGCID). 48 precipitants from a homemade screening kit based on the Wizard screen were loaded into three SlipChips, 16 precipitants in each Chip; the same loading procedure was the same as in the food dye experiments. Each SlipChip was then immersed into FC-70 in separate Petri dishes. The Petri dishes were incubated at room temperature and the results were monitored for two weeks. Images of areas containing crystals were taken by a SPOT Insight camera (Diagnostic Instruments, Inc., Sterling Heights, Mich.) coupled to a Leica MZ 16 Stereoscope.

Crystallization of glutaryl-CoA dehydrogenase from *Burkholderia pseudomallei* in well plates, not Using a SlipChip. Once a crystallization condition for glutaryl-CoA dehydrogenase was identified, the experiment was scaled up in a sitting-drop well plate (Hampton research) using the microbatch method. At the same mixing ratio identified by the screening experiments on the SlipChip, the protein sample was mixed with the precipitant to obtain a final volume of 3 μL in the well. In the reservoir, Millipore water was mixed with the precipitant to give the same precipitant concentration as in the well; the final volume was 600 μL. Each condition had one duplicate. The plate was then sealed with sealing tape (Hampton research) and incubated at room temperature. Images of crystals were taken by a SPOT Insight camera (Diagnostic Instruments, Inc., Sterling Heights, Mich.) coupled to a Leica MZ 16 Stereoscope.

X-ray diffraction and data processing. Crystals for x-ray diffraction were obtained from the well plate experiments. For precipitants that contained PEG-400, the mother liquor was used as a cryo-protectant, and the concentration of PEG-400 was changed to be 25% (w/v). For other precipitants, the mother liquor plus 20% (v/v) glycerol was used as a cryo-protectant. A crystal was first transferred from the original well to the well containing the cryo-protectant by using a nylon loop. Then the crystal was frozen in liquid nitrogen. The X-ray diffraction assays were performed at GM/CA Cat station 23 ID-D of the Advanced Photon Source (Argonne National Laboratory). X-ray data were collected at 100 K using a wavelength of 1.0332 Å.

The data were processed and analyzed using HKL-2000.

X-ray structure determination of glutaryl-CoA dehydrogenase. The structure of glutaryl-CoA dehydrogenase was solved by molecular replacement using the PDBid 3D6B structure as a starting model and the MOLREP program in CCP4 suite. The data collected from crystals grown in the condition containing PEG-400 were used. The rigid-body, positional, and temperature factor refinement was performed using maximum likelihood target with the program REFMAC5. The SigmaA-weighted 2Fobs-Fcalc and Fobs-Fcalc Fourier maps were calculated using CCP4. The Fourier maps were displayed and examined in COOT. The search for new solvent molecules was performed with help of COOT. The coordinates and structure factors have been deposited in the Protein Data Bank with entry code 3II9 (pending).

In certain embodiments of the SlipChip, multi-parameter screening can be performed for nanoliter protein crystallization combining free interface diffusion and microbatch methods. In certain embodiments of the present invention, a SlipChip-based free interface diffusion (FID) method and a SlipChip-based composite method that simultaneously performs microbatch and FID crystallization methods in a single device can be performed.

In one embodiment, the FID SlipChip was designed to screen multiple reagents, each at multiple diffusion equilibration times, and was used to screen conditions for crystallization of two proteins, enoyl-CoA hydratase from *Mycobacterium tuberculosis* and dihydrofolate reductase/thymidylate synthase from *Babesia bovis* against 48 different reagents at 5 different equilibration times each, consuming 12 μL of each protein for a total of 480 experiments using three SlipChips. The composite SlipChip was designed to screen multiple reagents, each at multiple mixing ratios and multiple equilibration times, and was used to screen conditions for crystallization of two proteins, enoyl-CoA hydratase from *Mycobacterium tuberculosis* and dihydrofolate reductase/thymidylate synthase from *Babesia bovis*. To prevent cross-contamination while keeping the solution in the neck ducts for FID stable, the plates of the SlipChip were etched with a pattern of nano-scale areas. This nanopattern was used to increase the contact angle of aqueous solutions on the surface of the silanized glass. Nanopatterning is generally described in Z. Burton and B. Bhushan, Nano letters, 2005, vol. 5, no8, pp. 1607-1613, incorporated by reference in its entirety. The composite SlipChip increased the number of successful crystallization conditions and identified more conditions for crystallization than separate FID and microbatch screenings. Crystallization experiments were scaled up in well plates using conditions identified during the SlipChip screenings, and X-ray diffraction data were obtained to yield the protein structure of dihydrofolate reductase/thymidylate synthase at 1.95 Å resolution. This free-interface diffusion approach provides a convenient and high-throughput method of setting up gradients in microfluidic devices, and can also be used for cell-based assays.

A SlipChip-based approach can be used to simultaneously perform two methods for protein crystallization, microbatch and free interface diffusion (FID), in a single microfluidic device. Currently, there are challenges to protein crystallization. To crystallize proteins, a large chemical space must be searched to determine the conditions required. The search for the right precipitants and the right concentrations of protein and precipitant is expedited by faster assays and smaller sample sizes, and a simple, fast, and controllable system advances the discovery of new protein structures. A particularly attractive method to crystallize proteins is nanoliter-scale FID because it explores the phase diagram for crystallization as both the concentration of protein and the concentration of precipitant are gradually changed by diffusion, provides a higher transient supersaturation level for crystal nucleation, and eliminates precipitation induced by fast mixing. Nanoliter-scale FID is consequently efficient for crystallization, but currently it is only implemented with valve-based systems. FID is mechanistically very similar to the well-established counter diffusion methods that are typically implemented on microliter scales, including chip-based and gel acupuncture-based approaches. The use of valves in FID requires external control equipment, and valves are often composed of PDMS. PDMS devices have the additional complication of requiring control of the atmosphere and evaporation. Valve-free approaches to implement FID simplify the method and make it more widely available. Different methods of crystallization explore different paths towards the equilibrated condition where crystals of protein form, and therefore yield different crystallization results. These methods can be modified to alter the kinetics of crystallization and thus explore different routes to form crystals of proteins; however, different methods require different techniques to combine the protein solution and precipitant solution. While it is desirable to use more than one method of crystallization, it is technologically challenging to use two techniques in one experiment.

The SlipChip technology described herein addresses these challenges. It has been demonstrated in both pre-loaded and user-loaded formats. In some embodiments, the user-loaded format can be used to demonstrate an FID technique based on a SlipChip and also combined FID and microbatch techniques in one "composite" SlipChip.

The inventors designed an embodiment of the SlipChip to incorporate the FID method. This SlipChip was designed to screen a sample against 16 different precipitants at five different equilibration times. Each equilibration time was investigated in duplicate, for a total of 160 assays in a single SlipChip. The SlipChip can be configured to form 16 separate fluidic paths for the precipitants, each containing 10 areas, and a single fluidic path for the protein sample containing 160 areas. To incorporate the FID method, when the SlipChip was "slipped" to connect the protein areas and the precipitant areas, the microducts (ducts 21 μm in depth) that had formed the continuous fluidic path for the protein sample became the neck duct connecting the protein area to the precipitant area. By gradually increasing the distance between the protein areas and the precipitant areas, the length of the neck was increased from 91 μm to 491 μm; by decreasing the width of the ducts, the width of the neck was decreased from 104 μm to 58 μm. The geometry of the necks, defined as the length of the neck duct divided by the cross-sectional area of the duct, was consequently altered.

A SlipChip was designed to screen a protein against 16 different precipitants using the FID method of crystallization. Multiple precipitants, as well as multiple equilibration times for mixing the protein with each precipitant, can be screened on the same SlipChip. The top plate contains ducts for the protein and ducts for the precipitant. The ducts for the protein will become the neck ducts that connect the protein areas and the precipitant areas, and these ducts gradually decrease in width from left to right, gradually changing the equilibration time. The bottom plate has areas for the protein and areas for the precipitant. The distance between the areas for the protein and areas for the precipitant is gradually increased from left to right, gradually changing the equilibration time. When the two plates are assembled, the fluidic path for the protein and the fluidic path for the precipitants are formed. After "slipping", protein and precipitant areas from the bottom plate are bridged by narrow ducts in the top plate.

The geometry of the neck controlled the equilibration time, and the inventors found that the equilibration time increased linearly with the neck geometry, consistent with numerical simulations. Equilibration time occurring in the steady state with fully developed diffusion profiles is different than the time to establish these profiles; the latter time scales with the square of distance. The FID assays were set up easily in the SlipChip, requiring no valves and only involving pipetting and slipping. In this approach, the ducts for the protein sample were used to set up the FID assays, so little sample was wasted. Because the necks were designed to be thin compared to the areas containing precipitant or protein, the change in volume caused by changing the neck geometry was negligible compared to the total volume of the crystallization assay. The volume of the neck constituted only 4-8% of the total volume of the crystallization trial. The inventors have demonstrated how changing the equilibration time affects protein crystallization.

Changing the geometry of the duct changes the equilibration time in the SlipChip. Each condition represents a different equilibration time, and was done in duplicate. Diffusion profiles were obtained for various neck geometries by using a model fluorescent dye, DTPA. Average intensities in the area for protein were measured by linescan through the areas. The diffusion profiles depended on the neck geometry. The 50% equilibration time and neck geometry are linearly related. 50% equilibration time was defined as the time it took for the average intensity in the protein areas to reach half of the maximum equilibrated intensity; neck geometry was defined by the length of the neck divided by the cross-sectional area of the neck. At the shortest equilibration time, only precipitates were obtained. As equilibration time increased, fewer, larger crystals were obtained.

The inventors first demonstrated the effect of equilibration time on the kinetics of crystallization by crystallizing the photosynthetic reaction center from *Blastochloris viridis* using the FID SlipChip. The inventors demonstrated that as the equilibration time increased, the protein progressed from precipitate to many small crystals to fewer larger crystals. The inventors then used the FID SlipChip to screen crystallization conditions for two proteins, enoyl-CoA hydratase from *Mycobacterium tuberculosis* and dihydrofolate reductase/thymidylate synthase from *Babesia bovis*. Approximately 12 µL of each protein was consumed to screen against a screening kit containing 48 precipitants for a total of 480 experiments. This was performed on three SlipChips, each SlipChip with 16 precipitants and five conditions in duplicate per precipitant, for a total of 160 experiments per chip and consuming 4 µL of protein per chip. The inventors also screened both proteins using certain embodiments of the user-loaded SlipChip using the microbatch method against the same precipitants, and compared the microbatch results to the FID results.

The two proteins assayed represent different kinetics of nucleation: enoyl-CoA hydratase nucleates quickly while dihydrofolate reductase/thymidylate synthase nucleates slowly. For enoyl-CoA hydratase, FID minimizes nucleation and yields crystals in conditions where only precipitation is observed in microbatch. Using the FID SlipChip, the inventors obtained crystals of enoyl-CoA hydratase under several conditions. Under conditions that yield crystals in both methods, such as for the photosynthetic reaction center from *Blastochloris viridis*, FID yields fewer large crystals while microbatch yields many small crystals. For dihydrofolate reductase/thymidylate synthase assays where crystals formed, few crystals were obtained in each trial, indicating that the crystallization of dihydrofolate reductase/thymidylate synthase is nucleation-limited. Only one precipitant condition produced crystals using the FID method, but three precipitant conditions produced crystals in the microbatch method. This implies that proteins with different nucleation kinetics will require different crystallization techniques, and using multiple techniques in parallel increases the likelihood of identifying suitable conditions to produce protein crystals.

In another embodiment of the SlipChip the two methods (FID and microbatch) were screened simultaneously in addition to identifying a precipitant and its concentration for crystallization. In certain embodiments a continuous fluidic path for the protein sample and 16 separate fluidic paths for different precipitants can be configured. In this embodiment, areas designed for microbatch experiments and areas designed for FID experiments were in each fluidic path, allowing a single protein to be screened against 16 precipitants each at multiple mixing ratios and equilibration times. In this embodiment FID areas have multiple mixing ratios (1:2, 1:1, and 2:1) for a total of 176 experiments per chip, five microbatch experiments and six FID experiments for each of 16 precipitants.

In the composite SlipChip, multiple precipitants and multiple volumes and equilibration times for mixing the protein can be screened on the same SlipChip using both microbatch and FID methods. The top plate contains areas for the protein and ducts for the precipitant (microbatch) and ducts for both the protein and precipitant (FID). The bottom plate has ducts for the protein and areas for the precipitant (microbatch) and areas for both the protein and precipitant (FID). When the two plates are assembled, the fluidic path for the protein and the fluidic paths for the precipitants are formed to fill areas for both microbatch and FID methods. In microbatch the two areas are aligned with one another, in FID the two areas are connected by a narrow duct.

In certain embodiments, unwanted cross-contamination could potentially occur during the slipping step: a thin film of solution can form between the two plates of the SlipChip, connecting the ducts and areas that should be separated. To minimize unwanted cross-contamination, a contact angle between the solutions and the plates of the SlipChip in the lubricant fluorocarbon of greater than ~130° is preferred, and in other experiments, it is preferred to spin-coat the plates with thin layers of fluorinated ethylene propylene. In certain embodiments of the FID method, the solution in the neck duct is not stable at such high contact angles and tends to break up to minimize the surface energy. The inventors solved this problem by patterning the surface of the SlipChip to make it more hydrophobic than the surface inside the areas and neck ducts. To do so, the inventors introduced an extra step of fine etching before washing off the coating left from the previous etching steps. This generated patterns of 10 µm diameter areas that were 250 nm deep. Without nanopatterning, the average contact angle of a 0.1% N,N-Dimethyldodecylamine N-oxide (LDAO) sample solution was only 112.2°, with nanopatterning, the average contact angle of the same LDAO sample solution was 134.2°. In addition, nanopatterning decreased the surface area of glass that was directly exposed to the solution edge during the slipping step. The small areas trapped lubricating fluid and created a barrier to prevent solution leakage.

The performance of the nanopatterning was affected by the geometry of the nanopattern, including the nano-scale area size, spacing, and etched depth. These parameters can be varied, and the contact angle of each nanopatterning can be measured. Both the depth and the surface area of the nano-scale areas should affect the contact angle. Silanized glass with nanopatterning typically had a contact angle higher than glass without nanopatterning, and the contact angle increased with the depth of etching. The contact angle was above 130° for those glass plates where the nanopatterning depth was in the range of 196 nm ~3.81 μm. For nanopatterns with a depth of 3.81 μm, the maximum contact angle was 153.62° (RSD=1.01%, n=5, measured after 5 min of droplet setup). The contact angle decreased with time, as observed by measuring the contact angle 5 min later. The amount of the decrease was affected by the nanopattern depth. Nanopatterns with less than 200 nm depth had a faster decrease in contact angle than those nanopatterns that were deeper than 200 nm. The composite SlipChip was also used to screen conditions for crystallization of the same two proteins studied using separate FID and microbatch experiments, enoyl-CoA hydratase from *Mycobacterium tuberculosis* and dihydrofolate reductase/thymidylate synthase from *Babesia bovis*. The composite approach made the search for relevant crystallization conditions more efficient, as two routes to nucleation and crystal growth were investigated simultaneously, while the same small amount of protein (~12 μL) was consumed to screen each protein against the same screening kit. Both microbatch and free-interface diffusion components of the composite SlipChip functioned, and identified crystallization conditions for both proteins. In the composite SlipChip, the majority of conditions identified by separate microbatch and FID screenings were also identified. For enoyl-CoA hydratase, two new conditions not identified in either of the individual screens were picked up by the hybrid screen.

Screening crystallization conditions for proteins using the composite SlipChip matched results from microbatch and FID methods. All areas contained reagent 41 (45% (W/V) PEG-3000, 0.1 M CHES, pH 9.5). Using the microbatch method, crystals formed at a mixing ratio of 2:1 (protein: precipitate). Using the FID method, crystals formed at a mixing ratio of 1:2. The composite method produced as many or more crystallization hits than either microbatch or FID alone for both enoyl-CoA hydratase and dihydrofolate reductase/thymidylate synthase.

The inventors scaled up one of the three conditions for crystallization of dihydrofolate reductase/thymidylate synthase identified in the microbatch SlipChip. The condition chosen was the protein sample at a mixing ratio of 0.33:0.57 with 20% (w/v) PEG-8000, 0.2 M NaCl and 0.1 M CHES, pH 9.5. The inventors scaled up dihydrofolate reductase/thymidylate synthase instead of enoyl-CoA hydratase because dihydrofolate reductase/thymidylate synthase is more difficult to crystallize, as indicated by fewer recognized hits. The precipitant, 20% (w/v) PEG-8000, 0.2 M NaCl and 0.1 M CHES, pH 9.5, produced crystals with the best-defined shape at the chosen mixing ratio. It is straightforward to translate the microbatch method crystallization trial from SlipChips to well plates, and the inventors successfully obtained crystals from the scale up approach. The inventors collected a full X-ray diffraction data set and determined the structure at a resolution of 1.95 Å, space group P212121. The structure has been deposited in the Protein Data Bank, PBDid: 3KJR. The same protein was screened in parallel using Seattle Structural Genomics Center for Infectious Disease (SSGCID) and Accelerated Technologies Center for Gene to 3D Structure (ATCG3D) facilities to yield crystals using microfluidic microbatch in a crystal card in conditions using 20% (w/v) PEG-8000, 0.1 M CHES pH 9.5. These crystals yielded a 2.35 Å structure, space group P1 (PDBid 3D6B). Screens were conducted double-blind, without any information about crystallization conditions shared until after the screens were completed and crystals were obtained—the screening of crystallization of dihydrofolate reductase/thymidylate synthase on the SlipChip and the concomitant scale up assays were performed without any knowledge of conditions obtained by the screening in facilities SSGCID and ATCG3D. Similar conditions, sharing the same PEG and buffer and differing only by the presence of NaCl in the SlipChip screen, were independently discovered to yield structures. The inventors obtained a higher resolution structure, with a different space group.

The inventors have demonstrated a SlipChip-based FID approach to crystallize proteins and a composite SlipChip-based approach to use microbatch and FID crystallization techniques simultaneously. Certain embodiments of the SlipChip provide a simple and easy-to-use method to set up over 160 experiments in free interface diffusion and 176 experiments in both microbatch and free interface diffusion, and all assays can be setup simultaneously with a single slip. For applications such as protein crystallization, where each trial does not necessarily need to be controlled individually, the absence of valves dramatically simplifies both the execution of assays and fabrication of devices. Fabrication of devices is further simplified by using a SlipChip platform, because the SlipChip is compatible with inexpensive molding technologies and common plastics. More advanced techniques already demonstrated in plug-based crystallization techniques are compatible with the SlipChip design. In addition to screening multiple precipitants, mixing ratios, and equilibration times, the composite SlipChip enables the comparison of two different protein crystallization techniques on the nanoliter scale in the same device. By using a single device, the surface chemistries and solutions used are the same, and any advantage of one method over the other can be identified and realized. Microbatch corresponds to rapid mixing through a larger interface, leading to more rapid nucleation. Free interface diffusion corresponds to slower mixing through a smaller interface, corresponding to slower nucleation. Control of the neck geometry enables the continuum of methods bridging microbatch and FID methods. Crystallization based on counter diffusion approaches is mechanistically similar to FID methods. Counter diffusion for crystallization can be implemented on the SlipChip on smaller scale and in more multiplexed format than in traditional methods. The composite SlipChip provides a platform on which to assay many proteins and the opportunity to learn more about important characteristics of protein crystallization.

After crystallization conditions are identified, high-quality crystals suitable for X-ray diffraction are preferred for characterizing the crystals and determining protein structures. To produce crystals large enough for X-ray diffraction, typically a minimum trial volume of ~10 nl is required, and even much smaller crystals can be analyzed using, for example, recent advances in synchrotron x-ray science, so the crystals obtained in the SlipChip can be large enough for structural characterization. There are several options for obtaining X-ray diffraction data from crystals grown in a SlipChip including extraction of the crystals or in situ diffraction. In certain embodiments, the SlipChip is not sealed, therefore, the two plates can be separated and crystals extracted as has been done for a well-based chip. Diffraction in situ can prevent damage to the crystals during post-crystallization manipulations and can increase throughput. X-ray diffraction in situ can be performed in the SlipChip since the SlipChip can be constructed of material that is compatible with in situ diffraction, such as PDMS, PMMA, and cyclo-olefin-copolymers, or, if necessary, the glass can be etched to create areas with sufficiently thin walls.

If certain crystals grown in a SlipChip don't yield high-quality X-ray diffraction data, the crystallization experiments can be scaled up using the conditions identified by the SlipChip screenings. Microbatch experiments are easily scaled-up in well plates. Another success has been achieved using the same strategy with ribose-phosphate pyrophosphokinase from *Burkholderia pseudomallei*. A condition (20% (w/v) PEG-3350, 0.2M magnesium formate, pH 5.9) found by conventional vapor diffusion method yielded crystals in space group of I222. The crystal structure was determined at 2.3 Å resolution (PDBid: 3DAH). In parallel using an embodiment of the SlipChip, the inventors found a different condition (11% (w/v) PEG-8000, 37 mM sodium citrate, pH 5.5) yielding crystals in space group of P43212. The inventors obtained a data set at 1.83 Å with crystals produced by scaling up. Using other techniques, the FID approach can be less trivial to scale up because the diffusion profiles and kinetics need to be replicated and thoughtfully controlled on a larger scale. The predictable diffusion profile the inventors determined for FID SlipChip enables the rational design of scaled up scalable SlipChips both down to, for example, picoliter-scales and up to, for example, microliter-scales.

The technology described here has many applications beyond protein crystallization. For example, the nanometer-scale etching used to create a superhydrophobic surface will impact surface patterning technologies. In addition, the techniques used for the FID method can be expanded to control equilibration times when combining solutions in other experiments. This control of equilibration can be useful for setting up concentration gradients in a range of applications, e.g. when studying chemotaxis and in other cell-based assays.

Example
Fabrication of SlipChip with Nanopatterning

The inventors followed the glass etching fabrication procedure described elsewhere in the application with the following modifications. A blank glass plate (Soda-lime glass, thickness: 0.7 mm; chromium coating: 1025 Å; AZ photoresist: 1 µm) was first cut to be 3 in ×1 in. Step 1: The glass etching fabrication procedure was followed until the point where the backside of the glass plate was sealed with PVC tape. Next, the inventors placed cross marks for aligning the second photomask on the edge of the glass plate; these marks were also taped to prevent etching. In this example, the etching time was ~30 min to etch areas that were 40 µm deep into the glass plate. The plate was thoroughly rinsed with Millipore water and dried with nitrogen gas. Step 2: Using another photomask containing the design for the ducts and an etching time of ~15 min, 20 µm deep ducts were etched on to the glass plate using the same procedure as in Step 1. Care was taken to align the glass plate with the photomask. During this step, the 40 µm deep areas were further etched to be 60 µm deep. The plate was thoroughly rinsed with Millipore water and dried with nitrogen gas. Step 3: After ducts and areas were etched into the plate, the plate was aligned with a nanopatterning photomask and the same procedure was followed as in Step 1. After removing the chromium coating, the glass plate was immersed in 50:25:37.5 mmol/L HF/NH4F/HNO3 etching solution, and etched for 20 min at room temperature (~23° C.) to produce ~250 nm deep patterns over the surface. Finally, the glass plate was rinsed with ethanol to strip the undeveloped photoresist, and immersed in the chromium etchant to remove the chromium coating. The glass was then rinsed with ethanol and Millipore water and dried with nitrogen gas. The method described here integrates nanometer-deep designs and various micrometer-deep designs on one glass substrate. It can also be used to create nanometer/micrometer hybrid ducts for other nanofluidic/microfluidic applications. The etched patterns were measured with a Veeco Dektak 150 profilometer (Figure S2). The glass plates were cleaned and subjected to an oxygen plasma treatment, and then the surfaces were rendered hydrophobic by silanization in a vacuum desiccator for 3 hours with tridecafluoro-1,1,2,2-tetrahydrooctyl-1-trichlorosilane as previously described. After silanization, the glass plates were baked in a 120° C. oven for 30 min, rinsed by immersing in a tank of FC-3283, and dried in a 60° C. oven overnight.

FEP Spin Coating

Spin coating FEP was performed as described elsewhere in this application.

Measuring Contact Angles of Nanopatterning

Glass plates were etched with nanopatterns by using the nanopatterning photomask described in Step 3 of Fabrication of SlipChip with nanopatterning, and different nanoscale area depths were obtained by controlling the etching time. All glass was silanized and cleaned before measuring contact angles. The glass plate was immersed into fluorocarbon in a glass tank. The plate, with patterned surface facing down, was clamped by two micro binderclips on each end to create a gap between the plate and the bottom of the tank. 5 µL of the measured aqueous solution was pipetted into the gap, and the aqueous droplet with 0.1% LDAO contacted the plate due to its buoyancy in the surrounding fluorocarbon (FC-40). The contact angle of the droplet on the substrate was then measured by using an optical contact angle meter (Ramé-Hart Instrument Co., Model 500). The contact angle was measured immediately after the droplet contacted the glass plate and again 5 min after contact.

Food Dye Assay in a FID Device

A FID device was made with the method described above without nanopatterning or FEP coating. The two plates of the device were assembled under FC-40. In the resulting orientation, fluidic ducts for all 16 reagents and one sample were formed. All the solutions used for food dye experiments were filtered with a 0.45 µm PVDF syringe filter before use. Four food dyes (yellow, pink, red, and blue) were diluted ~10 times from their stock solutions and were pipette-loaded into 16 reagent ducts. To load each duct, 4 µL of dye was first pushed through the inlet using a pipette until the dye solution emerged from the outlet. A green dye was diluted 20 times and was mixed with 0.04% (w/v) LDAO to mimic a protein sample. The green dye was then loaded through the sample inlet. Using a pipette, 10 µL of the dye was loaded into the Chip until all the sample ducts were fully filled. Once the sample was loaded, the SlipChip was slipped such that the connections between adjacent areas were disconnected and the vertical ducts formed a bridging diffusion duct for the sample areas and relative reagents areas under it. Sequential images (time interval of 3 min) were taken with a Leica MZ 16 Stereoscope with a Plan APO 0.63× objective.

Fluorescent Dye Diffusion Assay in a FID Device

A FID device was made with the method described above with nanopatterning. The SlipChip was assembled and solutions were loaded as described for the food dye experiment. 250 µM MPTS in PBS buffer (1×, pH 7.4) was loaded by pipetting into two reagent ducts. 0.01% (w/v) LDAO solution was loaded into the sample duct to fill all sample areas. The SlipChip were slipped under a Leica MZ 16 Stereoscope to form 20 free interface diffusion experiments with 5 different duct geometries. The starting time point of FID was recorded with a timer. The device was quickly transferred to a Leica DMI6000 microscope (Leica Microsystems) with a 5×0.4 Leica objective and a Hamamatsu ORCAER camera. A DAPI filter with an exposure time of 20 ms was used to collect MPTS fluorescence. To calibrate the microscope, the fluorescence intensity of a fluorescence reference slide for the DAPI filter was recorded and used for background correction. Images were acquired and analyzed by using Metamorph imaging system version 6.3r1 (Universal Imaging) with multi-dimension acquisition function. Images were taken every 10 minutes. To obtain the average intensity in the sample area, the inventors obtained linescans on each sample area. The intensity along the linescan was averaged, and the average intensity was plotted over time. The time was corrected by accounting for the delay between setting up the FID experiments and the start of imaging.

Food Dye Assay in a Hybrid Device

A hybrid SlipChip was made by using the nanopatterning method described above. It was assembled under FC-40. In the resulting orientation, fluidic ducts for both 16 reagents and one sample were formed. All the solutions used for food dye experiments were filtered with a 0.45 µm PVDF syringe filter before use. Four food dyes (yellow, pink, red, and blue, Ateco, Glen Cove, N.Y.) were diluted ~10 times from their stock solutions and were pipette-loaded into 16 reagent ducts. To load each duct, 4 µL of dye was first pushed through the inlet using a pipette until the dye solution emerged from the outlet. A green dye was diluted 20 times and was mixed with 0.04% (w/v) LDAO to mimic a protein sample. The green dye was then loaded through the sample inlet. Using a pipette, 10 µL of the dye was loaded into the Chip until all the sample ducts were fully filled. Once the sample was loaded, the SlipChip was slipped such that the reagent areas overlapped with the sample areas in the microbatch sections, and the reagent areas were connected to the sample areas by the necks (ducts connecting the fluidic path of the sample before slipping) in the FID sections.

Crystallization of Enoyl-CoA Hydratase from *Mycobacterium tuberculosis* with Microbatch SlipChip.

The protein sample was obtained from the Seattle Structural Genomics Center for Infectious Disease (SSGCID). The microbatch SlipChips were made by glass etching, surface-coated by fluorinated ethylene propylene (FEP), and assembled under lubricant fluorocarbon, a mixture of perfluoro-tri-n-butylamine and perfluoro-di-n-butylmethylamine (FC-40). 48 precipitants from a home-made screening kit were loaded into three assembled SlipChips, 16 precipitants in each Chip. Precipitants were combined with the protein sample by slipping. Each SlipChip was then immersed into FC-70 in separate Petri dishes. The Petri dishes were stored in a 23° C. incubator and the results were monitored for two weeks. Images of areas containing the crystallization trials were taken over the two weeks by using a SPOT Insight camera (Diagnostic Instruments, Inc., Sterling Heights, Mich.) coupled to a Leica MZ 16 Stereoscope.

Crystallization of Enoyl-CoA Hydratase with FID Chip

The FID SlipChip for protein crystallization was made by using the nanopatterning method described above. 48 precipitants from a home-made screening kit were loaded into three SlipChips, 16 precipitants in each Chip; the loading procedure was the same as in the food dye experiments of FID Chip. After slipping, the precipitant areas and protein areas were connected in pairs by the protein neck to initiate FID experiments. Each SlipChip was then immersed in FC-70 in separate Petri dishes. The Petri dishes were stored in a 23° C. incubator and the results were monitored for two weeks. Images of areas containing crystals were taken over the two weeks.

Crystallization of Enoyl-CoA Hydratase with Hybrid SlipChip.

The hybrid SlipChip for protein crystallization was made by using the nanopatterning method described above. 48 precipitants from a home-made screening kit were loaded into three hybrid SlipChips, 16 precipitants in each Chip; the loading procedure was the same as in the food dye experiments of the hybrid Chip. After one step of slipping, both microbatch and FID experiments were set up. Each SlipChip was then immersed in FC-70 in separate Petri dishes. The Petri dishes were stored in a 23° C. incubator and the results were monitored for two weeks. Images of areas containing crystals were taken over the two weeks.

Crystallization of Dihydrofolate Reductase/Thymidylate Synthase from *Babesia bovis* with Microbatch SlipChip.

The protein sample was obtained from SSGCID. The screening assays using microbatch SlipChips were performed in the same way as described for enoyl-CoA hydratase.

Crystallization of Dihydrofolate Reductase/Thymidylate Synthase with FID Chip

The protein sample was obtained from SSGCID. The screening assays using FID SlipChips were performed in the same way as described for enoyl-CoA hydratase.

Crystallization of Dihydrofolate Reductase/Thymidylate Synthase with Hybrid SlipChip The protein sample was obtained from SSGCID. The screening assays using hybrid SlipChips were performed in the same way as described for enoyl-CoA hydratase.

Visualization of Protein Crystals Using a UV-Microscope

To confirm the crystals obtained in all of the crystallization assays on SlipChips were indeed protein crystals, the inventors used a UV-microscope (PRS-1000, Korima Inc., Carson, Calif.). Both brightfield images and images under UV-light were taken. The crystals were confirmed as protein crystals when UV signals from the crystals were detected, and the corresponding crystallization conditions were identified as hits.

Crystallization of Dihydrofolate Reductase/Thymidylate Synthase in Well Plates.

Crystallization of dihydrofolate reductase/thymidylate synthase was performed in well plates as described for glutaryl-CoA dehydrogenase from *Burkholderia pseudomallei*.

X-Ray Diffraction and Data Processing

X-ray diffraction and data processing were performed as described elsewhere in this application.

X-Ray Structure Determination of Dihydrofolate Reductase/Thymidylate Synthase.

The structure of dihydrofolate reductase/thymidylate synthase was solved by molecular replacement using the PDBid 3I3R structure as a starting model and the MOLREP program in CCP4 suite. The data collected from crystals grown in the condition containing PEG-400 was used. Rigid-body, positional, and temperature factor refinements were performed using a maximum likelihood target with the program REFMAC5. The SigmaA-weighted 2Fobs-Fcalc and Fobs-Fcalc Fourier maps were calculated using CCP4. The Fourier maps were displayed and examined in COOT. The search for new solvent molecules was performed with help of COOT. The structure has been deposited in the Protein Data Bank, PBDid: 3KJR.

Quantifying Mixing Ratio: Characterization of Area Sizes

The original (before etching) area is a hexagon with two opposing right angles between the first and second sides and the fourth and fifth sides. The volume of the area is expressed in Equation 1, where W1 is the original width of the area (the distance between the third and sixth sides), L is the original length of the area (the length of the third and sixth sides), r is the expanding distance, and d is the depth of the area after etching.

$$\text{Volume} = W_1 L d + 0.5 W_1^2 d + 0.707 \pi r d W_1 + 0.666 \pi d r^2 + 0.5 \pi r d L \quad \text{Eq. 1}$$

The size of the areas after etching was measured by using a Leica MZ 16 Stereoscope calibrated by a micro-ruler. The expanding distance r was then calculated using Equation 2, where W2 is the width (along the same axis as W□) of the area after etching.

$$r = 0.5(W_2 - W_1) \quad \text{Eq. 2}$$

The inventors assumed that the etching speed was the same in all directions, so the original pattern of the area expanded the same distance in all directions. The expanding distance, r, was assumed to be the same as the depth, d. Therefore, the volume of the areas can be calculated by combining Equations 1 and 2.

$$\text{Volume} = W_1 L \frac{W_2 - W_1}{2} + 0.5 W_1^2 \frac{W_2 - W_1}{2} + 0.707 \pi \frac{(W_2 - W_1)^2}{4} W_1 + 0.666 \pi \frac{(W_2 - W_1)^3}{8} + 0.5 \pi \frac{(W_2 - W_1)^2}{4} L \quad \text{Eq. 3}$$

The areas of the SlipChip can be designed such that W1 was always 236 μm and L was varied to be 0, 20, 40, 60, 80, 100, 120, 140, 160, 180 and 200 μm. The angles of the hexagon are 90 or 135 degrees. By etching the areas to be 60 μm deep, the areas can be designed with volume of 4.0, 4.4, 4.8, 5.2, 5.6, 6.0, 6.4, 6.8, 7.2, 7.6 and 8.0 nL, respectively.

In certain embodiments of the present invention, the SlipChip can be used to perform bead-based assays such as bead based immunoassays. In certain embodiments, bead-based SlipChip methods can involve multi-step slipping, loading beads into the chip, handling beads in areas, transfer of beads from one layer to another, and then from one area to another area, by slipping. Washing beads can be performed by many mechanisms including back and forth sliding, forward sliding and serial dilution. Hydrophilic areas can be used to maintain thin layers of fluid in an area, can be used for effective serial dilution by creating small volumes that can be washed with large volumes and can be used to speed up diffusion in and out of the thin layer. Nano-scale areas which are very thin (between, for example, about 100 nm, 1 um, 10 um) can contain immobilized antibodies for very rapid immunoassays. Such immunoassays can be valuable for rapid analysis, for example to detect Parathyroid Hormone. In addition, removal of excess material by slipping over such an area can be used to evaluate weaker binding, for example in applications described in Maerkl S J, Quake S R. "A Systems Approach to Measuring the Binding Energy Landscapes of Transcription Factors" Science, 2007, 315:233-237. For SlipChip immunoassays, when beads are held down, or capture antibody is immobilized on the surface, washing can be performed directly by running fluid through aligned areas and ducts (to reduce cross-contamination, it is preferred to wash all areas in parallel, not sequentially).

Cell cultures can be grown, maintained, or assayed in areas. There may be at least one cell in an area, and analyzing can be performed by, for example, immunoassay. This may involve a secretion of the cell, a lysed cell, stimulating cells and then analyzing the result by any method including, for example, by immunoassay, or stimulating by slipping to add a reagent, and analyzing by any method including immunoassay.

The SlipChip can be used to analyze many samples which may be obtained from other devices including, for example, the chemistrode.

In some embodiments, many small-volume samples can be analyzed in parallel using bead-based ELISA assays in the SlipChip. Situations in which analyzing small-volume samples are important include, but are not limited to, analyzing samples from the chemistrode. Understanding biological systems can involve tools to deliver, capture, and interpret molecular signals with high temporal resolution. The newly developed chemistrode addresses this unmet need by recording molecular signals in an array of hundreds of nanoliter-volume plugs, which are subsequently analyzed by multiple independent techniques in parallel. The chemistrode can benefit from methods to analyze the nanoliter-volume recording plugs with high sensitivity, specificity, and throughput. Immunoassays are one of the most frequently used techniques for detecting molecular markers with high specificity and sensitivity in biological research. Developing immunoassays for these nL-plugs enhances the analyzing abilities of the chemistrode. Other situations in which analyzing small-volume samples are important include, but are not limited to, diagnostics and clinical research. For example, serially monitoring a tumor over time requires repeated sampling of small volumes and analyzing them. Also, to avoid unnecessary depletion of blood samples deposited in blood banks, testing requires analysis of small volumes. Other situations in which analyzing small-volume samples are important include, but are not limited to, single-cell analysis, nano-flow sampling from live tissue, e.g., the retina (Lu, Miao-Jen, et al. Exp Diabetes Res. 2007; 2007: 39765), small samples (e.g., material from an embryo). The biggest bottleneck in certain situations is processing (such as combining samples, separating samples with beads, and adding reagents) many small volumes in parallel. Typical methods for manipulating nanoliter droplets serially process plugs one-by-one. For certain embodiments, this is less preferred when indexing of plugs is important, because errors can accumulate. Many examples of current devices for arranging nanoliter droplets in arrays do not allow manipulations (adding reagents, handling beads) of droplets. Digital microfluidics works with microliter volumes. Many microfluidic devices rely on laminar flow to introduce the sample: these can have large dead volumes and/or adsorption problems. Certain embodiments of the SlipChip are capable of robustly handling many multi-step reactions in parallel without using complex instruments. The inventors developed a simple approach that uses a SlipChip to perform bead-based ELISA to analyze many small-volume samples in parallel. The inventors have designed certain embodiments of the SlipChip to incorporate multi-step slipping, and performed experiments to demonstrate loading and washing of beads. Multi-step slipping allows us to transfer beads from one layer to another, and then from one area to another area. In these embodiments, beads can be washed by two mechanisms: forward sliding with serial dilutions, and back and forth sliding. Hydrophilic areas maintain thin layers of fluid in the areas of this SlipChip. The hydrophilic areas also allow for effective serial dilution by creating small volumes that can be washed with larger volumes. The detection limit the inventors achieved with one embodiment of the SlipChip was down to the pM range, which is in the physiological concentration of many molecular markers.

An embodiment of the SlipChip has been designed to be able to perform 48 immunoassays in parallel. It contains two sections, section A and section B. Section A is used for loading many small volume samples: the design of this section is variable to accommodate the different requirements of different sources of samples. To demonstrate performing bead-based ELISA, a device was built with six groups of seven areas each (1 nL, 10 µm deep). When the areas for the sample (bottom plate) and ducts for the sample (top plate) are aligned, six separate fluidic paths are formed, and each fluidic path is filled by pipetting into an individual inlet. Each fluidic path also contains a separate outlet for the solutions. In these experiments, six standard calibrators were loaded into the six fluidic paths for the sample. Section B is used for performing the bead-based ELISA: this is the core section of the device. It contains six rows of 48 areas (9 nL, 80 µm deep). Areas in the first row are used to load the mixed solution containing magnetic beads coupled with the capture antibody and the enzyme-labeled detection antibody. Areas in the second, third, fourth, and fifth rows are used to load the washing buffer. Areas in the sixth row are used to load the solution containing the substrate. The top layer of an embodiment of the SlipChip may contain inlets, outlets, and ducts to load the sample, and inlets, outlets, and areas for the various reagents. The bottom layer of an embodiment of the SlipChip may contain the areas for the sample, and ducts to load the reagents.

In certain embodiments, a SlipChip may be composed of two layers of microfabricated glass. The top layer may contain all the inlets, outlets and ducts for the sample and areas for the reagents. The bottom layer may contain areas for the sample ducts for the reagents. For improved filling of the areas, the surfaces of the device can be silanized to be hydrophobic while keeping the areas hydrophilic. The areas can be protected during silanization to maintain a hydrophilic surface. A potential source of cross-contamination is the formation of a thin film of solution between the two plates of certain embodiments of the SlipChip that connect areas that should be separated after slipping. This is caused when the solutions wet the surface of the SlipChip. To minimize the wetting of the BSA-containing solutions on the surface of certain embodiments of the SlipChip except inside the areas and the ducts, a nanopattern can be fabricated on the surface outside the areas and the ducts. The nanopatterning increases the contact angle between the solution and the surface, preventing wetting of the surface.

In certain embodiments, using a SlipChip to perform immunoassays involves three general steps (a) preload reagents, (b) load samples, and (c) perform the assay. In certain embodiments reagents may be preloaded in eight steps: (1) A SlipChip is assembled so that the areas of row 1 are connected by reagent ducts. (2) The reagent solution containing, for example, capture-antibody coated superparamagnetic beads and enzyme-labeled detection antibody is injected into the SlipChip and the areas in row 1 are filled. (3) The chip is slipped to connect the areas of row 2 by ducts. (4) Fluorocarbon is injected through the ducts to remove any remaining solution in the ducts. (5) Washing buffer is injected to fill the areas in that row in the SlipChip. (6) The chip is slipped to connect the areas of the next row by ducts. (7) Steps (4), (5), and (6) are repeated three times to fill rows 3 and 4 with buffer. (8) Fluorocarbon is injected through the ducts to remove any remaining solution, and the enzymatic substrate is injected to fill row 6.

In one embodiment, samples are loaded in two steps: (1) The SlipChip is slipped to connect areas by ducts (this is the ready-to-use state for the users), (2) Solutions of the analyte are injected by pipetting through the inlets.

In certain embodiments, assays may be performed in five steps: (1) The SlipChip is slipped to combine the analyte and reagent solution of, for example, antibodies and beads, and the solution is incubated to allow an antibody sandwich to form, (2) A magnet is brought up against the back of the bottom layer to pull the beads down into the area of the bottom plate, and the assay solutions and the washing buffer are combined by slowly slipping the SlipChip so that the beads remain in the areas of the bottom plate, though the magnet is moved away, (3) Step (2) is repeated three times, (4) A magnet is used to pull the beads down into the area of the bottom plate, and the SlipChip is slipped to combine the antibody-sandwich and the substrate, (5) The increase of fluorescence is monitored using a fluorescence microscope. The fluorescence is correlated with the concentration of analyte using techniques known to those skilled in the art.

In one embodiment containing two sections, A and B, eight steps may be used to pre-load reagents into the SlipChip. The areas of row 1 of Section B can be connected by the reagent ducts. The reagent solution containing the capture-antibody coated superparamagnetic beads and enzyme-labeled detection antibody can be injected into the SlipChip to fill the areas in row 1 of Section B. The SlipChip can be slipped to connect the areas of row 2 of Section B by ducts. Fluorocarbon can be injected through the ducts to remove any remaining solution in the ducts. Washing buffer can be injected to fill the areas in that row in the SlipChip. The SlipChip can be slipped to connect the areas of the next row by ducts. These steps can be repeated three times to fill rows 3, 4, and 5 of Section B with buffer. Fluorocarbon can be injected through the ducts to remove any remaining solution, and the enzymatic substrate can be injected to fill row 6 of Section B. Two steps can be used to load the sample into this embodiment of the SlipChip: The SlipChip can be slipped to connect the areas in section A by the ducts for the sample. Solutions of the analyte can be injected by pipetting through the inlets. Five steps can be used to perform the immunoassay: The SlipChip can be slipped to combine the analyte and reagent solution of antibodies and beads, and incubate the solution to allow the antibody sandwich to form. A magnet can be used to pull the beads down into the area of the bottom plate, and the SlipChip can be slipped to combine the assay solutions and the washing buffer. Steps can be repeated as necessary. A magnet can be used to pull the beads down into the area of the bottom plate, and the SlipChip can be slipped to combine the antibody-sandwich and the substrate. The increase of fluorescence can be monitored using a fluorescence microscope.

It will be apparent to one skilled in the art that embodiments similar to those described above that contain, for example, rows 1 through 6, can be made in which a plurality of sets of, for example, six row sections can be built onto a single SlipChip, such that a plurality of assays can be performed in parallel.

In other embodiments, analyzing many, for example, nanoliter samples simultaneously using the SlipChip may be performed by using an insulin bead-based ELISA. To demonstrate this, the inventors injected a solution containing superparamagnetic beads coated with the capture-antibody, alkaline phosphatase-labeled anti-insulin monoclonal antibody, and blocking buffer in areas of a first row in a first section to form a sandwich complex. To detect the enzyme-labeled detection antibody, the inventors used a fluorescent substrate for the enzyme, fluorescein diphosphate (FDP), which becomes fluorescent upon hydrolysis by the enzyme alkaline phosphatase (ALP). The inventors injected six standard calibrator solutions of insulin (0 pM, 7 pM, 70 pM, 350 pM, 1050 pM, and 2100 pM) in the areas in a section of the same chip. Fluorescence intensity in each area was measured over time. The inventors found that the limit of detection, defined as three times the deviation of the background signal, was about 9 pM.

An insulin immunoassay may be performed with multiple small samples in parallel on a SlipChip. Fluorescence intensity of multiple, for example, nanoliter samples on the same SlipChip in different areas of the insulin immunoassay may be measured over time.

In certain embodiments of the SlipChip, superparamagnetic bead-based assays may be performed. The inventors have demonstrated these beads stayed in areas during slipping: the beads did not get trapped between the two plates, and there was <3% loss. For certain embodiments, retention of beads is preferred to improve the accuracy of the results. The beads can be moved using a moving magnet to facilitate mixing of solutions. For certain embodiments, this is preferred for both washing and transferring the beads from area to area. Moving beads with a magnet will increase mixing, increasing the efficiency of washing. A magnet can also be used to pull beads into a bottom area prior to slipping, increasing the number of beads that were transferred from row to row in the SlipChip. Residual enzyme-labeled detection antibody will diffuse into the washing buffer, and can be exponentially diluted to eventually reached a negligible level, washing the beads. In certain embodiments, after four cycles of washing, the residual reagents are diluted by a factor of $10^4$, assuming complete mixing in every washing cycle. The inventors demonstrated, in certain embodiments, that the level of enzyme-labeled detection antibody was below the detection limit after washing in the SlipChip.

Fabrication of SlipChip with hydrophilic areas. The inventors used the glass etching fabrication of SlipChip procedure described elsewhere in this application with the following modifications. A blank glass plate (Soda-lime glass, thickness: 0.7 mm; chromium coating: 1025 Å; AZ photoresist: 1 μm) was first cut to be 2 in ×1 in. After the photomask was removed from the glass plate, the glass plate was developed by immersing it in 0.5% NaOH solution for 1 min. In this example, certain areas on the front of the glass plate were also taped with PVC tape to form thinner areas. After the glass plate was taped with PVC tape, it was immersed in the etching solution and a 25° C. constant-temperature water bath shaker was used to control the etching speed. By controlling the etching time (~50 min), areas and ducts that were 70 μm deep were etched into the glass plate. The plate was thoroughly rinsed with Millipore water and dried with nitrogen gas.

Next, the tape protecting the thinner areas was removed and the plate was immersed in the etching solution for ~7 min. 10 μm deep areas were etched on to the glass plate where the tape was removed. During this step, the 70 μm deep areas and ducts were further etched to be 80 μm deep. The plate was thoroughly rinsed with Millipore water and dried with nitrogen gas.

After the ducts and areas were etched into the plate, the glass plate was rinsed with ethanol to strip the undeveloped photoresist. Then, the plate was coated with OmniCoat and baked at 200° C. for 1 min. Next, the plate was coated with a 10 μm thick layer of SU8 2010, and the plate was covered with a photomask that protected the areas on the plate that were to be hydrophobic. UV light was shined from the back of the glass plate. In the area exposed by the photomask, UV light only passed through the plate where the chromium coating was removed, so only the SU8 in the areas remained after developing. The SU8 in the areas protected the areas and prevented them from being made hydrophobic. OmniCoat on the exposed surface was developed by immersion in CD-26 for 4 min.

Next, a layer of S1813 positive photoresist was coated on top of the plate and baked at 95° C. for 1 min. The plate then was aligned with a nanopatterning photomask and the same procedure was followed as described for etching the areas and ducts. After removing the chromium coating, the glass plate was immersed in the glass etching solution described above that was diluted 10 times, and etched for 10 min at room temperature (~20° C.) to produce ~300 nm deep patterns over the surface. Finally, the glass plate was rinsed with ethanol to strip the undeveloped photoresist, and immersed in the chromium etchant to remove the chromium coating. The glass was then rinsed with ethanol and Millipore water and dried with nitrogen gas.

The etched patterns were measured with a Veeco Dektak 150 profilometer. The glass plates were cleaned and subjected to an oxygen plasma treatment, and then the surfaces were rendered hydrophobic by silanization in a vacuum desiccator for 3 hours with tridecafluoro-1,1,2,2-tetrahydrooctyl-1-trichlorosilane as previously described. After silanization, the glass plates were baked in a 120° C. oven for 30 min, rinsed by immersion into a tank of FC-3283, and dried in a 60° C. oven overnight. Finally, the SU8 in the areas was stripped by immersing the glass plates in Remover PG at 80° C. for 30 min.

Assembling a SlipChip. The SlipChip was assembled under FC-40. The bottom plate was first immersed into FC-40 in a Petri dish, with the patterns facing up. The top plate was then laid on top of the bottom plate, with the patterns facing down. The two plates were aligned into the positions shown in FIG. 3a, by moving them relative to each other and then fixed by using two micro binder clips. The SlipChip was ready for use after the extra FC-40 on the surface was removed.

Food Dye Illustration. All the food dye solutions were filtered with a 0.45 μm PVDF syringe filter before use. A solution of mouse monoclonal anti-insulin coupled to paramagnetic particles was concentrated six times by centrifuging. The resulting bead suspension and two food dyes (orange, and blue, Ateco, Glen Cove, N.Y., diluted ~10 times from their stock solutions) were pipette-loaded into the reagent ducts. To load each duct, 2.5 μL of dye was first pushed through the inlet using a pipette until the dye solution emerged from the outlet. After loading reagents, the SlipChip was slipped to form a continuous fluidic path for the sample. A red dye was diluted 10 times and then loaded through the sample inlet. Using a pipette, 2.5 μL of dye was loaded into each of the six fluidic sample path of the Chip.

Insulin bead-based ELISA. The loading procedure was similar to that for the food dye illustration. The reagent areas were loaded and the six sample paths were loaded with the six standard insulin solutions. After the areas for the antibodies and areas for the samples were combined the SlipChip was incubated for half an hour at 37° C. to allow complete reaction. The SlipChip was then slipped to perform the assay.

Images of areas were taken by a SPOT Insight camera (Diagnostic Instruments, Inc., Sterling Heights, Mich.) coupled to a Leica MZ 16 Stereoscope. The fluorescence intensity of the areas was measured by using a Leica DMI6000 microscope (Leica Microsystems) with a 20×0.4 NA Leica objective and a Hamamatsu ORCAER camera. A GFP filter was used to collect fluorescein fluorescence. Images were acquired and analyzed by using Metamorph imaging system version 6.3r1 (Universal Imaging). The maximum intensity of the images was first plotted against time, and then the initial increasing rates were extracted and subtracted by the rate of the negative control (the assay was the same except that no detection antibody was added), and the initial rates were plotted against the corresponding concentration to obtain a calibration curve.

In certain embodiments of the SlipChip an immunoassay can be performed in seven steps: (A) Nanoliter-volumes of analyte solution are deposited on the areas in the bottom layer of SlipChip immersed under fluorocarbon. (B) The SlipChip is assembled and the reagent solution containing the capture-antibody coated superparamagnetic beads and enzyme-labeled detection antibody is injected into the fluidic path formed by the ducts of the bottom plate and the areas of the top plate. (C) The SlipChip is slipped to combine the analyte and reagent solution, and a magnet is used to settle the beads down into the areas of the bottom plate. The solutions are incubated to allow antibody sandwiches to form. (D) The SlipChip is slipped back into the configuration in (B) and washing buffer is injected into the fluidic path formed by the ducts of the bottom plate and the areas of the top plate. (E) The SlipChip is slipped to combine the washing buffer and the assay solutions. Steps (D) and (E) are repeated to remove loosely bound enzyme-labeled detection antibody. (F) The SlipChip is slipped and the enzymatic substrate is injected into the fluidic path formed by the ducts of the bottom plate and the areas of the top plate. (G) The SlipChip is slipped a final time to combine the substrate and antibody-sandwich. The concentration of analyte is monitored by measuring the increase of fluorescence. The increase in fluorescence is correlated with the concentration of analyte. In one example of beads being loaded, transferred, and washed in an embodiment of the SlipChip, beads are uniformly loaded into the areas of the SlipChip by pipetting, beads are transferred from one layer to another by using magnets and slipping. The beads will stay in the areas during slipping. Beads can be moved using a moving magnet to facilitate mixing of solutions. In certain embodiments, this is preferred for efficient washing. In certain embodiments, such as certain enzymatic reactions, mixing is preferred to improve homogeneity of the reaction mixture.

In one example, manipulating superparamagnetic beads in a SlipChip involved the following: nanoliter-volume solutions were deposited in the bottom plate, and the SlipChip was assembled, beads suspended in a solution were injected into the SlipChip, slipping and magnetic force were used to settle the beads down into the areas of the bottom plate, the SlipChip was slipped back to the original configuration and buffer was injected into the SlipChip to remove any residual solution in the fluidic path.

Next, an example of washing superparamagnetic beads to remove substantially all loosely bound detection antibody in the SlipChip is described. The inventors first deposited solutions of enzyme-labeled detection antibody (alkaline phosphatase labeled anti-insulin monoclonal antibody) in areas 13-24 and 37-48 of the bottom plate. As a control, the inventors also deposited buffer solutions in wells 1-12 and 25-36. Then, the inventors injected the capture-antibody coated superparamagnetic beads suspended in the blocking buffer into the SlipChip. The inventors slipped the device and combined the beads with detection antibody. To introduce the washing buffer, the inventors settled the beads into the areas of the bottom plate using magnetic force and slipped the device. Washing buffer was injected. Next, the inventors slipped the device to combine washing buffer with the beads. Loosely bound detection antibody will diffuse into the washing buffer while the beads remain in the areas of the bottom plate. By repeating the wash steps, residual enzyme-labeled detection antibody was exponentially diluted and eventually reached a negligible level; at this point beads were considered to be washed. In one case, wash steps were repeated 12 times, and the amount of residual detection antibody was ~0.2% of the starting concentration assuming complete mixing in every washing cycle. To detect residual enzyme-labeled detection antibody, the inventors used a fluorescent substrate for the enzyme, fluorescein diphosphate (FDP), which becomes fluorescent upon hydrolysis by the enzyme alkaline phosphatase (ALP). The inventors slipped the device and injected FDP. Finally, the inventors slipped the device to combine the substrate and any residual enzyme-labeled detection antibody in the area. Fluorescence intensity in each area was measured. The inventors found that the fluorescence intensity was very weak and the same for areas deposited with ALP-antibody and areas deposited with buffer. The fluorescence intensities were also the same as the fluorescence of substrate solution mixed with buffer. This result indicated that the level of enzyme-labeled detection antibody was below the detection limit after washing. As a positive control, the inventors added FDP to the areas without washing by leaving out the washing steps. The areas deposited with ALP-antibody showed strong fluorescence, indicating that the reagents and the method were effective for detecting residual ALP-antibody. Together, these experiments show that residual detection antibody can be substantially removed from the beads by washing with back-and-forth slipping in the SlipChip.

The forward-slipping method in the SlipChip can be modified to incorporate analysis of single cells on-chip and to analyze samples collected in plugs. The inventors used the forward-slipping method to measure insulin secretion from single β-cells loaded on-chip (insulin secretion from mouse islets sampled by chemistrode). First, the inventors modified the design of section A to allow analysis of single cells loaded on-chip. In this design, Section A has two rows of areas (one in the bottom plate and one in the top plate) and Section B is the same as previously described. The inventors loaded and cultured single β-cells in the first row of areas on the top layer—this is the second row of areas in Section A. The inventors loaded glucose solutions in the row of areas on the bottom layer—the first row of areas in Section A. This design involved one additional slipping step to combine the β-cells and the glucose solutions. After the β-cells and the glucose solutions were combined, the inventors slipped the samples through section B to perform the insulin bead-based ELISA as described above. This design can be used to grow pure cultures of cells in the areas starting from a single cell. This design can also be used to stimulate and analyze single cells. The cell can be stimulated by slipping to bring it into contact with a particular reagent, and either the secretions of the cell or the cell lysates can be analyzed by immunoassay (as described previously) or by other methods.

The inventors also modified the design of section A to allow analysis of insulin secretion from single islets sampled by a chemistrode. In this design, Section A has two rows of areas in the top plate. The first row is loaded with the plugs captured using the chemistrode, the second row is preloaded with buffer. The six rows of section B are preloaded as described previously. The inventors stimulated a single islet by glucose and sampled the insulin release in plugs using the chemistrode. In this case, the chemistrode generated an array of plugs representing temporal resolution of insulin release. The SlipChip was assembled under fluorocarbon the inventors first directly deposited the sample plugs in the first row of areas on the top layer before assembling the two layers, then carefully aligned the two layers such that the first row of areas on the top layer was lined up with the row of wells in the bottom layer. The top row of this SlipChip design contained no inlets or outlets because the plugs were directly deposited onto the areas of the SlipChip. The inventors first slipped the sample to dilute it by slipping into buffer. The inventors then slipped the diluted sample through section B to perform the insulin bead-based ELISA as described above.

The SlipChip can also be designed with very thin areas (for example, about 100 nm, 1 µm, or 10 µm) that contain immobilized antibodies for very rapid immunoassays. Washing can also be done by an active method: if the beads are immobilized by a magnetic field or if the capture antibody is immobilized on the surface of the areas, the beads can be washed directly by running fluid through the aligned areas and ducts. To avoid cross-contamination in active washing, the areas are washed in parallel instead of sequentially. In certain embodiments, it is preferred to design the device so the pressure drop along the inlet duct and the outlet duct is smaller (10 fold for example) than the pressure drop along the individual fluid paths that are being washed. When nano-scale areas are washed, the flow resistance is likely to be high and this condition is likely to be satisfied. The inlet duct and the outlet duct for the washing fluid can be dead-ending, with narrow ducts pointing towards the other duct. When the areas containing immobilized antibodies are slipped and aligned to connect the inlet duct and the outlet duct, the washing fluid can pass through and wash the areas.

Certain embodiments of the SlipChip can be used to carry out sample preparation using beads: by transferring beads from area to area in the SlipChip and exposing them to different reagents, sample purification and preparation can be accomplished, for example as done in the Kingfisher system. Washing and concentrating can also be enhanced by a number of fields and effects, for example, electrical concentration uses electrical fields to concentrate molecules near nanopores or ducts.

Certain embodiments of the SlipChip are compatible with magnetic immunoassays, including, for example, those developed by the Philips Corporation. Certain embodiments of the SlipChip may be used to obtain epigenetic information. For example, acetylation, methylation, ubiquitylation, phosphorylation and sumoylation of histones can be analyzed, and certain embodiments of the SlipChip may be used to perform and analyze chromatin immuno-precipitation (ChIP), down to the single-cell level.

Certain embodiments of the SlipChip can be used to perform PCR experiments. At least three different SlipChip-based PCR examples follow: a preloaded SlipChip to perform multiplexed PCR experiments, a SlipChip designed for digital PCR experiments, and a procedure to trap bacteria onto beads and load the beads into a SlipChip for PCR.

Certain embodiments of the SlipChip may include slipping on top of an oil area, the use of non-fluorinated oil/mineral oil; and/or non-fluorinated silanization on glass, the use of dried reagents (for example, primers) with oil on top, and areas that are shallower than the area with the PCR mix so the PCR mix drop touches the primer. When slipping an area containing an aqueous solution over an area containing oil that optionally has reagents, the contents of the top area displaced the oil and then can react with the reagents deposited in the bottom. Some oil remains in the area to provide control of thermal expansion, and in some instances the total volume of oil may be greater than the volume of aqueous solution. Certain embodiments of the multiplexed PCR device may also include overlapping a larger square and a smaller circle. This geometry achieves two goals: it reduces errors due to thermal expansion so some oil is trapped in the larger square and it reduces errors due to touching the dried primer in the bottom area.

In certain embodiments of the SlipChip there are oval areas that overlap. In certain embodiments the oval areas (areas extended in the direction of filling) provide strong overlap, and low pressure drop for loading, and can be slipped a small distance to break up overlap among them and create overlap with oil areas. In certain embodiments the oval areas can be used to center droplets for better imaging of the droplets.

Certain embodiments of the SlipChip may be used to trap bacteria using magnetic beads. Bacteria from plasma may be trapped on beads and loaded into certain embodiments of the SlipChip and then analyzed using, for example, PCR reactions.

The devices and methods described here can be used for a number of applications. In particular, applications that require changes in temperature can be performed using these devices. Applications include analysis of DNA by PCR and RNA by RT-PCR, including analysis of mRNA. Other applications include processes that require thermal denaturation of enzymes and other molecules, processes that require thermal activation or inactivation of components and reactions, and processes that require non-ambient temperature (e.g., many catalysis reactions).

Certain embodiments of the SlipChip can be used for a number of applications involving human, animal and environmental samples that include, but are not limited to, samples from blood, urine, CSF, stool, eye, ear, genital tracts, lower respiratory tracts, nose, and throat. These applications include measurement of viral loads for viral infections such as HIV and hepatitis, analysis of mutations and drug resistance of viruses and bacteria and fungi, panels for identification of viruses and bacteria, analysis of cancer cells and their mutations, genetic variability, clonal evolution, and drug resistance. Microbes of interest include, but are not limited to, *Staphylococcus aureus*, Beta-hemolytic streptococci, *Streptococcus pneumonia*, Enterococcus, *Erysipelothrix, Listeria monocytogenes, Haemophilus influenza, Pseudomonas aeruginosa*, Mold, *Actinomyces* sp., lecithinase or lipase positive anaerobic Gram-positive organisms, and the *Bacteroides fragilis* group.

Viral detection can be performed on the SlipChip using many different assays including but not limited to nucleic acid testing (NAT) technology to amplify and detect viral target RNA or DNA sequences. In some embodiments, HIV detection can be performed on the slipchip using NAT technology to amplify and detect HIV target sequences.

Capturing cells on beads or area surfaces of certain embodiments of the SlipChip is attractive for analysis and manipulation of cells, e.g., multiplexed PCR analysis, relevant for applications, including but not limited to, cancer diagnostics, prenatal diagnostics and infectious disease.

In certain embodiments, SlipChip devices were fabricated by using glass etching fabrication of SlipChip as described elsewhere in this application, except for the following changes: In this example, ~45 minutes of etching yielded a depth of ~60 microns. Access holes were drilled with a diamond drill bit 0.030 inches in diameter. The surfaces of the etched glass plates were cleaned with Millipore water, followed by ethanol and subjected to an oxygen plasma treatment before silanization. The glass was silanized by using dichlorodimethylsilane (a non-fluorinated silane) in vapor phase for one hour. Then the glass slides were rinsed with chloroform, acetone, and ethanol, and finally dried with nitrogen gas.

The following describes one embodiment of a preloaded multiplexed PCR SlipChip. The top plate of the PCR SlipChip contained square sample areas of 640 µm in length, 70 µm in depth and the bottom plate contained ducts for the samples and preloaded circular areas containing different PCR primer sets. The circular areas were 560 µm in diameter and 30 µm in depth. The areas in the bottom plate were first loaded with 0.5 µL of primer solution (1 µM), and dried at room temperature. Then, the bottom plate was placed in a Petri dish containing mineral oil. Fluorinated or non-fluorinated mineral oils may be used in PCR SlipChip experiments. By placing the bottom plate in a Petri dish containing oil, a layer of oil formed on top of the preloaded dry primer. The areas containing primer were designed to be smaller in both depth and width than the top areas containing the PCR master mix. This allowed the droplet containing the PCR master mix loaded in the top area to efficiently reach the primer in the bottom area through the layer of oil on top of the primer. Next, the top plate of the PCR SlipChip was aligned on top of the bottom plate such that the sample areas and sample ducts lined up to form a continuous fluidic path. The PCR mixture containing EvaGreen supermix (Bio-rad), 1 mg/mL BSA (Roche) and either DNA template or water (for the control set) was flowed through the fluidic path to load the sample areas. The PCR SlipChip was slipped to align the square sample areas with the circular primer areas. Because there was a layer of oil between the two areas, the aqueous PCR mixture formed a droplet within the areas to reduce surface tension. When the PCR mixture touched the primer on the bottom of the primer area, the PCR primer dissolved in the reaction mixture. After the SlipChip was slipped, thermocycling was performed using an Eppendorf mastercycler with an in-situ adapter. PCR readout was performed by using fluorescence measurements and gel electrophoresis of the sample areas.

During thermocycling, the aqueous solution in the areas expanded in volume due to the increase in temperature. In certain embodiments, when using a SlipChip with only square areas, the aqueous solution can fill the square area, risking, after an increase in temperature, the aqueous solution leaking out of the areas, resulting in a loss of material and unmonitorable changes in concentration. When a smaller, circular area containing oil was brought into contact with a square area containing aqueous solution, the aqueous solution forms a droplet within the area, providing room for expansion during thermocycling. Certain shapes and sizes of the bottom area are preferable for forming a single droplet of consistent size in the center of the two areas. Consistently sized droplets minimize variations in the concentration of reagents within the droplets.

The inventors set up the experiments in this embodiment of the PCR SlipChip to have two rows of control areas with no template and two rows of areas with 5 pg/µL of S. aureus gDNA. The inventors found that no contamination occurred in the SlipChip, as only areas containing template showed amplification. All areas containing template showed amplification, verifying the robustness of the PCR SlipChip. Fluorescence intensity measurements and gel electrophoresis showed that areas without template had no DNA present after thermocycling and areas with template only contained one DNA sample.

Quantitative data analysis confirmed no contamination in the PCR SlipChip. To further verify that there was no contamination or cross-contamination in the SlipChip, we preloaded the bottom chips with two different primer sets, alternating primer sets for the nuc gene (from S. aureus) and the mecA gene (from MRSA). 5 pg/µL S. aureus genomic DNA was injected into chips as described above. Since the nuc gene is present only in S. aureus genomic DNA, while the mecA gene is present only in MRSA, only the areas loaded with primers for the nuc gene showed an increase in fluorescence, and other areas containing mecA gene did not show fluorescence. A linescan of the fluorescence intensity quantitatively showed that areas without template did not show significant fluorescence.

In certain embodiments, thermocycling is performed by placing the entire PCR SlipChip into a thermocycler that will raise and lower the ambient temperature surrounding the device. In different embodiments of the PCR SlipChip, thermocycling takes place within the device. Here, the thermocycler is replaced by a steady temperature distribution within the device, and the areas are physically moved from one temperature to the next. Aqueous droplets are first formed by slipping to combine areas containing aqueous solution with areas containing oil as previously described. Certain embodiments of the SlipChip are designed such that the aqueous droplets that are formed can be moved by slipping without loss of solution. These droplets are then slipped to regions of the SlipChip that are maintained at a specific temperature for a specified period of time. The temperature distribution within certain embodiments of the SlipChip can be generated by using, for example, IR heaters or a thermoelectric device under a P2i coating. The size of these "hotspots" and "coldspots" can be small enough to accommodate individual areas, or large enough to accommodate rows or arrays of areas. For example, a rotary device can move areas from the cold half of the device to the hot half of the device. The presence of multiple temperature spots within the device can be used to add another dimension to certain embodiments of the PCR SlipChip device: annealing temperature. As different primers have different annealing temperatures, a wider range of primers can be screened on this device.

The following describes one embodiment of a digital PCR SlipChip. One embodiment of the SlipChip contained 1,280 areas, and each area was about 5 nL in volume, and was fabricated using the photolithographic and wet chemical etching techniques described above. This embodiment contained oval-shaped ducts or areas; the two plates were patterned with overlapping oval areas of dimensions 400 µm×200 µm and 50 µm in depth. The two plates were also patterned with circular areas of dimensions 200 µm in diameter and 50 µm in depth. By using overlapping oval areas, the pressure drop in the device was small, allowing for filling by simple pipetting. By slipping the SlipChip a short distance, the oval areas were separated and were overlaid on top of circular areas containing a layer of oil. For digital PCR, a primer was added to the PCR mixture instead of being preloaded into the circular areas. The oval areas were designed so that the width of the oval areas was the same as the diameter of the circular areas. The design enabled the droplets to be centered in the areas, allowing for better imaging. The design also produced droplets of consistent size, therefore producing droplets with consistent concentrations of reagents. The design created an aqueous droplet surrounded by oil within the area, as in the previously described PCR SlipChip, allowing room for thermal expansion during thermocycling.

Certain embodiments of the digital PCR SlipChip were able to detect template DNA at concentrations as low as 100 fg/10 µL.

The dynamic range of digital PCR can be increased by, for example, using a combination of large and small areas. For example, in a device containing 2,000 areas, one would get a larger dynamic range and higher confidence in the statistics if 1,000 areas contained 1 nL of solution and 1,000 areas contained 10 nL of solution. The distribution of area sizes that gives the best dynamic range and highest confidence interval can be predicted.

In certain embodiments of the digital PCR SlipChip, multiple area sizes can be designed by using a rotational design. The large areas can be placed on the outside at a lower density, and the small areas can be placed on the inside at a higher density. As this embodiment of the SlipChip is rotated to slip, the large areas will move more than small areas and all the areas will each contact their corresponding areas on the bottom plate simultaneously.

In certain embodiments of the SlipChip, trapping bacteria can be performed using magnetic beads. The inventors used magnetic beads (Bug Trap version C) to capture MRSA from human pooled plasma (HPP). HPP was spiked with MRSA for a final concentration of 1×107 cfu/mL of MRSA. Then, 100 µL of this solution was incubated with Bug Trap beads for 20 minutes at room temperature. The beads were pulled down with magnets, and washed with 1×PBS buffer five times. Then, the beads were mixed with EvaGreen PCR supermix, 1 mg/mL BSA, primers and injected into a SlipChip for thermal cycling. The SlipChip design used here was the same as for the multiplex PCR experiments.

The techniques described herein may be used for parallel analysis of many individual cells, viruses, particles, molecules, and other objects. For example, certain embodiments of the SlipChip may be used to perform such measurements on populations of cancer cells to determine variability and heterogeneity of genetic makeup, phenotype, dynamics of responses, including responses to potential treatments and combination of treatments. SlipChip can be used to evaluate cells and tissues, for example blood cells, for markers of radiation damage, resulting, for example, from radiation therapy, industrial accidents or acts of war or acts of terrorism. This analysis may be used to estimate the radiation dose received by a person, and such knowledge may be used to take appropriate countermeausures, e.g. adjusting the dose of radiotherapy, administration of chelation therapy or ingestion of non-radioactive isotopes or additional methods. These markers can be, for example, markers of double-stranded DNA breaks. Proteins, mRNA, miRNA markers and small molecules may be used, both general markers and organ-specific markers. One example of such marker is phosphorylation of Histone H2AX. The markers can be analyzed on SlipChip, for example, via enzyme assays, via immunoassays, electrophoresis, western blotting, via nucleic acid amplification techniques, including analysis of RNA levels, and combinations of methods. Measurements performed at single-cell level would provide further valuable information to distinguish a dose of radiation received globally from a dose received locally, even from circulating cells. For example, global damage could lead to similar levels of damage shown by the damaged cells or a single-peak distribution of famage, while local damage could lead to a variation of levels of damage shown by cells, or a bimodal or a more complex distribution of damage. Amplification of genetic material from individual viruses followed by genotyping the viruses to determine their resistance patterns enables early detection of resistant phenotypes, preferred for treatment in, for example, HIV and Hepatitis infections.

The techniques described herein may be integrated with multiphase flow techniques including plug-based and/or droplet-based microfluidic systems and other techniques. Certain embodiments of the SlipChip are suitable for the analysis of arrays of droplets, plugs and other fluid volumes surrounded by an immiscible fluid, including volumes generated on a SlipChip directly or generated externally and introduced into the SlipChip, such as plugs generated by a chemistrode or elsewhere.

This application describes a SlipChip device used for separation that can be integrated with a number of different separation techniques and sample types. This is a more detailed description of capabilities already described in U.S. provisional application 61/162,922 (see, for example, sections 00102, 00104, 00122, and 00188). The SlipChip was constructed as described for the SlipChip used for FID protein crystallization above.

In certain embodiments, the SlipChip may be used for diffusion-based separation. Many medical diagnostics rely on isolated clear bodily fluids such as blood plasma to diagnose diseases, but generating clear body fluids often requires expensive centrifuges, time, and labor. A SlipChip can be designed to let small molecular weight proteins, nuclear acids, and viruses in whole blood diffuse into an area containing buffer while red blood cells are retained in the original areas. This separation is based on a difference in diffusion coefficients. For example, in 5 minutes, the Hepatitis B virus can diffuse 600 µm but a red blood cell can only diffuse 4 µm. For example, the inventors designed a SlipChip in which whole blood is mixed with 5 µmol/L 8-methoxypyrene-1,3,6 trisulfonic acid (MPTS) and the mixture is loaded into a left area by pipetting a 10 µL blood sample. 1×PBS buffer was loaded into right areas. The device was slipped to connect the blood areas with the buffer areas. The MPTS diffused into the buffer areas in 30 min, while the blood cells did not move.

This SlipChip design can utilize a separation medium in the ducts or areas to induce a separation. At least one area/duct can contain the separation medium. Examples of separation media that can be integrated into the areas include, but are not limited to, gels (e.g., silica gel or polyacrylamide gels), buffers, polymer filters and membranes, binding agents, chromatography media, surfaces of living cells, biological membranes (i.e. lipid bilayers) with and without proteins, arrays of particles, and nanoparticles. Alternatively, the separation medium can be on the surface of the device. For example, thin layer chromatography (TLC), gel electrophoresis, and isoelectric focusing can be implemented on a SlipChip. Separation can also be driven by diffusion and external fields and environments. Examples of fields and environments to induce separation include magnetic fields, electric fields, optical fields, gravitational fields, a chemical gradient, a temperature gradient, active transport, and shear forces. Fields may be produced by elements that have been integrated on-chip or externally. For example, electrodes can be incorporated into the areas and/or ducts or other areas of the SlipChip, or can be applied externally via the inlets and outlets of the SlipChip. With the integration of electrodes into the SlipChip, one can use electrophoresis to do separation without pretreatment of samples by placing a gel in the ducts for electrophoresis. Fields can be switched on/off or modulated in strength by slipping the SlipChip from one position to another. Separations can also enabled by tags that modify objects' properties with respect to an applied field. For example, magnetic susceptibility, electrophoretic mobility, and diffusion coefficients can be modified by binding the object of interest to another object. Surface modified magnetic beads can be utilized to bind specific bacteria, followed by separation by magnetic fields. The SlipChip can be used to separate and detect small molecules such as drugs and their metabolites and complexes, hormones, environmental pollutants, antibiotics, nicotine and its metabolites, drugs of abuse, stress hormones, other molecules associated with chronic and acute stress. These separation methods can also be used for separation of cells and isolation of cells from biological fluids. Such cells of interest include circulating tumor cells, fetal cells in blood, stem cells, bacterial and fungal cells, T-cells and B-cells, and other subpopulations of cells expressing specific markers. These cells can be isolated from blood, urine, cerebral spinal fluid, interstitial fluid, tear fluid, amniotic fluid, bone marrow, and tissue biopsies. For example, a separation may be useful to determine the aggregation states and post-translational modifications of proteins and peptides involved in neurodegenerative diseases.

This SlipChip can also be used to study objects that can move independently, such as cells and organisms. Chemotaxis (active transport), thermotaxis, and magnetotaxis can be studied by setting up chemical, thermal, and magnetic gradients within the SlipChip. For example, chemotaxis can be used to isolate bacteria or leukocytes in blood.

Separations can be integrated with all the other capabilities of the SlipChip. For example, after slipping to separate a mixture into various fractions, the SlipChip can be slipped a second time to introduce reagents to visualize detection, such as in delivering antibodies for Western blotting. Also, detection of phosphorylation and glycosylation levels in cells is important for diagnostics and drug discovery. Combining separation with immunostaining is attractive for detection of phosphorylation and glycosylation, and the SlipChip may be used to implement such measurements of phosphorylation and glycosylation down to single-cell levels. A series of slips can be used to isolate a single cell, lyse it, perform a separation, stain the separated fraction with antibody, and perform a detection assay. After an initial separation, multiple fields can be combined in a single step or multiple steps to perform one-dimensional, two-dimensional, or higher dimensional separations. For example, separations may be combined with protein crystallization. By continuing separation during crystallization, various aggregation states of proteins during crystallization can be separated. This separation can yield crystals of high quality and purity.

In certain embodiments of the SlipChip strong intrinsic mixing can be generated by vortex magnetic fields. See Martin, Shea-Rohwer, Phys Rev E Stat Nonlin Soft Matter Phys. 2009 July; 80(1 Pt 2):016312 incorporated by reference in its entirety. "Vortex" magnetic fields can be applied to a suspension of spherical magnetic particles, which create strong, homogeneous mixing throughout the fluid volume. Stirring a laminar flow within a microchannel can be done by applying an alternating magnetic field to ferrimagnetic beads inside a channel. See Rida and Gijs Anal Chem. 2004 Nov. 1; 76(21):6239-46 incorporated by reference in its entirety. Stir-bar strategies using microscale magnetic bars exposed to a spatially uniform rotating magnetic field can be used. Permanent structures that can be used include fabricated magnetic rods driven by a standard magnetic stirrer. Beads bound to microchains can also be used for mixing. Mixing can be achieved by exposing beads to a simple rotating field. Beads can provide a modest level of mixing within a fluid. Permanent magnets (and magnetic stirrers) to create vortex magnetic fields are preferred for certain embodiments because of the simplicity of the setup. Other methods of mixing commonly used in microfluidic devices, including ultrasonic mixing, "bubble mixers", and mixing and flow driven by electrical fields, including alternating current dielectrophoresis, can be used on SlipChip.

An example of using a magnetic stirrer and strong permanent magnet.

A microfluidic device containing 1 micron magnetic beads was placed 1-1.5 cm away from a rotating strong magnet and 4 strong magnets were added on top at approx. the same distance. Strong mixing did occur inside the ~6 nL areas. Without the top magnets, or rotating magnet below, the strong mixing stops. Without being bound by theory, it is thought that a vortex magnetic field was generated.

Buffering chambers can be used in any of the devices described herein. These are preferably closer to the inlet, upstream of the set of areas and ducts. They are capable of trapping some of a sample and, for example, can prevent overshooting when a small amount of sample is pushed too far into a SlipChip. Buffering chambers are preferred when loading with positive displacement devices (pipettes, etc).

In SlipChips used to perform FID crystallization, differently-sized ducts that connect areas (for example, differing in at least one of length, width and depth) on the same device can be used to create a plurality of diffusion profiles across different areas.

For certain embodiments of the SlipChip, it is preferable to have varying degrees of overlap between areas and/or ducts within a set of overlapping areas and/or ducts.

In SlipChips used to perform certain reactions, including FID crystallization, a plurality of ducts can connect to a single area to create multiple concentration gradients connected to the same area.

A SlipChip can be designed to perform more than one type of reaction. For example, a device can be configured to carry out both FID crystallization and microbatch crystallization on the same device. In some embodiments, a branching supply duct is used to the sample between the regions of the device used for the different reactions.

SlipChips similar to the devices described above for carrying out FID crystallization can be used for other types of experiments. For example, a cell-migration or cell polarization assay can be carried out in such a device. One slips the device to connect at least two areas, creating a gradient along which cells can migrate up or down, or in response to which cells may polarize. One can connect multiple areas to establish complex gradients and countergradients. In addition, such devices can be used to co-culture and monitor cell-cell interactions.

Many fields and forces can be used to transfer a volume from one area to another area. Examples of fields that can enable transfer of volumes between areas include surface tension, magnetic fields, electric fields, gravitational fields, temperature gradients, and shear forces. In certain embodiments, the SlipChip can be used for metering and transferring multiple volumes of liquid into a single volume. The SlipChip can be designed with areas of varying volumes, to transfer and mix samples of different volumes into a single volume. The ability to transfer and mix samples of different volumes into a single volume can be used as a general method for rehydrating dry reagents and can be followed by relevant assays. It can be used for unidirectional transfer of reagents in assays, for PCR and other applications that require thermal expansion, in protein crystallization experiments, blood coagulation, assays and reactions, for adding reagents to arrays of trapped droplets, as on "drop spot arrays" and in other arrays as described, for example in the following publications: Schmitz, C. H. J.; Rowat, A. C.; Koster, S.; Weitz, D. A., Lab Chip 2009, 9, 44-49; Shim, J. U.; Olguin, L. F.; Whyte, G.; Scott, D.; Babtie, A.; Abell, C.; Huck, W. T. S.; Hollfelder, F., J. Am. Chem. Soc. 2009, 131, 15251-15256, which are herein incorporated by reference. Different geometries, sizes, and surface modifications of the areas and plates of the SlipChip can be utilized to transfer and compartmentalize droplets in the areas. As the droplet shape and volume is restricted by the area shape and area volume, areas can be filled to differing extents, including areas that are fully filled, small droplets trapped within bigger areas, and droplets that are contained in areas that are only slightly bigger than the droplet. Areas of different sizes and different extents of filling can be used to transfer and combine volumes in certain embodiments of a SlipChip.

One example of how to use these combinations of area and droplet sizes to transfer volumes in the SlipChip involves the following: One can slip and overlap one area fully filled with one substance with a larger area containing a droplet composed of a second substance. When these two areas come into contact, the liquid in the first area merges with the droplet in the larger and remains in the larger area to minimize the surface tension.

Different geometries can be used to trap droplets that are smaller than the area. For example, sloped areas can be used to confine the droplet or a three-layer SlipChip can be used to confine a droplet in a middle layer. These designs can be used to precisely position the droplets and can be used to avoid the escape of the droplet while slipping. In addition, they are also very useful for devices that need to be opened to extract droplets for off-chip analysis.

The SlipChip can also be used to induce mixing in droplets. In certain embodiments, if an area is not completely filled, there is an additional layer of lubricating fluid between the solution in the area and the lubricating fluid between the two plates of the SlipChip. As the SlipChip is slipped, the motion of the two plates can induce mixing in the droplet, transmitted by the motion of the lubricating fluid. A nonlinear or irreversible slipping pattern can be used to enhance mixing.

In certain embodiments, in areas that are not completely filled, the presence of an additional layer of lubricating fluid between the solution and the surface of the other plate of the SlipChip can prevent cross-contamination. The additional barrier between the solution and the facing plate of the SlipChip will reduce the possibility of residue being left on the surface of the SlipChip, in addition to, or as an alternative to adjusting the contact angle of the solution by surface modifications.

Surface modification of an area can be used to control positioning and mass transfer in the areas. For example, one can create an area with a hydrophilic bottom surface that will trap the droplet in the bottom, as the bottom of the area will be preferentially wetted by the aqueous solution. In another example, the entire area can be made hydrophilic, so that an aqueous solution will wet the area. Different solutions can have different shapes and surface curvatures (surface energy) in the same size area. Surface modification can also be used to transfer solutions from one area to another. For example, two areas can be connected with a hydrophilic bridge, connecting one area that is not fully filled to another that is full. Using surface tension and diffusion, substances can be transported from one area to another.

One mechanism of transferring a volume of fluid from a first area (e.g., a metering area) to a second area (e.g., a reactor area) is when the first area and the second area have geometries such that the volume of fluid inside the first area has a higher surface tension than the volume of fluid inside the second area. For example, this condition can be satisfied when the first area is shallower and smaller than the second area. The user can load the first area using a duct and then slip such that the first area and second area overlap. The droplet in the first area prefers to go into the bigger area because of surface tension. This approach can be applied for example to rehydrate a preloaded dry reagent. This approach can also be used to combine multiple reagents within the same volume; for example two, three, four, five or more reagents can be added sequentially to the same volume without loss of the reagents already added.

In another example of transferring droplets using surface tension, a surface of a reactor area can be modified to be hydrophilic, while the remaining surfaces of the SlipChip device are hydrophobic. When using hydrophilic reactor areas and hydrophobic metering areas, the relative size of the areas is unimportant, as an aqueous solution being transferred by the metering area will preferentially wet the hydrophilic surface of the reactor area. For example, large and small fully filled hydrophobic areas, as well as partially filled hydrophobic areas, can be used to fill the reactor area.

A multiplexed SlipChip for high efficiency screening of many combinations was developed based on the multi-step transferring strategy. The device can be used to set up a reaction matrix, each area with a different combination of solutions. More steps can be carried out to introduce third and fourth reagents in both vertical and horizontal directions. For example, such an N×N design can be used to rehydrate a dry reagent, add a sample, add reagents (in, for example, the vertical direction), and then add another set of reagents (in, in this example, the horizontal direction). The device can also be designed with areas of different volumes, adding an additional dimension to the multiplexed screening. The device can utilize the mechanisms of volume transfer based on surface tension described above.

Other mechanisms that can be used to transfer solutions from a first area to a second area are described. The density differences of the liquids can be used to float a droplet or deposit a droplet into a larger area. If magnetic beads are added to a droplet in a first area, a magnet can be used to move the droplet into a second area. One can also integrate electrodes onto certain embodiments of the SlipChip to move droplets containing charged solutions or particles. After filling a second area with a first solution, one can slip back and fill the second area with another solution, then slip to overlap the two areas again to combine metered volumes of different solutions. The solutions can also be incubated between fillings. The user can control the number of solutions and the volume of each solution filled into a reactor area. For example, an array of small areas with different volumes can be used to meter exact volumes of different solutions into a reactor area.

If the volume of a reactor area is larger than the volume of the droplets that are metered into it, there is room for thermal expansion. This is useful for applications where the temperature is increased (as in thermocycling for PCR, for example), because the solution will not spill out when thermal expansion occurs. If the reactor area is full when a metering area is brought into contact with it, the solution in the metering area will mix with the solution in the reactor area. When the metering area is slipped away, it will transport a metered volume of the mixed solution. Mixing techniques can be integrated with the SlipChip to ensure good mixing of the two solutions.

An embodiment of a SlipChip which uses small areas to meter and transfer solutions to larger areas for mixing is described. This device contains 10 rows, where each row contains 20 larger areas, 20 smaller areas, and a duct, and each row can be filled with a different solution. The larger areas (620 µm×240 µm size, 60 µm deep, 6.8 nL volume) and duct (300 µm width, 60 µm deep) are in the bottom plate, and the smaller areas (620 µm×120 µm wide, 35 µm deep, 2 nL volume) are in the top plate. The SlipChip device was assembled under fluorocarbon. The fluorocarbon oil filled the areas, ducts, and the gap between the two plates. A red food dye solution was filled into the fluidic path formed by the smaller areas and the duct. The device was slipped to align the smaller areas with the larger areas. Due to the surface tension of the aqueous solution, the solution was transferred from the smaller areas into the larger areas. The device was slipped back to its original position to form a continuous fluidic path through the smaller areas and the duct, and a blue food dye solution was filled into the smaller areas. The device was again slipped to align the smaller areas with the larger areas, and the red and blue food dye were combined in the larger area and mixed. Between fillings the different food dye solutions, the fluidic path was washed with water and FC40 to reduce contamination.

In some embodiments the SlipChip can be used for metabolism profiling. All people metabolize drugs differently. Determining personal metabolism is possible with genetics but is expensive, and faces challenges when trying to deal with combinatorial interactions. Additional challenges are present because liver enzymes can be induced and also inhibited. A functional test is therefore useful. A SlipChip based device for metabolism profiling can be used in the office or at home. There is also a need to characterize nicotine metabolites to optimize smoking cessation. The SlipChip is useful for this, since it can be used away from a laboratory. It can for example, be used at drugstores with a SlipChip equipped with thin-layer chromatography capabilities, to aid in selecting among nicotine patches with different doses. Shear-driven chromatography can be used to improve thin-layer chromatography on a SlipChip. Detection and quantification can be performed on such devices using, for example, a cell phone or visual detection device.

A SlipChip for measuring substance metabolism is useful, for example, in situations where a simple device is needed to determine the concentration of the drug or the ratio between a drug and one or more of its metabolites, or where dosing is important. Measuring the concentration of a substance in saliva is preferred. Measuring the concentration of a substance that partitions into saliva regardless of the source of the saliva is preferred. Such a device can also be useful in situations where monitoring, rather than diagnosing, is important, for example over long term periods of time where a patient is already taking one or more drugs and some metabolic enzymes may be inhibited. In such a case, it is useful to monitor the metabolism of the one or more drugs over time to avoid overdosing. This kind of device is also useful during phase I, II or III drug trials to minimize side effects and improve outcomes, or for detecting pesticides on foods. Two-dimensional separations by thin-layer chromatography or other techniques can be used to improve concentration and separation (for example, one can concentrate the sample in one dimension and then separate in the other, using different solvent phases).

In some embodiments, a SlipChip for metabolism profiling can include a discontinuous bridging duct to enable multi-step slipping without cross-contamination, on-chip serial dilution, and patterning of the device to create hydrophilic areas.

SlipChip is applicable to a multitude of approaches and techniques to enable personalized medicine. The applications include testing patient samples for diagnostics and drug development and treatment monitoring.

SlipChip may be used to evaluate kidney function of patients, including by analysis of blood, urine, saliva and other samples. It includes analysis of creatinine and analysis of other markers such as Neutrophil gelatinase-associated lipocalin (NGAL), Cystatin C and other markers. Markers can be analyzed using immunoassays, enzyme assays, and other assays as described elsewhere in this application.

SlipChip can be used to evaluate liver function, including enzymatic assays tests and immunoassay tests. Targets include Alanine transaminase (ALT), Aspartate transaminase (AST), Alkaline phosphatase (ALP), Gamma glutamyl transpeptidase (GGT), Beta-Hexosaminidase (β-HEX), Lactate dehydrogenase (LDH), 5' Nucleotidase (5'NTD). Additional tests, such as coagulation tests (e.g. INR), serum glucose, total and direct bilirubin (BIL), Serum albumin can be performed on SlipChip using the methods described in this application.

From the foregoing, it will be observed that numerous variations and modifications may be effected without departing from the spirit and scope of the invention. It is to be understood that no limitation with respect to the specific embodiment illustrated herein is intended or should be inferred. It is, of course, intended to cover by the appended claims all such modifications as fall within the scope of the claims.

In certain embodiments, the SlipChip can be used to generate concentration profiles by serial dilution. Serial dilution is one of the most common and fundamental laboratory techniques, with applications including immunoassays, cell culture assays, and determining the kinetics of enzymatic assays. Several microfluidic methods exist to create dilutions, including simple diffusional mixing of laminar flow, multi-step fluid-dividers that split and recombine multiple streams, and mixing multiple streams with flow rates proportional to the desired final concentration. However, many microfluidic devices rely on continuous flow, which suffers from large dead volume, adsorption, pressure drop limit, and other limitations. In certain embodiments, the SlipChip is capable of robustly handling multiplexed multi-step reactions in parallel without using complex instruments. The inventors developed a simple approach that uses the SlipChip to perform serial dilutions. The inventors have designed a SlipChip to incorporate multi-step slipping and multiple mixing ratios, controlled by adjusting area sizes. This method can handle many samples in parallel, can require, in certain embodiments, small volumes of sample (nanoliters for each area), and is useful for quantitative multiplexed assays. In one embodiment, a serial dilution SlipChip is designed to perform eight serial dilution steps in parallel. It contains two parts: a row of shallow areas that contains sample and an array of deep areas that are filled with buffer solutions for dilution. Using the SlipChip to perform serial dilutions involves, in certain embodiments, three general steps: (a) loading buffers, (b) loading samples, and (c) multi-step slipping to dilute. After filling the SlipChip by, for example, pipetting, the two plates of the chip are slipped to separate ducts from areas. As the ducts are separated from the areas, they are also moved out of the slipping path. The areas containing sample are brought into contact with the areas containing buffer, and the sample is diluted. The mixing ratio, or dilution factor, is determined by the ratio of area volumes. Further steps of slipping operate by the same principle and thus serial dilutions are performed. In one example, the serial dilution SlipChip was composed of two layers of microfabricated glass: The top layer contains all the inlets and outlets, ducts for the sample, and areas for the buffer solution. All areas are 76 µm deep and ducts are 30 µm deep. The bottom layer contains 10 µm deep areas for the sample and 30 µm deep ducts for the buffer solution. The surfaces of the device were silanized to be hydrophobic while keeping the 10 µm deep areas hydrophilic. The inventors used relatively thin, 10 µm deep areas to decrease diffusion time in and out of the area. The inventors made the area hydrophilic to control the shape (and the volume) of the water droplet within the hydrophilic area, and also to prevent de-wetting from the shallow area. The 10 µm deep areas were temporarily masked during silanization to maintain a hydrophilic surface. Fluorescent dye was used to quantify the dilution using this SlipChip. After 4 slipping steps, a ~$10^4$-fold dilution was observed.

For fabrication of the SlipChip with hydrophilic areas the inventors followed the glass etching fabrication of SlipChip procedure described elsewhere in this application with the following modifications. A blank glass plate (Soda-lime glass, thickness: 0.7 mm; chromium coating: 1025 Å; AZ 1500 photoresist: 1 µm) was first cut to be 3 in×1 in.

After the photomask was removed from the glass plate, the glass plate was developed by immersing it in 0.5% NaOH solution for 2 min. After the glass plate was taped and immersed in the etching solution, a 25° C. constant-temperature water bath shaker was used to control the etching speed. By controlling the etching time (~30 min), areas that were 46 µm deep were etched into the glass plate. The depth of the areas was verified using a specially designed structure that indicates, without magnification, that a certain etch depth has been passed. This structure consists of an array of squares with a width equal to double the distance to be etched. The squares are originally covered with chrome. After the desired etch depth has been reached, the chrome is removed, producing an obvious contrast difference that can be seen with the naked eye. The plate was taken out and thoroughly rinsed with Millipore water and dried with nitrogen gas. Using another photomask containing the design for the ducts and an etching time of ~20 min, 30 µm deep ducts were etched into the glass plate. The plate was thoroughly rinsed with Millipore water and dried with nitrogen gas. The inventors used the same protocol to make 10 µm deep areas and 30 µm deep ducts in the bottom plate.

After the glass plate was rinsed with ethanol to strip the undeveloped photoresist, the glass plate was piranha cleaned (1 part 30% hydrogen peroxide, 3 parts sulfuric acid), washed twice with Millipore water, and then dehydrated on a 220° C. hot plate for more than 2 hours. The plate was cooled down to room temperature and spin-coated with OmniCoat (MicroChem, USA) and baked at 200° C. for 1 min. The plate was cooled down to room temperature and spin-coated with a 20 µm thick layer of SU8 2025. The plate was next covered with a photomask that protected the areas on the plate that were to be hydrophobic. UV light was shined from the back of the glass plate, to take advantage of the preexisting chrome mask. In the area exposed by the photomask, UV light only passed through the plate where the chromium coating was removed, so only the SU8 in the areas remained after developing. The SU8 in the areas protected the areas and prevented them from being made hydrophobic. OmniCoat on the exposed surface was developed by immersion in MF-319 for 30 sec and rinsed with Millipore water for 2 minutes.

Finally, the glass plate was immersed in the chromium etchant to remove the chromium coating. The glass was then rinsed with ethanol and Millipore water and dried by baking in a 120° C. oven overnight.

The glass plates were cleaned and subjected to an air plasma treatment at 300 mTorr for 100 seconds, and then the surfaces were rendered hydrophobic by silanization in a vacuum desiccator for 5 hours with tridecafluoro-1,1,2,2-tetrahydrooctyl-1-trichlorosilane as previously described. After silanization, the glass plates were rinsed by (in this order) 3×20 ml anhydrous toluene, 3×30 ml anhydrous ethanol, 3×30 ml ethanol/$H_2O$ (50%:50%, v:v), and 3×30 ml Millipore water. The plates were baked in a 120° C. oven for 15 minutes. Finally, the SU8 in the areas was stripped by immersing the glass plates in Remover PG at 80° C. for 30 min. The plates were then rinsed with chloroform, acetone, and then ethanol and blown dry with nitrogen.

The SlipChip was assembled under FC-40. The bottom plate was first immersed into FC-40 in a Petri dish, with the patterns facing up. The top plate was then laid on top of the bottom plate, with the patterns facing up. After ~3 mins, the top plate was then flipped carefully to prevent trapping of air bubbles when assembling the SlipChip. If necessary, air bubbles can be removed by quickly placing the chip in a vacuum desiccator. The two plates were aligned by moving them relative to each other and were then fixed by using four micro binder clips. The SlipChip was kept in FC-40 during the process of loading.

All the fluorescent dye solutions were filtered with a 0.22 µm PVDF syringe filter (Millipore) before use. Alexa Fluor 488 hydrazide (1.6 mM, Invitrogen) in PBS buffer (1×, pH 7.4) was loaded by pippetting into the sample duct. 1×PBS buffer solution was loaded into the buffer duct. The SlipChip was slipped under a Leica MZ 16 stereoscope to first form isolated droplets. Then the sample areas were combined with the buffer areas sequentially. After each slipping step, the inventors waited for 3 minutes to allow for the diffusion of the fluorescent dye. After 4 steps of slipping, the device was quickly transferred to a Leica DMI6000 microscope (Leica Microsystems) with a 20×0.7 NA Leica objective and a Hamamatsu ORCAER camera. A L5 filter with an exposure time of 30 ms was used to collect Alexa Fluor 488 fluorescence. Images were acquired and analyzed by using Metamorph imaging system version 6.3r1 (Universal Imaging). To calibrate the microscope, the fluorescence intensity of a fluorescence reference slide for the L5 filter was recorded and used for background correction. 80 nM, 160 nM, 400 nM and 800 nM Alexa Fluor 488 hydrazide solutions in PBS buffer were used to obtain the calibration curve to determine the concentration of fluorescent dyes after four slipping steps. Area depth was measured with a Veeco Dektak 150 profilometer and volume of the areas was calculated with the assumption that etching is isotropic.

Certain embodiments of the SlipChip can also be used to perform other multi-step reactions, including but not limited to determining IC50, EC50 assays and other concentration curves (e.g. CP450, etc). IC50 assays can be performed via serial dilutions of DMSO compound libraries to achieve dilutions of $2 \times 10^7$ in 100% DMSO or DMSO/water mixtures and assays can be performed with each dilution to ascertain the IC50 of the compound of interest. The SlipChip is an ideal platform to make dilutions of libraries and perform subsequent screening on the generated dilution library in a multiplexed manner. Other multi-step reactions which can be performed on the SlipChip include measuring enzymatic kinetics and quantifying concentrations by PCR by serial dilution (either combined with real time PCR or using end point PCR). For example, the user can perform an HIV viral load test by PCR. The user can serially dilute an unknown sample over a wide dynamic range and extract the concentration from PCR results with the assumption that the HIV virus follows a Poisson distribution. Other multi-step reactions which can be performed on the SlipChip include sensitivity testing, both drug and toxin, using serial dilutions of the substance of interest which are then administered (on-chip or off-chip) to a test organism or human subject, and isolation of rare cells or molecules, especially from samples with unknown initial concentration: in a dense cell population/high concentration mixture, a rare cell or molecule will be difficult to find. Serial dilution offers a convenient method to obtain the concentrations necessary for stochastic confinement (or digital PCR, etc.) when the initial concentration is unknown. Multi-step reactions which can be performed on the SlipChip include bacterial culture density (or the concentration of particles in solution) which can be quickly estimated through serial dilution and back-calculation. Determining antibody titer and serial dilution is one possible method to either eliminate non-specific binding, or identify it as a false-positive.

In certain embodiments of the present invention, high throughput nanoliter digital PCR can be performed on the SlipChip. The SlipChip has been shown to be free of cross contamination, and it has been previously validated by performing protein crystallization and immunoassays. The inventors have also demonstrated the SlipChip can be applied to high throughput multiplex PCR. The inventors have used the SlipChip platform for performing digital PCR. In certain embodiments, over one thousand nanoliter compartments can be formed simultaneously by one slipping step after a sample has been introduced via pipetting. When a low concentration of nucleic acid is loaded into the device, there can be less than one copy of nucleic acid per compartment. In this case, a "yes-or-no" digital readout of end-point fluorescence can be used to detect the presence of nucleic acid in each compartment, and the concentration of nucleic acid in the original sample can be calculated. Such a digital PCR SlipChip" has been used to amplify *Staphylococcus aureus* genomic DNA. It has also been used to amplify RNA from HIV via RT-PCR. The digital PCR SlipChip offers a new strategy for quantification of nucleic acids, study of cell heterogeneity, diagnostics of prenatal disease, and improvement of point-of-care devices. When combined with isothermal reactions and visual readout, the PCR SlipChip platform is a powerful tool for diagnostics in resource-limited settings.

Manipulating volumes of fluid is the basis of modern laboratory practice. It is critical in research and development, from new biomarkers and drugs to new materials and processes. It is a critical part of analytical science in diagnostics, food and water safety, and biodefense. In these areas, SlipChip technology can be useful. SlipChips can be designed to encode a complex program for parallel manipulation of many fluid volumes. The SlipChip, in certain embodiments, comprises two plates that can move relative to one another. The program is encoded into each SlipChip as a pattern of areas imprinted into the plates. Each area remains isolated until it overlaps with an area on the opposite plate. The encoded program is executed by moving—or slipping—the two plates relative to one another. As plates move, areas in the two plates come in and out of contact in a precisely defined sequence, creating and breaking up transient fluidic pathways, and bringing reagents in and out of contact. One or multiple samples can be introduced via such fluidic pathways. The program is executed by bringing the samples into contact with reagents either loaded by the user into a transient pathway, or pre-loaded onto the SlipChip. Very complex programs can be executed on thousands of areas very easily for the user. The smaller the volumes, the more precious are the samples and reagents, the larger the number of interacting samples and reagents, and the more complex the manipulations, the more beneficial the SlipChip. The SlipChip satisfied the seven unmet needs that are framing development of new fluidic technologies: it enables miniaturization, smoothly and precisely scalable from picoliter to nanoliter to microliter volumes. The SlipChip enables experiments that simply cannot be done on large scale, e.g. interrogating individual cells, both for human cells and microbial cells, or counting molecules. The SlipChip minimizes consumption of reagents and samples, reduces waste, especially relevant for expensive reagents, rare samples (biopsy samples, rare cells, banked samples), toxic, radioactive, and biohazard waste. Certain embodiments of the SlipChip enable multiplexed experimentation, with thousands of experiments easily performed in parallel in miniaturized format. SlipChip enables "one sample, one assay, many times", as required for detecting variability in properties of individual cells or genotypes. Examples include diagnosing cancer by analyzing biopsies and circulating tumor cells, analyzing rare and drug resistant genotypes in HIV, and emerging methods for diagnosing stroke. Certain embodiments of the SlipChip enable massively simplified "one assay, many samples" testing as is done by central labs such as Quest Diagnostics. Certain embodiments of the SlipChip enable "one sample, many assays", as in multiparameter diagnostics necessary for diagnosis of complex conditions. Certain embodiments of the SlipChip enable "many samples, many assays" experiments required for biomarker discovery and validation. The SlipChip satisfies demand for speed: cutting test-to-result time. By performing analysis at a single-cell level and removing the requirement for cell culture, certain embodiments of the SlipChip accelerate microbiological testing critical for diagnosis of sepsis and food, water, and environmental safety. By providing a simplified platform, certain embodiments of the SlipChip enable portable point-of-use devices critical for diagnosis of acute conditions (such as stroke and heart attack). Certain embodiments of the SlipChip satisfy demand for sensitivity down to single-molecule level in "digital" formats. Detecting molecules one at a time is attractive for sensitive detection and for quantification, for nucleic acids and proteins. The SlipChip is an ideal platform for such "digital" formats that require thousands of experiments (to get an accurate count) in small volumes (to get each molecule to a high enough concentration so the detection chemistry works) and multi-step manipulations (e.g. for heterogeneous immunoassays). This capability has wide-ranging implications, from counting gene copy number in individual cancer cells to diagnosing heart attacks and traumatic brain injury (TBI). The SlipChip minimizes manual labor, reduces errors, increases reproducibility, increases throughput, essential in well-equipped laboratories, point-of-care, and resource-poor settings. It enables complex pre-programmed multistep procedures on the microscale, including sample preparation and processing, as required for genetic testing. It supports reagents loaded by the user, or preloaded at the factory and stored on board, minimizing handling. A SlipChip with preloaded reagents functions as a "liquid-phase microarray", with the potential of revolutionizing multiplexed solution-phase assays just as gene-chips revolutionized DNA hybridization assays. It enables these complex procedures to be performed outside of the laboratory, as required for bench-top discovery work, point of care and home testing, and resource-poor environments. The SlipChip platform supports all common experimental methods. For example, it supports PCR and other nucleic-acid testing, immunoassays and handling of beads, enzyme assays and cell-based assays, required for a broad range of applications. It supports commonly used readout mechanisms (optical, magnetic and electrical). It is uniquely suitable for chemistry with, for example, simple Teflon and glass devices. Certain embodiments of the SlipChip decrease costs. Certain embodiments require no valves and are simple to manufacture by standard plastics technologies. The platform can be simple to operate with no or minimal equipment needed. This combination of low cost and simplicity makes the SlipChip superior to other microfluidic lab on a chip technologies, which can require complex instrumentation to run the chips (robotics, pumps, actuators), and can require complex chips with integrated valves. The SlipChip is superior to the robotic workstations which are capital-intensive and cannot match the performance of the SlipChip at the low-volume range due to problems with evaporation and precision.

Certain embodiments of the SlipChip can be used on many single cells/single particles/single samples/single molecules at a time. They can also be used for 3D tissue models, with associated fluidics for maintenance, perturbing, and analysis.

The SlipChip can be used in academic, pharmaceutical, diagnostic segments, providing reagents and equipment. Certain embodiments of the SlipChip allow the miniaturization and simplification of standard laboratory protocols, measurement of concentration of nucleic acids DNA/RNA ("digital PCR"), protein crystallization, and unique capabilities in single-cell analysis. The SlipChip can also bring value to companies selling libraries of compounds by packaging them in SlipChips. Currently, these libraries can be sold only to screening centers, and testing is expensive. 10,000 times less, for example, of each compound can be loaded on a SlipChip and tested. The SlipChip can reducing the barrier for users testing reagents; preloaded SlipChips with a panel of reagent formulations can be distributed to users who can rapidly and efficiently test which of the formulations is optimal for their application, and order that formulation in larger quantity (perhaps also on SlipChips). Certain embodiments of the SlipChip can also be used for genetic testing in forensics which needs highly simplified approaches.

Other areas where the SlipChip may be useful include food, water and environmental safety. Current methods of bacterial detection require overnight culture before testing. Certain embodiments of the SlipChip can provide answers in ~1 hour without culture, overcoming this costly time lag. Certain embodiments of the SlipChip enable on-site testing, critical for remote locations (for example, space missions, rural areas). It can also be used for livestock diagnostics/agricultural testing. Certain embodiments of the SlipChip allow miniaturizing and accelerating existing diagnostic tests in home, point of care and clinical testing. The simplicity of the technology makes it attractive for point of care, home and military use; high performance could make the same platform attractive for central lab instruments, saving money in FDA costs needed to approve currently disparate platforms used for clinical lab and point of care technologies. Certain embodiments of the SlipChip can be used for accelerated microbiological testing in sepsis, a cause of death for over 100,000 people just in the US. Many of these deaths are preventable by a more rapid diagnosis. Diagnostics include genetic testing and screening for drug resistance, as in MRSA and drug-resistant HIV genotypes, phenotypic testing for drug resistance, testing for coagulopathies and associated testing and monitoring of blood coagulation, cell-based immunodiagnostics/allergy profiling, diagnostics for the developing world (for example, HIV, malaria, TB, etc.), home and point of care diagnostics for monitoring organ function and treatment, especially with expensive biologics, general metabolic tests for monitoring drug treatment and drug metabolism, to ensure safety and efficacy. These are important both to consumers and, potentially, drug developers to monitor clinical trials. Warfarin is the best known example, but there are many more. The SlipChip can also be used for new diagnostics approaches including but not limited to discovering new biomarkers via single-cell analyses as in cancer, prenatal, and stroke diagnostics; discovering new panels of biomarkers using multiplexed analyses as in Alzheimer's disease and cancer (possibly in conjunction with the chemistrode for pulse-chase diagnostics); it can enable clinical studies and validation of these biomarkers, enable the use of these biomarkers in diagnostics in point of care and clinical formats. It can also be used for maintaining proper mental status for patients with psychiatric disorders—including, for example, for home testing, remote monitoring, patient networks, and other non-traditional approaches. The SlipChip can also be used for new therapeutic approaches including but not limited to integration of biomarker discovery and validation with drug discovery and diagnostics and complex tissue culture models with integrated analysis.

The SlipChip can also be used as a test to modify behavior or help people make choices, rather than offer a medical treatment. For example, the nicotine patch and other smoking cessation products are available without a prescription. It is well-known that the metabolic rate of nicotine strongly affects the success rate of smoking cessation and should guide the kind of patch the person should be buying. Such a test can be implemented on a SlipChip and sold to people who are quitting smoking, classifying people into three classes of low-medium-high nicotine metabolizers and suggesting appropriate smoking cessation products. A test, taken daily, suggests the dosing of the patch to provide a smooth cessation experience. A kit can include such tests with smoking cessation products. SlipChip tests can also optimize performance: levels of hydration and dehydration, diet, caffeine and other legal substances, exercise levels can all be monitored and/or modified to achieve top performance with the guidance of proper tests. Such tests can by used by those whose performance at a given time matters: competitive athletes, military, students, sports enthusiasts and people whose time is too valuable to be wasting in the afternoon lull. A "Stress chip" can be used for analyzing for markers of acute and chronic stress in the general population. Managing stress is perhaps one of the most important avenues of improving life satisfaction. Such a test would provide more immediate feedback to individuals on their life style to reduce the possibility of stress-related health conditions. This is much less expensive than waiting for development of chronic inflammation or cardiovascular conditions, and then interfering. To employers, military and law enforcement, and insurers it is valuable to evaluate and manage human resources. An "addiction SlipChip" could be used to perform panels, or combinations of panels, testing for liver damage associated with alcohol consumption, nicotine and its metabolite levels associated with smoking, levels of blood glucose and glycosylated hemoglobins associated with metabolic and eating disorders, levels of caffeine and its metabolites, and levels of drugs of abuse. A "baby chip", "organic chip", and "chronic chip" are additional applications to satisfy the need-to-know of first-time parents, health fanatics, or people at high risk for chronic conditions who are most likely to be proactive in wanting information and monitoring. For a simple SlipChip with a cell-phone readout, partnering with, for example, Google or Microsoft is attractive, as a way for people to organize results of their tests and optionally link them with blogs that reflect diet, exercise and behavior. Healthy people can use their Google Health service to mine for an incredible wealth of information, which can be used to improve tests and to offer advertisement and new products. Certain embodiments of the SlipChip can be used for maintaining health and performance, in addition to treating disease. Analyzing testable salivary markers linked to performance (both short term, and long term as in health status) and individualized to each person via simple testing platform, can improve quality of life and productivity of the society.

In certain embodiments, the SlipChip can be used to implement genetic algorithms (GA) to discover new homogeneous catalysts using the oxidation of methane by molecular oxygen as a model system. In one example demonstrated by the inventors, the parameters of the GA were the catalyst, a cocatalyst capable of using molecular oxygen as the terminal oxidant, and ligands that could tune the catalytic system. The GA required running hundreds of reactions to discover and optimize catalyst systems of high fitness, and microfluidics enabled these numerous reactions to be run in parallel. The small scale and volumes of microfluidics offer significant safety benefits. The microfluidic system included methods to form diverse arrays of plugs containing catalysts, introduce gaseous reagents at high pressure, run reactions in parallel, and detect catalyst activity using an in situ indicator system. Platinum (II) was identified as an active catalyst and iron (II) and the polyoxometalate $H_5PMo_{10}V_2O_{40}$ (POM-V2) were identified as active cocatalysts. The Pt/Fe system was further optimized and characterized using NMR experiments. After optimization, turnover numbers of approximately 50 were achieved with approximately equal production of methanol and formic acid. The Pt/Fe system demonstrated the compatibility of iron with the entire catalytic cycle. This approach of GA-guided evolution has the potential to significantly accelerate discovery in catalysis and other areas where exploration of chemical space is preferred. Kreutz, et al., *J Am Chem Soc.* 2010 Mar. 10; 132(9):3128-32 is incorporated in its entirety by reference.

In certain embodiments, the SlipChip platform can be used to perform digital PCR with instrument free sample loading and small sample volume. In one example, the PCR master mixture was introduced into the SlipChip by pipetting. The fluidic path was formed by overlapping elongated areas, and broken by simple sliding to generate 1280 reaction compartments (2.6 nL each) simultaneously. After thermal cycling, end-point fluorescence intensity was used to detect the presence of nucleic acid. Digital PCR on the SlipChip was validated using *Staphylococcus aureus* genomic DNA. When the template in the PCR master mixture was diluted, the fraction of positive areas decreased proportionally, as expected by a statistical distribution. No cross contamination was observed during the experiments. Digital reverse transcription PCR (RT-PCR) was also demonstrated on a SlipChip by amplifying RNA from HIV. The SlipChip provides an easily available strategy to count nucleic acids by using PCR and RT-PCR, as well as to perform single cell analysis, prenatal diagnostics, and point-of-care diagnostics. With isothermal PCR and visual readout, the digital PCR on the SlipChip can be designed to be instrument free, and can be widely applied for research and diagnostics in resource limited area.

The general idea behind digital PCR is to separate the molecules of nucleic acid by placing one molecule or less into a compartment. As the number of compartments is increased and the size of the compartments is decreased, the probability of trapping a single molecule in each compartment increases. At the single molecule level, confining the molecule in a small volume also increases the relative concentration, thus increasing the sensitivity. The number of positive areas can be counted and the total number of target molecules in the sample can be calculated.

Digital PCR has been previously demonstrated on a multiwell plate, and a number of groups have shown how to implement this method in a microfluidic format. Valve-controlled microfluidic chips have adapted digital PCR for various applications, for example cell analysis and prenatal diagnosis; however, this method still requires a complex multilayer soft lithography fabrication process and a electrical pneumatic system to accurately control the "open/close" state of the valves. Another system for digital PCR uses picoliter droplets in a microfluidic device for single-copy PCR and RT-PCR. Although a large number of picoliter droplets can be generated by using a microfluidic T-junction, this method requires high-precision pumps to accurately control the flow rate in order to form droplets of uniform size. Emulsion PCR, microdroplet, and engineered nanoliter droplets can be also potentially be used for digital PCR, but these systems require either mechanical agitation or pumps to generate the small volume droplets. A microfluidic chamber for high throughput nanoliter volume qPCR can also be adapted for digital PCR, but it still requires mechanical loading and manual sealing operations. To date, digital PCR is still restricted to high-end users. A simple, inexpensive platform is still an unmet need to make digital PCR a routine procedure in laboratory or resource limited settings. The inventors have demonstrated such a system based on the SlipChip platform. The SlipChip is an advantageous platform for digital PCR due to its inherent simplicity. All samples can be loaded by simple pippetting. The SlipChip can handle multistep processes on many small volumes in the context of protein crystallization and immunoassays. Multiplexed PCR was successfully demonstrated in SlipChip: no cross-contamination was seen when different pre-loaded primers were used to screen a sample to identify the presence of pathogens, and the design of the SlipChip was modified to allow room for thermal expansion of an aqueous PCR solution during thermocycling. The SlipChip has also been shown to be capable of performing digital PCR by dividing a sample into thousands of nanoliter areas.

Example. All solvents and salts purchased from commercial sources were used as received unless otherwise stated.

SsoFast EvaGreen Supermix (2×) was purchased from Bio-Rad Laboratories (Hercules, Calif.). Bovine serum albumin (BSA) was purchased from Roche Diagnostics (Indianapolis, Ind.). All primers were ordered from Integrated DNA Technologies (Coralville, Iowa). Mineral oil (DNase, RNase, Protease free) and DEPC-treated nuclease-free water were purchased from Fisher Scientific (Hanover Park, Ill.). Dichlorodimethylsilane was purchased from Sigma-Aldrich (St. Louis, Mo.). *Staphylococcus aureus* genomic DNA (ATCC number 6538D-5) was purchased from American Type Culture Collection (Manassas, Va.). Soda-lime glass plates coated with chromium and photoresist were purchased from Telic Company (Valencia, Calif.). Spectrum food colors (red food dye) were purchased from August Thomsen Corp (Glen Cove, N.Y.). PCR tubes and barrier pipette tips were purchased from Molecular BioProducts (San Diego, Calif.). Small binder clips (clip size ¾") were purchased from Officemax (Itasca, Ill.). Mastercycler and in situ adapter were purchased from Eppendorf (Hamburg, Germany). Teflon tubing (O.D. 250 μm, I.D. 200 μm) was purchased from Zeus (Orangeburg, S.C.). Teflon tubing (I.D. 370 μm) was obtained from Weico Wire & Cable (Edgewood, N.Y.). Photomasks were obtained from CAD/Art Services, Inc. (Bandon, Oreg.). Amorphous diamond coated drill bits were obtained from Harvey Tool (0.030 inch cutter diameter, Rowley, Mass.).

The procedure for fabricating the SlipChip was based on the glass etching fabrication of SlipChip procedure described elsewhere herein, with the following modifications. The soda-lime glass plate coated with chromium and photoresist was aligned with a photomask containing the design for the areas (both circular and elongated) of the SlipChip, and exposed to UV light for 40 seconds. After removing the exposed photoresist and chromium layers, the glass plate was immersed in a glass etching solution for 35 min at 40° C. to produce areas that were 50 μm deep.

The glass plate with an etched pattern of areas was thoroughly cleaned with Millipore water and ethanol and dried with nitrogen gas. The glass plate was oxidized in a plasma cleaner for 100 seconds and immediately placed in a desiccator with 50 μL of dichlorodimethylsilane. A vacuum was then applied for one hour for gas-phase silanization. The silanized glass plate was rinsed with chloroform, acetone, and ethanol, and then dried with nitrogen gas. In order to be reused, the glass plate could be cleaned with piranha acid (3:1 sulfuric acid:hydrogen peroxide) and silanized again as described above.

The mineral oil was filtered and degassed before using. The SlipChip was assembled under mineral oil. The bottom plate was first immersed into the oil in a Petri dish, with the patterned side facing up. The top plate was then laid on top of the bottom plate with the patterned side facing down. The two plates were aligned and fixed using binder clips.

Two primer sequences for the nuc gene found in *S. aureus* were selected from a previous publication: 5'-GCGATT-GATGGTGATACGGTT-3' (primer 1) and 5'-AGCCAAGC-CTTGACGAACTAAAGC-3' (primer 2). The reaction master mixture consisted of 10 μL of 2× SsoFast EvaGreen Supermix, 0.5 μL of primer 1 (10 μmol/L), 0.5 μL of primer 2 (10 μmol/L), 2 μL of 10 mg/mL BSA solution, 5 μL of RNase free water and 2 μL of *S. aureus* gDNA solution. The *S. aureus* gDNA solution was serially diluted using 1×BSA solution (0.01 mg/mL) to give a range of final template concentrations: 10 ng/μL, 1 ng/μL, 100 pg/μL, 10 pg/μL, 1 pg/μL, and 100 fg/μL. The amplification was performed using a PCR thermocycling machine (Eppendorf). To amplify the DNA, an initialization step of 2 min at 94° C. was used to activate the enzyme. Next, a total 35 cycles of amplification were performed as follows: a DNA denaturation step of 1 min at 94° C., a primer annealing step of 30 sec at 55° C., and a DNA extension step of 30 sec at 72° C. After the final cycle, a final elongation step was performed for 5 min at 72° C. Then the PCR products were stored in the cycler at 4° C. before imaging.

There are 2.9 million total base pairs in *S. aureus* gDNA (GenBank accession number NC_009632). The average molecular mass per base pair was approximated to be 660 to simplify the calculation. Therefore, 1 ng of *S. aureus* gDNA has $3.15 \times 10^5$ copies. The volume of reaction solution in each compartment was 2.6 nL, and the total number of areas in the device was 1280. Thus, each area contained on average 944 copies when the starting concentration of *S. aureus* gDNA was 1 ng/μL.

Bright field images were acquired by Leica stereoscope. All fluorescence images were acquired by using a digital camera (C4742, Hamamatsu Photonics, Japan) mounted to a Leica DMI 6000 B epi-fluorescence microscope with a 5×/0.15 NA objective and L5 filter at room temperature. All fluorescence images were corrected by a background image obtained with a standard fluorescent slide and then stitched together using MetaMorph software (Molecular Devices, Sunnyvale, Calif.). The intensity levels were adjusted to the same values for all images.

The design of the device was symmetric to increase the density of areas. Arrays of circular areas filled with oil were designed in both the top and bottom plates, and overlapping elongated areas in both top and bottom plates were used to introduce the sample. Upon slipping, isolated compartments were created, and an aqueous droplet of uniform size was generated in each individual compartment. This SlipChip contained no ducts; instead, each plate contained rows of elongated areas and circular areas for a total of 1,280 reaction compartments. The elongated areas were 400 μm long, 200 μm wide, and 50 μm deep, and the circular areas were 200 μm in diameter and 50 μm in depth. In the initial configuration, the elongated areas in the top and bottom plates overlapped to form a continuous fluidic path. By using overlapping elongated areas instead of areas connected by ducts, the pressure drop in the device was small, allowing many areas to be filled by simple pipetting, and a 3.4 μL sample filled the entire device. By slipping the top plate relative to the bottom plate a short distance, the elongated areas were separated and each was centered on top of a circular area containing a layer of lubricating fluid (mineral oil). For digital PCR, the primer was added to the PCR mixture instead of being preloaded into the circular areas. The elongated areas were designed so that the width of the elongated areas was the same as the diameter of the circular areas. Advantages of this design include: (1) The design enables the droplets to be centered in the areas, allowing for better imaging. (2) The design also produces droplets of consistent volume (~2.6 nL), (3) The design creates an aqueous droplet surrounded by oil within the area, as in the previously described multiplexed PCR SlipChip, allowing room for thermal expansion during thermal cycling.

During thermal cycling, the lubricating fluid and the aqueous PCR mixture expand more than the glass material of the SlipChip due to the different thermal expansion coefficients of the three materials. When using certain embodiments of a SlipChip with overlapping areas of the same size and geometry, the aqueous solution will completely fill the areas. During the temperature increase required for thermal cycling, the aqueous solution can expand and leak out of the areas, resulting in a loss of material and changes in the concentration of reagents. For the multiplexed PCR SlipChip, this problem was solved by overlapping a square area containing an aqueous PCR mixture with a circular area containing oil, producing a droplet suspended in oil and centered in the square area. For digital PCR, the inventors achieved the same result by using elongated areas containing the aqueous PCR mixture centered over circular areas filled with the lubricating fluid.

The inventors demonstrated digital PCR on the SlipChip with 10 fg/μL of S aureus gDNA. At this concentration, there was less than 1 copy of gDNA per 100 areas on average, and PCR amplification of a single copy of gDNA was achieved. A linescan of the digital PCR SlipChip before and after thermal cycling shows that the fluorescence intensity for areas containing a single DNA template increased significantly while the fluorescence intensity for areas without a DNA template did not increase. This linescan also verified that there was no cross-contamination in the SlipChip, as the fluorescence intensity for empty areas adjacent to an area containing DNA template did not change.

The inventors quantified the performance of this device using five concentrations of genomic DNA from S. aureus. The digital PCR SlipChip was able to detect template DNA at concentrations as low as 1 fg/μL. The inventors determined that single copy target DNA amplification was achieved when less than one-third of the total areas showed the signal of amplification. The expected concentration of the DNA template was presented as number of copies per area (cpw), and the concentration of the original DNA stock solution was measured spectrophotometrically by Nano-Drop (Thermo Scientific). The detailed method for calculating the cpw is presented elsewhere herein. As the DNA template in the PCR master mixture was diluted, the fraction of positive areas decreased proportionally. The inventors saw no evidence of contamination, as a control sample containing no template DNA did not give any positive results.

The inventors repeated the experiments for each concentration (n≥3), and generated a calibration curve to relate the fraction of areas showing a positive PCR result and the expected copy number of template per area. A Poisson distribution was assumed to calculate the expected fraction of positive areas. The fraction of positive areas was slightly lower than the expected value from the Poisson distribution; this could be caused by non-specific absorption during sample preparation. The inventors performed reverse-transcription PCR (RT-PCR) using the digital PCR SlipChip to quantify viral load with RNA purified from HIV. They demonstrated that the SlipChip was capable of quantifying the amount of nucleic acid present in a sample using standard thermal cycling PCR techniques. The SlipChip contained 1,280 areas designed to separate a 3.4 μL sample into 1,280 droplets of ~2.6 nL each, and was capable of detecting the template DNA at single copy level. The upper limit of concentration that could be detected using this device can be increased by increasing the number of areas on the SlipChip, and the sensitivity of the device can be improved by decreasing the area volume. The inventors have incorporated up to 16,384 areas of picolitre volume on a single SlipChip with dimensions of 1.5 inch by 1 inch. Digital PCR SlipChips can also be made to screen multiple samples on the same chip as in SlipChips designed for protein crystallization experiments and multiplex PCR. Multiplex digital PCR SlipChip can be made to count multiple targets in one experiment without interference by increasing the number of areas and using a microarray technique to pre-load different dry primer sets in the circular areas. Other improvements to the digital PCR SlipChip design include incorporating non-thermal cycling methods such as LAMP or NASBA, and increasing the dynamic range of the digital PCR SlipChip by using a combination of large and small areas. For example, in a device containing 2,000 areas, one would get a larger dynamic range and higher confidence in the statistics if 1,000 areas contained 1 nL of solution and 1,000 areas contained 10 nL of solution. The distribution of area sizes that gives the best dynamic range and highest confidence interval can be predicted. Additional improvements include incorporating real-time PCR and multi-color probes, such as the Taqman system and molecular beacons (using appropriate imaging devices known in the art). Multi-color probes can be used to apply digital PCR for multigene detection within a single cell to study heterogeneity and also to provide a method to integrate internal positive controls. The SlipChip can be made to perform nucleic acid (DNA/RNA) extraction and purification on the same chip before digital PCR for "sample in, result out" applications.

Another application of digital PCR on SlipChip is the detection of rare cells in the presence of large amount of normal cells, such as distinguishing between mutant and wild-type template DNA. With traditional techniques, it is difficult to quantify the faction of mutant due to the interference of a large population of normal cells. Digital PCR on SlipChip is a robust and easy method to increase the fraction of rare cells by confining them in areas of small volume.

This platform makes digital PCR widely available, and provides a very simple lab-based quantification of nucleic acids. The SlipChip provides an easily available method to perform prenatal diagnostics. The device can also be used for single cell analysis such as detection of mutations, monitoring of gene expression, and analysis of heterogeneity, as well as for inexpensive diagnostics, especially in resource-limited settings. Non-thermal cycling methods, nucleic acid purification methods, and simple readouts can be incorporated into the digital PCR SlipChip.

In certain embodiments, nanoliter multiplex PCR arrays can be performed on the SlipChip. In one example, the SlipChip platform was used to perform high throughput nanoliter multiplex PCR. The advantages of using the SlipChip platform for multiplex PCR include the ability to preload arrays of dry primers, instrument-free sample loading, small sample volume, and high throughput capacity. The SlipChip was designed to preload one primer pair per reaction compartment, and to screen up to 384 different primer pairs with less than 30 nanoliters of sample per reaction compartment. The inventors used both a 40-area and 384-area design of the SlipChip for multiplexed PCR. Both platforms were found to be free from cross-contamination, and end point fluorescence detection was used for readout. Multiple samples can also be screened on the same SlipChip simultaneously. Multiplex PCR was performed on the 384-area SlipChip with 20 different primer sets to identify 16 bacteria and fungi species commonly presented in blood infections. The SlipChip was able to correctly identify five different bacterial or fungal species in separate experiments.

Since its introduction, multiplex PCR has been successfully applied in many areas, including genetic analysis of cancer cells, monitoring of genetic variability and clonal evolution, and identification of infectious diseases caused by viruses, bacteria, fungi, and parasites. The conventional method for performing multiplex PCR is to load multiple primers to amplify multiple target templates in one reaction compartment. The throughput of this approach is generally limited to less than 10 targets per compartment because of poor sensitivity or specificity and uneven amplification rates of different targets, as well as interference of different primers and the number of fluorescent probes required for detection. Multiplex PCR can also be performed with PCR microarrays, but this method usually requires a large amount of reagent and samples. Another conventional strategy is to use many miniaturized compartments each with primer set for different target, but this approach is hindered by limitations in small volume liquid handling and the cost of instrumentation.

Microfluidic technology has been demonstrated to have more advantages over traditional PCR platforms, including, but not limited to, small reaction volume, high-throughput capacity, and portability. A number of groups have developed "Lab-on-a-Chip" microfluidic platforms for PCR, and micro-droplet based PCR has been demonstrated for single copy nucleic acid detection. However, most microfluidic PCR systems still require complicated fabrication, and rely on pumps or sophisticated valves to control fluid flow. A microfluidic platform with pump-free easy loading, small reaction volumes, and high-throughput capacity is still an unmet need for multiplex PCR.

The SlipChip allows microliter solutions to be effectively distributed to hundreds of nanoliter compartments with high precision without requiring pumps or a loading machine. An important feature of the SlipChip is that it allows preloading and storage of multiple reagents without cross contamination. The inventors made SlipChips to perform high-throughput, multiplex PCR. An array of primer sets was directly deposited in the areas of the SlipChip using manual deposition and allowed to dry at room temperature. Methods for microarray fabrication, such as inkjet, microjet deposition and spotting technologies, can also be applied to fabricate of the array of primers on the SlipChip. Here, the inventors describe a SlipChip that is capable of performing 384 simultaneous PCR reactions to identify up to 384 different templates in a single 10 μL sample with end-point fluorescence detection. The SlipChip can be setup easily by users with simple pipetting and PCR reactions are initiated by slipping without relying on pumps or other instruments.

Example. All solvents and salts purchased from commercial sources were used as received unless otherwise stated. All primers were ordered from Integrated DNA Technologies (Coralville, Iowa). Primer sequences are listed elsewhere herein. Bovine serum albumin (BSA) was purchased from Roche Diagnostics (Indianapolis, Ind.). SsoFast EvaGreen Supermix (2×) was purchased from Bio-Rad Laboratories (Hercules, Calif.). Mineral oil (DNase, RNase, Protease free), Agar, 100 bp PCR DNA ladder, and DEPC-treated and nuclease-free water were obtained from Fisher Scientific (Hanover Park, Ill.). Dichlorodimethylsilane was purchased from Sigma-Aldrich (St. Louis, Mo.). *Staphylococcus aureus* genomic DNA (ATCC number 6538D-5), *Candida albicans* (ATCC 10231), *Staphylococcus aureus* (ATCC 25923), methicillin resistant *Staphylococcus aureus* (MRSA, ATCC 43300), *Escherichia coli* (ATCC 39391), and *Pseudomonas aeruginosa* (ATCC 27853) were purchased from American Type Culture Collection (Manassas, Va.). YM Broth and LB Broth were purchased from Becton, Dickinson and Company (Sparks, Md.). Soda-lime glass plates coated with chromium and photoresist were purchased from Telic Company (Valencia, Calif.). Spectrum food colors (green, red, and blue food dye) were purchased from August Thomsen Corp (Glen Cove, N.Y.). Barrier pipette tips and PCR tubes were purchased from Molecular BioProducts (San Diego, Calif.). Small binder clips (clip size ¾") were obtained from Officemax (Itasca, Ill.). Mastercycler and in situ adapter were purchased from Eppendorf (Hamburg, Germany). Teflon tubing (I.D. 370 μm) was obtained from Weico Wire & Cable (Edgewood, N.Y.), and teflon tubing (O.D. 250 μm, I.D. 200 μm) was purchased from Zeus (Orangeburg, S.C.). Photomasks were purchased from CAD/Art Services, Inc. (Bandon, Oreg.). Red quantum dots (QDs), Qdot 655 ITK, and kit for pBad His B plasmid were purchased from Invitrogen (Carlsbad, Calif.). Green QDs were obtained from Ocean Nanotech (Springdale, Ark.). MinElute PCR Purification Kit was obtained from Qiagen (Valencia, Calif.).

The procedure for fabrication of SlipChip from glass was based on the glass etching fabrication of SlipChip procedure described in detail elsewhere herein, with the following modifications. The glass plate was aligned with a photomask containing the design for the areas and the ducts, and exposed to UV light for 40 seconds. The top slide for both the 40-area design and the 384-area design contained the square areas that were etched to be 70 μm deep. The bottom slide for both the 40-area design and the 384-area design contained the circular areas that were etched to be 30 μm deep. A through hole was drilled in the top plate as an inlet for the solution. The final volume of a single compartment (a pair of overlapping square and circular areas) for the 40-area design was around 25.9 nL and for the 384-area design was around 7.1 nL.

The glass slide with etched areas was thoroughly rinsed with Millipore water and ethanol and then dried with nitrogen gas. The glass slide was oxidized in a plasma cleaner for 100 seconds and then immediately transferred into a desiccator. 50 μL of dichlorodimethylsilane was injected into the desiccator and a vacuum was then applied to perform gas phase silanization for an hour. The silanized glass slide was cleaned with chloroform, acetone, and ethanol, and then dried with nitrogen gas. The silanized glass slide was used for PCR experiments within one day. The patterned glass slide could be re-used after it was cleaned with piranha solution (3:1 sulfuric acid:hydrogen peroxide) and silanized again as described above.

For the 40-area SlipChip design, the concentration of each primer was 0.05 μM. The solution of primer was flowed in Teflon tubing (200 μm ID) connected to a 50 μL Hamilton glass syringe. A volume of 0.1 μL of primer solution, controlled by a Harvard syringe pump, was deposited into the circular areas. The solution was allowed to dry at room temperate, and the preloaded SlipChip was used for experiments within one day.

For the 384-area SlipChip design, the concentration of each primer was 0.1 μM. All primer sequences are described in Table 1. A volume of 0.02 μL of primer solution was deposited into the circular areas on the bottom plate. The solution was allowed to dry at room temperature, and the preloaded SlipChip was used within one day.

TABLE 1

Name and sequence of deposited primer sets in the 384-well SlipChip. Primer sets used in the 40-well SlipChip are marked with asterisks.

| Name of primer sets | Target DNA/pathogen |
|---|---|
| pBad | GCGTCA CACTTT GCT ATG CC GCTTCT GCGTTC TGA TTT AAT CTG |

TABLE 1-continued

Name and sequence of deposited primer sets in the 384-well SlipChip. Primer sets used in the 40-well SlipChip are marked with asterisks.

| Name of primer sets | Target DNA/pathogen |
|---|---|
| E coli nlp | ATA ATC CTC GTC ATT TGC AG<br>{Palka-Santini, 2009 #20}<br>GACTTC GGGTGA TTG ATA AG |
| S pyogene fah | TTA AAT ACG CTA AAG CCC TCT<br>{Palka-Santini, 2009 #20}<br>AGG GTG CTT AAT TTG ACA AG |
| S pyogene OppA | CCC AGT TCA ATT AGA TTA CCC<br>{Palka-Santini, 2009 #20}<br>TTG ACT TAG CCT TTG CTT TC |
| S pneumoniae cinASP | GGCTGT AGG AGA CAATGA AG<br>{Palka-Santini, 2009 #20}<br>CTT TGT TGA CAG ACGTAG AGT G |
| S pneumoniae plySP | ATT TCG AGT GTT GCT TAT GG<br>{Palka-Santini, 2009 #20}<br>GTA AAGTGA GCC GTC AAATC |
| E faecium bglB | TCT TCA TTT GTT GAA TAT GCT G<br>{Palka-Santini, 2009 #20}<br>TGG AAT CGA ACC TGT TTATC |
| E faecalis ace | TAG TTG GAA TGA CCG AGA AC<br>{Palka-Santini, 2009 #20}<br>AGT GTA ACG GAC GAT AAA GG |
| P aerugino vic | TTC CCT CGC AGA GAA AAC ATC<br>{Qin, 2003 #17}<br>CCT GGT TGA TCA GGT CGA TCT |
| S agalactia cpsY | CGA CGA TAA TTC CTT AAT TGC<br>{Palka-Santini, 2009 #20}<br>TCA GGA CTG TTT ATT TTT ATG ATT |
| Pseu general 16S | GAC GGG TGA GTA ATG CCT A<br>{Qin, 2003 #17}<br>CAC TGG TGT TCC TTC CTA TA |
| S aureus nuc ** | GCGATTGATGGTGATACGGTT<br>{Brakstad, 1992 #18}<br>AGCCAAGCCTTGACGAACTAAAGC |
| S epid agrC | GAT GAT ATT AAT CTA TTT CCG TTT G<br>{Palka-Santini, 2009 #20}<br>TCA GGA CTG TTT ATT TTT ATG ATT |
| S mutans dltA | AGATAT GAT TGC AAC AAT TGA A<br>{Palka-Santini, 2009 #20}<br>CGC ATG ATT GAT TTG ATA AG |
| P mirabil aad | CGCTAT TAA CCT TGC TGA AC<br>{Palka-Santini, 2009 #20}<br>CCT TTC TCA CTC ACC ACATC |
| MRSA mecA ** | CAAGATATGAAGTGGTAAATGGT<br>{Shrestha, 2002 #19}<br>TTTACGACTTGTTGCATACCATC |
| C troplicalis ctr | CAA TCC TAC CGC CAG AGG TTA T<br>{Luo, 2002 #16}<br>TGG CCA CTA GCA AAA TAA GCG T |
| C glabrata cgl | TTA TCA CAC GAC TCG ACA CT<br>{Luo, 2002 #16}<br>CCC ACA TAC TGA TAT GGC CTA CAA |
| C albicans calb | TTT ATC AAC TTG TCA CAC CAG A<br>{Luo, 2002 #16}<br>ATC CCG CCT TAC CAC TAC CG |
| K pneumonia cim | AAT TTA ACC TGG TTT GAT AAG AA<br>{Palka-Santini, 2009 #20}<br>CAA AAT ATG AAC TAT CAG AAA GAT TG |
| K pneumonia acoA | TAA CGG CAA AGA CGC TAA<br>{Palka-Santini, 2009 #20}<br>TGA CCA GGG CTT CTA CTT C |

*Staphylococcus aureus*, methicillin resistant *Staphylococcus aureus*, *Escherichia coli*, and *Pseudomonas aeruginosa* were cultured in LB broth for 6-8 hours to an exponential phase. *Candida albicans* was cultured in YM broth for 8 hours. The cells were collected and washed with 1× PBS buffer. The number of cells was counted under a microscope and the concentration was normalized to be approximately $1 \times 10^7$ cfu/mL. The final concentration of pathogens was $1 \times 10^6$ cfu/mL after mixing with the PCR master mixture.

The SlipChip was assembled under mineral oil, which was filtered and degassed before experiments. The bottom plate was first immersed into the oil in a Petri dish, with the patterned side facing up. The top plate was then laid on top of the bottom plate with the patterned side facing down. The two plates were aligned and fixed using binder clips.

Thermal expansion was studied using a fluorescence stereomicroscope, MZ FLIII (Leica, Germany), equipped with a GFP filter set and 11.2 Color Mosaic camera (Diagnostic Instruments Inc., MI). This stereomicroscope allowed simultaneous observation of red and green quantum dots, both excited with a blue light. The gap between the two plates of the SlipChip was filled with mineral oil stained with green fluorescent quantum dots (QDs). To stain the oil, the original 1% QDs solution in toluene was filtered through 0.22 micron microcentrifuge Amicon filters (Millipore, Mass.) and sonicated in ultrasonic bath (Fisher Scientific, NJ) for 10 min. A 10% solution of QDs in mineral oil was thoroughly vortexed and kept for at least 10 min under vacuum before filling the device.

Stained mineral oil was deposited between the slides of the SlipChip; excess oil was removed by rinsing the assembled device sequentially with chloroform, acetone, and ethanol. The SlipChip areas were filled by injecting an aqueous solution of red QDs through the fluidic path created by the areas and ducts. Red QDs 655 ITK were diluted 1:10 in 10 mM Tris-HCl buffer, pH 8.0, containing 1 mM EDTA and 50 mM NaCl. The SlipChip was placed under the stereoscope on the Mastercycler and multiple heating cycles were performed to observe aqueous thermal expansion.

For reactions in the 40-area SlipChip, the reaction master mixture consisted of 10 μL of 2× SsoFast EvaGreen SuperMix, 2 μL of 10 mg/mL BSA solution, 6 μL of RNase free water, and 2 μL of 1 ng/μL *S aureus* gDNA (replaced with 2 μL of RNase free water for control experiments). The final concentration of gDNA template was 100 pg/uL. For reactions in the 384-area SlipChip, a 331-bp long piece of dsDNA amplified from His B plasmid (pBad template) was used as a template for a PCR control reaction (Primer 1: GCG TCA CAC TTT GCT ATG CC; Primer 2: GCT TCT GCG TTC TGA TTT AAT CTG). The pBad template was purified using a MinElute PCR Purification Kit (Qiagen).

The reaction master mixture for the 384-area SlipChip consisted of 10 μL of 2× SsoFast EvaGreen SuperMix, 2 μL of 10 mg/mL BSA solution, 1 μL of 100 pg/μL pBad template, 2 μL of cell suspension, and 5 μL of RNase free water. The PCR master mixture was injected into the SlipChip by pipetting. The square areas on the top plate were moved to overlay the circular areas on the bottom plate. The SlipChip was then placed on an in situ adaptor in the Mastercycler (Eppendorf) for thermal cycling. An initial step of 15 min at 94° C. was used to lyse the cells and activate the enzyme for reaction. Next, a total 35 cycles of amplification were performed as follows: a DNA denaturation step of 1 min at 94° C., a primer annealing step of 30 sec at 55° C., and a DNA extension step of 30 sec at 72° C. After the final cycle, the DNA extension step was performed for 5 min at 72° C. Then the SlipChip was kept in the cycler at 4° C. before imaging.

Bright field images were acquired by using Leica stereoscope. All fluorescence images were acquired using a Leica DMI 6000 B epi-fluorescence microscope with a 5×/0.15 NA objective and L5 filter at room temperature. The intensity level of fluorescence images was adjusted to be the same values for all images. All fluorescence images were corrected by a background image obtained with a standard fluorescent slide. Fluorescence images were stitched together using MetaMorph software (Molecular Devices, Sunnyvale, Calif.).

The inventors have performed PCR on the SlipChip with a design containing forty areas and two inlets for two different samples. This device can be used to simultaneously screen two different samples with up to 20 different primer sets for each sample. The top plate contained the fluid inlet, square areas (side length of 640 μm, depth of 70 μm) and rectangular areas (length of 570 μm, width of 230 μm, depth of 70 μm). The bottom plate contained circular areas (diameter of 560 μm, depth of 30 μm) and the ducts for introduction of the sample (width of 150 μm, depth of 30 μm). Different primer sets were preloaded into the bottom circular areas and allowed to dry under room temperature. The top and bottom plates were then submerged under mineral oil and assembled to form a continuous fluidic path. The PCR master mixture, a solution containing SsoFast EvaGreen Supermix, 1 mg/mL BSA, and template (or water for the control experiments), was introduced into the SlipChip by pipetting. In this geometry, the sample fluid spontaneously broke up into discrete volumes even before sliding. This breakup of a continuous stream into discrete volumes can be used for applications where compartmentalization is required, such as stochastic confinement and digital PCR. Immediately after injection of sample, the top plate was slipped down to overlap the square areas with the circular areas on the bottom plate, and the dry primers preloaded in the circular areas dissolved in the sample introduced from square areas. The rectangular areas on the top plate also aligned with the middle of the duct on the bottom plate. The aqueous solution formed a circular droplet in the areas due to surface tension, and the volume of solution in each compartment was estimated to be 25.9 nL by using AutoCAD software.

The inventors addressed the issue of thermal expansion during thermal cycling by careful design of the SlipChip. The material of the SlipChip (glass), the lubricating fluid (mineral oil), and the sample (the aqueous PCR mixture) have different thermal expansion coefficients. It is known that the mineral oil and aqueous mixture should expand more than the glass when the temperature of the SlipChip was increased from the annealing temperature (55° C.) to the dissociation temperature (95° C.). The unique design of this SlipChip held the aqueous solution within the area by using area geometry. Dichlorodimethylsilane was applied to render the surface of the SlipChip hydrophobic. The inventors used an aqueous solution containing red quantum dots and mineral oil containing green quantum dots to study the fluid movement during thermal cycling. When using the SlipChip with only square areas, the aqueous solution filled the square area. After an increase in temperature, the aqueous solution leaked out of the areas, resulting in a loss of material and unpredictable changes in concentration. The inventors found that when a smaller, circular area containing oil in the bottom plate was brought into contact with a square area containing aqueous solution in the top plate, the aqueous solution would form a droplet surrounded by mineral oil within the hydrophobic area due to the surface tension, providing room for expansion during thermal cycling. When the temperature was increased, the aqueous solution expanded to fill the reaction compartment and the mineral oil expanded and moved through the gap between the top and bottom plates in the SlipChip, serving as a buffer material. Without this design, in certain embodiments leakage has been observed during thermal cycling. The inventors determined that the shape and size of the bottom area can be used to form a single droplet of consistent size in the center of the two areas. Consistent size of the droplets formed ensured that the concentration of reagents within the droplets remained the same in all droplets. The rectangular areas on the top plate overlapped with the ducts on the bottom plate to address the issue of thermal expansion of the solution remaining in the duct.

The inventors performed PCR in an embodiment of the SlipChip by amplifying nuc gene in *S. aureus* genomic DNA. Primers for the *S. aureus* nuc gene were preloaded into the circular areas of the bottom plate of the SlipChip and allowed to dry under room temperature. The PCR master mixture, containing EvaGreen supermix, 100 pg/μL *S. aureus* genomic DNA (gDNA), and 1 mg/mL BSA, was injected into the ducts to fill two rows of areas. Two other rows of areas were filled with the same aqueous PCR mixture but replaced gDNA template by RNase free water. The square areas in the top plate and circular areas in the bottom plate were overlapped by sliding the two plates of the SlipChip relative to one another. The SlipChip was placed into the thermal cycler on a flat in situ adaptor for PCR amplification. The inventors showed that no cross contamination occurred between different rows in the SlipChip as only areas containing template showed amplification. Fluorescence intensity increased significantly after thermal cycling only in the areas containing gDNA, and all 20 areas containing template showed amplification, verifying the robustness of the PCR SlipChip. After thermal cycling, the solution in the SlipChip was flowed out and collected, and a gel electrophoresis experiment was performed. The image of the gel showed successful on-chip amplification and the correct size of the amplification product (~270 bp).

Next, the inventors tested the cross contamination among adjacent areas by preloading the primer sets for the nuc gene in *S. aureus* and mecA in Methicillin-resistant *Staphylococcus aureus* (MRSA) on the chip alternatively in the same row, and injecting PCR master mixture containing 100 pg/μL of *S. aureus* genomic DNA into the SlipChip (primer sets can be found in Table 1). Because the nuc gene is commonly present in *S. aureus* but the mecA gene is not, all ten areas preloaded with the primers for the nuc gene showed a significant increase in fluorescence intensity after thermal cycling, and none of the areas loaded with primers for the mecA gene increased in fluorescence intensity. Combined with the results above, the inventors demonstrated each area was an isolated reaction condition, and there was no communication among areas.

Furthermore, the inventors demonstrated that the SlipChip containing 384 areas, which can be preloaded with up to 384 different primer sets, can be applied for high-throughput multiplex PCR. The inventors designed this platform for 16 different pathogens that are commonly present in blood infections by using 20 different primer sets preloaded on the SlipChip. Primer sequences were selected from previous publications, and the PCR master mixture was combined with cells at a final concentration of approximately $10^6$ cfu/mL. This guaranteed the presence of targeted cells in each individual area. The inventors have demonstrated that PCR on SlipChip can detect a single molecule. A SlipChip was made with 28 independent regions, and a primer set for each pathogen was preloaded as 4 by 4 matrices for the convenience of imaging. Primers for pBad template were preloaded in the two columns of areas at the edges of the SlipChip as a positive internal control. A purified pBad 331 bp template (final concentration 1 pg/uL) was added to the PCR master mixture before loading. Two columns next to the areas containing primers for pBad were left empty as a negative control for leakage.

The SlipChip was able to robustly identify cells, as only the regions preloaded with the appropriate primers showed a significant increase in fluorescent signal. The regions for positive controls showed an increase in fluorescent signal and regions for negative controls did not. The SlipChip was able to correctly identify S. aureus, MRSA, Candida albicans, P. aeruginosa, and E. coli. The inventors demonstrated high-throughput multiplex PCR on the SlipChip. In certain embodiments, the SlipChip can perform 384 nanoliter-scale reactions for multiplex PCR with a prefabricated array of primer sets. The PCR SlipChip can be loaded simply by pipetting, avoiding any requirements for complex injection methods. The inventors have shown that an embodiment of a PCR SlipChip can screen one sample for 16 different pathogens on the same SlipChip, and that there was no detectable cross contamination. The inventors have also demonstrated that two different samples can be introduced and tested simultaneously on a single preloaded SlipChip. The multiplexed PCR SlipChip can be designed with a larger number of inlets for simultaneous screening of multiple samples, for use with non-thermal cycling nucleic acid amplification methods such as LAMP, RPA or NASBA, and/or with a larger number of areas to allow for more conditions to be screened in a single experiment. PCR SlipChips can be made to use the primer sets established by current PCR microarray technology, but with a much smaller size and reaction volume. One can also adapt the current technologies of microarray printing to preload primers and to fabricate SlipChips.

In addition to distinguishing a large number of different species in one experiment, certain embodiments of the SlipChip are capable of providing quantitative results, by, for example, integrating real-time imaging techniques for multiplex real-time PCR, or using a large number of areas for each primer set to enable counting the number of all amplicons in one experiment to perform multiplex digital PCR.

In addition to being used for multiplex PCR for screening of specific genes, certain embodiments of the SlipChip can be used for additional applications. Multiplexed PCR and other nucleic acid amplification chemistries on SlipChip can be used for high-throughput DNA amplification before sequencing, for example enrichment methods for targeted sequencing, that can currently performed in well plates and by droplet-based methods (as described, for example, in Microdroplet-based PCR enrichment for large-scale targeted sequencing Tewhey, R. et al., Nat. Biotechnol. 2009, 27, 1025-1031). PCR on a SlipChip can also be used for the detection of genomic diseases, genetic mutations, and food or water contaminants. The current platform can also be adapted to perform reverse transcription PCR for RNA amplification for, for example, RNA virus detection, study of gene expression, and investigation cell heterogeneity.

The SlipChip can be fabricated from inexpensive materials such as glass or plastic, and, in certain embodiments, requires no complex equipment or specialized knowledge to operate. When dried reagents are preloaded onto the SlipChip, it is also easy to transport and store. It can be integrated with isothermal amplification methods and simple readouts.

The SlipChip can also be used in other applications that require prefabricated arrays of reagents with multiplex and high throughput capacity, such as, for example, protein crystallization, immunoassays, DNA hybridization, DNA-protein interaction, and chromatin immuno-precipitation (ChIP).

In certain embodiments, combinatorial biocatalysis can be performed on the SlipChip. Combinatorial biocatalysis is similar in concept to combinatorial synthesis in organic chemistry. Combinatorial biocatalysis can provide a diverse library of derivatives from a single lead compound by sequentially combining biocatalytic reactions via enzymes. Combinatorial biocatalysis enables the generation of a huge number of enzymatic products in parallel sequence of either different substrates or different enzymes. The lead compound bearing multi-functional groups (e.g., carboxyl group, hydroxyl group, acyl group, amine group, etc.) is a potential molecule to apply. Combinatorial biocatalysis requires many steps of sequential mixing and reactions. If the amount of a lead compound is very tiny and expensive, a 96, 384 or even 1,536 well plate may require too much volume for the thousands of reactions that may be needed. In addition, there can be limitations in testing synthesized derivatives because of the limited amount available. Analysis of products on a standard multiwell plate can be difficult in terms of both concentration and volume. Certain embodiments of the Slipchip can provide appropriate confined volumes and sufficient numbers of reaction centers without a complicated apparatus. The Slipchip is an attractive solution for high throughput drug discovery/drug screening. Possible applications of combinatorial biocatalysis include biocatalysis (enzyme screening, enzyme evolution, optimization of reaction conditions), bioengineering (system development, robotics, industrialization), bioprocess engineering (reaction system optimization, downstream process, scale-up, commercialization), medicinal chemistry (novel drug candidates, derivatization, ADME toxicity tests), food chemistry and engineering (natural colorants, antioxidants, food additives), agricultural chemistry (functional dairy products, emulsifiers) and environmental chemistry (natural pesticides).

In certain embodiments of the present invention, high throughput enzyme screening can be performed in the SlipChip. Screening enzymes is a huge research/industrial field in worldwide. Researchers typically apply their enzyme candidate to certified chemical libraries. Typically robotics and manual labor are used, but the amount of enzyme samples is typically a limiting factor. Similar problems occur as in combinatorial biocatalysis (see above). A variety of chemical libraries can be provided in a Slipchip with different substrates. Chemical libraries as the target substrates preferably cover a large spectrum of functional groups as well as having a target-specific focus on the particular enzyme being tested. The Slipchip can contain different ranges of chemical libraries with appropriate amounts of reactants. Users can then flow a small amount of enzyme solution into the device and analyze each area in a Slipchip. For example, if someone has a putative lipase/esterase sample, a Slipchip containing various chemical libraries testing for hydrolysis (e.g., one can contain C2 ester, C3 ester, C4 ester, . . . C14 ester, C16 ester . . . , etc.). Possible applications of high throughput enzyme screening include, but are not limited to, determining stereo-specificity, regio-specificity, hydrophobicity, hydrolysis and/or reverse-hydrolysis reactivity, the pH range, the temperature range for hyper-thermostable enzymes, the pressure range for hyper-barostable enzymes, the ionic strength range, and tolerance for high-salt conditions.

In certain embodiments, the SlipChip can be used for enzymatic tests for the screening of novel enzymes. Once a potential enzyme is isolated from a microorganism, it is typical to run enzymatic reactions in a 96-well plate to evaluate the substrate specificity, reactivity, selectivity, and stability. For this analysis, typically one tests the enzyme against a chemical library. A pre-loaded chip can be provided that contains multiple substrates for use as a simple test screening kit for enzyme samples.

In certain embodiments of the present invention, the SlipChip can be used as a platform that reduces the complexity of sample collection, concentration, and preparation (SCCP); processes diagnostically relevant samples with viscosities ranging from urine to sputum; and allows processing of large, milliliter-scale sample volumes to capture low concentrations of analytes, and concentrating them to small, nanoliter-scale volumes for easy detection, all in a manner compatible with a wide range of amplification, detection, and readout components.

The SlipChip platform overcomes several key challenges that face healthcare and diagnostic technologies in resource-limited settings. Diagnostic assays require a complex sequence of steps, from sample preparation to amplification to detection and readout. These steps are difficult to perform in resource-limited settings, as they require either highly skilled technicians or complex automation. The difficulty increases further for assays requiring high sensitivity (little room for error and contamination), quantification (complex protocols and equipment), and multiplexing (the process must be repeated multiple times for multiple analytes). The SlipChip platform can encode for all the steps necessary for a complete diagnostic device, from sample collection, concentration, and preparation, to amplification, detection, and readout.

The SlipChip platform can ease sample preparation, and open new assay techniques to point-of-care (POC) applications. It can, for example: (i) accept small or large volumes (allowing for high sensitivity) of diagnostically relevant samples such as blood, sputum, urine or feces; (ii) manipulate them through many sample preparation steps to isolate the molecules of interest; and (iii) concentrate them into smaller volumes that can be used directly by an amplification or detection component.

In certain embodiments, the SlipChip can be used for the rapid, simple extraction of diagnostically relevant biomarkers from raw sample inputs. Certain embodiments of the SlipChip can be used to address many areas of current significant unmet need including but not limited to the following: (1) sample preparation of whole blood and plasma for isolation of viral RNA for quantification of HIV viral load (for monitoring antiretroviral therapy and for diagnosing infants, for example); (2) sample preparation of sputum for isolation of both RNA and DNA nucleic acids from pathogens that cause pneumonia (for determining when antibiotic treatment should be administered, for example).

Quantitative monitoring of HIV viral load during treatment in resource-limited settings to prevent widespread drug resistance has been identified as a major barrier to HIV/AIDS care worldwide. Diagnosis of HIV infections in infants over few weeks of age can be performed by quantifying viral load, and is preferred in resource-limited settings, as early diagnosis of HIV infection and administration of HIV antiretroviral drug treatment drastically reduces the rate of infant mortality.

At present, no HIV viral load quantification platform is available that can be used in resource-limited settings; centralized testing of viral load is not universally suitable. Existing centralized viral load assays require significant technical expertise and instrumentation. Installing complex instruments in resource-limited settings has generally failed, and transporting samples to centralized labs has also proven problematic. Dried blood spots (DBS, spots of whole blood dried on filter paper) are the only realistic option for transporting samples in these settings. In addition to technical issues of isolating viral RNA quantitatively from DBS, this approach is not well-suited for traveling clinics, as results must be obtained without delay so the result of the test can be actionable. Moreover, the use of DBS still requires quantitative RNA testing that assumes sophisticated equipment and technical expertise.

In certain embodiments, the SlipChip can be used for quantitative and sensitive measurement of HIV viral load in resource-limiting settings by performing multistep sample processing in a self-contained format. Certain embodiments of the SlipChip can accept, for example, 100-200 µl of whole blood or plasma, and produce purified viral RNA with >30% yield in 20-50 µl with quality sufficient for subsequent isothermal amplification performed on the Digital SlipChip or another amplification component.

Accurate diagnosis of the cause of acute lower respiratory infections (ALRIs) such as pneumonia could save hundreds of thousands of lives every year and preferably involves concurrent multiplexed detection of bacteria and viruses, and quantification to distinguish lower levels (corresponding to bacterial colonization) from higher levels (corresponding to bacterial infections). In developing countries ALRIs, particularly pneumonia, are the leading cause of death in children under 5 years of age (>2 million/year), due to inadequate treatment caused by the lack of accurate, low cost, readily available diagnostic tools. Poor diagnostic capabilities also lead to overuse of antibiotics, advancing the emergence of drug resistant strains. Bacterial infections, particularly *Streptococcus pneumoniae* and *Haemophilus influenzae* type b, which can be easily treated with antibiotics, must be distinguished from viral or other causes. A major challenge is differentiating bacterial infection from colonization of the upper respiratory tract, and a simple qualitative yes/no test is not effective. Diagnosis can be dramatically improved by implementing a quantitative multiplexed test of sputum for, for example, 16 common bacterial and viral pathogens. For example, a medium level of *S. pneumoniae* bacterium in the absence of significant levels of other pathogens is likely to indicate *S. pneumoniae* infection, while a medium level of *S. pneumoniae* bacterium in the presence of a very high level of respiratory syncytial virus (RSV) would indicate RSV infection as a more likely cause.

In certain embodiments, the SlipChip can be used to isolate RNA and DNA of pathogens that cause pneumonia from sputum in >30% yield with >5-10 fold increase in concentration for downstream quantitative and sensitive detection on a Digital SlipChip or another component.

Certain embodiments of the SlipChip can be programmed to perform complex manipulations of volumes from mL to nL. They can be used to easily process hundreds or thousands of nanoliter volumes in parallel by simple slipping, for example, two plates. The inventors have demonstrated that larger volumes can be incorporated into this platform (e.g., 200 µL of whole blood). This multi-scale capability is useful. For example, to capture 50 HIV viruses at 500/mL HIV viral load, one needs to handle at least 100 µL of plasma, while concentrating samples into smaller volumes reduces losses during processing and provides output more suitable for amplification and quantification (e.g., using a digital PCR SlipChip). Serial dilution by 105-fold and washing by dilution have been demonstrated on the SlipChip. Quantitative handling of beads has been demonstrated in nL-volume immunoassays in the pM range, handling and detecting a few thousands of protein molecules. Local heating and cooling can be programmed into the SlipChip via simple chemistry, by programming heat- or cold-generating reagents to combine at the required step. Temperature control can be also achieved via external or internal on-chip means, including electrical and thermoelectric heating and cooling, and a number of approaches used to conduct PCR reactions. These features can be used for reliable isolation of target nucleic acids with at least 30% yield, with 10-fold concentration, and can optimize the trade-offs between yield and concentration.

In certain embodiments, the SlipChip can be encoded to extract HIV RNA from whole blood or plasma for downstream HIV viral load analysis. The SlipChip can use 100 to 200 µL of plasma (prepared on chip or off chip) with 500 to $10^6$/mL HIV viral load and isolate viral RNA into 10-30 µL of solution with >30% yield. This output is sufficient for a digital SlipChip to measure the viral load with a dynamic range from 500 to 106 copies per mL, and less than 3 fold error with 95% confidence. Quality and quantity of isolated HIV RNA can be quantified by real time RT-PCR.

In certain embodiments, the SlipChip can be encoded to extract RNA and DNA from sputum for identification and quantification of pathogens that cause pneumonia. They can handle, for example, 200-500 µL of sputum for RNA and DNA isolation in >30% yield, concentrating it in, for example, 20-50 µL of amplification-ready solution. The highly parallel processing on the SlipChip enables optional enhancements that include: (i) parallel purification of DNA and RNA simultaneously from the same sample, and (ii) multiple sputum samples processed on the same device from a single patient to ensure at least one high-quality sample, or from multiple patients to increase throughput. These features, combined with SlipChip components for amplification, readout, and integration, provide solutions to urgent global diagnostics problems including quantification of HIV viral load and multiplexed quantitative analysis of pneumonia pathogens. The sputum sample processing protocol can be easily adaptable to the isolation of DNA from *Mycobacterium tuberculosis* for molecular diagnosis of TB and identification of drug resistant strains, and is expandable to isolation of nucleic acids from feces. HIV protocols are adaptable to isolation of *Plasmodium* DNA from blood for diagnosis of malaria.

In certain embodiments, the SlipChip can be used to provide signal amplification and improve detection, in a manner compatible with a wide range of existing and future amplification chemistry components.

In certain embodiments, the SlipChip can be used to dramatically enhance signal amplification and detection chemistries by leveraging the advantages of the SlipChip platform to implement the principle of "stochastic confinement". The SlipChip can be used to, for example, (i) increase sensitivity of existing technologies to the single-molecule or single-cell level; (ii) increase specificity and reduced interference and background reactions; (iii) robustly quantify over a large dynamic range; iv) perform multiplexed experiments.

In certain embodiments, the SlipChip can be used as an open platform that component builders can use to enable robustness, quantification, sensitivity, and specificity of amplification chemistry components for diagnostic applications in resource-limited settings. The SlipChip can be used to address many areas of current significant unmet need including but not limited to the following: (1) quantification of HIV viral load (for monitoring antiretroviral therapy and for diagnosing infants, for example), and (2) multiplexed quantitative detection of bacterial and viral pathogens that cause pneumonia (for determining when antibiotic treatment should be administered, for example).

In certain embodiments, the SlipChip can be used for quantification of HIV viral load for, for example, monitoring antiretroviral therapy and for diagnosing infants. In certain embodiments, the SlipChip can be used for highly quantitative and sensitive measurement of HIV viral load by converting simple qualitative amplification chemistries to a "digital" format with end-point readout, this is sometimes referred to herein as a "Digital SlipChip".

In certain embodiments, the SlipChip can be used for multiplexed pathogen detection to diagnose the cause of pneumonia. At the present, quantitative multiplexed diagnostics of pneumonia pathogens is an unmet need under resource-limited settings. Single-analyte tests can be done by isothermal techniques, but their value is limited in the absence of quantification and multiplexing. Multiplexed quantitative detection can be accomplished by real time PCR, but this has not been useful in point of care, resource limited settings. In certain embodiments, the SlipChip can be used for quantitative and sensitive detection of pneumonia pathogens by combining multiplexing and conversion of amplification chemistries to a "digital" format with end-point readout.

In certain embodiments, the SlipChip can be used for (i) increased sensitivity of existing technologies to the single-molecule or single-cell level; (ii) reduced interference and background reactions; (iii) robust quantitation over a large dynamic range; (iv) practically unlimited multiplexing applications. Certain embodiments of the SlipChip can encode, as a sequence of areas in the two plates, essentially any program to manipulate fluid volumes.

In certain embodiments, the SlipChip can be used for multivolume stochastic confinement. The SlipChip can split a sample into, for example, hundreds or thousands of small volumes of different sizes in a "digital" format (zero versus one or more molecules of analyte per area), prior to amplification. Confinement of molecules in small areas (i) increases concentration of molecules, (ii) isolates these molecules from interfering molecules, (iii) enables quantification from endpoint readout by maximum likelihood estimation, with large dynamic range provided by multiple volumes used simultaneously on the same chip.

The SlipChip is compatible with both digital PCR and digital isothermal recombinase-polymerase amplification (RPA) amplification technologies using commercially available stock reagents. Many other isothermal techniques can be performed, including but not limited to loop-mediated isothermal amplification (LAMP) and nucleic acid sequence-based amplification (NASBA), for quantification of analytes (even in the presence of interference).

In certain embodiments, the SlipChip can have a dynamic range of $500\text{-}10^6$/mL for analysis of HIV viral load using multivolume stochastic confinement. In certain embodiments, the SlipChip can be designed as a rotary multivolume Digital SlipChip. This design can have hundreds of areas with volumes ranging from, for example, 0.37 nL to 250 nL, and can quantify HIV viral RNA with a dynamic range of $500\text{-}10^6$ copies/mL, in 3-fold changes with 95% confidence. The inventors have confirmed that HIV RNA can be detected on the Digital SlipChip platform.

In certain embodiments, the SlipChip can be used for detection and quantification in sputum samples of 16 pathogens involved in pneumonia. In certain embodiments, the SlipChip can contain preloaded reagents for isothermal amplification chemistry for 16 pathogens (with an optional additional reverse transcription step for detection of RNA viruses). The inventors have demonstrated multiplexed detection of pathogens using preloaded reagents on a 384-plex uniform-area SlipChip platform. Different areas of the proposed chip can be used to tune the dynamic range of the device into the appropriate range, for example: outer areas with larger areas for sensitive detection of CMV, HRV, and other pathogens in the range of $10^2\text{-}10^5$/mL, and inner areas with smaller areas for detection and quantification in the $10^2\text{-}10^6$/mL range of colonizing pathogens such as *S. pneumonia* and *H. influenzae* type b. The SlipChip's capabilities of sample preparation, visual readout, and integration have the potential to provide solutions to two areas of urgent global diagnostics needs—quantification of HIV viral load and multiplexed quantitative analysis of pneumonia pathogens. Diagnosis of tuberculosis can be performed by stochastic confinement on the SlipChip which would amplify physiological responses of *Mycobacterium tuberculosis* and enable rapid detection and phenotypic testing of drug resistance. Quantification of CD4 count in AIDS patients can be performed efficiently using multivolume stochastic confinement.

In certain embodiments, the SlipChip can be used for readout and signal transduction. In certain embodiments, the SlipChip can accept output from multiplexed amplification and detection component technologies, e.g., 1000's of separate amplified nucleic acid products produced during detection of pathogens, and convert them to a readout for analysis and interpretation by eye or by using a simple cell phone camera. The SlipChip can enhance signal processing and readout by leveraging the advantages of the SlipChip platform to implement multistep and multiplexed processing, generating a visual readout for any diagnostic test. In certain embodiments, the SlipChip can be used for (i) technically complex processing without dependence on user expertise; (ii) access to more diverse amplification, processing and detection chemistry than currently available in POC, expanding the diagnostic tool box; (iii) quantifiable visual readout without infrastructure.

In certain embodiments, the SlipChip can be used for rapid visual analysis for diagnostics in two areas of current significant unmet need in resource-limited settings: 1) quantification of HIV viral load (for, for example, monitoring antiretroviral therapy and for diagnosing infants), and 2) multiplexed quantitative detection of bacterial and viral pathogens that cause pneumonia (for, for example, determining when antibiotic treatment should be administered).

In certain embodiments, the SlipChip can be used for multiplexed visual readout for determination of HIV viral load in regions with no infrastructure. In certain embodiments, the SlipChip can be used for quantitative and sensitive measurement of HIV viral load in regions without suitable infrastructure by performing multistep processing in a self contained format and generating an easy to interpret visual readout. It can accept products of nucleic acid amplification technology (NAT) performed on the SlipChip or another amplification component, and convert it to a visual readout allowing for more immediate treatment plans to take effect.

In certain embodiments, the SlipChip can be used for multiplexed visual detection and analysis to determine the cause of pneumonia.

In certain embodiments, the SlipChip can be used to (i) Accept, for example, thousands of mixtures containing amplified nucleic acids, e.g. from a Digital SlipChip or another component, and (ii) Carry out multistep processing of these mixtures to produce a quantitative visual readout from each. Other technologies have not yet been able to meet these needs, which are preferred for converting to visual readout the quantitative, highly multiplexed "digital" tests, such as the HIV viral load test or the pneumonia panel provided by the Digital SlipChip. Certain embodiments of the SlipChip can encode, as a sequence of areas in the two plates, essentially any program to manipulate fluid volumes. Certain embodiments of the SlipChip can process multiple volumes, through multiple steps of detection, amplification, and visual readout.

In certain embodiments, the SlipChip can accept, for example, thousands of areas, for example, 0.3-300 nL in volume with isothermally amplified nucleic acids in each area, and produce a visual readout from each area by a multistep process. In certain embodiments, an area larger than 250 μm×250 μm with absorbance above 1 is easily visible on the SlipChip. For larger areas with higher concentrations of nucleic acids, direct detection by hybridization capture of gold or selenium particles can be used. For smaller areas with lower concentrations, the user can transfer samples into larger areas and perform additional amplification chemistry. Amplification chemistry can be modified to provide visual detection, and such modifications are already well established for lateral flow readouts. Certain embodiments of the SlipChip can support all of the preferably included steps (for example, capture of molecules on beads and surfaces, magnetic manipulation, optional washing by dilution) using preloaded reagents by slipping, without requiring technical expertise of the user. In certain embodiments, the SlipChip can be used for LAMP and RPA and other isothermal amplification technologies.

Example. For one RPA experiment, a TwistAmp Basic kit was purchased from TwistDx. (Cambridge, United Kingdom) The RPA supermix was prepared from a single tube containing RPA enzymes and reagents (freeze-dried Basic reaction pellet), by addition of a mixture of 20 μl rehydration buffer and 8 μl control 1× primer/probe mix. A positive control solution was prepared by mixing 5 μl positive control template (10 copies/μl) with 14 μl of RPA supermix, while 5 μl water was added in 14 μl of RPA supermix as negative control solution.

A solution of 50 nl magnesium acetate (9.3 mM) was deposited into each circular area on the bottom plate of a 40-area SlipChip through the Teflon tubing (200 µm ID) connected to a 50 µL Hamilton glass syringe controlled by a Harvard syringe pump. The solution was let dry under room temperature for 10 minutes.

The SlipChip was assembled under degassed mineral oil. The bottom plate was first immersed into the oil in a Petri dish, with the patterned side facing up. The top plate was then laid on top of the bottom plate with the patterned side facing down. The two plates were aligned and fixed using binder clips.

Negative control solution (5 µl) was injected into the top two rows through one inlet by pipetting, while the positive control solution (5 µl) was loaded into the bottom two rows through a separate inlet. The fluidic path was broken by slipping and the top plate was moved to overlay with the circular areas, which contain preloaded dry magnesium acetate, on the bottom plate. The volume of the reaction mixture in each area was 27 nL with a predicted Mg acetate concentration of 17 mM. The SlipChip was immediately placed in a 39° C. incubator, and the fluorescence intensity was acquired using a Leica DMI 6000 B epi-fluorescence microscope. The fluorescence images were acquired using a 5×/0.15 NA objective and L5 filter immediately after slipping and 20 min after incubating at 39° C.

Experiment one, with dry magnesium acetate, was performed as described above. However, magnesium acetate solution can alternatively be loaded into the SlipChip in then aqueous phase, and then slid over to mix with RPA supermix to initiate the reaction. In Experiment two, premixing magnesium acetate solution with RPA supermix was done. A solution of 1 µl of 280 mM magnesium acetate was added to 19 µl negative control solution, and the solution was injected into the top two rows of a 40-area SlipChip. Another solution of 1 µl of 280 mM magnesium acetate was added to 19 µl positive control solution, and the solution was loaded into the bottom two rows through a separate inlet. The fluidic path was broken by slipping and the top plate was moved to overlay with the circular areas containing mineral oil. The SlipChip was immediately placed in a 39° C. incubator, and the fluorescence intensity was acquired by using a Leica DMI 6000 B epi-fluorescence microscope. The fluorescence images were acquired by using a 5×/0.15 NA objective and L5 filter immediately after slipping and 20 min after incubating at 39° C. In experiment one, out of 40 areas only two, corresponding to the positive control solution lit up. In experiment two, out of 40 areas three, corresponding to the positive control solution, lit up. In both experiments, the areas corresponding to the negative control solution all remained dark.

The SlipChip is compatible with a wide range of visual detection chemistries. Multistep processing on certain embodiments of the SlipChip can utilize standard visualization chemistries already established in the "dip stick" lateral flow devices (see for example, U.S. patent application Ser. No. 12/425,121, incorporated by reference herein in its entirety), or enable new chemistries. The autocatalytic reduction of silver (I) ions, initiated on the surface of gold nanoparticles (AuNPs), provides a very high degree of amplification, rapidly producing visually observable silver deposition. In SlipChip experiments in a 55 nL volume at 5 pM analyte (~165,000 molecules) this chemistry produced a visible signal that was clearly distinguishable from background. The signal was generated within 10 min. Additional chemistries that can be performed on the SlipChip include but are not limited to direct label capture, Alkaline Phosphatase (AP) to generate a visual product from NBT and BCIP, and polymerization-based amplifications.

In certain embodiments, the SlipChip can be used for visual quantification of HIV viral load on the SlipChip with a dynamic range of, for example, 500-106. The RPA products from HIV RNA from the SlipChip or other amplification components can be processed through additional steps on the SlipChip to perform, for example, hybridization, purification and visual signal generation for direct visual analysis of HIV viral load.

In certain embodiments, the SlipChip can be used for visualizing detection and quantification of, for example, 16 pathogens involved in pneumonia. The additional areas for hybridization and visual amplification can either be incorporated within a two-layer device, or within a multilayer device to increase density. The SlipChip can be used in other areas where multiplexed, multistep readouts are needed. This includes, but is not limited to, other diagnostic needs that rely on amplification of nucleic acids (e.g., in identification and diagnosis of malaria parasites or STDs), multiplexed immunoassays (e.g., in identification of pathogens responsible for persistent diarrhea or STDs), and in rapid visual detection and counting of *Mycobacterium tuberculosis* bacteria.

In certain embodiments, ELISA-based methods of determining viral load, such as ExaVir Load (Cavidi AB), can be performed in the SlipChip. ExaVir Load determines viral load based on quantification of Reverse Transcriptase activity, it can measure any HIV type or subtype, including O and N-group. Unfortunately Exavir Load and similar assays are slow and not quantitative. Such assays require a long incubation time for DNA synthesis to get detectable amount of DNA at low viral loads. However, if the assay is performed in certain embodiments of the SlipChip using stochastic confinement and a digital readout, the high local concentration allows shorter incubation times. For example, the ExaVir Load measuring range is up to 600,000/mL. This is determined by the synthesized DNA saturating all templates anchored on the bottom of the well in the incubation time (typically, 1 day). In a SlipChip area with, for example, 10 nL volume and a depth of 100 µm, one viron in a well is 100,000/mL, but the area is only about ~1/300 compared to a well in a 96-well plate. Assuming the speed of consuming the templates depends on the concentration of the viron, one would only need ~1/50 time, that is, typically approximately one hour, to saturate the templates in SlipChip.

Other methods can be performed in conjunction with ExaVir Load such as radical initiation/polymerization amplification in order to increase amplification. One can further enhance amplification by adding a small amount of radical chain terminator as an inhibitor to establish a threshold. This reduces the number of washing steps required.

In certain embodiments, the SlipChip can be stackable. A stackable SlipChip can be used in many areas of current significant unmet need, including but not limited to the following: (1) quantification of HIV viral load (for, for example, monitoring antiretroviral therapy and for diagnosing infants), and (2) multiplexed quantitative detection bacterial and viral pathogens that cause, for example, pneumonia (for, for example, determining when antibiotic treatment should be administered). A stackable SlipChip can be used for a complete blood-to-answer diagnostic solution for quantification of HIV viral load. In certain embodiments, a stackable SlipChip can be used for quantitative and sensitive measurement of HIV viral load by integrating different SlipChip technologies, for example: (i) SlipChip for sample prep and concentration to isolate HIV viral RNA from blood, (ii) Digital SlipChip to quantify the viral load by isothermal amplification and counting of RNA molecules, and (iii) a SlipChip to convert amplified nucleic acids into a readout detectable by eye or, for example, with a cell phone camera.

In certain embodiments, a stackable SlipChip can be used for multiplexed pathogen detection for diagnosis of the cause of, for example, pneumonia. In certain embodiments, a stackable Slipchip can be used for quantitative and sensitive detection of pneumonia pathogens at the point of care by integrating different SlipChip technologies, including, for example: (i) a SlipChip for sample prep and concentration to isolate from sputum RNA and DNA pathogens responsible for pneumonia, (ii) a Digital SlipChip for multiplexed identification and quantification of nucleic acids from a panel of, for example, 16 pathogens responsible for pneumonia, (iii) the SlipChip to convert amplified nucleic acids into visual readout detectable by eye or, for example, with a cell phone camera.

In certain embodiments, the stackable SlipChip can be used for integration of multiple SlipChip components among themselves or with other chemistry and hardware components. Certain embodiments of the SlipChip can encode, as a sequence of areas in the two plates, essentially any program to manipulate fluid volumes. They can be used for sample concentration and preparation, multiplexed amplification for identification and quantification of nucleic acids, and conversion of amplified nucleic acids to visual or, for example, cell-phone readout. The stackable SlipChip can be used for complete diagnostic tests by integrating these components with one another or with other components developed by others. There are many methods of integration for stackable SlipChips, including but not limited to the following: stacking of pre-made component chips to exchange a limited number of inputs/outputs, and fabricating multiple stacked layers to create complete SlipChip components that exchange hundreds or thousands of inputs/outputs. The stackable SlipChip can control slipping, trapping of beads, and control fluid movements through stacks, including capillary and pressure-driven flow. Slipping the individual layers of a stackable SlipChip can create and break up the fluidic paths through the stack, so even a simple wick or pressure source can cause highly controlled reconfigurable movement of fluids through the stack.

In certain embodiments, the stackable SlipChip can be used for integrating pre-made component SlipChips with few inputs-outputs. In certain embodiments, the stackable SlipChip can be used for the integration of a concentrating SlipChip with a Digital SlipChip. A single connection between the components of the stack can be sufficient for HIV viral load measurements, and a few connections (e.g., to separately handle solutions from RNA and DNA preparation modules) can be sufficient to identify and quantify nucleic acids from, for example, pneumonia pathogens. This approach is attractive because as long as the input-output configuration standards are established, the components can be individually optimized and then easily integrated.

In certain embodiments, the stackable SlipChip can be used for direct integration of SlipChip layers. This approach takes layouts of component SlipChips, and integrates them in stacks that allow direct sample transfer from areas in one layer into areas of another layer. This approach is valuable for integration of components that handle hundreds or thousands of sample volumes, for example a Digital SlipChip to amplify nucleic acids and a readout SlipChip to perform multistep processing of each volume to create a visual readout. It also provides significant simplification of the overall device, as a single Digital SlipChip layer can be integrated with either one of several different types of readout SlipChips, depending on the needs of the diagnostic device. In certain embodiments, the stackable SlipChip allows a complete test for measuring HIV viral load with dynamic range of 500-106/mL. In certain embodiments, the stackable SlipChip can be used for detection and quantification in sputum samples of, for example, 16 pneumonia pathogens.

In certain embodiments, the SlipChip can be used for the amplification of cascades to count molecules of traumatic brain injury (TBI) biomarkers. TBI is a major health issue in the military. Mild TBI (mTBI) is of special significance as it encompasses the majority of cases, is harder to diagnose, and can result in long-term disability. Current diagnostic techniques, magnetic resonance imaging and computer tomography, are impractical in battlefield settings and are limited by cost and low sensitivity. An unmet need is to diagnose and initiate appropriate treatment for TBI at the point-of-care (POC).

Biomarkers can be used to diagnose TBI, but there is a need for improved (1) detection and, especially, quantification of low (pM) levels of panels of biomarkers in blood (Quantification is critical because both absolute levels and time-dependent changes in levels of biomarkers are needed for proper assessment of TBI.), and (2) function in a portable lightweight device without extra equipment to perform and read the assay. Qualitative results can be obtained from known dip-stick type devices, but quantification requires a separate reader and can be unreliable. Quantification at low concentrations enables detection of biomarkers in blood or urine and potentially even saliva, which are simpler and safer to collect in field settings than the current "gold standard" cerebrospinal fluid.

Assays development has two opposing requirements: amplification and quantification. Low starting concentrations and the need for strong, easily detectable signal require a very high degree of amplification. However, such amplification is generally difficult to quantify and is too sensitive, with even small amounts of spurious interference triggering the amplification cascade, leading to errors and false positives. This challenge can be addressed by single-molecule detection in thousands of areas of, for example, nanoliter, picoliter, or femtoliter volumes, by combining "stochastic confinement" and chemical amplification. "Digital" approaches to count single molecules are routine for nucleic acids by PCR (digital PCR) and have been demonstrated for enzymes. These approaches use "stochastic confinement": the sample is separated into, for example, hundreds or thousands of small volumes, or areas, so statistically each area contains zero or one molecule of the target analyte. Stochastic confinement has several advantages, including: (1) Strong, qualitative yes/no amplification chemistry leads to a quantitative result by counting positive areas; (2) Artifacts, e.g. false initiation or inhibition of amplification, are restricted to individual areas; (3) Sensitivity and specificity of assays are increased because the effective concentration of a single molecule is higher in a smaller volume (increased signal) and interfering molecules are statistically excluded (decreased noise). Amplification is initiated (e.g., by thermal cycling in PCR), and the number of positive areas, corrected by Poisson statistics, corresponds to the number of molecules in the sample. One can use "stochastic confinement" and chemical amplification for single molecule immunoassays for digital biomarker detection.

Stochastic confinement and amplification can be used for "barcoded" visual readout, to provide immediate measurement, interpretation, and treatment suggestions. Visual readout is important in, for example, far-forward military settings away from the sophisticated imaging instruments of hospitals and laboratories. Visual readout of multiplexed assay volumes can be structured as a digital pattern of dots, like a barcode, so that the pattern can be interpreted by eye or with a cell phone camera. Capturing the image is useful for making time course measurements and to automate or delegate decision-making. The pattern could be analyzed and interpreted immediately via on-board software or a central facility to instruct the best course of action. "Digital" counting of TBI biomarkers, for example, enables diagnosis in far-forward military settings. After a series of amplification steps, a visual signal is generated that can be rapidly imaged and analyzed using, for example, a cell phone camera to provide immediate instruction.

Multistep processing of, for example, thousands of, for example, nanoliter, picoliter or femtoliter volumes can be achieved by using the SlipChip. Sophisticated fluid manipulation on a SlipChip can be used to perform the multi-step heterogeneous immunoassays and other chemistries that are preferred for detection of TBI biomarkers at the single-molecule level. The SlipChip is a microfluidic platform that can be used to encode a complex program for parallel manipulation of thousands of small volumes. Heterogeneous immunoassays can be performed quantitatively with amplification on certain embodiments of the SlipChip. To detect low levels of protein biomarkers in TBI, heterogeneous immunoassays are useful because a large excess of capture antibody can be used to drive binding. For these assays, multi-step processing is preferred, including washing steps and addition of reagents for signal amplification. The inventors have demonstrated a bead-based immunoassay with pM-level sensitivity for the metabolic marker insulin, using nanoliter volumes on SlipChip. Stochastic confinement on the SlipChip can be used for the counting of single DNA molecules after amplification by digital PCR. The inventors demonstrated that single molecules of DNA can be detected and their concentration quantified by counting the number of positive areas out of 1,280 total areas, each 2.6 nL in volume.

In certain embodiments, the SlipChip can be used for: (1) Quantitative detection of TBI biomarkers with high sensitivity which can be accomplished by counting single molecules after a very high degree of amplification. (2) A multistep amplification cascade which can give the sensitivity needed to detect and count single molecules of the TBI biomarkers of interest in visual readout. (3) Stochastic confinement of molecules of TBI biomarkers in tiny (for example, femtoliter to picoliter) volumes which can be used for standard heterogeneous immunoassay chemistries for molecular recognition.

Ubiquitin C-terminal Hydrolase-L1 (UCH-L1) is a marker for neuronal cell body injury, and SBDP 150 is a product of αII-spectrin cleavage by calpain and a marker linked to axonal injury. These are present at 4 to 130 pM and 7 to 70 pM, respectively, in blood during TBI. There are commercial monoclonal antibodies against them that can be used in these assays. Certain embodiments of the SlipChip can be used to quantify a range of ~0.02-200 pM concentrations, or down to 0.001 pM with coincidence detection.

Single-molecule microscopy can be used to verify the presence of a single molecule of interest in areas used for amplification and visual readout. Samples can be imaged on Alba microscopy system (ISS, Champaign, Ill.). Target biomarkers, antibodies, DNA probes and even gold nanoparticles (AuNPs) can be labeled with quantum dots (QDs, enhanced by blinking). Lanthanide dyes with long lifetimes can be used in a time-gated mode in strongly fluorescent human samples of plasma.

In certain embodiments, the SlipChip can be used to partition and manipulate samples in small volumes. The SlipChip enables formation and manipulation of a wide range of volumes, for example, from tens of nanoliters (area dimensions, for example, 500×500×50 µm3) to tens of picoliters (50×50×5 $\mu m^3$) to tens of femtoliters (5×5×0.5 $\mu m^3$). Appropriate control reactions on, for example, the microliter scale can be performed to confirm that reagents and assays perform as expected. Stochastic confinement can be used to isolate single molecules: for example, at 9 pM concentration, areas 0.2 pL in volume contain on average a single molecule. The advantages and limitation for each size of area, such as extremely rapid transport versus increased complexity of fabrication for femtoliter areas can be determined for a given application. If small volumes are less preferred for a given application, short equilibration times can be used to capture single biomarker molecules from larger volumes. Characterization by single-molecule microscopy can be used to ensure improved representation of the actual concentration.

To analyze single-molecule assays, Poisson statistics can be used to calculate the initial concentration of analyte from the number of positive and negative areas observed. To establish accuracy and precision of the single-molecule immunoassay with visual readout, the user can analyze biomarker concentrations in buffer, artificial plasma, and archived normal human plasma un-spiked and spiked with biomarker at 0.02 pM-200 pM in log-scale concentration steps (n≥5 samples per concentration). To perform the assay in the context of TBI, archived human plasma from 12 individual TBI patients (Banyan) can be analyzed ≥3 times to assess precision of the assay and measure levels of biomarkers in mTBI patients.

In certain embodiments, the SlipChip can be used to achieve multistep threshold amplification of single molecules with visual readout in a multiplexing format. For simple visualization by eye or a cell-phone camera, the optical properties (absorbance or reflectance) of positive areas can be equivalent to an absorbance of 0.5 to 1 in a 200 µm×200 µm area.

The autocatalytic reduction of silver (I) ions, initiated on gold nanoparticle (AuNP) surfaces, provides a very high degree of amplification producing visually observable silver deposition. For use in immunoassays, an AuNP is conjugated to the detection antibody. In the SlipChip this chemistry can produce a visible signal that is clearly distinguishable from the background in a 55 nL volume with 5 pM AuNP (165,000 AuNP per area). Amplification conditions can be modified to achieve lower detection limits and the starting volume can be reduced to 200 fL so a 5 µM concentration will produce an average of 0.6 molecules per area. Robust amplification from single particles to generate a visual signal from >95% of particles with <1% false positives, on a device containing at least 200 areas can be achieved.

Dark field microscopy can be used to track anti-UCH-L1 antibody conjugated to 150 nm AuNPs at the single molecule level. Alternatively, a fluorescence microscopy system (e.g., an Alba system) can be used to track fluorescently labeled AuNPs.

For certain applications, two-stage amplification is preferred to visualize the signal, as the signal from sub-picoliter areas may not be intense enough to detect visually. The output from the first stage of AuNP-catalyzed amplification can initiate amplification in a second set of areas that are large enough to be visually observed. As silver deposition is autocatalytic, potential signal generation in the absence of AuNPs (background) is a concern. During the first stage of amplification, true positives generate a strong signal and background noise generates a weak signal. A threshold can be introduced such that only an input signal that is stronger than a critical level generates further amplification. Passivating the gold surface by the addition of high affinity thiols can suppress both background and sub-threshold concentrations of AuNPs for over 1 hr. The use of a threshold can ensure that visual signal appears after the second stage of amplification only from areas that initially contained AuNP.

PCR can be used as an additional amplification step to increase the signal-to-noise ratio from the amplification chemistry and single-molecule amplification of nucleic acids by standard PCR are well known. Single-molecule immuno-PCR combined with stochastic confinement can be performed. The user can conjugate, for example, anti-UCH-L1 detection antibody to a DNA sequence. The DNA serves as a template for PCR amplification, producing many copies of the sequence. Each copy of PCR product can be designed to hybridize to two probes: one that immobilizes it on the surface of the area or a bead, and one that links it to a signaling molecule. Alkaline phosphatase (AP) with NBT/BCIP and AuNP-catalyzed silver deposition have both been used to generate a visual signal from PCR products.

In certain embodiments, the SlipChip can be used for quantitative single-molecule PCR and isothermal DNA amplification. Standard PCR can be performed on the SlipChip because it is robust and well-characterized, but the required thermocycling is not always preferred, for example, for field use. Isothermal techniques are preferred for certain field applications. The inventors have demonstrated single-molecule detection using isothermal recombinase polymerase amplification (RPA) on the SlipChip platform.

Other chemistries for amplification combined with stochastic confinement can be used on the SlipChip. Photoinitiated systems have proven to be very sensitive and can function at the single molecule level. Polymerizations can generate visual signals, and attaching multiple radical photoiniators to an antibody has shown promise for visual readout. Photoacid generators linked to autocatalytic acid generation are used extensively in photoresists that require extreme sensitivity.

A single sandwich-complex can provide a clearly observable signal on the SlipChip, and the immunoassay for, for example, TBI biomarkers (e.g., UCH-L1) can be used to detect down to the single molecule level.

Stochastic confinement isolates single molecules of analyte in SlipChip areas containing capture antibody: a device with, for example, 1000 areas of, for example, 0.5 pL volume can allow for detection of single molecules in the range of 0.2-200 pM. Capture efficiency can be assessed using, for example, target biomarker labeled with fluorescent quantum dots (QD) by tracking biomarker-containing areas before and after washing using, for example, a fluorescence microscopy system, and comparing results to calculated prediction. For example, a 1 pL area containing one biomarker molecule and 0.1 µM capture antibody ($K_d$=1 nM) is predicted to capture the biomarker with 99% efficiency. The user can label the detection antibody with a different QD, and directly visualize binding. The user can measure colocalization of the two labels to quantify formation of the immuno-sandwich complex and quantify background off-target binding of detection antibodies. This allows quantification of improvements from altering assay conditions (concentrations, buffers, surface chemistries, etc) to optimize single-molecule binding with low background.

Single molecule measurements often suffer from high background and weak signal from single analyte molecules. Stochastic confinement can increase the signal intensity in positive areas, but this does not necessarily decrease the number of false-positive areas due to non-specific binding of the detection antibody (background binding), and may not be alleviated using traditional methods described above. One solution to decrease background binding is to attach the detection antibody to a magnetic bead, so that unbound antibody can be more easily removed from the areas and removal can be further enhanced using acoustic techniques. For applications with a high background signal, coincidence detection using colocalization of two detection antibodies can be used to directly measure and correct for the background signal.

After loading areas with single molecules of analyte and obtaining predicted binding of antibodies, amplification chemistry can be performed and then the user can evaluate the entire immunoassay in buffer and in artificial plasma. The user can stochastically confine samples to isolate single molecules, form the immuno-sandwich complex, amplify using the chosen amplification chemistry, and image to count the number of positive areas. The user can evaluate sensitivity, specificity, linearity (or the dose-response relationship in general), and deviation from expected results over the range of concentrations.

The user can use a labeled biomarker to apply pre-amplification visualization to confirm the presence and location of single molecules. Tracking how many antigen-containing areas result in visual signal and how many blank areas result in visual signal can quantify the performance of the system.

The SlipChip single-molecule approach can be used for coincidence detection to lower the signal due to background binding and also directly distinguish background binding from on-target binding, quantifying the background binding. The user can use two detection antibodies, labeled with different fluorophores against two different epitopes of the target biomarker (for example, three antibodies are available for three distinct epitopes of UCH-L1 (Banyan Biomarkers)) and use two-color detection. The user can detect coincidence initially directly with an appropriate fluorescence microscope and then by amplification to give two-color visual readout or conditional readout (e.g., requiring capture of both horse radish peroxidase and glucose oxidase to generate color after PCR). Background binding gives a signal with low coincidence, predicted by Poisson distribution. On-target binding gives easily distinguishable above-random coincidence (for example, >98% confidence even for a 25-area chip). Without single-molecule coincidence detection, these signals may appear indistinguishable, with 5 units of binding for either detection antibody. If necessary, the background signal can be lowered even further by requiring that only tags in close proximity produce a signal. For example, fluorescence resonance energy transfer or fluorescence cross-correlation spectroscopy can be used for characterization with paired detection aptamers initiating rolling circle amplification (RCA) only when the two aptamers are in close proximity, as when bound to analyte.

Human samples can have higher background signal from nonspecific binding due to many other substances in plasma, and varied background concentration in different human samples. The user can conduct single-molecule immunoassays for biomarkers in plasma samples, by first verifying that binding occurs specifically using single-molecule fluorescence microscopy measurements and then applying amplification chemistry to get visual readouts.

The user can detect biomarkers quantitatively and with visual readout in human samples by counting single molecules after multistep amplification in, for example, sub-nanoliter volumes. A user can use aptamers instead of antibodies, isothermal amplification instead of PCR, engineer devices to carry out the assays under field conditions, and design software for communication devices to interpret results of the assays and suggest actions. The SlipChip can also accelerate drug discovery for, for example, TBI, and discovery and testing of biomarkers. Its high sensitivity can be used in the development of biomarkers in more accessible fluids such saliva, urine or tear fluid. This can also enable detection of non-protein biomarkers such as mRNA or miRNA.

In certain embodiments of the SlipChip, stochastic confinement can be combined with coincidence detection to allow sample-specific background correction to quantify samples that have a high level of nonspecific binding. To eliminate amplification of noise, the user can introduce a threshold such that only input signal that is stronger than a critical level generates further amplification.

In certain embodiments, the SlipChip can be used for combinatorial biocatalysis using many different organisms, including but not limited to extremophiles. Many researchers use plate assays for the screening of general thermophiles (preferring about 45° C. to about 80° C.), whereas for the hyperthermophile (preferring about 80 to about 122° C.), it is difficult to run standard plate experiments because of the evaporation and melting of agar media. Most known hyperthermophiles are anaerobic, sulfur requiring, and slow growing organisms. The SlipChip can be used to culture many organisms including thermophiles and hyperthermophiles. Many of the biocatalytic reactions run by hyperthermophiles are biomass degradation (e.g., capable of cellulase production and reaction). The SlipChip can be used for novel enzyme screening or culturing community-based cultures.

The following patents and applications are herein incorporated by reference in their entirety: U.S. Ser. No. 12/257,495 "Automated analyzer for clinical laboratory", U.S. Ser. No. 12/411,020 "Integrated microfluidic assay devices and methods", U.S. Pat. No. 3,996,345 "Fluorescence quenching with immunological pairs in immunoassays", U.S. Pat. No. 5,686,315 "Assay device for one step detection of analyte" and PCT/US2007/20810 "Integrated microfluidic assay devices and methods".

In certain embodiments, the SlipChip may be used as cell-cell communication devices, where the surface is wetted by reaction fluid instead of lubricating fluid. Areas that connect by very thin ducts, which may be nanopatterned, along the surface can be used to monitor cell-cell interactions without contact, or to filter solutions (if flow is induced from one area to another) for, for example, sample preparation and bead-based chemistries. In some instances, both surfaces will be hydrophilic, but in others, only one surface can be hydrophilic. Hydrophilic nanopatterns can be used.

Certain embodiments of the SlipChip can be used to analyze plugs which can come from any plug making system or device, including for example, the chemistrode. Reagents in certain embodiments of the SlipChip can be bathed in a lubricant or carrier fluid. Protein adsorption on certain embodiments of the SlipChip can be controlled at interfaces by controlling surface chemistry using, for example, flourous soluble surfactants. Certain embodiments of the SlipChip can be used to store reagents without risk of contamination.

In some embodiments, the SlipChip can be an opening and closing device. This can be used for isolating and analyzing rare cells, particles, and/or beads carrying cells or molecules of interest, out of large volumes. This is relevant to a number of different kinds of cells including but not limited to circulating tumor cells, microbial cells in bodily fluids, purification of other cells. This can be done using many different approaches including but not limited to standard loading and capture and using an open SlipChip that is used to capture, and then assembling afterwards. One plate of the SlipChip can act as a filter or as a capture surface, solving the problem of analyzing large volumes with only a few cells of interest. Such devices can be used for, for example, analysis of samples that may be difficult to load otherwise, for example, aerosols of bacteria and viruses generated during coughing, or tissue slides from which a user would like to analyze the sample without losing track of spatial relationships among cells, as is done for tumors and biopsies. In addition, a user can open the chip for analysis by methods that benefit from direct access (for example mass-spectrometry, including analysis of areas of the SlipChip by DESI and MALDI techniques). When SlipChip is constructed using materials that can be penetrated (including PDMS, polyurethane, other elastomers, and sealing tape manufactured by 3M), contents of areas can be accessed directly, for example by puncturing the material with a needle.

In certain embodiments of the present invention, surface tension can be used to prevent leakage ("surface tension seal"). Two halves of the device can be made of, for example, plastic which are then made very hydrophobic using for example, plasma treatment. A closed path around the chip can be made hydrophilic. The hydrophobic areas are wetted with a hydrophobic liquid. To prevent evaporation, there can be a liquid reservoir in contact with appropriate areas. The two halves of the SlipChip can be clamped together and the aqueous solutions added to the chip will not leak between the plates because of capillary pressure. Similarly, the hydrophobic solution is stopped by the hydrophilic layer. The highest pressure the device can withstand is governed by the capillary pressure.

When clamping the two sides of a SlipChip together, if the layers are very thin, then it is preferred to apply pressure uniformly over the surface. With a pre-strained holding device the SlipChip can be made very thin, pre-clamped together at the factory, and peeled apart. Alternatively, two rigid glass slides can be used as holders and, if necessary, imaging can be performed through them. The glass slides can be removed if x-ray diffraction is to be performed. However, in certain embodiments, clamping is not necessary. For example, two glass slides, if wet, stick together very tightly; similar ideas can be used to keep the layers of a SlipChip together. If the opposing surfaces are rigid and flat, a very high capillary pressure is produced, and the rigidity requires that when separating the slides the contact must be broken over a large area simultaneously, requiring high force. Applications include, but are not limited to protein crystallization, for example for membrane protein crystallization.

In certain SlipChip applications in which precise metering of a sample is preferred, a well can be overfilled, and then excess can be pushed away by the adjacent layer. Alternatively, the device can have a set of redundant pathways, wherein each path for purification and/or analysis takes, for example, 5 µL, and as the user loads the sample into the device, the first 5 µL is filled, then the second, etc. Such a device has a robust system that can do quantitative analysis on, for example, 10 μL and on 50 μL of plasma.

In certain embodiments of the present invention, the SlipChip may be in a centrifuge tube. This kind of device can be used for reconcentration of cells/particles by sticking a SlipChip at the bottom of a centrifuge tube.

The chemistrode, a microfluidic device that relies on two-phase laminar flow, can acquire repeated samples and maintain them for analysis. The chemistrode is a microprobe that performs like an electrode (delivers and records signals) but uses chemical rather than electrical signals. Chemistrodes for sampling secretions from tissue in an isolated area, and needle-like chemistrodes for sampling soil suspensions have been demonstrated.

Chemistrodes are compatible with parallel chip-based nanoliter assays down to single-molecule methods, ensuring that many small volumes can be sampled and analyzed from a single animal. Detection of single-molecules of the metabolic marker insulin has been achieved using a competitive immunoassay and fluorescence correlation spectroscopy (FCS). Droplets obtained by the chemistrode also can be analyzed on a SlipChip. The chemistrode, combined with FCS or SlipChip for analysis, can continuously sample biofluids from live animals for quantitative analysis.

Certain embodiments of the SlipChip can process many nanoliter volumes from a chemistrode to perform, for example, multi-step heterogeneous immunoassays at picomolar levels required for detection of biomarkers (TBI biomarkers, for example).

Certain embodiments of the SlipChip can be used for inexpensive and simple measurement of HIV viral load at the point of care (POC). Such a test is urgently needed to provide proper care to patients on antiretroviral therapies in resource-limited settings, and to control the emergence and spread of drug-resistant strains of HIV worldwide. While a number of qualitative yes/no diagnostic tools have been developed, there is still an unmet need for quantitative viral load measurement in resource-limited settings. Although PCR-based assays with real-time readout are quantitative, these assays require equipment and environments too complex for POC in resource-limited settings. Also, isolation and concentration of viral RNA from plasma is challenging for most POC approaches. Certain embodiments of the SlipChip can encode a complex program (algorithm) for manipulation of many fluid volumes in parallel. Certain embodiments of the SlipChip consist of two plates that move—or "slip"—relative to one another, lubricated by inert fluid that is immiscible with the sample fluid and also provides control of surface chemistry and prevents cross-contamination. The program is encoded into the plates as a pattern of areas containing reagents, and is executed by slipping. Slipping brings areas (or wells) in the two plates in and out of contact to execute a diagnostic assay. Manipulations on multiple scales, e.g., from 100 pL to 100 μL, can be performed on the same chip. Such SlipChips facilitate integration of upstream sample preparation to isolate and concentrate viral RNA and permit quantification of viral particles via nucleic acid amplification using "digital" (single molecule) detection with downstream signal amplification to enable readout as simple as an image taken with, for example, a cell phone camera.

One can target different HIV-1 subtypes, including the A, C, and G subtypes predominantly found in India and Nigeria.

Currently available qualitative POC diagnostics tests are not suitable for the quantitative monitoring needed. The HIV antibody test has been incorporated into a dipstick format that can be readily used in resource-limited settings. However, this test does not reflect the effect of HIV antiretroviral therapy (ART) as it only provides information on the patient's serostatus. The p24 antigen test has low sensitivity and works only at a very high level of HIV viremia ($>10^5$ particles/ml), and therefore cannot be used to monitor ART. Methods for CD4 cell counts are currently not widely available, and the counts can be low in a number of illnesses and may not reflect HIV infection. In addition, HIV viral dynamics and resistance to therapy can only be inferred, since CD4 counts are slow to reflect changes in viral load that are happening on a more rapid timescale. The ExaVir-Load from Cavidi AB has potential for use in resource-limited settings, but testing requires about 3 days, is expensive, and has an extra burden of proof to connect it to the established clinical practice.

Quantitative measurement of HIV viral load by nucleic acid testing is urgently needed for resource-limited settings. The main goal of ART is formulated as to reduce the HIV RNA level in plasma as much as possible for as long as possible. This requires quantification, which is currently based on direct nucleic acid testing (NAT) by real time reverse transcriptase-polymerase chain reaction (RT-PCR), Nucleic Acid Sequence Based Amplification (NASBA), and transcription-mediated amplification (TMA) on automated machines in centralized laboratories. Quantification of the HIV viral load is used to guide when to begin HIV antiretroviral drug treatment, provide information on the degree of initial antiretroviral effect achieved, assess the risk of disease progression, and guide decision making on when to switch to a different ART regimen.

At present, no HIV viral load quantification platform is available that can be used in resource-limited settings, as described elsewhere in this application. A preferred device has a number of preferred characteristics: a wide dynamic range to measure viral loads from, for example, 500 to 1,000,000 particles/mL in plasma; use, for example, 100-200 μL of whole blood or plasma; be quantitative enough to distinguish, for example, 3-5 fold changes in viral loads with 90-95% probability; be low in cost; be easy to use; provide results in under, for example, 2-4 hours (within one visit); require only simple and robust equipment; and have a simple readout.

Digital direct nucleic acid testing (NAT) is a technological advance that enables quantification of DNA or RNA levels with higher sensitivity and does not require real-time readout. For certain applications, real-time RT-PCR provides accurate viral loads and can be used, but for others, it is too complex in regard to required expertise and equipment. To obtain quantitative results without the necessity for real-time measurements, single-molecule detection has emerged as preferred. Digital NAT is based on the concept of confining and visualizing single copies of nucleic acid in a series of small volumes. The number of small volumes that generate a nucleic acid product directly corresponds to the number of molecules present in the original sample, making the results highly quantitative. The detection sensitivity of samples with high background is increased in digital platforms, since each molecule being detected is partitioned into individual small volumes (or stochastically confined), apart from inhibiting contaminants.

Certain embodiments of the SlipChip provide a simple way of compartmentalizing a large number of small (for example, picoliter to nanoliter) fluid volumes in parallel without external instrumentation. The SlipChip can be used to perform digital NAT for HIV treatment and diagnosis in resource-limited settings. Certain embodiments of the Slip- Chip readily form thousands of nanoliter reactor chambers while not requiring costly pump-based filling systems—a series of connected wells can be simply filled by a single pipetting step, and wells are subsequently separated into individual nanoliter reactors by slipping one plate next to the other. The SlipChip can be highly multiplexed but does not require valves.

Certain embodiments of the SlipChip maintain compartmentalization of all reactions even under stringent conditions required during sensitive assays and thermal cycling. By altering the geometry of the wells, an aqueous droplet can be suspended in the well, surrounded by a lubricating fluid. In certain embodiments, during temperature changes associated with thermal cycling, the fluids expand but the aqueous droplet containing the PCR reaction does not leak out of the wells.

Certain embodiments of the SlipChip facilitate the addition of multiple reagents in separate steps to all compartmentalized reaction volumes in parallel without external instrumentation or cross-contamination between neighboring reaction volumes, as is preferred for both digital isothermal NAT and subsequent amplification of the NAT readout. Isothermal NAT is advantageous for resource-limited settings because it does not require thermal cycling, eliminating the need for a major piece of equipment. However, it is not currently used commercially as POC because of the technical difficulty of controlling the initiation of amplification reactions, as the reaction is initiated immediately upon mixing the PCR mixture with the template RNA. Because amplification starts prior to loading the sample into the digital platform, the digital readout is not necessarily an accurate reflection of original target concentration of RNA. When template nucleic acid is amplified prior to stochastic confinement, false positives can occur. Certain embodiments of the SlipChip solve this problem. First of all, reagents can be added instantaneously at any user-specified start time after loading of the RNA template by slipping the wells containing sample into contact with wells containing the reagent. Secondly, digital PCR can utilize end-point readout so reaction time is not critical. In addition, there is no cross contamination between neighboring reaction volumes. The SlipChip facilitates manipulation of varying reaction volumes, as preferred for RNA isolation. The SlipChip can be fabricated in any geometry with varying well diameters and varying depths, for example depths ranging from several microns to millimeters. Each reaction volume containing a single nucleic acid can truly be digitally interpreted. As an alternative to using fluorescence readouts, colorimetric enzymatic amplification reactions can be used to detect NAT products. The SlipChip can also accomplish the simultaneous addition of multiple reagents to all reaction volumes.

In certain embodiments of the SlipChip, molecules or viral particles can be captured by magnetic beads, and pulled from a large volume into a small volume by use of magnets, enabling on-chip concentration. Likewise, small volumes can be added to large volumes, enabling on-chip dilution.

Interfacial chemistry in certain embodiments of the SlipChip can be controlled at the interface of the lubricating fluid and the reaction fluid, simplifying fabrication. The interfacial chemistry between two immiscible liquids can be controlled by, for example, adding surfactants. Because the lubricating fluids used in certain SlipChips can be the same as the carrier fluids used in previous droplet-based work (see for example, U.S. Pat. No. 7,129,091, and PCT/US2009/046255, both incorporated in their entirety herein) the interfacial chemistry can be controlled in an analogous manner. For a non-fluorinated lubricating fluid (such as mineral oil), a surfactant can be added to the aqueous reaction fluid; for a fluorinated lubricating fluid, a fluorinated oil-soluble surfactant can be added to the lubricating fluid. Examples of different lubricating fluids that have been used in the SlipChip include mineral oil for a single-molecule PCR SlipChip and fluorinated oils for a SlipChip for immunoassays achieving pM detection limits.

Possible surface treatments for a SlipChip include, but are not limited to, dichlorodimethylsilane (appropriate for glass devices) and gas phase silanization.

A glass SlipChip with uniform well volumes can have, for example, a dynamic range of detection of 5,000 to 100,000 HIV particles/mL. An advantage of such a design is that every well is an identical replicate if loaded with the same solution, since the surface-to-volume ratio is kept constant. In one experiment, the concentration of a dye loaded in a SlipChip with uniform well volume had a coefficient of variation of 3.2%. A uniform well device can have, for example, 1280 reaction volumes, with 640 elongated wells in the top piece and 640 elongated wells in the bottom piece of the SlipChip to conserve space. The elongated wells can initially overlap for filling. After filling, the elongated wells can be slipped over circular wells containing, for example, mineral oil. This design promotes the formation of an aqueous droplet surrounded by a volume of mineral oil upon slipping. The aqueous droplet can expand upon heating, displacing mineral oil between the two plates of the SlipChip, and preventing the aqueous phase from leaking out of the well and causing cross-contamination due to thermal expansion. Each circular well can be, for example, 50 µm in diameter and depth.

This device can be made from glass using standard photolithographic and wet chemical etching techniques. Surface chemistries can be controlled by rendering the surface of the SlipChip hydrophobic by silanization with, for example, dichlorodimethylsiloxane, which is amenable to PCR. Mineral oil can be used as the lubricating fluid between the two plates of the SlipChip and as the wetting layer surrounding the aqueous phase containing the reaction mixture.

A commercially available Access RT-PCR kit from Promega, with a known concentration of the commercially available HIV standard (8E5 LAV deletion mutation strain of HIV-1) and EvaGreen dye to detect product can be used. One can use primers for amplification of the HIV-1 long-terminal repeat (LTR) region, which contains sequences that are conserved between all HIV-1 subtypes in M, N, and O groups. These primers are suitable for amplifying all subtypes of HIV-1 found in India and Nigeria (A, C, and G) as well as the subtype predominant in the US (B). The primers are: A1352 sense, position 607 in the published sequence alignment from the Los Alamos HIV Sequence Database, GRAACCCACTGCTTAASSCTCAA; A1355 antisense, position 708, GAGGGATCTCTAGNYACCAGAGT.

In an experiment, reliable filling of 1280 wells was achieved using 6.5 µL of initial sample, and a reproducible digital readout was attained for both PCR and RT-PCR. A 1280-well SlipChip was characterized for digital PCR using *Staphylococcus aureus* genomic DNA. Results were both reproducible and quantitative. In addition, an experiment demonstrated that the biochemistry of RT-PCR using the 8E5 LAV deletion mutation strain of HIV-1 and the A1352 and A1355 sense and antisense primers is compatible with digital SlipChip platforms.

Internal controls can be built into the SlipChip to validate results that are obtained in the field. For example, 100 wells can be preloaded with primers to detect control RNA that can be added to the sample. The primers can be dispensed either manually or by simple robotics prior to assembly of the two plates of the SlipChip.

An embodiment of a circular SlipChip that generates multiple reaction volumes on one chip has been demonstratedError! Reference source not found. An advantage of this design is that its dynamic range can cover a range of detection of, for example, 500 to 1,000,000 HIV particles/mL. In certain embodiments, the wells initially overlap with ducts to enable filling and are then slipped into discrete reaction volumes by rotating the device. Exemplary dimensions for this SlipChip of varying well volumes are 128 wells of 200 nL volume (39-1667 RNA molecules/mL), 128 wells of 20 nL volume (391-16667 RNA molecules/mL), 256 wells of 2 nL volume (1953-166,667 molecules/mL), and 512 wells of 0.5 nL volume (7813-1,333,333 molecules/mL). These well sizes allow checking the internal consistency of the SlipChip due to the overlap in dynamic range of the larger and smaller volumes. The device can incorporate internal controls.

Such a device can, alternatively, use surfactants in the aqueous sample solution or use fluorinated oil instead of mineral oil.

In certain embodiments, it can be preferable to achieve an equivalently large dynamic range by on-chip serial dilution, which, in certain embodiments, contains larger wells. Exemplary dimensions for this design are five rows containing 100 wells in each row, and a shallow well containing 20 nL of sample is slipped over a preloaded well containing 180 nL dilution buffer, achieving a 10 fold dilution with each slip.

SlipChips can be made of many materials, including, for example, glass, polycarbonate, polypropylene and other plastics. Both polypropylene and polycarbonate are known to be compatible with PCR. Plastic devices can be coated with different surface coatings, surfactants and oils.

Certain embodiments of the SlipChip can be used to control the initiation of HIV RNA transcription into cDNA by reverse transcriptase (RT) and subsequent amplification reactions. Initiation of cDNA synthesis and amplification is controlled by slipping wells containing the reaction mixture and template RNA in the upper piece of the SlipChip over preloaded dried primers in the bottom piece of the SlipChip. The primers can, for example, be loaded manually for initial testing using Teflon tubing with an I.D. of, for example, 50 µm, or using simple robotics.

A 384-well SlipChip preloaded with primers for the detection of different bacterial species successfully distinguished methicillin-resistant *Staphylococcus aureus* (MRSA) from methicillin-sensitive *S. aureus* (MSSA). Two columns at either end of the SlipChip were preloaded with pBad primer, and pBad template DNA was loaded into all wells as a positive control.

Isothermal amplification technologies that can be used including NASBA, and RT-RPA These amplification techniques can operate at 40° C. (a lower temperature preferred for certain POC devices): NASBA (product: RNA), RT-RPA (product: DNA), RT-LAMP using one of LAMP HIV-RNA 6-primer sets, transcription-mediated amplification (TMA, 41° C.), helicase-dependent amplification (HAD, 65° C.), and strand-displacement amplification (SDA, 37° C.), Amplification methods preferable for POC are those that do not require large temperature differences from ambient and can be initiated in one mixing step, however, NASBA and RPA contain heat-labile enzymes. Therefore, one can exclude the denaturation step from standard protocols and adjust the primer annealing temperature to 40° C. If, for certain embodiments, annealing at 40° C. gives lower sensitivity, one can select a 100-120 nucleotide long amplification target in the genomic RNA conservative in different HIV-1 subtypes that has weak secondary structure which allows efficient primer annealing at 40° C.

In an experiment, a $Mg^{2+}$ solution was preloaded into all wells of a SlipChip, and all other reagents for RPA in solution were used to fill remaining wells. The original concentration of control template provided with the kit was 2 molecules/µL. Approximately 500 nL was analyzed.

Several diagnostic NAT tests incorporate an internal control within the same tube or well as the RNA of interest, and quantify the internal control by using a specific probe conjugated to a different fluorophore than that of the probe recognizing the amplified target RNA. One can incorporate an internal control using control template RNA (e.g., 3,569 nt-long bacteriophage MS2 genomic RNA) mixed with, for example, HIV RNA and all amplification reagents into the SlipChip. One can independently and simultaneously analyze HIV RNA and internal control template by preloading three quarters of the wells on the chip with a dry reaction mixture containing HIV primers, and the other quarter with internal control, using, for example, SYBR Green detection to quantify the load of HIV and the internal control.

Visual readouts are preferred for certain resource-limited POC settings. One can modify the SlipChip to incorporate additional steps and slips useful for a visual readout. Obtaining a visual readout can comprise hybridization of a nucleic acid product to an enzyme, washing to remove excess enzyme, addition of a substrate that the enzyme will convert to a visual signal, and incubation to amplify the visual signal. To make visualization easier, the well size can be increased to allow more visual signal to be produced. A cell phone camera, for example, can serve to record, analyze and document the results.

Hybridization of single-stranded RNA (generated by NASBA) can be achieved in one step using surface immobilization, magnetic beads and shallow wells.

Alkaline Phosphatase can be used for enzyme-based detection. Alkaline phosphatase has a well established BCIP/NBT ((5-bromo-4-chloro-3-indoyl phosphate, disodium salt)/(nitro blue tetrazolium chloride)) substrate for visualization. This substrate forms a very strong blue-colored precipitate at the site of enzymatic activity. For certain applications, the expected 100 nM of product R/DNA binds enough enzyme to easily and rapidly consume the BCIP substrate to generate the approximately 1 mM of products preferred for producing a dark, easily identifiable signal.

Gold nanoparticles or colored magnetic beads that can either be concentrated from a larger well into a small spot or amplified using silver amplification (for gold nanoparticles) can also be used to generate a strong visual signal.

A cell phone camera can easily record data and provide rapid analysis using simple software to count and calculate the desired information. The camera preferably can resolve and identify spots. By focusing, for example, a 1 megapixel camera on a 1280 well layout, each well image contains approximately 80 pixels. Using a 2 megapixel camera, each well image contains approximately 200 pixels. This number of pixels is sufficient for reliable counting. Both resolutions are common levels in many cameras, and are readily available even in resource-limited settings. The samples can be transferred to larger wells during visual signal development to facilitate detection.

For certain applications, it is preferred to attain a final concentration of purified RNA that corresponds to at least 40% of the initial HIV viral load present in patient blood, or 200 to 400,000 molecules/mL isolated. Calculations based on Poisson statistics indicate that 40% recovery is adequate to reliably quantify initial viral loads from the patient at 500 to 1,000,000 molecules/mL.

Exemplary Isolation Protocols Include:

Protocol 1: Modified Boom's isolating RNA from plasma via lysis of viral particles with chaotropic salts followed by trapping of RNA on silica magnetic beads (MagPrep® beads, Merck KGaA).

Protocol 2: Modified Boom's protocol isolating RNA from plasma via lysis of viral particles with chaotropic salts followed by trapping of RNA on iron-oxide beads.

Protocol 3: Isolating RNA from whole blood via capture of viral particles on antibody-coated magnetic beads (Viro-Adembeads, Ademtech, France) followed by a soft lysis procedure (heating at 95° C. or treating with a weak alkali).

For each protocol, on a SlipChip one can reduce the number of washing steps to two.

Example: To obtain the HIV RNA used in a 1280-well digital SlipChip, HIV-1 was purified from Acrometrix Opti-Qual HIV-1 High Positive Control ($1.7 \times 10^6$ mutant HIV-1 particles/mL; 18 pg HIV RNA/mL, 1 OD260=37 µg/mL) using a Qiagen QiaAmpViral purification kit, which contains complete lysis, carrier RNA, and silica minicolumns.

An embodiment of a circular SlipChip platform can accommodate all steps of the RNA isolation process using magnetic capture beads.

Certain embodiments of the SlipChip can sample whole blood or plasma and yield a measurable readout indicating HIV viral load.

Nanoliters of solution can be stored for greater than 6 months in fluorocarbon in a plastic SlipChip. One can store SlipChips in blister packs. One can use, for example, Drierite-type Cobalt-based solid dessicants to estimate water flux, and/or to create a dry boundary between the regions of a SlipChip.

A sample can be pre-stored in a big well on certain embodiments of a SlipChip. Because, in certain embodiments, the sample is surrounded by the lubricating oil, such as fluorocarbon (FC) or paraffin oil, evaporation is prevented. When pressure is applied through an inlet, the sample flows into wells via the fluidic path until it reaches a dead-end. Once the sample stops automatically, the sample wells are slipped into reagent wells to initiate reaction. When loading hundreds of wells with different volumes, it is preferable to make sure all wells will be filled. The dead-end filling facilitates doing so. All wells upstream of the dead-end are filled completely and the user does not have to determine when to stop since loading stops automatically when the sample reaches the dead-end.

A stackable, rotary SlipChip embodiment offers additional capability through modularity. Different reagent types, such as wet and dry reagents, can be stored on different layers of the rotary device. Further, if standard configurations are used, different detection systems can be easily mixed and matched simply by introducing a different rotary layer into the system. The RNA purification cycle described below can also be used for other assay types.

Filling methods include, but are not limited to, pressure driven well filling, centrifugal force, and dead-end filling.

In certain embodiments, a sample, first collected in a larger big well, is preferably transferred to a second step for processing. Dead-end filling provides both a driving force and a stopping mechanism to transfer the sample. That is, connecting such a sample to a controlled pressure source drives it to desired channels or wells from the first layer to the second layer and then stopping automatically without leaking when it reaches the end. It restarts when it is connected to an opening in a third layer. The pressure source can be as simple as an air-loaded syringe. This method is not limited to filling within one layer of a rotary system. It can fill different layers through holes by controlling the pressure.

Certain embodiments of the SlipChip provide a platform for storing solutions and dry reagents for use for POC diagnostics.

Experiments show that nanoliters of solution can be stored for greater than six months in fluorocarbon in a plastic SlipChip.

Water adsorption can be reduced by adding an external drying agent, or adding a desiccant trap in the chip between the wet areas and the dry areas to minimize crosstalk through fluorocarbons. Alternatively, one can modify the designs so the reagents are loaded dry and the device is configured to allow later addition of a solvent.

The reagents and enzymes used in amplification assays can be freeze-dried, optionally in the presence of stabilizing agents (e.g., at protein:trehalose:mannitol ratio as 1:20:100) using known freeze-drying methods. Reagents can be stored, for example, dry, under mineral or fluorocarbon oil, stored in air or sealed under vacuum.

A possible design of a SlipChip: 4 stacked layers (numbered 1 to 4, starting on the top), layers 1 and 2 together form a SlipChip, as do layers 3 and 4. Layer 2 has a hole in the bottom for transferring samples into layer 3. One can use standard positions of the through-hole inlets/outlets so any two SlipChips can be integrated with one another.

In certain embodiments, a sample can be pre-stored in a big well on-Chip. Surrounding the well with lubricating oil (such as FC or paraffin oil) can prevent evaporation. When pressure is applied through an inlet, a sample flows into wells via the fluidic path until it reaches a dead-end. Once the sample stops automatically, the sample wells can be slipped into reagent wells to initiate reaction. When loading, for example, hundreds of wells with different volumes, it is preferred to make sure all wells will be filled. The dead-end filling design can be used to do so. In this design, all wells are filled completely and a user does not have to determine when to stop since loading stops automatically when the sample reaches the dead end.

One can array the droplets into the wells in a SlipChip, which may be done manually or robotically. One can use an alternative self-arraying design where droplets from the chemistrode, or from other sources of plugs (for example, those formed using the techniques described in U.S. Pat. No. 7,129,091, incorporated by reference herein in its entirety) are flowed into the chip and trapped spontaneously by known droplet trapping mechanisms. Wu, L.; Li, G. P.; Xu, W.; Bachman, M., Appl. Phys. Lett. 2006, 89, Boukellal, H.; Selimovic, S.; Jia, Y. W.; Cristobal, G.; Fraden, S., Simple, robust storage of drops and fluids in a microfluidic device. Lab on a Chip, 2009. 9(2): p. 331-338 and Hong Shen, Qun Fang and Zhao-Lun Fang, A microfluidic chip based sequential injection system with trapped droplet liquid—liquid extraction and chemiluminescence detection, Lab Chip, 2006, 6, 1387-1389, describe methods for droplet-trapping, and all are incorporated by reference herein in their entirety. PCT/US2008/001544, published as WO2008097559A2, and U.S. Pat. No. 7,556,776 are also incorporated by reference herein in their entirety Certain embodiments of the Slipchip can be used in combination with these techniques, for example by creating discrete volumes using these techniques and then slipping reagents on top of them.

Possible applications of a SlipChip include, but are not limited to: detecting viral pneumonias; using ELISA to detect cardiac markers, including but not limited to GPBB, myoglobin, CK-MB and Troponin T; testing food, including, for example, milk, wine, baby formula, barley, beans, dried fruit, fruit juice, grains, maize, milk, dairy food, nuts, rice, grain, wheat, beef, meat, seafood, chicken, dog food; testing food for the presence of antibiotics (for example, chloramphenicol), pesticides (including for example organophosphate pesticides (assayed by cholinesterase inhibition), endrin, perthane, carbaryl, tetradifon, diphenylamine, aldrin, dieldrin, benzene hexachloride, chlordane, chlordecone, DDT, DDE, TDE, dicofol, ethylene dibromide, heptachlor, lindane, and/or mirex), natural toxins (including, for example, aflatoxin, ochratoxin and/or mycotoxin), residues, and allergens (including, for example, almond, egg, gliadin, hazelnut, milk, mustard, seafood, peanut or soy residues); testing for sulfites in shrimp; testing for *salmonella, listeria*, and/or *E. coli*; testing for deoxynivalenol (DON), fumonisin, T-2/HT-2 toxins, zearalenone, histamine, patulin; blood typing; using PCR for Influenza A Subtyping (including H1N1) HAI Screens (including MRSA and/or VRE), testing for cystic fibrosis, newborn screening, cancer prognosis, gene expression clustering, ADME/Tox pharmaceutical R&D screening, sepsis detection, HBV/HCV/HIV blood donor screening, HCV quantitation, HIV subtyping, HIV quantitation, HIV drug resistance, HPV subtyping, running the Ashkenazi panel, prenatal screening of chromosomes, e.g., chromosomes 13, 18, 21, X and Y, avian flu strain subtyping, cancer diagnosis, cancer recurrence detection, organ transplantation typing, organ transplantation monitoring, high-throughput screening; molecular testing of blood for infectious diseases; genotype/viral load testing; quantitative measurement of viral load in infected patients (HIV, HCV); testing for sexually transmitted disease including *chlamydia*/gonorrhea/HPV and drug resistance; prognostics (e.g., drug effectiveness); pharmacogenomics and theranostics (pharmaceutical/diagnostic pairings); using PCR to test for, for example, *chlamydia* and/or gonorrhea, *mycobacterium tuberculosis*, HCV quantitation, HIV drug resistance testing, HBV in blood donations, HCV/HIV in blood donations, drug metabolizing enzymes, Factor II (prothrombin), Factor V leiden, HPV genotyping, *gardnerella*, trichonomonas, *vaginalis* and *candida* spp., *legionella* pneumophilia, MRSA, *Staphylococcus aureus*, Group B Streptococci; using immunoassays to test for Group A Streptococci, Group B Streptococci, West Nile (WNV), Cytomegalovirus, Cystic Fibrosis Screening; B-Cell Chronic Lymphocytic Leukemia Chromosomal 8 enumeration (CML, AML, MPD, MDS, for example), HER-2 Status, initial diagnosis and recurrence monitoring of bladder cancer, sex mismatched bone marrow transplant testing, detecting mutations in HIV-1 virus associated with drug resistance; real-time tests for infectious diseases and FISH tests for certain types of cancer, including cervical, esophageal and melanoma; active screening to identify patients colonized with MRSA; genetic tests for hereditary diseases, including breast and ovarian cancer, hereditary melanoma; testing for adenomatous polyposis syndromes; testing for hereditary nonpolyposis colorectal cancer (HNPCC); chemical Q&A testing, including testing active ingredient presence and/or quantity and/or for contaminants; testing pesticides; testing fertilizers; testing petroleum; industrial fermentation process control; testing water, fruit, vegetables, food, soap oils, milk, dairy foods, beverages, eggs; screening for and/or analyzing irregular proteins or amino acids, free fatty acids, lactic acid, peroxides, ammonia, chloride, glucose, phenols, urea; test for *campylobacter*; analyzing marine algae; testing in slaughter houses and farms; blood tests for colorectal cancer monitoring; skin patch cocaine testing for professional drivers; pneumonia panel testing (using, for example, RT-PCR) for *mycoplasma* pneumonia, *Chlamydia*, pneumonia and *legionella* pneumonia; screening newborns for, for example, common phenylketonuria, sickle cell disease, and hypothyroidism; and testing for BNP/Pro, hs-CRP, or homocysteine. In addition, a point of care test for C-Reactive protein on SlipChip may be used for monitoring pain during therapy and during clinical trials.

Organisms that can be detected in certain embodiments of the SlipChip using, for example PCR and/or immunoassay methods known to those skilled in the art include, but are not limited to: *Streptococcus pneumoniae, Haemophilus influenzae* type b, *Staphylococcus aureus, Escherichia coli, Pseudomonas aeruginosa, Chlamydophila pneumoniae, Mycoplasma pneumoniae, Legionella pneumophila, Streptococcus agalactiae, Mycobacterium tuberculosis, Klebsiella pneumoniae, Moraxella catarrhalis, Chlamydophila psittaci, Streptococcus viridans, Coxiella burnetii, Cryptococcus neoformans, Enterobacter*, respiratory syncytial viruses (RSV), influenza viruses (A and B), Human parainfluenza viruses, cytomegalovirus (CMV), Human rhinovirus (HRV), Coronavirus (e.g., SARS), adenovirus, metapneumovirus, Herpes simplex viruses, Human bocavirus, *Giardia lamblia, Cryptosporidium parvum*, enteroaggregative *Escherichia coli* (EAggEC), *Vibrio cholerae, Shigella dysenteriae* type 1 (Sd1), enterotoxigenic *E. coli* (ETEC), *Entamoeba histolytica, Campylobacter, Salmonella, Clostridium difficile*, rotavirus, norovirus, adenovirus, and astroviruses.

Devices and methods that use certain embodiments of the SlipChip to isolate or capture targets such as, for example, rare cells or beads carrying cells of interest out of samples such as, for example, bodily fluids are described. Such devices and methods are preferred for the downstream analysis of captured targets and the samples that carry them. For example, rare cells, particles such as beads or aggregates, or molecules can be captured out of bodily fluids including, for example, blood, saliva, breath vapor, tears, CSF, or urine, or from other samples, including soil suspensions, environmental water samples, tissue homogenates, gasses, liquids, solids or gels. The approach is beneficial when analyzing samples with low concentrations of analytes, for example organisms, organelles, molecules, macromolecules, DNA, protein, and carbohydrates, rare nucleic acids or proteins, markers and biomarkers of genetic or infectious disease, environmental pollutants, cells or vesicles, including host cells such as epithelial cells, circulating tumor cells, cells of the immune system, red blood cells, platelets, exosomes, microvesicles, non-host cells, including fetal cells and sperm. (See e.g., U.S. Ser. No. 10/823,503 incorporated herein by reference). Another example includes the analysis of rare cells, such as circulating cancer cells or fetal cells in maternal blood for prenatal diagnostics. This approach may be beneficial for rapid early diagnostics of infections by capturing and further analyzing microbial cells in blood, sputum, bone marrow aspirates and other bodily fluids such as urine and cerebral spinal fluid. Analysis of both beads and cells may benefit from stochastic confinement (See e.g., PCT/US08/71374 incorporated herein by reference).

Isolation or capture of targets is important for characterization or analysis of a wide variety of systems. One example is analyzing rare cells in bodily fluids—an example that is important for applications including, but not limited to, cancer (circulating tumor cells (CTCs), invasive tumor cells in draining lymph nodes), immunity (CD4 counts, antigen-specific cells, etc), infection (microbial cells), prenatal diagnostics (fetal cells or nucleated red blood cells in maternal blood) and stroke (transcriptionally-altered peripheral blood mononuclear cells (PBMCs)). A "rare cell" can be either a cell of one type (e.g., CTCs) in a mixture with an abundance of cells of other types (e.g., stromal cells, lyphocytes), or can be a cell with an unusual phenotype or genotype (e.g., upregulated transcription) in a mixture of normal cells of the same type (e.g., PBMCs).

Isolation or capture of CTCs can be important for cancer diagnostics and monitoring. Metastases are the major cause of death from cancer because they are often resistant to conventional therapies (there is much heterogeneity in cancer cells in metastases). CTCs are cells that have detached from a main tumor and circulate in the blood stream. When adhering to other tissues, they can act as a seed for growth of additional tumors by creating a microenvironment around themselves in the invaded tissue. CTCs are observed at very low concentrations in the blood (between one cell in $10^6$ to $10^9$). The amount of CTCs varies considerably in different cancer types, with some cancers having no CTCs in most cases (ovarian cancer) to others having CTCs in nearly every case (breast cancer). Much recent research has focused on methods for improving the detection of such cells, and much progress has been made (see Current methods section below). However, most of these methods provide only enumeration of CTCs, while a few can provide analysis by PCR or staining. In the present invention methods and devices that can be used to capture CTCs for a wide variety of downstream analyses and manipulations are described.

While CTCs can provide information from the blood stream, analysis of solid tumor samples or lymph node biopsies can provide information about the primary tumor. However, solid tumor biopsy samples are often limited to those from a fine needle aspirate or fine needle biopsy, due to the difficulty of accessing an internally located tumor without risk or major inconvenience to the patient. These samples may provide as few as 200 cells, including a mixture of tumor cells and stromal or lymphoid (non-tumor) cells. There is a need to capture or isolate the tumor cells from these samples and provide multiplexed analysis, despite small numbers of target cells. Similarly, there is a need for rapid capture and analysis on an intraoperative timeframe (<40 min) to determine whether samples such as sentinel lymph node biopsies are metastatic, thus alleviating the need for a second surgery in positive cases. The present invention provides methods and devices to capture and isolate tumor cells from these samples despite the presence of a large number of stromal or lymphoid cells, and enables rapid analysis and manipulation such as PCR for mutations such as in kRAS2 (common for solid tumors), or RT-PCR for specific mRNAs including MUC1 for breast cancer.

Another important application of capture and isolation is analysis of the immune system. The human bloodstream contains several million cells per mL, including T- and B-lymphocytes, monocytes, dendritic cells, neutrophils, and red blood cells, in addition to >$10^8$ platelets per mL. For conditions such as cancer as well as autoimmunity, allergy, and infection, the frequency of T-cells that are specific for a particular antigen (tumor antigens, self-antigens, allergens, or antigens from pathogens, respectively) is often predictive of disease progression. However, these cells are quite rare, occurring at a frequency of 0.002% to 0.2%, or 2 in 1,000 to 100,000 cells. Current methods for analysis focus on enumeration (flow cytometry, ELISPOT) and offer little further analysis. The present invention provides devices and methods to capture and isolate such cells (e.g., by affinity capture with MHC-antigen complexes, by screening for antigen-stimulated cytokine secretion, etc.) and provides downstream analysis including, but not limited to, PCR, further stimulus-response assays, and culturing. Such methods can provide insight into the molecular mechanisms of tumors, autoimmunity and other conditions. For example, it can be used to determine whether T-cells that are specific for self-antigens are also more sensitive to stimulation by cytokines, thus aggravating autoimmune responses. SlipChip may be used to perform assays for all of the applications for which ELISPOT technique can be used. Stochastic confinement on SlipChip would provide more rapid and sensitive assays.

Some current methods provide capture of targets but have provided little or no downstream analysis or processing. Current methods for capture include, filtration by size or morphology, affinity capture, such as with antibody-coated magnetic beads or rods (e.g., Cell Search, MagSweeper, or RoboSCell technologies), microfluidic posts (e.g., CTC-chip or exosome capture), or microfluidic channel walls, functional capture, by unique behaviors including metastatic invasion of collagen adhesion matrices, negative selection by removing all other targets, capture by magnetic, optical, other properties (e.g., by dielectrophoretic field-flow fractionation or photoacoustics), and screening all targets visually and collecting those of interest, including by flow cytometry, fiber optic arrays, or laser scanning (Laser-Enabled Analysis and Processing, LEAP™, by Cytellect).

In contrast to the above-listed methods, certain embodiments of the SlipChip enable a multitude of upstream or downstream applications, including combining upstream sample preparation with capture and downstream multi- or single-cell analysis and manipulation. Examples of the types of analysis that can be carried out include, but are not limited to, PCR and other nucleic-acid based tests, immunoassays, staining, including immunostaining, histological staining, and mass-spectrometry. Procedures that can be carried out after isolation include, but are not limited to, cultivation, including cultivation of single cells, pure cultures (one cell type), mixed co-cultures, or spatially-organized co-cultures, stimulus-response assays, including but not limited to antigen, pathogen, or cytokine challenges, receptor binding and chemotaxis assays.

Targets can be selected by size or morphology, for example by filtration. For example, samples can be passed through a filtration device by a process such as aspiration or flow. Filtration devices, such as sieves or porous membranes, retain targets larger than the filtration in the capture area. They can be used to isolate larger targets, or to remove material from smaller targets of interest. Captured targets can then be slipped into an analysis area for further manipulation. Reagents for detection of targets of interest can be included at various stages, including being mixed with the sample before filtration, or being preloaded on the device, as shown below. A filter (for example one with submicron sized pores) can be placed in a channel, in a channel, the sample can be flowed through the filter, and then a wash, preferably smaller in volume than the original sample, can be flowed in the reverse direction to resuspend what the filter collected.

Capture by hydrodynamics can be used, for example, for samples containing targets with hydrodynamic properties distinct from other constituents of the sample. For example, arrays of nanopillars have been used to separate objects according to their hydrodynamic and diffusion properties. Differences in hydrodynamics of objects moving next to a boundary are also well established. A skimming method in which small cells were able to go into narrow side channels, and large cells were not (also useful for separating plasma from cells) has been described. Encapsulation of cells into droplets followed by sorting hydrodynamically to exclude empty droplets and collect cells of desired size has been described. Targets can be sorted by utilizing density changes. For example, species could be encapsulated in droplets with a detection reagent, such that targets in droplets produce a molecule that makes the droplet less dense and cause the droplet to float to an upper portion of the SlipChip. Any of these methods can be utilized on SlipChip, and then the captured targets can be slipped to another area for analysis and manipulation.

Capture by electrical, optical, magnetic and other properties can be used, for example when targets themselves inherently have distinct electrical, optical, magnetic properties, or when those properties can be induced. For example, selective binding of magnetic particles to microorganisms changes the organisms' magnetic properties, and may be used to separate those organisms from the rest of the sample using magnetic fields.

Targets of interest can be captured by their affinity for a capture agent, which can be either specific or non-specific for the target of interest. In certain embodiments, the bulk of the sample is not captured by the device, while the desired targets, such microorganisms, cells, or molecules can be preferentially bound and enriched.

Capture agents (or capture elements) can include affinity reagents, including antibodies, aptamers, non-specific capture agents, including for example a hydrophilic patch to which a droplet or cell can stick and others described herein. Several capture elements can be patterned on the same plate. For example, one row can be patterned with capture agents against bacteria, another row with capture agents against fungi. After assembly of the plates, detection reagents against bacteria and fungi can be added to the corresponding areas, to detect bacteria and fungi from the same sample.

Targets of interest can be captured by a unique behavior. For example, cells can be loaded into SlipChip wells coated with a substance such as a collagen adhesion matrix. Metastatic cells will migrate into the gel, while other cells will not. Other cells can be washed away and the gel dissolved, leaving metastatic cells isolated in wells that can be slipped to another area for analysis.

The SlipChip is also capable of arraying species (cells, beads, etc) across the different areas of a chip, and then applying detection agents to all of them in order to identify the location of the desired targets. These can then be isolated by slipping to another area for further analysis and manipulation. For example, all cells in a sample can be loaded into wells, then identified with a labeled affinity reagent (such as a fluorescently-labeled antibody for markers of interest, such as CD4 or EpCAM. Those wells containing labeled cells could then be slipped into an analysis area for further analysis or manipulation, for example, by PCR, cell culture and/or immunoassay.

One can carry out off-SlipChip binding to carriers with subsequent capture of carriers on a SlipChip. Carriers can be, for example, magnetic particles, particles coated with DNA, antibodies, and/or other targeting molecules. In certain embodiments, the target of interest binds to the carrier, and the carrier is captured on a SlipChip by a capture area. Binding is accomplished by methods including, but not limited to, those using affinity, electrical, optical, magnetic, or other properties. Capture of the carrier can be accomplished by methods such as those described above for capture of targets. For example, rare cells in a sample solution can bind to magnetic beads coated with antibodies, and the magnetic beads are then captured in SlipChip wells adjacent to a magnet.

Capture can be done in either a closed device (two or more plates together) or an open device (one or multiple plates separately exposed to sample). For a closed device, sample can be loaded by several means, including, for example, though an open hole, through induced flow or through aspiration into a channel. For an open device, one plate of the SlipChip may act as a filter or as a capture surface. An advantage of an open device is that large volumes of sample can be rapidly processed and rare targets quickly captured. This is useful for targets such as CTCs, which may be present at rates as low as 0.5-50 cells per mL of blood. In addition, open devices can be useful for analysis of samples that may be difficult to load otherwise, for example, aerosols of bacteria or viruses generated during coughing, or for analysis of samples on tissue slides, for which keeping track of spatial relationships among cells is preferred, as is done for, for example, tumor biopsies. In addition, opening the chip for analysis by methods that benefit from direct access (for example, mass-spectrometry) is advantageous. An exemplary method of collecting material on an open SlipChip comprises, exposing at least one plate of a SlipChip to a sample, allowing at least one target to transfer to the plate (for example, by affinity capture or filtration capture), optionally removing the SlipChip from the environment, bringing the second plate of the SlipChip into contact with the first plate, and slipping the plates to bring at least one area on each plate into contact with one another to induce a reaction/interaction with the target, for analysis or manipulation.

Capture methods can be combined with other techniques including stochastic confinement, multistep amplification of detection signals, and visual readouts. For example, targets such as cells from the sample can be stochastically confined into separate small volumes that accelerate detection and/or make it more sensitive. An application includes the stochastic confinement of immune cells from blood samples into, for example, nanoliter volumes, followed by slipping the device to perform an immunoassay for CD4 in order to identify CD4+ cells. This provides a CD4 count. Identified CD4-positive cells can then be isolated and slipped to another area for further analysis, such as PCR.

Capture methods can be combined with downstream analysis and manipulation, including, for example, stimulus-response assays and directed crawling assays. Stimulation-response assays are useful for detection and characterization of cells whose phenotypes are not apparent under resting conditions, for example for the detection of liquid tumors. Captured cells can be stimulated, such as with cytokines, and their response assayed by a set of parallel analyses and manipulations including ELISA for secreted signals including cytokines and proteases, staining for phosphorylation status to determine signaling pathways, PCR, RT-PCR, and culturing. Directional crawling assays may be used to distinguish cells with varying phenotypes. For example, metastatic cells crawl rapidly and directionally when mechanically confined; captured CTCs can be slipped into channels such as long straight ducts in order to assess this behavior.

Similarly, chemotactic gradients can be established, for example by loading one well of certain embodiments of a SlipChip with a chemotactic agent and slipping so that it is connected with another well or a duct, establishing a gradient by diffusion (as in FID devices and bridging devices). Flow can also be used to establish gradients. These gradients can be used to analyze chemotaxis of captured cells, which is relevant to inflammation, tumor regression and metastasis, autoimmunity, and infections.

Captured targets that are isolated individually can be monitored over time, with or without treatment or stimulation, providing time-resolved single target information that cannot be obtained in bulk cultures. For example, single cells can be monitored for proliferation, expression of a reporter (monitored, for example, by fluorescence) and/or secretion of a signal.

Wells containing captured cells can be manipulated to analyze the behavior of the cells. For example, wells can be analyzed for deposition of extracellular matrices. The surface of the chip can be modified by micro- or nano-scale topologies, or with modifications such as chemical surface treatments, to alter the dynamics and products of extracellular matrix formation. In another example, stimulants, including but not limited to chemical or cellular stimuli, can be applied to induce behaviors such as proliferation or differentiation; this is useful in the study of many cell types including lymphocytes, monocytes, and stem cells. Captured cells of different types can be brought together into a co-culture, either mixed or spatially-defined, in order to analyze cell-cell interactions. In one example, antigen-presenting cells can be cultured with T-cells, in order to analyze the dynamics of the T-cell response to antigen recognition. In another example, antigen-activated memory T-cells can be cultured in a well that is fluidically connected to another well via a duct too small for cells to pass through. Other cells, for example, naïve T-cells or B-cells, or epithelial cells, can be cultured in the other well, in order to analyze the effects of soluble signals such as cytokines.

Hydrophilic bridges can be used in certain embodiments of a SlipChip to allow for cell-cell interactions by connecting wells. An experiment to screen antibiotic resistance is described. The device and methods described here can be used, for example, for screening antibiotic resistance, for studying cell-cell communication without bringing cells into physical contact, for building spatial confined microbial communities, for understanding diversity and evolution of microecological systems, and for extracting or separating viruses, bacteria, and/or cells based on their size, motility and/or chemotaxis.

Experimental Section
Chemicals and Materials

All solvents and salts purchased from commercial sources were used as received unless otherwise stated. FC-40 (a mixture of perfluoro-tri-n-butylmethylamine and perfluoro-di-n-butylmethylamine) was obtained from 3M (St. Paul, Minn.). Food dyes were purchased from Ateco (Glen Cove, N.Y.). Tridecafluoro-1, 1, 2, 2-tetrahydrooctyl-1-trichlorosilane was purchased from United Chemical Technologies, Inc. (Bristol, Pa.). Alexa Fluor® 488 dye (Alexa-488) was purchased from Invitrogen (Eugene, Oreg.). Soda-☐ lime glass plates with chromium and photoresist coating were purchased from Telic Company (Valencia, Calif.). Amorphous diamond coated drill bits were obtained from Harvey Tool (0.035 inch cutter diameter, Rowley, Mass.). Fluorescence reference slides were purchased from Microscopy/Microscopy Education (McKinney, Tex.). Binderclips (5/32' inch capacity, ½' inch size) were purchased from Officemax (Itasca, Ill.). Pipettors were obtained from Eppendorf Inc. (Westbury, N.Y.). Fisherbrand pipettor tips were from Fisher Scientific (Hanover Park, Ill.).

Chip Design and Fabrication. SlipChip was fabricated using glass etching fabrication of SlipChip as described elsewhere in this application, with the following modifications. About 25 minutes of etching yielded a depth of about 30 µm. After etching, the tape was removed from the plates. The plates were then thoroughly rinsed with Millipore water and dried with nitrogen gas. The hydrophilic bridge surface was created by aligning a photomask containing the black patterns of hydrophilic bridge parts only to the bottom plate, then following the glass etching fabrication procedure described elsewhere. Access holes were drilled with a diamond drill bit 0.035 inches in diameter. The surfaces of the etched glass plates were cleaned with Millipore water, followed by ethanol and subjected to an oxygen plasma treatment before silanization. As the glass surface of the hydrophilic bridge pattern was not silanized, it remained hydrophilic after removing the chromium layer on the hydrophilic bridge pattern. The plate was then rinsed with Millipore water and ethanol and dried with nitrogen gas thoroughly.

Assembling the SlipChip. The SlipChip was assembled under a mixture of FC-40 and 0.4 mg/ml RfOEG. A 50 µl mixture of FC-40 and 0.4 mg/ml RfOEG was spread onto the bottom plate in a Petri dish, with the patterns facing up. The top plate was then laid on top of the bottom plate, with the patterns facing down. The two plates were aligned into position by moving them relative to each other and then fixed by using two micro binder clips. The SlipChip was ready for use after the extra FC-40 on the surface was removed.

Food Dye Experiments. All the solutions used for food dye experiments were filtered with a 0.45 µm PVDF syringe filter before use. Two food dyes (blue and yellow, Ateco, Glen Cove, N.Y.) were pipet-loaded into 20 reagent channels. To load each channel, 10 µL of dye was pushed through the inlets using a pipette until the dye solution emerged from the air supply channel. After loading reagents, the Chip was slipped to align two reagent wells over the hydrophilic part. The hydrophilic bridge was completely wetted by slightly slipping the wells left and right. Then two wells were connected by a wetting layer created by the reagents left on the hydrophilic surface.

Diffusion test using fluorescence dyes. The loading procedure was similar to that for the food dye experiments. Alexa488 (44 µM) and MPTS (400 µM) were dissolved in 10 mM TRIS buffer. The Alexa488 solution and MPTS solution were loaded into the device. The 10 inlets in one half of the device were loaded with Alexa488, each path containing 10 wells. 10 inlets on the other half of the device were loaded with MPTS. After the wells with fluorescent dyes were connected with hydrophilic bridges, the diffusion processes were imaged for 3 h in the dark using a Leica DMI6000 fluorescent microscope with a 10×0.4 NA Leica objective and a Hamamatsu ORCAER camera. GFP and DAPI filters were used to collect Alexa☐488 and MPTS fluorescence. An exposure time of 30 ms for both Alexa488 and MPTS was used.

Measuring fluorescence. Images were acquired and analyzed using Metamorph imaging system version 6.3r1 (Universal Imaging). To extract the intensity of the fluorescent signal, a region of 100 pixels by 100 pixels was selected in the middle of every well of interest. To calibrate the microscope, the fluorescent intensity of fluorescence reference slides for GFP and DAPI were recorded and used for background correction.

Data analysis. To calibrate the intensity measurements, the background intensity was first subtracted from all the fluorescent images. The intensity of each well was then extracted from the integrated intensity of a 100 pixel by 100 pixel region located at the center of each well.

Antibiotic screening experiments with *Escherichia coli*. *Escherichia coli* with plasmid pDsRed was provided by Professor Benjamin S. Glick (University of Chicago). Stocks of cells were stored at −80° C. Before each experiment, stocks were streaked onto LB agar plates (Difco LB Broth, Miller, containing 2% (wt/vol) Alfa Aesar agar powder) containing 100 µg/ml ampicillin. Plates were incubated overnight at 30° C. Colonies were inoculated in culture tubes containing 3 mL of LB with ampicilin (100 µg/ml) and subcultured overnight at 30° C., 160 rpm. The bacteria culture loaded into the device was re-inoculated from the overnight culture and cultured to the log phase. A bacteria cell density of $2.5 \times 10^7$ cells/ml was loaded via half of the inlets of the hydrophilic bridge device. Different concentrations of Chloramphenicol and Kanamycin (0.01 µg/ml, 0.1 µg/ml, 1 µg/ml, 10 µg/ml and 100 µg/ml for each antibiotic) were loaded into the other half of the device. Air supply channels were sucked dry to allow for air transport for *E. coli* growth. After the wells with bacteria and antibiotics were connected with hydrophilic bridges, the growth of *E. coli* was imaged for 16 h in the dark using a Leica DMI6000 fluorescent microscope with a 10×0.4 NA Leica objective and a Hamamatsu ORCAER camera. A Texas red filter was used to collect DsRed fluorescence. An exposure time of 40 ms was used. Images were acquired and analyzed by using Metamorph imaging system version 6.3r1 (Universal Imaging). To compare and quantify the bacteria growth, the threshold area percentage was measured for every pair of wells. This was done by selecting the features in the image by thresholding and measuring the 'red' pixel numbers. The threshold area percentage represents the percentage of red pixel number over the whole pixel numbers in the measuring region. Here, the entire measuring region for every image was the same.

Results

A SlipChip to perform 10 independent interaction experiments at the same time was prepared. Each experiment contained 9 duplicate trials. In one trial, two wells (1.5 nL each) are separated by a submicron-thick hydrophilic bridge which is 300 µm×40 µm in size. The top plate containing pairing wells was aligned with bottom plate containing microchannels and hydrophilic square patterns. Two rows with pairing wells were separately loaded with blue solution containing cell A and yellow solution containing cell B. After loading, the top plate wells are slipped relative to the bottom plate to break the continuous stream into compartments and generate pairing wells connected through hydrophilic bridges to start diffusion. Small molecules diffuse through the submicron thick hydrophilic bridges. At equilibrium, both wells were green. Cells A and B do not cross the hydrophilic bridge, but chemicals they secrete can be exchanged through the hydrophilic bridge.

A hydrophilic bridge device was tested with food dye. Blue and yellow dyes were loaded separately into 20 loading channels. After slipping, two wells were connected by the hydrophilic bridge. Bidirectional diffusion of two food dyes between two wells through the communication hydrophilic bridge was evidenced by a uniform green color in both columns of wells.

In another experiment, one set of wells was initially loaded with MPTS and these were paired with wells filled with Alexa488 (Green). The two dyes diffused towards each other through hydrophilic surface of connected bridge. Overlaid brightfield and fluorescent images show diffusion of fluorescent dyes from one set of wells to the other. Complete mixing was achieved after ~55 minutes for Alexa488 and ~45 minutes for MPTS.

Antibiotic screening was performed in a hydrophilic bridge device Bright field and fluorescent images showed *E. coli* growing in wells on one side of the hydrophilic bridge. Chloramphenicol (CLR) and kanamycin (Kana) were loaded into the wells on the other side. Concentrations for each antibiotic were 0.01 µg/ml, 0.1 µg/ml, 1 µg/ml, 10 µg/ml and 100 µg/ml. *E. coli* cells (density of $2.5 \times 10^7$ cells/ml) were loaded into the first set of wells in pairs of columns. Data were analyzed after 16 h from when *E. coli* was first exposed to different concentration of antibiotics. The threshold area for grown *E. coli* DsRed was selected and the threshold area percentage was measured for each pair of wells. The threshold area percentage indirectly represents the growth difference under different antibiotics concentration.

In certain embodiments, fabrication and operation of the SlipChip does not require lubricating fluid. The SlipChip can be operated without lubricating fluid dispensed between the plates. For such "dry" operation, it is preferable that the reaction fluids have a high contact angle (for example, an angle above 130 degrees) on the surfaces of the device. This high contact angle can be achieved via multiple approaches and their combinations, including the use of nanoporous and microporous polymers, phase separation of block copolymers, surface coatings, surface roughness and a number of other approaches, for aqueous solutions these are known as approaches for creating hydrophobic and superhydrophobic surfaces. Porous polymers may be used to create superhydrophobic surfaces, for example as described in Levkin P A, Svec F, Frechet J M J, Advanced Functional Materials, 2009 19 (12):1993-1998. An example of SlipChip operating without lubricating fluid is described.

SlipChips were made from plastics by hot embossing using glass molds. Fabricating glass molds—A glass mold was prepared by glass etching. The glass plate (3 mm thick) with chromium and photoresist coatings (Telic Company, Valencia, Calif.) was covered by a photomask containing the SlipChip design (patterns were shades on clear background) and was exposed to UV light for 1 min. Immediately after exposure, the glass plate was developed by immersing it in 0.1 mol/L NaOH solution for 2 min. Only the areas of the photoresist that were exposed to the UV light dissolved in the solution. The exposed underlying chromium layer was removed using a chromium etchant (a solution of 0.6:0.365 mol/L $HClO_4/(NH_4)_2Ce(NO_3)_6$). As a result, the patterns in the design were still covered by chromium and photoresist coatings. The plate was thoroughly rinsed with Millipore water and dried with nitrogen gas, and the back of the glass plate was taped with PVC sealing tape (McMaster-Carr) to protect the back side of glass. The taped glass plate was then carefully immersed in a plastic container with a glass etching solution (1:0.5:0.75 mol/L HF/NH4F/HNO3) to etch the bare glass surface of the plate (areas on the plate where both photoresist and chromium coatings were removed). A 40° C. constant-temperature water bath shaker was used to control the etching speed. By controlling the etching time (~55 min), the etching depth was 60 µm. The photoresist and chromium coatings that covered the patterns were then sequentially removed by ethanol and the chromium etchant. Consequently, the non-etched patterns stood as 60 µm-high pillars. The glass plate with positive patterns was then coated with another chromium layer. An array of holes (5 µm by 5 µm) was formed by ablating the chromium layer using a Resonetics RapidX 250 excimer laser operating at 193 nm. The fluence was adjusted to ablate a 150 nm layer of Cr in a single pulse, without affecting the glass. The glass was subsequently etched with HF using the Cr as an etch mask.

Resulating holes become posts in the hot embossed plastic piece, which significantly increases the contact angle. Fabricating plastic SlipChips—The glass mold was used to emboss the chip pattern into 1/16" fluorinated ethylene propylene (FEP, McMaster-Carr). The chips were embossed at 260° C., 400 lbs/in2 for 20 minutes in a Carver 3889 hot press. The chips were rapidly cooled to room temperature before pressure was removed.

In certain embodiments, operation of plastic SlipChips can be done without lubricating fluid. A dead-end filling method was adopted to load a dry FEP SlipChip with aqueous solutions. Following the assembly of the FEP SlipChip in the absence of any lubricating fluid, the SlipChip was sandwiched between two glass slides. The top glass slide had access holes aligned to the inlets of the SlipChip. The "sandwich" was fixed with paper clips. Solutions were all loaded by directly pipetting a 1 μL volume into the inlets. The pipette tips were pushed against the inlets through the access holes in the top glass slide. The loading process spontaneously stopped when the solution reached the dead-end. 0.1 M Fe (NO3)3 was used as a reagent and 0.3 M KSCN was used as a sample. After loading, the top plate of the SlipChip was slipped relative to the bottom plate and solutions were combined while the Chip remained sandwiched between the two glass plates throughout the process. Reaction between Fe (NO3)3 solution and KSCN solution produced red solution of various complexes including Fe(SCN)3. No evidence was found for cross-contamination or liquid residue left behind after slipping, and the red complex did not form in the ducts.

In one example of a simple chemical reaction in a dry FEP device, the two plates of the SlipChip were aligned in the absence of lubricating fluid to form the fluidic paths for the reagent and the sample. The reagent and sample solutions were loaded into the SlipChip via pipetting. The SlipChip was slipped to combine the reagents with the sample. The reaction progress was monitored by observing the color change from clear to red.

In certain embodiments, multivolume stochastic confinement can be performed on the SlipChip for digital detection by PCR and other techniques. The inventors have developed a multivolume stochastic confinement method on SlipChip for quantification of target species or molecules over a large dynamic range using digital detection. Detection can be achieved through various methods, including PCR, cell culture, enzymatic and isothermal amplification methods. The principal of stochastic confinement is laid out in the patent application PCT/US/2008/071374, Stochastic Confinement to Detect, Manipulate, and Utilize Molecules and Organisms. Potential applications of multivolume stochastic confinement include, but are not limited to, diagnosing, monitoring or detecting disease biomarkers, testing environmental or food samples, and isolating, characterizing, and analyzing cultures or other biological samples.

Digital PCR commonly uses microwells or emulsions of the same volume, so requires very high numbers of compartments (1000's to millions) to achieve high precision and a large dynamic range. SlipChip can be designed to perform digital measurements within wells of multiple volumes. Some advantages of this method over single volume methods include a large dynamic range with fewer wells, and increased precision achieved by overlapping ranges for the different sized wells. Arrays of wells with multiple reaction volumes can be designed on a single chip to achieve the entire desired range of detection. The approach is analogous to serial dilution methods and the statistical analysis can be performed with the same mathematical calculations. Instead of the multivolume approach, SlipChip can be used to perform serial dilution followed by analysis The multivolume approach has been used in microbiology, such as the IDEXX Quanti-Tray®/2000, for detection and enumeration of microbes. These and other applications can also be implemented on SlipChip. The multi-volume approach can be applied to digital PCR on SlipChip. Three possible modes of operation include: (1) Injection of the sample premixed with PCR reagents into the chip, then compartmentalization via slipping to perform digital PCR. (2) Separately preloading or user-loading reagents such as primers, optionally in a multiplexed format, and then mixing with the sample via slipping to initiate the reaction. (3) Combinations of the above.

In addition to standard PCR techniques, SlipChip is compatible with isothermal amplification techniques such as loop-mediated amplification (LAMP), recombinase polymerase amplification (RPA), nucleic acid sequence based amplification (NASBA), transcription-mediated amplification (TMA), helicase-dependent amplification (HAD), rolling-circle amplification (RCA), and strand-displacement amplification (SDA). The multivolume SlipChip can be used to digitize such platforms. The multivolume SlipChip could be applied to other systems that are compatible with stochastic confinement (patent application PCT/US/2008/071374, Stochastic Confinement to Detect, Manipulate, and Utilize Molecules and Organisms), including analysis or detection of cells.

One example of an application for the multivolume SlipChip is the measurement of HIV viral load. For HIV viral load measurements at the point of care, one desired goal is a dynamic range of 500 to 1,000,000 HIV particles/mL of blood plasma with the ability to distinguish concentration changes of at least 3 fold over the entire range. An example of a system that satisfies this was demonstrated by the inventors. This example is composed of 128 wells of 50 nL volume, 128 wells of 10 nL volume, 256 wells of 2 nL volume and 512 wells of 0.4 nL volume. The larger number of smaller volume wells can be used to increase resolution or alternatively can be used with an internal standard to calibrate the system. Accounting for two copies of RNA per HIV viral particle, this design has a lower detection limit of 200 HIV particles/mL and a dynamic range where 3 fold resolution can be achieved of 600-3,500,000 HIV particles/mL, and will greatly exceed that resolution over much of the range. This calculation needs to be adjusted for the effects of sample losses and concentration during sample preparation, and this can be done for example using an internal standard detected on the same device using a probe with a different color, or using different primers preloaded into specific wells.

This design could be applied to point of care testing. Alternatively, measurements in the range of 40-10,000,000 particles/mL might be required. A device can be designed to achieve this range. One example of such a device uses a total sample volume of 75 μL for the lower limit of detection and the smallest well volumes to be on the order of 0.25 nL. Being able to preconcentrate samples would allow for smaller volumes to be used.

The multivolume SlipChip method for digital measurements can also be applied to other diseases where accurate information on infection load is useful such as for hepatitis B viral load.

A similar layout to that described above can be used for other applications such as diagnosing the cause of pneumonia. Because pneumonia can be caused by many different species, accurate diagnosis requires a highly multiplexed test to detect the majority of potential pathogens. It also requires quantification to differentiate lower levels (corresponding to normal bacterial colonization of the upper respiratory tract) from higher levels (corresponding to bacterial infection of the lower respiratory tract). By splitting the design into 16 equal sections, 16 different species of bacteria and viruses can be detected over an approximately 1000 fold concentration range. An alternative design for pneumonia detection would allow for low detection limits for potential viral species, and a sufficiently large dynamic range for detection of potential bacterial causes and differentiation of colonization vs. infection. The design would include eight sets of 12×200 nL wells and 12×50 nL wells for viral detection. These sets would have a detection range of about 1000 particles/mL to about 30,000 particles/mL. It would also include eight sets of 24×25 nL wells and 24×2.5 nL wells for bacterial detection and more precise quantification. These sets have a detection range of about 4000 bacteria/mL up to about 800,000 bacteria/mL, with 3 fold resolution over much of that range. The detection ranges and designs can be adjusted as necessary to meet the requirements of the test, including changing well size or number or preconcentrating the samples being tested. As has been demonstrated in existing digital PCR literature, this approach can be used in any application where real-time PCR has been applied. This approach can combine digital analysis with multiplexing on a single device, for example, by adding multiple samples (such as blood, urine, or sputum) or running multiple tests on the same sample, or a combination.

To design the devices and analyze the results, several methods or their combinations can be used. Device design is dependent both on the desired detection range and the resolution achievable over the range. One method uses statistical approaches based on the poisson or binomial distributions, to calculate the concentration in the form of a "Most Probable Number (MPN)", as presented in the following equation:

$$\sum s_i v_i = \sum \frac{((n_i - s_i) * v_i * e^{(-v_i d)})}{1 - e^{(-v_i d)}}$$

Where $n_i$ is the total number of wells at the ith dilution/well size, $s_i$ is the number of sterile/empty/unreactive wells at that level, $v_i$ is the fraction of the original sample solution contained at that level (so a 10 fold dilution or reduction in well volume by a factor of 10 would give a value for $v_i$ of 0.1), and d is the original concentration, so the equation needs to be solved for d.

The lower limit of detection is dependent on the total sample volume contained in all of the wells. The upper limit of detection is set by the sample volume and number of wells at the smallest volume. Several methods or their combination can be used to establish the confidence intervals (CIs) for given results and determine the resolution of the system. Equation-based approximations are useful because CI values can be obtained rapidly, but they are only average approximations so may not be accurate for a given result. They are useful for directing system/device design, to make sure that the desired performance is reasonable to expect. Another set of methods that are commonly used are known as "exact" methods, because they utilize the actual probabilities for all potential results. These methods are predominantly based on existing work applied to single dilution/volume systems commonly referred to as the Clopper-Pearson (CP) and Sterne methods named for their creators. The CIs can be used to determine the resolution of a given system, and as this is dependent on number of wells and the dilution factor, the desired resolution will also govern well sizes and numbers. The following inequality is used to determine the factor/fold of resolution:

$$d1+95\% \text{ CI for } d1 \leq d2 - 95\% \text{ CI for } d2$$

When the two sides are equal then d1/d2=X, which is the factor/fold of resolution, and is typically set to be at most 3 fold in the examples described throughout.

Several SlipChip designs can be used to implement multivolume stochastic confinement, including rotating SlipChip devices, stacked multilayer SlipChip devices, and devices that require sliding in one or two directions. Wells of different volumes can be made in the same layer or by combining wells and through holes in multiple layers. In addition, wells of different volume can be made by creating wells of the same depth but different lateral dimensions, or by varying the depth of the wells. Keeping the volume constant but increasing the depth of wells reduces their lateral dimensions and is useful for increasing the density of wells. For applications that require thermal expansion, devices can be optionally designed so wells are brought into contact with reservoirs containing lubricating fluid or another fluid, as described in recent papers.

In one example, the device includes 128 wells of 50 nL volume, 128 wells of 10 nL volume, 256 wells of 2 nL volume and 512 wells of 0.4 nL volume. The larger number of smaller volume wells can be used to increase resolution or alternatively can be used with an internal standard to calibrate the system. When considering a solution containing purified HIV RNA, use of a nucleic acid amplification technique for detection, and accounting for two copies of RNA per HIV viral particle, this design has a lower detection limit of 200 HIV particles/mL and a dynamic range where 3 fold resolution can be achieved of 600-3,500,000 HIV particles/mL. This design will greatly exceed that resolution over much of the range. This calculation needs to be adjusted for the effects of sample losses and concentration during sample preparation, and this can be done for example using an internal standard detected on the same device using a probe with a different color, or using different primers preloaded into specific wells. For PCR applications, this design optionally includes smaller wells containing oil that are brought into contact with larger wells containing aqueous solution. When the smaller wells are brought into contact with the larger wells, the aqueous solution spontaneously forms a droplet surrounded by oil in the compartment, allowing for room for thermal expansion during thermal cycling. The wells and ducts can be patterned separately on the top and bottom plates. The wells can be fabricated by the techniques described elsewhere in this application. In some designs, the wells initially overlap with ducts to generate continuous fluidic path to enable filling. Filling can be achieved by using pipetting or other mechanical or chemical driven pressure. Dead-filling or through holes as outlets can be used to evenly fill the entire chip. The SlipChip can be slipped into discrete reaction volumes, for example by rotational motion of the device, and compartments of different volumes are generated simultaneously.

In one example of a multivolume device made in glass, the device includes 15 wells of each volume, with 135 wells in total; the volumes are: 0.25 nL, 0.72 nL, 1.95 nL, 5.24 nL, 14.1 nL, 38.1 nL, 103 nL, 278 nL, and 511 nL. This provides a detection limit of about 200 particles/mL with a dynamic range of at least 3 fold resolution from about 800-2,400,000 particles/mL. The procedure for fabricating this SlipChip was based the procedure described in previous work. In general, the structure was patterned by using photolithography and then etched by using a glass etching solution (1:0.5:0.75 mol/L $HF/NH_4F/HNO_3$). The device was silanized by dichlorodimethylsilane to provide a hydrophobic surface. A solution of orange food dye was injected into the device, and wells of different volumes were generated after slipping.

In another design the device has 88 large wells, 272 medium wells and 216 small wells. The design could be applied to quantification of HIV viral load. Considering two copies of RNA per HIV particle and well volumes of 50, 5 and 0.5 nL respectively this design gives a detection limit of about 250 HIV particles/mL and a dynamic range with at least 3 fold resolution from about 800-3,300,000 HIV particles/mL, with better resolution over much of the range. The overall range for the individual well sizes has higher precision due to overlap of detection ranges.

Two examples of circular SlipChips to perform digital measurements are described. In the first example a SlipChip designed to measure HIV viral load contains 88 wells of 50 nL each (dynamic range $950-2.5 \times 10^4$ particles/mL), 272 wells of 5 nL each (dynamic range $3.0 \times 10^3 - 3.5 \times 10^5$/mL), and 216 wells of 0.5 nL each (dynamic range $3.8 \times 10^4 - 3.3 \times 10^6$/mL) to give a total dynamic range (after 4 fold concentration) of 800-3,300,000 particles/mL with at least 3 fold resolution. In the second example a SlipChip designed to identify and quantify pneumonia pathogens and distinguish between bacterial colonization and infection contains 16 regions: 8 regions containing 6×400 nL wells and 26×50 nL wells for a detection range of about $800-4 \times 10^5$ particles/mL for detection of viral and noncolonizing bacterial detection, and 8 regions containing 5×400 nL wells and 8×50 nL wells and 27×5 nL wells with a detection range of about $10^3-4*10^6$ particles/mL for bacterial detection. It can achieve 3 fold resolution over at least the middle portion of the range to distinguish infection from colonization.

For multiplexed detection, the device can be separated into multiple regions. Different inlets for different samples can be used to fill each region. In addition, different primers and chemistries can be preloaded into different regions. The regions may have the same sensitivity and dynamic range, or different sensitivity and dynamic range. Different sensitivity is needed, for example, for multiplexed detections of pathogens in pneumonia, where a $800-10^5$/mL range is needed for low level detection and moderate quantification, and detection in the range of $10^2-10^6$/mL is needed for pathogens such as *S. pneumonia* and *H. influenzae* type b, for improved quantification to distinguish colonization from infection. For example, in one design there are 16 regions: 8 regions containing 6×400 nL wells and 26×50 nL wells for a detection range of several hundred to about 40,000 particles/mL to detect viruses, and 8 regions containing 5×400 nL wells and 8×50 nL wells and 27×5 nL wells for a detection range of about 1000 to 400,000 particles/mL to detect bacteria and discriminate between colonization and infection. The design can be applied to detection and quantification of pneumonia-causing pathogens.

The SlipChip is compatible with various readout technologies, including colorimetric or fluorescence readout. These readout methods can be applied either in real time or at the end point. In certain embodiments, the user can use the SlipChip platform to enrich sample and perform sample preparation from milliliter scale of sample for further analysis, such as PCR, isothermal amplification and immunoassays. This method can be applied together with other Slip-Chip application to provide means for diagnostics, monitoring or detecting disease biomarkers, and testing environmental or food samples. In certain embodiments, the SlipChip can be used to synthesize composite particles in a high-throughput or combinatorial manner. SlipChip may be used to fabricate particles, including solid or hydrogel particles made from different polymers and hydrogels with many applications, including surface decoration and protection, food additives, Sustained Release Capsules, chromatography, flow cytometry, drug delivery and encapsulation of cells for implantations. Particle with precise size, shape, and composition have found applications in MEMS (micro electro mechanical system), photonics, diagnostics, and tissue engineering. However, the synthesis of such particles using existing techniques like seed polymerization is time consuming and expensive. Microfluidics has proved to be a powerful tool for making spherical particles or non spherical particles, or even janus particles. However, it is difficult to form arbitrary shapes or form composite particles with these methods. In general, SlipChip can be used to make rather arbitrary particles, by using SlipChip as a mold. Methods include using SlipChip to fill molds, slip away ducts used for filling areas of the molds and forming particles. Methods of inducing formation of particles may include curing using thermal energy, optical, ultra-violet light, chemical binding agents, and so on. Methods of forming particles, and materials for fabricating or coating SlipChip molds, may be adapted from those used by Liquidia Technologies. The use of lubricating fluid, for example fluorinated lubricating fluid, in the SlipChip during particle formation may substantially facilitate release of particles after formation. Slipping of several areas of slipchip filled with precursor of particle material in contact and then inducing particle formation can be used to create composite particles of complex shapes and compositions. Particles may be released by slipping or by simply dis-assembling the SlipChip. Particles with gradient properties may be created by bringing together precursors with different properties.

In certain embodiments, a SlipChip platform, called the matrix slipchip, can be used to perform n×m reactions with n+m loading steps. SlipChip designs to mix two, three, and four components are described. Two experiments with bacterial cells are described: culturing bacterial cells on the matrix SlipChip and screening bacteria-bacteria interactions on the matrix SlipChip. Features to highlight include high throughput: 1024 parallel experiment in <4 cm×4 cm space; save precious reagents and samples; mixing multiple times with precise time and volume control; the device is reusable and reconfigurable: after each use, the device can be opened and washed for second use. An 8 inlet top plate can be used with a different bottom plate containing a different number of inlets, such as 8 inlets, 16 inlets and 32 inlets, based on need, since the central design is same; open the device to extract the content of nanoliter droplets for scale up culture, detection, etc. or using permeable layers, such as tape-sealed layers, to access the results of the experiments; nanoliter aerobic cell culture with sufficient air supply and without evaporation. or anaerobic culture; air supply channel; nanopost pattern for oxygen transport; easily generate duplication for reproduce and improve data quality, a lot of duplication wells make it possible to extract more products from the device for further usage and analysis; transfer of beads, cells from wells on one plate to wells on another plate by gravity or magnetic force; the device and methods described here can be used for a number of applications. In particular, the SlipChip could be used as a platform for performing high throughput screening, especially of protein crystallization, multiplex genome sequencing, cell-cell interaction, protein-protein interaction, and drug screening, etc.

Matrix SlipChip has a number of additional applications. ThermoFluor Assays and other assays that reflect protein stability (for example by monitoring fluorescence of hydrophobic dye akin to 1-anilinonaphthalene-8-sulfonic acid (ANS)) can be used to monitor stability of protein molecules as a function of temperature or changes in chemical conditions. These assays are useful to monitor ligand binding in drug discovery, and optimization of ligand and buffer conditions for crystallography. It will be obvious to those skilled in the art that SlipChip and Matrix SlipChip will enable a number of additional applications, including but not limited to those marketed by Fluidigm, including measurements of Copy Number Variation, Gene Expression, Protein Crystallization, Sample Quantification for Next Gen Sequencing, Single Cell Gene Expression, SNP Genotyping.

The Matrix SlipChip was composed of a top plate and a bottom plate with complementary patterns. It was fabricated by using soda-lime glass plates with chromium and photoresist coating (Telic Company, Valencia, Calif.). Microchannels and wells on the glass plates were made by using standard photolithographic and wet chemical etching techniques. Briefly, the glass plate with photoresist coating was aligned with a photomask containing the design of the microchannels and wells and exposed to UV light for 1 min. The photomask was removed, and the glass plate was developed by immersing it in 0.1 mol/L NaOH solution for 2 min. The exposed underlying chromium layer was removed using a chromium etchant (a solution of 0.6:0.365 M $HClO_4/(NH_4)_2Ce(NO_3)_6$). The plate was rinsed with Millipore water and dried with nitrogen gas, and the back of the glass plate was taped with PVC sealing tape (McMaster-Carr) to protect the back side of glass. The taped glass plate was then carefully immersed in a plastic container with a glass etching solution (1:0.5:0.75 M $HF/NH_4F/HNO_3$) to etch the glass surface that was exposed after the chromium coating was removed. A 40° C. constant-temperature water bath shaker was used to control the etching speed. ~25 minutes of etching yielded a depth of ~30 μm. After etching, the tape was removed from the plates. The plate was then thoroughly rinsed with Millipore water and dried with nitrogen gas. Access holes were drilled with a diamond drill bit 0.030 inches in diameter. The surfaces of the etched glass plates were cleaned with Millipore water, followed by ethanol and subjected to an oxygen plasma treatment before silanization.

To culture aerobic cells in the SlipChip, a nanopost pattern was fabricated on the top plate to improve the oxygen supply. To make the nanopost pattern, after etching the 30 μm patterns, the top plate was cleaned with water and dried with nitrogen gas. We utilized the original photoresist and chromium coating still cover those areas that were not etched. The plate was aligned with a nanopost photomask and the same procedure was followed as described above, through the step that removed the exposed underlying chromium. After removing the chromium coating, the top plate was immersed in 1:0.5:0.75 M HF/NH4F/HNO3 mol/L HF/NH4F/HNO3 etching solution, and etched for 30~90 s at room temperature (~23° C.) to produce the desired nanopost height over the surface. Finally, the top plate and the bottom plate (which has no nanoposts) were rinsed with ethanol to strip the undeveloped photoresist, and immersed in the chromium etchant to strip off the chromium coating. The glass was then rinsed with ethanol and Millipore water and dried with nitrogen gas.

The glass plates were cleaned and subjected to an oxygen plasma treatment, and then the surfaces were rendered hydrophobic by silanization in a vacuum dessicator for 3 hours with Tridecafluoro-1,1,2,2-tetrahydrooctyl-1-trichlorosilane as previously described. After silanization, the glass plates were baked in a 120° C. oven for 30 min, rinsed by immersing in a tank of FC-3283, and dried in a 60° C. oven overnight.

Before use, the bottom plate and top plate of the matrix SlipChip were cleaned with soap, Millipore water and 100% ethanol sequentially, and dried with nitrogen, and placed in clean Petri dish with the etched pattern facing up. 50 μL FC-40 (3M) fluorinated oil with 0.4 mg/mL RfOEG3 was spread onto the surface of bottom plate, and then the top plate was placed (patterned side down) onto the bottom plate. FC-40 totally wet the silanized surface and spread between two plates. The two plates were aligned by slipping them relative to each other and then fixed by using two micro binder clips. The SlipChip was ready for use after the extra FC-40 on the surface was removed. Both plates of the Matrix SlipChip contained elliptical wells. The wells were 200 μm wide and 400 μm long, etched to be 30 μm deep, with volume of approximately 2 nL. Connecting microchannels were 860 μm long and 80 μm wide, with depth of 30 μm. Before loading solution, the oil in the channels and wells were sucked up by applying vacuum at the inlet of the device. Four food dyes (red, orange, green, and blue, Ateco, Glen Cove, N.Y.) were diluted ~20 times from their stock solutions and were filtered with a 0.45 μm PVDF syringe filter before use. Solutions were pipet-loaded into wells in 32 columns from 8 inlets. To load each channel, 8 μL of dye was first pushed through the inlet using a pipette until the dye solution emerged from the outlet. After loading reagents, the top plate was first slipped down and then slipped left, to form continuous fluidic paths in rows. The same four food dye solutions were loaded through the 8 inlets from the left side to fill 32 rows of wells. Using a pipette, 8 μL of dye was loaded into the Chip until all the channels in row were fully filled. Once the rows was loaded, the top plate was slipped again to mix the 1024 wells in columns on the top plate and 1024 wells in rows on the bottom plate.

The inventors designed a following 3-component and 4-component matrix SlipChip to incorporate mixing of more than 2 components in one compartment. The food dye experiments were performed with the similar procedure described for the 2-component Matrix SlipChip, except an extra washing step was needed to load two sets of adjacent wells using the same connection channels.

In the step by step operation of three components mixing matrix SlipChip, a first set of wells in the bottom plate are filled. Optionally, the chip is slipped and the same ducts are used to fill the second set of wells in the bottom plate. SlipChip is slipped (e.g. in X and Y directions) so that the horizontal rows are aligned, and the wells in the top plate are filled and the SlipChip is slipped so that the wells overlap, combining solutions in the two adjacent bottom wells with the solution in the top well.

In the step by step operation of four components mixing matrix SlipChip, a first set of wells in the bottom plate are filled. Optionally the chip is slipped and the second set of wells is filled. SlipChip is slipped so that the horizontal rows are aligned, and the first set of wells in the top plate is filled. The SlipChip is slipped so that the second set of horizontal wells in the top plate is filled. The connecting channels were first washed with buffer. The SlipChip is slipped so that the wells overlap, combining solutions in the two adjacent bottom wells with the solutions in the two adjacent top wells.

In the step by step operation of four component matrix SlipChip using food dyes the first step was loading the first set of vertical wells. The second step was slipping to fill the second set of vertical wells followed by slipping to align the horizontal wells and ducts. Then the first set of horizontal wells were filled followed by the slipping and filling of the second set of horizontal wells and finally slipping to combine solutions in 4 wells.

The success of culturing different bacteria cells (including aerobic or anaerobic strains) on SlipChip is fundamental for further study of cell-to-drug screening, bacteria antibiotic resistance, bacteria quorum sensing, and multi species community interactions, etc. Compared with conventional methods, the matrix SlipChip can use nanoliter volumes to observe single cell or small group of cells, increase the throughput, and save time and reagents.

To be able to culture and grow aerobic bacteria in nanoliter wells in matrix SlipChip, the user needs to continuously supply oxygen to these wells. This was achieved on the slipchip by the following features: To culture cells in the isolated wells, the inventors connected horizontal wells and channels and loaded the resulting fluidic path with air to form a breathing channel. Each isolated well could get its oxygen supply from 2 nearby breathing channels. The distance between the well and breathing channel was 240 μm. The matrix SlipChip used FC-40 as lubrication oil, which has a very high solubility of oxygen and good oxygen permeability. A nanometer to micrometer thick FC-40 film can support the transportation of oxygen. Since oxygen supply efficiency of the breathing channel is limited by the thickness of the FC-40 film between two plates, the inventors fabricated a nanoposts pattern on the top plate. This increased the thickness of the FC-40 film from estimated 500 nm to 1.5 μm. As shown in Error! Reference source not found. D) to F), this increase efficiently increased the growth of E coli DS red cell in SlipChip.

The homogeneity of culture in SlipChip was tested as describe in the following:

*Escherichia coli* with plasmid pDsred was obtained. Stocks of cells were stored at −80° C. Before each experiment, stocks were streaked onto LB agar plates (Difco LB Broth, Miller, containing 2% (wt/vol) agar powder, Alfa Aesar) containing 100 μg/ml Ampicillin. Plates were incubated overnight at 30° C. Colonies were inoculated in culture tubes containing 3 mL of LB media with Ampicilin (100 μg/ml) and subcultured overnight at 30° C., 160 rpm. The bacteria culture that was loaded into the device was re-inoculated from the overnight culture and cultured to the log phase. When loading cells into the device, the bacteria cell density was adjusted to $1.1 \times 10^7$ cells/mL to obtain ~22 cell per well.

The 32×32 matrix SlipChip was prepared as described previously. The cell suspension was shaken before pipette loading from 8 inlets in the top plate. 8 μL of cell suspension was loaded into each inlet. After loading, the device was slipped to disconnect wells in column from channels and connect the channels and wells in rows to serve as air supply channels. The oil in the air supply channel was removed with a vacuum to allow for air transport for *E. coli* growth.

The micro binder clips were removed, and the 32×32 matrix SlipChip was carefully placed into a Petri dish. 2 small caps with 50 μL FC-40 and one small cap with 100 μL H2O was kept in the Petri dish beside the SlipChip to supply moisture in the dish. The Petri dish was wrapped with Parafilm to avoid escape of moisture.

The growth of *E. coli* was imaged every 2 hours for 16 hours in the dark using a Leica DMI6000 fluorescent microscope with a 10×0.4 NA Leica objective and Hamamatsu ORCAER camera. Texas red filter was used to collect Dsred fluorescence. An exposure time of 40 ms was used. To calibrate the microscope, the fluorescent intensity of a fluorescence reference slide for the Texas red filter was recorded and used for background correction. Images were acquired and analyzed by using Metamorph imaging system version 6.3r1 (Universal Imaging) with multi-dimension acquisition function. To compare and quantify the bacteria growth, a measure circle was drawn to cover the well and the integrated fluorescent intensity with background substrate was measured for every well. The 32×32 matrix of wells were grouped as 16×16 units, each with 2×2 wells, and the average intensity for each unit was gathered for 3 different devices (no nanoposts, 426 nm nanoposts, and 940 nm nanoposts, respectively). The results qualified that the nanopost pattern can improve the growth of *E. coli* on the matrix SlipChip.

For cell culture on a device with a breathing channel there were vertical isolated wells loaded with bacteria culture and horizontal wells and channels connected and loaded with air to supply oxygen to the bacteria wells. The nanoposts on the top plate accelerated oxygen exchange. The nanoposts are 20 μm by 20 μm in size and 900 nm in height, the spacing between nanoposts are 80 μm. The nanoposts will maintain a gap of greater than 1 μm that is filled with FC-40 oil within the device. This oil is air permeable and accelerates the exchange of oxygen from breathing channel and bacteria wells. Different nanopattern heights were used to culture *E. coli* DS red: no nanoposts; 426 nm nanoposts; 940 nm nanoposts. With increase of nanopost height, there is better and more even growth in the device.

A 32×32 matrix SlipChip with 16 inlets (each inlet distributed solution to 2 columns) was prepared as previously described. The device was aligned so that the fluidic paths formed in columns. Three antibiotics, Chloramphenicol, Kanamycin, and Streptomycin, were dissolved in LB broth media with different concentrations (0.01 μg/mL, 0.1 μg/mL, 1 μg/mL, 10 μg/mL and 100 μg/mL for each antibiotic), and were loaded into the wells in columns. The device was then slipped to connect wells in rows to load *Escherichia coli* with plasmid pDsred. *E. coli* was cultured as described in the previous part. The bacteria cell density was counted and adjusted to ~$2.4 \times 10^7$ cells/mL to obtain about 48 *E. Coli* cells in each well. Then the device was slipped to bring wells on the bottom plate with *E. coli* into contact with the wells on top plate with antibiotic solution. The device was kept still for 30 min with top plate facing down, so that majority of *E. coli* cells were settled down in the well in the top plate by gravity. Then the device was slowly slipped so that continuous fluidic paths were formed in rows again to serve as air supply channels. The solutions in the air supply channels were removed with vacuum to allow air transport for *E. coli* growth.

The matrix SlipChip was put into a Petri dish and growth of *E. coli* was imaged for 16 hours as previously described. The same data analysis was carried out for every well at time point of 16 hour and the intergrated fluorescent intensity from *E. Coli* cells were plotted as a gray scale map. For each antibiotic concentration and the control without antibiotics, there are 64 wells in 2 parallel columns. The average intensity of these 64 wells was plotted.

A control experiment on 96-well plate was carried out for the same cell sample and antibiotic concentrations. Basically, 100 µL aliquot of cell suspension was added into the wells, then 100 µL of antibiotics with different concentrations. The OD unit was measured in a microplate reader at 0 h and after 16 hours. A *E. coli* growth inhibition breakpoint similar to that obtained with the matrix SlipChip was seen for all three antibiotics.

For the antibiotic screening in 32×32 matrix SlipChip, after 16 hrs, integrated intensity indicate growth of *E. coli* on 32×32 SlipChip after 1:1 mixing with control (LB broth media) and three antibiotics (Chloramphenicol, Kanamycin and Streptomycin) with different concentrations. Concentrations for each antibiotic were 0.01 µg/ml, 0.1 µg/ml, 1 µg/ml, 10 µg/ml, 100 µg/ml. The initial *E. coli* cells density was $2.4 \times 10^7$ cells/mL. Data were analyzed after 16 hours of incubation. The average fluorescent intensity from *E. coli* after cultured 16 hour with different antibiotics concentration. The breakpoint represents the growth difference under different antibiotics concentration.

In certain embodiments, analog-to-digital conversion of concentration with visual or cell-phone readout can be performed on the slipchip. Using chemistry with threshold can convert analog readout to digital readout. A definition of a threshold can be found in patent application Stochastic Confinement to Detect, Manipulate, And Utilize Molecules and Organisms (Pub. No. WO/2009/048673, International Application No. PCT/US2008/071374). An analog readout, in the case of assays, is a signal that corresponds to the amount of a certain substance, is expressed on a continuous scale, and therefore requires equipment to read. A digital readout is expressed as a digit, which, in this case, is a yes/no value (yes being above the threshold value and no being below the threshold value). Such analog-to-digital conversion, when coupled with assays that give visual readout, can be performed in a SlipChip without special equipment. The threshold-based analog-to-digital conversion allows the result to be realized and semi-quantified by the naked eye or to be captured by a simple camera, such as a cell phone camera which can send the picture out for further analysis or storage. This approach works with various assays and various threshold chemistries. Particularly, the inventors have demonstrated two types of threshold chemistries, with enzymes and with gold nanoparticles (Au NPs). Enzyme: A threshold exists when an inhibitor binds tightly to an enzyme and inhibits the enzyme from performing the catalysis function. When there is a small amount of enzyme, there will be enough inhibitor to inhibit all the enzyme molecules from performing the catalytic function. When there is a larger amount of enzyme, there will not be enough inhibitor to suppress the enzymatic reaction. As a result, for a certain amount of inhibitor, there will be a threshold, meaning that only when the enzyme concentration exceeds that threshold can the inventors observe a signal. Thus, the threshold position depends on the amount of inhibitor. Here the inventors used the inhibitor syn-(S)-TZ2PIQ-A5[1] which binds tightly to acetylcholinesterase (AChE) in a 1-to-1 ratio. The threshold amount of AChE is set by the amount of inhibitor. AChE hydrolyzes acetylthiocholine to give out thiocholine. Thiocholine reacts with stach/$I_2$ complex. The reaction causes a color change from dark blue to clear. Gold nanoparticles (Au NP): Au NPs can catalyze the reduction of silver (I) ion (in the presence of hydroquinone), which is colorless, to silver (0) particles, which are black precipitates. Via a tight Au-S bond, the thiol forms a layer on the surface of Au NPs. The layer will block the interaction between Au NPs surface and reactants in the solution. When there is small amount of Au NPs, there will be enough thiol to coat the surface of all the Au NPs, inhibiting the contact between Au and silver and suppressing the silver enhancement reaction. When there is larger amount of Au, there will not be enough thiol to coat the entire surface of Au, and silver enhancement will take place quickly. Only when Au NPs are in excess compared with the amount of thiol would there be surface exposed to silver, thus the threshold position depended on the amount of thiol.

The threshold chemistries can be coupled with assays. For example, the threshold can be coupled to the reporter molecule of an immunoassay. The inventors herein reported an experimental result in which an immunoassay for cystatin C in the SlipChip gave visual digital readout by utilizing the threshold of AChE, which is the reporter molecule. The inventors also showed that the threshold for Au NP worked in SlipChip to give visual digital readout, thus demonstrating the potential of applying this threshold to assays such as immunoassays.

A sandwich immunoassay for insulin has been successful demonstrated in the SlipChip. However, the readout for the assay still required a fluorescent microscope. Here the inventors modified the assay for cystatin C, with AChE as the reporter enzyme. The assay gave digital readout due to thresholds set by different amounts of the inhibitor syn-(S)-TZ2PIQ-A5, and gave visual readout by the color changing reaction of thiocholine (a product of the enzymatic reaction) with the dark blue starch/I2 complex to make the mixture colorless. The amount of cystatin C correlates linearly with the amount of AChE. By using different amounts of inhibitor, the inventors can set different thresholds for AChE. The concentration of AChE will make the reaction proceed at certain threshold values and is inhibited at other threshold values. Such result will indicate the range of concentration of AChE, and thus, the range of concentration of cystatin C.

This SlipChip was similar to the one used to perform bead-based immunoassays, with the modifications of larger dimensions, a change in the number of wells in each row, an additional row for reagents in the top plate, and varied depths in that row to allow for multiple threshold concentrations to be evaluated on a single SlipChip.

For the SlipChip for immunoassay with threshold, diamond wells dimensions were 780 µm×780 µm. Ducts were 380 µm wide and 90 µm deep. The spacing between the rows and columns were 2.5 and 1.5 mm, respectively. The bottom plate of the SlipChip contained wells to hold sample and ducts to load the reagents. In the top plate, the ducts were used to load the sample. The wells in row 1 on the top plate were loaded with the capturing mixture. Rows 2-5 were filled with buffers for washing, row 6 was loaded with the inhibitor, and row 7 was loaded with the substrate. The wells in row 6 were divided into 5 sets of [5, 6, 6, 6, 6] wells with respective depths of [16, 21, 28, 51, 90] µm. Other wells on the top plate were 90 µm deep. Wells on the bottom plate were 7 µm deep. For the immunoassay, the plates were aligned to load the capturing mixture. The plates were slipped and aligned many times to load reagents and then slipped and aligned to load the analyte. The plates were slipped so that the row of wells in the bottom plate came into contact with each row of wells in the top plate sequentially, and then slipped to show the final results.

Before performing the whole enzymatic immunoassay in SlipChip, the inventors validated the use of the AChE threshold by showing the simple threshold of just AChE and the inhibitor syn-(S)-TZ2PIQ-A5 in a SlipChip. Indeed, at a final inhibitor concentration of 5 nM, AChE showed a threshold at 5 nM (final concentration), as expected. The reactions with concentrations of AChE >5 nM gave almost clear solutions, while the reactions with concentrations of AChE ≤5 nM remained dark blue.

For enzyme threshold chemistry in SlipChip, the top plate had four rows of wells that were connected to the same inlet. The bottom plate had four rows of wells with separate inlets and outlets. The depth of the wells on the top plate was 80 µm and the depth of the wells on the bottom plate was 60 µm. A solution of inhibitor was loaded into the wells on the top plate. Four different solutions of AChE with different concentrations were loaded into the wells on the bottom plate. The bottom plate was slipped relative to the top plate to allow the wells both plates to overlap. After a 30-minute incubation, the two plates were slipped back to the original position. The substrate mixture was loaded into the wells on the top plate. The SlipChip was slipped again to bring the wells of the top and bottom plate back into contact, and the reaction was monitored with the stereoscope.

The inventors also obtained preliminary results for the other type of threshold-generating reaction, silver reduction using Au NPs. The inventors have shown the threshold in Au NPs on a well plate. Here, the inventors demonstrated that this threshold can be performed in a SlipChip. In this experiment the inventors used a constant concentration of Au NPs while varying the amount of thiol inhibitor. When the concentration of 2-mercaptoethanol was below 110 µM, the thiol did not completely cover the surface of the Au NPs, so the reduction of Ag (I) proceeded as indicated by the dark color. But when concentration of 2-mercaptoethanol was above 330 µM, the reaction was suppressed and no signal was observed. Au NPs are commonly used tags in biological applications, enabling the coupling of this method to a wide range of detection reaction.

For threshold of AChE and immunoassay in SlipChip bioconjugation: bead-Ab: cystatin C antibody clone 24 (Genway, cat#20-511-242278) was conjugated to tosylated paramagnetic beads (Invitrogen, cat#65501) using the manufacturer's instruction. Ab-biotin: cystatin C antibody clone 10 (Genway, cat#20-511-242277) was conjugated to biotin using Lightning Link kit (Innova Biosciences, cat#704-0010) using the manufacturer's instruction.

The solutions were prepared as follows: Phosphate buffer: sodium phosphate 0.1 M, pH 7 with pluronic F127 (BASF) 1 mg/mL. BAB: pluronic F127 1 mg/mL in 1×DPBS (Gibco) pH 7. WB: BAB with extra 0.2 M NaCl (0.337 mM NaCl total) Starch solution: A suspension of cornmeal in phosphate buffer was boiled for 10 minutes and cooled down to room temperature. The supernatant was then filtered through a syringe filter with a 5-µm membrane to give the starch solution. Substrate mixture 1: 45 µL starch solution, 5 µL acetylthiocholine solution (0.4 M in phosphate buffer), and 1 µL of the 620 µL solution of NaI (18.64 mg) and I2 (1.55 mg) in water were mixed in a 600-µL microcentrifuge tube by vortexing. Substrate mixture 2: 98 µL starch solution, 1 µL acetylthiocholine solution (0.4 M in phosphate buffer), and 1 µL of the 4.016 mL solution of NaI (798.07 mg) and I2 (101.93 M) in phosphate buffer were mixed in a 600-µL microcentrifuge tube by vortexing. Capturing mixture: 2.5 mg/mL bead-Ab, 0.025 mg/mL Ab-biotin and 25 mg/mL AChE-avidin (Cayman Chemicals, cat#400045) in BAB.

The fabrication of features on the SlipChip was performed as follows: The SlipChip for simple threshold was fabricated as previously described. The dimensions of the wells were 1960 µm×400 µm×80 µm on the top plate and 1920 µm×360 µm×60 µm on the bottom plate. On the SlipChip for immunoassay with threshold, all features except the wells in row 6 of the top plate and the wells of the bottom plate were fabricated as previously described. Wells in row 6 of the top plate and wells in the bottom plate were formed using laser drilling (Resonetics RapidX250 system, with demagnification of 7, constant energy mode of 130 mJ, 75-mm lens, fluence of 2.5 J/cm2).

The coating of the SlipChip was performed as follows: The surface treatment of the SlipChip for simple threshold was performed as previously described. The SlipChip for immunoassay with threshold was coated with FEP to have a robust coating to prevent wetting of the areas not containing any features (wells or ducts) by aqueous solution. The bare glass chips were cleaned in $H_2SO_4$ 98%: $H_2O_2$ 30% (3:1 v/v) for 1 hour. They were then dip-coated in FEP emulsion (Fuel Cell Earth LLC, cat#TE9568-250) diluted 3 times with Millipore water with the speeds of going in and out of the solution of 10.8 and 1.8 cm/min, respectively. The coated chips were baked on a hot plate from room temperature (21-23° C.) to 250° C., and at 250° C. for 5 min, then cooling in air at room temperature. The FEP layer in wells in row 6 of the top plate and in the bottom plate were removed by layer drilling (70 mJ with 50% attenuator, with other parameters the same as when drilling wells) and subsequently, manual application of a needle (Beckton-Dickinson, cat#305109) under a microscope.

The operation of the SlipChip was performed as follows: The SlipChip was assembled by dropping 0.5 mL of FC-40 (3M) onto the bottom plate, putting the top plate on top of the bottom plate, and clamping the two plates with clothespins. Each row of the SlipChip was loaded by sticking a 10-µL pipet containing 10 µL of the solution in the inlet hole and pushing the solution out of the pipet.

The loading of the reagents and sample into the SlipChip was performed as follows: The SlipChip for simple threshold: First, the inhibitor solution was loaded into 4 rows in parallel via an inlet connected to 4 rows; AChE (SigmaAldrich, cat#C2888) solutions in phosphate buffer were loaded into 4 rows one by one from 4 separate inlets. The chip was slipped so that each row of the AChE solutions overlapped with a row of the inhibitor solution. The chip was then incubated for 30 minutes before being slipped back to the original position. An excess amount (~100 µL) of substrate mixture 1 was loaded into the wells in 4 parallel rows. The chip was then slipped again so that the substrate mixture came into contact with the mixture of AChE and inhibitor formed in the previous step. The final concentrations of AChE were ~4, 5, 6, and 7 nM, and the final concentration of inhibitor was ~5 nM. The reaction was monitored a Leica MZ 16 stereoscope (Leica Microsystems) with a Plan APO 0.63x objective. The SlipChip for immunoassay with threshold: After the assembly of the two plates, they were aligned so that wells in row 1 of the top plate were connected by the ducts in the bottom plate. The capturing mixture was then loaded into the first row of wells. The plates were then slipped relative to each other so that the wells in the second row of the top plate were connected by the ducts in the bottom plate, and WB was loaded into the second row. Similarly, wells in rows 3 through 7 were loaded with WB, phosphate buffer, phosphate buffer, inhibitor solution, and substrate mixture 2, respectively. Then the plates were aligned so that the wells in the bottom plate were connected by the ducts in the top plate, and the cystatin C sample (in BAB) was loaded in the wells of the bottom plate.

The SlipChip was slipped so that wells of the bottom plate were overlapped with the first row of wells in the top plate. The mixture of the sample and the capturing mixture were incubated for 30 minutes at room temperature (21-23° C.).

A magnet was used to pull the beads to the bottom of the wells in the bottom plate. The chip was slipped so that the wells in the bottom plate overlapped with the second row of wells in the top plate, and was incubated for 2 minutes. The wells in the bottom plate were sequentially brought into contact with wells in rows 3 through 7 of the top plate with incubation time of 2, 2, 2, 30, and 120 minutes. Finally, the beads were pulled to the bottom of the wells in the bottom plate and the wells were separated from the wells in row 7 of the top plate. The results were read in the wells in row 7 of the top plate, and wells in the bottom plate which contained beads were used as markers of positions of the wells in row 7 of the top plate, in case the reaction proceeded in the wells. The picture of the result was taken with an inexpensive cell-phone camera (Nokia 3555b).

The fabrication of SlipChip was performed as follows: The inventors followed the fabrication procedure previously described with the following modifications. The glass plate with photoresist coating was aligned with a photomask and exposed to UV light for 1 min. The size of wells was 1920 µm (length)×360 µm (width) decided by the. The chip used for Au NPs threshold had 5 wells in each row and 20 wells in total. Immediately after exposure, the photomask was removed from the glass plate and the glass plate was developed in 0.1 mol/L NaOH solution and a chromium etchant (a solution of 0.6:0.365 mol/L $HClO_4/(NH_4)_2Ce(NO_3)_6$) separately. The taped glass plate was then carefully immersed in a plastic container with a glass etching solution (1:0.5:0.75 mol/L $HF/NH_4F/HNO_3$) to etch the glass surface that was exposed after the chromium coating was removed. 80 µm deep wells and ducts were etched into the glass plate. Finally, the glass plate was rinsed with ethanol to strip the undeveloped photoresist, and immersed in the chromium etchant to remove the chromium coating. The etched patterns were verified using a Veeco Dektak 150 profilometer. After subjected to an oxygen plasma treatment, the surfaces were rendered hydrophobic by silanization in a vacuum desiccator for 3 hours with tridecafluoro-1,1,2,2-tetrahydrooctyl-1-trichlorosilane.

Preparation of silver enhancement solution before mixing on SlipChipwas performed as follows: Solution A: 3 µL 200 mM citrate buffer was mixed together with 15 µL 100 mM $AgNO_3$ solution and 82 µL Millipore water. Solution B (B1-B4): 4 µL 0.15 mM Au NPs was mixed with 30 µL 100 mM hydroquinone solution and different volume of 1 mM mercaptoethanol solution (0, 10, 30, 50 µL), the total volume was fixed to 90 µL by compensating with Millipore water.

Experiment of Au NPs-based threshold on SlipChipwas performed as follows: The SlipChip was assembled, loaded and slipped as described previously. First, solution A was pipetted into 4 rows in parallel via an inlet connected to 4 rows; solution B1 to B2 were pipetted into 4 rows one by one from 4 separate inlets. Then one plate of glass was slipped relative to the other for the wells in different plates to overlap with each other. The whole chip was put into darkness after mixing and results were examined every 5 minutes by taking microphotographs with a Leica MZ 16 Stereoscope (Leica Microsystems) with a Plan APO 0.63x objective.

The idea of using threshold to get analog-to-digital conversion of concentration can also be applied to other assays (besides immunoassay as described herein) making it relevant to many diagnostic needs. For example, a threshold in nucleic acid can be set using set amounts of immobilized complementary fragment to bind to the nucleic acid and physically removing the bound molecules. Such threshold could be applied to give digital readout in nucleic acid quantification relevant in HIV, HBV, HCV, and other infections. The SlipChip, when combined with the analog-to-digital conversion, could be commercialized and presents an attractive platform for an equipment-free, point-of-care device that could be widely utilized.

In certain embodiments, dead-end filling of SlipChip can be performed including control of the surface chemistry and the gap size between the plates for lubricated and dry SlipChips.

This describes some of the current work to load SlipChips via dead-end filling. In the process which we call "dead-end filling", the fluid that fills the SlipChip after assembly (either lubricating fluid or air) is dissipated through the gap between the two plates of the SlipChip. This SlipChip design has no outlets (in the conventional sense) in the fluidic paths filled by dead end filling.

This method can be used to make a slipchip with inlets compatible with the standard SBS format, e.g. 96 or 384 or 1536 well plate; standard equipment can be used to dispense the solutions into the plate and after pressurization desired volumes would be formed inside the slipchip, slipping may be used to drive the processes. The standard SBS plate, with appropriate openings, can be used as one of the layers of the slipchip; may be designed to inject solutions through one of the wells, and observe through another well, etc.

Device fabrication was performed as follows: Soda-lime glass plates with chromium and photoresist coating (Telic Company, Valencia, Calif.) were used to fabricate devices. The standard method to make glass SlipChip was used. Briefly, the photoresist-coated glass plate was exposed to ultraviolet light covered by a photomask with designs of the wells and ducts. Following removal of the photoresist using 0.1 M NaOH solution, the exposed chromium coating was removed by a chromium-etching solution. The patterns were then etched in glass etching solution in a 40° C. shaker. After glass etching, the remaining photoresist and chromium coatings were removed by ethanol and chromium-etching solution, respectively. The surfaces of the etched glass plates were cleaned and subjected to an oxygen plasma treatment, and then the surfaces were rendered hydrophobic by silanization in a vacuum desiccator as previously described. Inlet holes were drilled with a diamond drill bit 0.035 inch in diameter.

Surface tension was measured as follows: The surface tension of aqueous solution in fluorocarbon was measured as previously reported with some modifications. Briefly, droplets of an aqueous solution of interest were formed at the end of a disposable droplet extrusion tip. The tip was assembled by using quick-set epoxy to glue polyimide-coated glass tubing to one 10 µL disposable pipet tip. The tip was then inversely inserted through an drilled hole of a 1 mL polystyrene cuvette and fixed by using epoxy glue. The polyimide tubing was connected to a 50 µL Hamilton Gastight syringe by using 30-gauge Teflon tubing. The syringe was then filled with the aqueous solution and the 1 mL cuvette was filled with fluorocarbon. The formed droplets were imaged using Model 250 Standard Digital Goniometer & DROPimage Advanced software (Rame-Hart Instrument Co).

Viscosity was measured by using the Cannon-Fenske calibrated viscometers manufactured by Cannon Instrument Company (State College, Pa.). The instructions accompanying the product were followed to take the measurements.

Contact angles were measured following the same protocol reported previously.[3,4] Briefly, 4 µL of a solution to be measured was pipetted on the substrate of interest. The contact angle of the droplet on the substrate was then measured by using an optical contact angle meter (Ramé-Hart Instrument Co., Model 500).

Measuring and controlling the gap between two plates of a SlipChip was performed as follows: Gap measurements were done on DMI6000 epi-fluorescence microscope manufactured by Leica (Germany) equipped with Hamamatsu digital cooled CCD camera (Japan). This cooled camera has linear response on light intensity, which allows precise intensity measurements. Gap between the slides was measured with using mineral oil (Fisher Scientific, NJ) stained with green fluorescent quantum dots (QDs) (Ocean Nanotech, Ark.). Original 1% QDs solution in toluene was filtered through 0.22 micron microcentrifuge Amicon filters (Millipore, Mass.) and sonicated in an ultrasonic bath (Fisher Scientific, NJ) for 10 min. 10% solution of QDs in mineral oil was thoroughly vortexed and kept for at least 10 min under vacuum before filling the device.

Stained mineral oil was deposited between the two plates of the SlipChip; excess oil was removed by rinsing the assembled device sequentially with chloroform, acetone, and ethanol. The two plates were clamped with 8 paper clips and kept for at least 1 hour under pressure before the measurements. Image acquisition, image processing, and measurements were done by using Metamorph software (Universal Imaging Corporation). Images were acquired at reduced field of illumination to avoid leaching of fluorescent light from the much brighter features used as a reference to relatively dim surrounding areas. Fluorescence images were treated according to a standard procedure, which include subtraction of the background camera noise and compensating for the uniformity of field of illumination. SlipChip has features of known depths, allowing for the estimation of the depths of unknown features, including the gap between the slides, by simply comparing fluorescence intensities from these features. To determine precise distance between the slides we applied a self-recursive procedure according to the formula:

$$d_{i+1} = (w + d_i) \times I_s / I_w$$

Here $w$ is the depth of the known feature (well), $d_0 = 0$; $d_i$–gap size, $I_s$ and $I_w$ are intensities acquired from the surrounding surface and from the well. The inventors usually conducted i=1-2 iterations to obtain reliable distance.

To validate this procedure and check for linearity we performed fluorescence measurements from the series of wells of known depths. These reference wells were made on a Laser Ablation System (Resonetics, NH). Depths of all features were measured with using a profilometer (Dektak 150, Veeco, Calif.). Fluorescence intensities acquired from the wells were found to be linear with the well depth. Difference in distances obtained with both techniques was within ~5%. Therefore, one can use fluorescence intensities to measure gaps between the SlipChip plates.

To control gaps between the slides the inventors use fluorescent silica beads of two different sizes. In particular, the inventors used beads with diameter of 1.5 μm and 3.86 μm respectively, obtained from Corpuscular Inc., NY. These beads were silanized before use to make them compatible with the hydrocarbon oil. Silanization was performed as follows: beads were rinsed and sonicated with acetone three times; 5% dichlorodimethylsilane was added to beads in acetone and exposed for 30 min at room temperature. Beads were rinsed once with acetone and twice with chloroform. The appropriate amount of beads was added to fluorescently stained hydrocarbon oil to obtain relatively uniform bead distribution. The gap between the SlipChip plates was measured as described above for each case.

Each device consists of two plates. Approximately 300 μL of the lubricant FC was pipetted on the bottom plate and the top plate was slowly placed on top the bottom plate to avoid trapping air bubbles in channels. The plates, in close contact, were then aligned under microscope and fixed by paper clips.

Testing the physical model (change pressure (home source and barometer) and observe leaking, solution) was performed as follows: Pressure control. Pressure was provided by a adjustable N2 source. The N2 source was bifurcated into two ends, one of which was connected to a barometer indicating the output pressure in the system and the other was connected to the SlipChip. Loading solutions. 4 μL of a green dye was pipetted on top of the inlets of an assembled device. An O-ring, made from PDMS and ~5 mm in height, was then sandwiched between the assembled device and a glass plate and fixed by paper clips. The glass plate bore a nanoport assembly (Upchurch Scientific). The assembly was then connected to the pressure source and solutions were loaded into the channels in the SlipChip. Any solution leakage was observed in the FC-receiving channel. Characterization of loading speed. The channel part between two circles was used to characterize the loading speed. The speed is the average volumetric flow rate, defined as Qave=V/t. V (m$^3$) is the volume of the channel part to be filled with solution and t (s) is the time recorded to fill the channel part.

5 solutions were used to load the FC-lubricated device: a green dye solution was used to load the fluidic path for sample; red, blue, orange, and yellow dyes were used to load the 16 fluidic paths for reagents. The surface of the plates was patterned with wells (approximately 12 μm long, 12 μm wide and 2 μm deep) with ~8 μm spacing. Such wells facilitate dissipation of lubricating FC. The same sample loading procedure that was used to test the physical model was used to load the sample and multiple reagent solutions simultaneously, except that all solutions were first loaded into big reservoir wells ahead of the fluidic paths. After loading, the top plate was slipped relative to the bottom one to bring reagent wells in contact with sample wells and to mix the solution inside.

In order to describe filling process in more details the inventors use equations for the pressure balance. The pressure applied at the inlet has to overcome the capillary pressure at the interface between phase 1 and phase 2.

$$\Delta P_{flow} = P_0 - \Delta P_{cap} \quad \text{Equation 1:}$$

ΔPflow is the pressure difference between the opposite ends of the channel filled with the aqueous phase 1 generated by the resistance of fluids flow, P0 is the pressure applied at the inlet to drive phase 1 into the fluidic path; and ΔPcap is the capillary pressure generated at the interface of phase 1 and phase 2 inside the filling channel. Generally it is difficult to determine precise shape of the interface even in rectangular channels, 5,6 especially if this interface is formed partially by the solid surface, partially by the liquid interface, like in this case. According to the Young-Laplace equation, the approximate pressure difference at the interface between phase 1 and phase 2 in rectangular channel will be $$\Delta P_{cap} = \sigma(1/R_w + 1/R_h) = 2\sigma\left(\frac{1}{w} + \frac{1}{h}\right)\cos\theta^7.$$

Here σ is the surface tension, $R_w$ ($R_w$=w/2 cos θ) and $R_h$ ($R_h$=h/2 cos θ) are the interface approximate curvatures in horizontal (width w) and vertical (height h) directions; θ is a contact angle.

When $P_0$ is larger than $P_{cap}$, $P_{flow}$ is positive and the channel is filled with phase 1. The larger the difference between these pressures the faster filling. Viscous drag forces will prevent the channel to fill out instantaneously. The detailed analysis of the viscous drag during flow through the solid rectangular channel has been discussed previously. The channel is formed (at least partially) by the fluorocarbon oil surrounding aqueous phase. The sealing pressure, $P_{seal}$ (Pa) (Equation 2) prevents phase 1 from leaking out of the channel.

$$P_{seal} = 2 \times \gamma \times \cos \theta / d < 2 \times \gamma / d = P_{seal,max} \quad \text{Equation 2:}$$

Here: γ (N/m) is the surface tension between the aqueous solution (phase 1) and the FC (phase 2); θ is contact angle between phase 1 and surface of the SlipChip in phase 2 and is required to be larger than 90° to prevent capillarity of phase 1; d (m) is the gap distance between the two plates of the SlipChip. The maximal pressure, $P_{seal,max}$ (Pa) exists assuming □=180□□ The inlet pressure must be smaller than the sealing pressure (Equation 3) to avoid leakage into the gap, if the pressure is higher, the aqueous solution will flow between the plates, causing leaking.

$$P_0 < P_{seal,max} \quad \text{Equation 3:}$$

Dissipation of FC limits the filling speed. The inventors used equations to make the prediction, and found that changing the related parameters affects loading speed while changing the unrelated parameters does not. In the testing SlipChip, $\Delta P_{flow}$ includes three terms (Equation 5): $\Delta P_1$, the pressure difference due to flow resistance of the aqueous in the loading channel; $\Delta P_2$, the pressure difference due to flow resistance of phase 2 in the loading channel; and $\Delta P_3$, the pressure difference due to flow resistance of FC between the two plates of a SlipChip. Equation 6, obtained by combining equation 1 and equation 5, expresses the pressure difference along the system. The pressure difference due to flow resistance can be expressed in equation 7.[7] $\mu_i$ is the viscosity of the corresponding fluid, so here $\mu_i$ (Pa·S) is the viscosity of the aqueous phase, $\mu_2$ and $\mu_3$ are the same, equal to the viscosity of the lubricating phase; $L_i$ (m) is the average length of the fluid path. The inventors assume L1 and L2 are the same, equal to half length of the whole loading channel. L3 equals to the distance between the loading channel and the large receiving channel; $Q_i$ (m³/s) is the flow rate discharge. Due to mass conservation, $Q_1$, $Q_2$ and $Q_3$ are the same; $h_i$ is the height of the fluid path, therefore, h1 and h2 are the same, equal to the height of the channel. h3 equals to the gap of the SlipChip; $w_i$ is the width of the fluid path. $w_1$ and $w_2$ are the same, equal to the width of the loading channel. The inventors assume $w_3$ is half length of the loading channel because it is difficult to determine the flow profile of the lubrication fluorocarbon along the loading channel between two plates.

$$\Delta P_{flow} = \Delta P_1 + \Delta P_2 + \Delta P_3 \quad \text{Equation 5:}$$

$$\Delta P_{inlet} = \Delta P_1 + \Delta P_2 + \Delta P_3 + \Delta P_{cap} + AP \quad \text{Equation 6:}$$

$$\Delta P_i = \frac{\pi^4 \mu_i L_i Q_i}{8 h_i^3 w_i \left(1 - \frac{2 h_i}{\pi w_i} \tanh\left(\frac{\pi w_i}{2 h_i}\right)\right)} \quad \text{Equation 7}$$

Hyperbolic tangent will asymptotically go to 1 when channel aspect ratio will increase (height will decrease and/or width of the channel will increase). At the same time pressure drop ΔP in the channel will change proportionally to 1/h³w□ when aspect ratio □ w/h □ asymptotically goes to ∞. $\Delta P_3$ is much larger than $\Delta P_1$ or $\Delta P_2$ because of $h_3 \ll h_{1 and 2} < w_i$ (equation 8). The inventors designed the testing chip to make sure $\Delta P_{inlet}$ was much larger than $\Delta P_{cap}$. Therefore, $\Delta P_{inlet}$ is approximately the same as $\Delta P_3$. By combining equation 7 and 10 with approximation at $h_3 \ll w_3$, the inventors obtained equation 10, which indicates that the loading rate of the aqueous solution, at a fixed inlet pressure, was determined by the dissipation of the lubricating fluorocarbon, including its viscosity, its dissipation dimension.

$$\Delta P_3 \gg \Delta P_1 \approx \Delta P_2 \quad \text{Equation 8:}$$

$$\Delta P_{inlet} \approx \Delta P_3 \quad \text{Equation 9:}$$

$$Q = Q_3 = \frac{8 h_3^3 \times w_3 \times \Delta P_{inlet}}{\pi^4 \mu_3 \times L_3} \quad \text{Equation 10}$$

The inventors experimentally tested the prediction by varying $h_3$ and $\mu_3$ while keeping $w_3$, $L_3$ and $\Delta P_{inlet}$ constant at $1 \times 10^4$ μm, $2 \times 10^3$ μm and $5.3 \times 10^3$ Pa respectively. Approximately, the loading rate increased with $h_3^3$ and $\mu_3$ independently. Furthermore, the inventors confirmed that change of other parameters related to $\Delta P_1$, $\Delta P_2$ and $\Delta P_{cap}$ did not have large effects on the loading rate.

SlipChip can be loaded by dead-end filling. The inventors used the physical model and designed a system to use dead-end filling to load multiple solutions into SlipChips at the same time. The inventors used a previously reported design, relevant to the user-loaded SlipChip screening conditions for protein crystallization with 16 different precipitants and 11 mixing ratios for each precipitant. The inventors made the following modifications to simplify the design: the ducts were made straight without turns optimal for loading; no narrow channels were used to balance the pressure. In addition, the inventors added an inlet reservoir for each loading solution. It was designed not only for buffering the flow as described in the testing SlipChip, but for storage and preventing evaporation as well. The inventors also designed smaller outlet reservoirs to prevent undesirable back flow. To minimize the flow pressure generated by dissipation of lubricating fluid between plates while maintaining the same sealing pressure, receiving channels were designed near the fluidic path so that the flowing distance of LF was be minimized. The inventors made small patterns (~2 μm in depth) on the contacting surface of SlipChip to further lower the flow pressure between plates.

Filling spontaneously ceased when the solution reached the end of the fluidic path even though other solutions were still being loaded. As a result, all the solutions can be loaded using a single pressure source.

To simplify pipetting of solutions into the SlipChip and allow for stable storage of solutions, the design can be modified such that the reservoir next to the inlet has multiple access holes. In this design, the lubricating fluid can exit the reservoir through one of the access holes, decreasing the pressure resistance to allow for easy loading. The solution remains surrounded by the lubricating fluid, allowing for stable storage reducing evaporation. To dispense the solution, pressure is applied at all the access holes to push the solution into the channel to be loaded. The shape of the reservoir can be designed such that the aqueous droplet moves spontaneously away from the access holes and into the proximity with the loading channel.

From the foregoing, it will be observed that numerous variations and modifications may be effected without departing from the spirit and scope of the invention. It is to be understood that no limitation with respect to the specific embodiment illustrated herein is intended or should be inferred. It is, of course, intended to cover by the appended claims all such modifications as fall within the scope of the claims.

The invention claimed is:

1. A reaction system for carrying out a reaction, the reaction system comprising:
   a first part having a first surface;
   a plurality of first areas located along a portion of the first surface; and
   a second part having a second surface opposed to the first surface;
   a plurality of second areas located along a portion of the second surface;
   wherein at least one of the first surface of the first part and the second surface of the second part is configured to move relative to the other between a first position, wherein at least some of said plurality of first areas are exposed to at least some of said plurality of second areas so as to form a plurality of rows, each row comprising overlapping first areas and second areas in fluidic communication along said row;
   a second position, wherein at least some of said plurality of first areas are exposed to at least some of said plurality of second areas so as to form a plurality of columns, each column comprising overlapping first areas and second areas in fluidic communication along said column;
   wherein the first part and the second part are engaged with each other before and after the relative motion; and
   wherein the first and second areas are configured to maintain at least one substance.

2. The reaction system of claim 1, further comprising a plurality of channels in said first or second part, wherein said plurality of channels are in fluidic communication with said plurality of rows of overlapping first and second areas in said first position.

3. The reaction system of claim 2, wherein said plurality of channels comprise inlet ducts or outlet ducts.

4. The reaction system of claim 1, further comprising a plurality of channels in said first or second part, wherein said plurality of channels are in fluidic communication with said plurality of columns of overlapping first and second areas in said second position.

5. The reaction system of claim 4, wherein said plurality of channels comprise inlet ducts or outlet ducts.

6. The reaction system of claim 1, wherein said relative motion is linear, rotational, or a combination of both.

7. The reaction system of claim 1, wherein said plurality of first areas are arranged in said first surface along rows extending parallel to one another.

8. The reaction system of claim 1, wherein said plurality of second areas are arranged in said second surface along rows extending parallel to one another.

9. The reaction system of claim 1, wherein said plurality of first areas or said plurality of second areas comprise ducts.

10. The reaction system of claim 1, wherein at least one first area or second area comprises a capture element.

11. The reaction system of claim 10, wherein the capture element is selected from the group consisting of antibodies, affinity-proteins, aptamers, beads, particles and biological cells.

12. The reaction system of claim 11, wherein the capture element is surface-bound antibodies or bead-bound antibodies.

13. The reaction system of claim 1, wherein the reaction comprises a synthetic reaction, a neutralization reaction, a decomposition reaction, a displacement reaction, a reduction-oxidation reaction, a precipitation, a crystallization, a combustion reaction, or a polymerization reaction.

14. The reaction system of claim 1, wherein the reaction produces or consumes a gaseous product.

\* \* \* \* \*